US 7,842,701 B2
(12) United States Patent
Fukumoto et al.

(10) Patent No.: US 7,842,701 B2
(45) Date of Patent: Nov. 30, 2010

(54) PYRAZOLOQUINOLONE DERIVATIVE AND USE THEREOF

(75) Inventors: Shoji Fukumoto, Osaka (JP); Takeshi Yamamoto, Osaka (JP); Masanori Okaniwa, Osaka (JP); Toshimasa Tanaka, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 863 days.

(21) Appl. No.: 10/589,443

(22) PCT Filed: Feb. 18, 2005

(86) PCT No.: PCT/JP2005/003086

§ 371 (c)(1), (2), (4) Date: May 7, 2007

(87) PCT Pub. No.: WO2005/080392

PCT Pub. Date: Sep. 1, 2005

(65) Prior Publication Data

US 2007/0281963 A1 Dec. 6, 2007

(30) Foreign Application Priority Data

Feb. 19, 2004 (JP) ............... 2004-042491

(51) Int. Cl.
*A61K 31/437* (2006.01)
*C07D 471/06* (2006.01)

(52) U.S. Cl. ........................................ 514/293; 546/82

(58) Field of Classification Search ............. 514/293; 546/82

See application file for complete search history.

(56) References Cited

U.S. PATENT DOCUMENTS

| 6,051,577 | A | 4/2000 | Altmann |
| 6,268,391 | B1 | 7/2001 | Dickerson et al. |

FOREIGN PATENT DOCUMENTS

| EP | 0 476 544 | 3/1992 |
| JP | 5-132484 | 5/1993 |
| JP | 2000-506537 | 5/2000 |
| JP | 2002-514228 | 5/2002 |
| WO | WO 95/32205 | 11/1995 |
| WO | WO 01/42247 | 6/2001 |
| WO | WO 01/47892 | 7/2001 |
| WO | WO 03/004492 | 1/2003 |
| WO | WO 03/008409 | 1/2003 |

OTHER PUBLICATIONS

Cecchi et al. "Synthesis and Binding Studies of 1-Arylpyrazolo [4,5-c]- and 2-Arylpyrazolo [4,3-c] Quinolin-4-Ones". *Farmaco. Edizione Scientifica.* 1995. vol. 40 pp. 509-516.
International Search Report dated Apr. 5, 2005.

*Primary Examiner*—Taofiq A Solola
(74) *Attorney, Agent, or Firm*—Hamre, Schumann, Mueller & Larson, P.C.

(57) ABSTRACT

The present invention provides a pyarzoloquinolone derivative having kinase inhibitory activity. The derivative is represented by the formula:

(I)

wherein $R^1$ is an aryl group which may be substituted, or an aromatic heterocyclic group which may be substituted; $R^2$ is a hydrogen atom, an amino group which may be substituted, a hydroxy group which may be substituted, or a thiol group which may be substituted; $R^3$, $R^4$, $R^5$ and $R^6$, which may be identical or different, are each (1) a hydrogen atom, (2) a nitro group, (3) a cyano group, (4) a halogen atom, (5) a hydrocarbon group which may be substituted, (6) an amino group which may be substituted, (7) a hydroxy group which may be substituted, or (8) a thiol group which may be substituted; and $R^3$ and $R^4$, $R^4$ and $R^5$, and $R^5$ and $R^6$ may respectively form a ring together with the adjacent carbon atom, or salt thereof.

4 Claims, No Drawings

PYRAZOLOQUINOLONE DERIVATIVE AND USE THEREOF

TECHNICAL FIELD

The present invention relates to a pyarzoloquinolone derivative which is useful as protein kinase (tyrosine kinase, etc.; in particular, Src) inhibitor, and use thereof.

BACKGROUND ART

A protein kinase transmits signals related to proliferation, intercellular communication, survival and the like, by phosphorylating tyrosine, serine or threonine in the protein itself or in other proteins. Such signals take an important role in proliferation, survival and the like of normal cells. However, genetic mutation, overexpression or activation of a molecule having protein kinase activity in cancer cells causes uncontrollableness of the signals, and leads to abnormal accentuation of the signals. For example, receptor type tyrosine kinases such as EGFR, HER2, IGFR, PDGFR and the like, non-receptor type tyrosine kinases such as Src, FAK, Met and the like, and serine threonine kinase such as Akt, c-raf, MEK and the like are overexpressed or activated in cancer cells, and for example, tyrosine kinases such as EGFR, Ab1, F1t-3 and the like, and serine threonine kinase such as b-raf and the like are reported to have genetic mutations (Genes and Development, Vol. 17, p. 2998 (2003)). In addition, when the gene of such a protein kinase is transfected to normal cells and overexpressed, the cells turn into cancer cells. Tumor development, tumor growth and malignant alteration of tumor are closely related to the accentuation of signals by protein kinases. Accordingly, a compound inhibiting protein kinases is believed to be useful as a drug for the prophylaxis and/or treatment of cancer, due to the ability to inhibit the proliferation of cancer cells, or to block the survival signals, and the like.

Abnormal protein kinases are also involved in other various diseases, in addition to cancer. For example, arteriosclerosis is related to the signals from PDGF receptors, etc.; nephritis to the signals from PDGF receptors, etc.; multiple sclerosis to the signals from Lck, etc.; viral diseases such as AIDS to the signals from Mos, etc.; psoriasis to the signals form EGF receptors, etc.; diabetic retinopathy to the signals from VEGF receptors, etc.; rhinitis to the signals from Syk, etc.; asthma to the signals from Syk, JAK3, $I_{KK\beta}$, etc.; glaucoma to the signals from ROCK, etc.; allergic diseases to the signals from Lyn, etc.; cardiac failure to the signals from ROCK, etc.; subarachnoid hemorrhage to the signals from ROCK or Rho, etc.; impotence to the signals from ROCK, etc.; Parkinson's disease to the signals from Jun, etc.; cerebral ischemic disease to the signals from Jun, Src, GSK-3, etc.; ischemic heart diseases such as myocardial infarction, angina pectoris and the like to the signals from p38MAP kinases, etc.; chronic rheumatoid arthritis to the signals from $I_{KK}1$, etc.; thrombosis to the signals from PKC, etc.; obesity to the signals from GSK-3, VEGF receptors, etc.; diabetes mellitus to the signals from GSK-3, etc.; chronic obstructive lung disease to the signals from GSK-3, etc.; osteoporosis to the signals from Src, etc.; and the rejection response associated with transplantation to the signals from Lck, etc. Therefore, such compound inhibiting protein kinases is believed to be useful as a drug for the prophylaxis and/or treatment of these diseases.

The Src family members are non-receptor type tyrosine kinases consisting of at least 9 members (Src, Fyn, Yes, Blk, Yrk, Fgr, Hck, Lck and Lyn) (Annual Review of Cell Development and Biology, Vol. 13, p. 513 (1997)). Among these, Src is in particular highly related to cancer. For example, when the level of Src protein is reduced, tumor growth is inhibited (Cell Growth and Differentiation, Vol. 8, p. 269 (1997)), while when the level of Src protein is increased, tumor growth is accelerated (Cell Growth and Differentiation, Vol. 8, p. 1287 (1997)). Further, Src has increased activity in colon cancer, breast cancer, pancreatic cancer, ovarian cancer, esophageal cancer, lung cancer, cervical cancer, stomach cancer and the like (Biochimica et Biophysica Acta, Vol. 1602, p. 114 (2002)), and it is reported that cancer with activated Src is highly metastatic and shows poor prognosis (Cancer Research, Vol. 94, p. 344 (2002)). Moreover, when the level of Src protein is reduced in cancer cells, the amount of VEGF produced is decreased (Journal Biological Chemistry, Vol. 273, p. 1052 (1998)). Since Src is involved in the proliferation signals of VEGF in vascular endothelial cells (Molecular cell, Vol. 4, p. 915 (1999)), Src also plays an important role in angiogenesis. Therefore, Src promotes proliferation of cancer cells directly or through angiogenesis, and thus, a compound inhibiting Src is believed to be useful as a drug for the prophylaxis and/or treatment of cancer such as, for example, colon cancer, breast cancer, pancreatic cancer, ovarian cancer, esophageal cancer, lung cancer, cervical cancer, stomach cancer and the like.

In addition, a knock-out mouse lacking Src gene develops marble bones disease, which is a disease caused by the lack of osteoclast activity (Cell, Vol. 64, p. 693 (1991)). It has been found that in such a mouse, there is no change in the number of osteoclast cells, but the function thereof is impaired. Further, the Src expression is high in the osteoclast cells, and osteoporosis develops when the activity of osteoclast cells predominates over the activity of osteoblast cells. Accordingly, a compound inhibiting Src is believed to be useful as a drug for the prophylaxis and/or treatment of osteoporosis. Furthermore, since creation of space inside the bone where cancer cells can proliferate under the activation of osteoclast cells, plays an important role in osseous metastasis, a compound inhibiting Src can be used as a drug for the prophylaxis and/or treatment of osseous metastasis of cancer cells (Cancer Research, Vol. 63, p. 5028 (2003)).

For the literature describing kinase inhibitors, particularly Src inhibitors, for example, JP-A No. 2003-519127, WO 03/004492, and WO 03/008409 may be mentioned.

Further, for the literature disclosing a compound similar to the pyrazoloquinolone derivative of the present patent application, for example, the following literatures are available.

EP-A No. 476544 describes a compound represented by the formula:

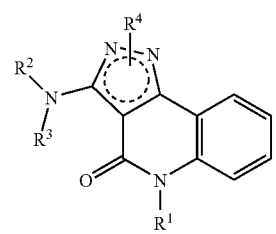

wherein $R^1$, $R^2$ and $R^3$ are each a hydrogen atom or a lower alkyl group; $R^4$ is a hydrogen atom, a lower alkyl group, a lower haloalkyl group, or a lower alkoxy-carbonyl group; and broken line represents two conjugated double bonds existing in the pyrazole ring, or a salt thereof as a therapeutic agent for inflammation and hepatic failure.

JP-A No. 5-132484 describes a compound represented by the formula:

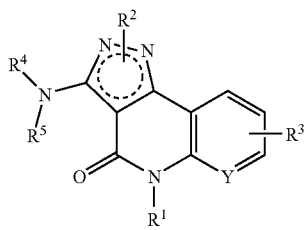

wherein $R^1$ is a hydrogen atom, a lower alkyl group, a lower alkenyl group, a carboxy-lower alkyl group, a lower alkoxy-carbonyl-lower alkyl group, a halogen-substituted lower alkyl group, a phenyl-lower alkyl group, or a phenyl group which may be substituted with a group selected from a halogen atom and a lower alkoxy group; $R^2$ is a hydrogen atom, a lower alkyl group, a phenyl group, a hydroxy-lower alkyl group, a cyano-lower alkyl group, a carboxy-lower alkyl group, a lower alkoxy-carbonyl-lower alkyl group, a halogen-substituted lower alkyl group, or a lower alkoxy-carbonyl group; $R^3$ is a hydrogen atom, or a halogen atom; $R^4$ and $R^5$ may be identical or different, and are each a hydrogen atom, a lower alkanoyl group, a lower alkylsulfonyl group, a lower alkyl group, a lower alkenyl group, a formyl group or a carboxy-lower alkyl group; $R^2$ and $R^4$ may be bonded to each other to form the group —CH$_2$—CH$_2$—CO— or the group —CH=CH—; Y is the group —CH= or a nitrogen atom; and broken line represents two double bonds existing in the pyrazole ring, as an agent for the prophylaxis and/or treatment of chronic arthritic rheumatism, nephritis, psoriasis, systemic erythematosus, and low back pain.

WO 95/32205 describes a compound represented by the formula:

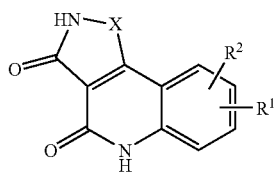

wherein $R^1$ and $R^2$ are each independently a hydrogen atom, a lower alkyl group, a lower alkoxy group or the like; and X is —CH=CH—, —NH— or the like, as an agent for the prophylaxis and/or treatment of ischemia and hyperlipidemia.

WO 01/42247 describes a compound represented by the formula:

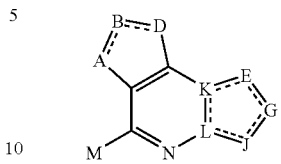

wherein A, B and D may be identical or different, and are each a nitrogen atom, an oxygen atom, a sulfur atom or the like; E and G may be identical or different, and are each a nitrogen atom, an oxygen atom, a sulfur atom or the like; J is a nitrogen atom, a substituted carbon atom or the like; K and L may be identical or different, and are each a carbon atom or a nitrogen atom; M is a hydrogen atom, a hydroxy group which may be substituted or the like, as an agent for the prophylaxis and/or treatment of depression and mania.

It is strongly demanded to develop a compound which has excellent kinase inhibitory activity, particularly Src inhibitory activity, and which is useful as a medicine.

DISCLOSURE OF THE INVENTION

The inventors of the present invention conducted various investigation on heterocyclic compounds having kinase inhibitory activity, particularly Src inhibitory activity. As a result, they synthesized for the first time a compound represented by the formula (hereinafter, may be simply referred to as Compound (I)):

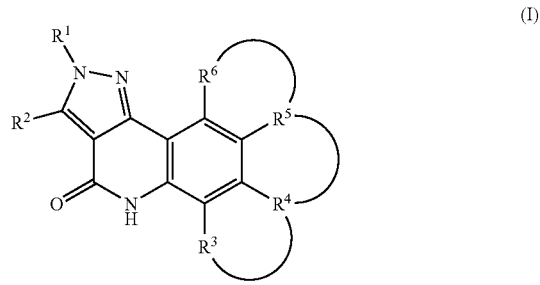

wherein $R^1$ is an aryl group which may be substituted, or an aromatic heterocyclic group which may be substituted; $R^2$ is a hydrogen atom, an amino group which may be substituted, a hydroxy group which may be substituted, or a thiol group which may be substituted; $R^3$, $R^4$, $R^5$ and $R^6$, which may be identical or different, are each (1) a hydrogen atom, (2) a nitro group, (3) a cyano group, (4) a halogen atom, (5) a hydrocarbon group which may be substituted, (6) an amino group which may be substituted, (7) a hydroxy group which may be substituted, or (8) a thiol group which may be substituted; and $R^3$ and $R^4$, $R^4$ and $R^5$, and $R^5$ and $R^6$ may respectively form a ring together with the adjacent carbon atom, a compound represented by the formula (hereinafter, may be simply referred to as Compound (I′)):

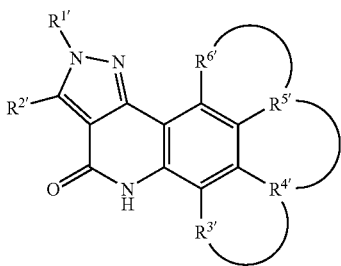

wherein $R^{1'}$ is a cycloalkyl group which may be substituted; $R^{2'}$ is a hydrogen atom, an amino group which may be substituted, a hydroxy group which may be substituted, or a thiol group which may be substituted; $R^{3'}$, $R^{4'}$, $R^{5'}$ and $R^{6'}$, which may be identical or different, are each (1) a hydrogen atom, (2) a nitro group, (3) a cyano group, (4) a halogen atom, (5) a hydrocarbon group which may be substituted, (6) an amino group which may be substituted, (7) a hydroxy group which may be substituted, or (8) a thiol group which maybe substituted; and $R^{3'}$ and $R^{4'}$, $R^{4'}$ and $R^{5'}$, and $R^{5'}$ and $R^{6'}$ may respectively form a ring together with the adjacent carbon atom, or a salt thereof, and also found that this compound or a salt thereof has excellent kinase inhibitory activity, particularly Src inhibitory activity, based on the specific chemical structure. The inventors completed the invention based on this founding.

Thus, the invention provides the following:

[1] A compound represented by the formula:

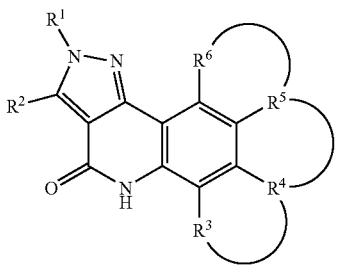

wherein $R^1$ is an aryl group which may be substituted, or an aromatic heterocyclic group which may be substituted; $R^2$ is a hydrogen atom, an amino group which may be substituted, a hydroxy group which may be substituted, or a thiol group which may be substituted; $R^3$, $R^4$, $R^5$ and $R^6$, which may be identical or different, are each (1) a hydrogen atom, (2) a nitro group, (3) a cyano group, (4) a halogen atom, (5) a hydrocarbon group which may be substituted, (6) an amino group which may be substituted, (7) a hydroxy group which may be substituted, or (8) a thiol group which may be substituted; and $R^3$ and $R^4$, $R^4$ and $R^5$, and $R^5$ and $R^6$ may respectively form a ring together with the adjacent carbon atom, or a salt thereof.

[2] The compound according to [1] above, wherein $R^1$ is (1) a phenyl group which may be substituted with 1 to 5 substituents selected from: (1') a $C_{1-6}$ alkyl group which may be substituted with a substituent selected from a $C_{1-6}$ alkyl group, a $C_{2-6}$ alkenyl group, a $C_{2-6}$ alkynyl group, a $C_{6-12}$ aryl group, a $C_{7-14}$ aralkyl group, a hydroxy group, a $C_{1-6}$ alkoxy group, a $C_{6-12}$ aryloxy group, a $C_{7-14}$ aralkyloxy group, a $C_{1-6}$ alkyl-carbonyloxy group, a $C_{2-6}$ alkenyl-carbonyloxy group, a $C_{2-6}$ alkynyl-carbonyloxy group, a $C_{1-6}$ alkylthio group, a $C_{6-12}$ arylthio group, a $C_{7-14}$ aralkylthio group, a carboxy group, a $C_{1-6}$ alkyl-carbonyl group, a $C_{2-6}$ alkenyl-carbonyl group, a $C_{2-6}$ alkynyl-carbonyl group, a $C_{6-12}$ aryl-carbonyl group, a $_{7-14}$ aralkyl-carbonyl group, a $C_{1-6}$ alkoxy-carbonyl group, a $C_{2-6}$ alkenyloxy-carbonyl group, a $C_{2-6}$ alkynyloxy-carbonyl group, a $C_{6-12}$ aryloxy-carbonyl group, a $C_{7-14}$ aralkyloxy-carbonyl group, a carbamoyl group, a mono-$C_{1-6}$ alkyl-carbamoyl group, a di-$C_{1-6}$ alkylcabamoyl group, a $C_{1-6}$ alkylsulfonyl group, a $C_{2-6}$ alkenylsulfonyl group, a $C_{2-6}$ alkynylsulfonyl group, an amino group, a mono-$C_{1-6}$ alkylamino group, a di-$C_{1-6}$ alkylamino group, a mono-$C_{2-6}$ alkenylamino group, a di-$C_{2-6}$ alkenylamino group, a mono-$C_{2-6}$ alkynylamino group, a di-$C_{2-6}$ alkynylamino group, a mono-$C_{6-12}$ arylamino group, a di-$C_{6-12}$ arylamino group, a mono-$C_{7-14}$ aralkylamino group, a di-$C_{7-14}$ aralkylamino group, a halogen atom, an azido group, a nitro group, a cyano group, a 5- to 8-membered heterocyclic group (this heterocyclic group may be substituted with a halogen atom, a hydroxy group, or a $C_{1-6}$ alkyl group which may be halogenated), a 5- to 8-membered heterocyclic-oxy group (this heterocyclic moiety may be substituted with a halogen atom, a hydroxy group, or a $C_{1-6}$ alkyl group which may be halogenated), a 5- to 8-membered heterocyclic-carbonyl group (this heterocyclic moiety may be substituted with a halogen atom, a hydroxy group, or a $C_{1-6}$ alkyl group which may be halogenated), a $C_{1-4}$ alkylene group, and a $C_{1-4}$ alkylenedioxy group (hereinafter, simply referred to as Substituent Group C); (2') a $C_{2-6}$ alkenyl group which may be substituted with a substituent selected from the Substituent Group C; (3') a $C_{2-6}$ alkynyl group which may be substituted with a substituent selected from the Substituent Group C; (4') a $C_{6-12}$ aryl group which may be substituted with a substituent selected from the Substituent Group C; (5') a $C_{7-14}$ aralkyl group which may be substituted with a substituent selected from the Substituent Group C; (6') a hydroxy group; (7') a $C_{1-6}$ alkoxy group which may be substituted with a substituent selected from the Substituent Group C; (8') a $C_{6-12}$ aryloxy group which may be substituted with a substituent selected from the Substituent Group C; (9') a $C_{7-14}$ aralkyloxy group which may be substituted with a substituent selected from the Substituent Group C; (10') a $C_{1-6}$ alkyl-carbonyloxy group which may be substituted with a substituent selected from the Substituent Group C; (11') a $C_{2-6}$ alkenyl-carbonyloxy group which may be substituted with a substituent selected from the Substituent Group C; (12') a $C_{2-6}$ alkynyl-carbonyloxy group which may be substituted with a substituent selected from the Substituent Group C; (13') a $C_{1-6}$ alkylthio group which may be substituted with a substituent selected from the Substituent Group C; (14') a $C_{6-12}$ arylthio group which may be substituted with a substituent selected from the Substituent Group C; (15') a $C_{7-14}$ aralkylthio group which may be substituted with a substituent selected from the Substituent Group C; (16') a carboxy group; (17') a $C_{1-6}$ alkyl-carbonyl group which may be substituted with a substituent selected from the Substituent Group C; (18') a $C_{2-6}$ alkenyl-carbonyl group which may be substituted with a substituent selected from the Substituent Group C; (19') a $C_{2-6}$ alkynyl-carbonyl group which may be substituted with a substituent selected from the Substituent Group C; (20') a $C_{6-12}$ aryl-carbonyl group which may be substituted with a substituent selected from the Substituent Group C; (21') a $C_{7-14}$ aralkyl-carbonyl group which may be substituted with a substituent selected from the Substituent Group C; (22') a $C_{1-6}$ alkoxy-carbonyl group which may be substituted with a substituent selected from the Substituent Group C; (23') a $C_{2-6}$ alkenyloxy-carbonyl group which may be substituted with a substituent selected from the Substituent Group C; (24') a $C_{2-6}$ alkynyloxy-carbonyl group which may be substituted with a substituent selected from the Substituent Group C; (25') a $C_{6-12}$ aryloxy-carbonyl group which may be substituted with a substituent selected from the Substituent Group C; (26') a $C_{7-14}$ aralkyloxy-carbonyl group which may be substituted with a substituent selected from the Substituent Group C; (27') a carbamoyl group; (28') a mono-$C_{1-6}$ alkyl-carbamoyl group which may be substituted with a substituent selected from the Substituent Group C; (29') a di-$C_{1-6}$ alkyl-carbamoyl group which may be substituted with a substituent selected from the Substituent Group C; (30') a $C_{1-6}$ alkylsulfonyl group which may be substituted with a substituent selected from the Substituent Group C; (31') a $C_{2-6}$ alkenylsulfonyl group which may be substituted with a substituent selected from the Substituent Group C; (32') a $C_{2-6}$ alkynylsulfonyl group which may be substituted with a substituent selected from the Substituent Group C; (33') an amino group; (34') a mono-$C_{1-6}$ alkylamino group which may be substituted with a substituent selected from the Substituent Group C; (35') a di-$C_{1-6}$ alkylamino group which may be substituted with a substituent selected from the Substituent Group C; (36') a mono-$C_{2-6}$ alkenylamino group which may be substituted with a substituent selected from the Substituent Group C; (37') a di-$C_{2-6}$ alkenylamino group which may be substituted with a substituent selected from the Substituent Group C; (38') a mono-$C_{2-6}$ alkynylamino group which may be substituted with a substituent selected from the Substituent Group C; (39') a di-$C_{2-6}$ alkynylamino group which may be substituted with a substituent selected from the Substituent Group C; (40') a mono-$C_{6-12}$ arylamino group which may be substituted with a substituent selected from the Substituent Group C; (41') a di-$C_{6-12}$ arylamino group which may be substituted with a substituent selected from the Substituent Group C; (42') a mono-$C_{7-14}$ aralkylamino group which may be substituted with a substituent selected from the Substituent Group C; (43') a di-$C_{7-14}$ aralkylamino group which may be substituted with a substituent selected from the Substituent Group C; (44') a mono-5- to 8-membered heterocyclic amino group which may be substituted with a substituent selected from the Substituent Group C; (45') a di-5- to 8-membered heterocyclic amino group which may be substituted with a substituent selected from the Substituent Group C; (46') a ($C_{1-6}$ alkyl which may be substituted with a substituent selected from the Substituent Group C)(5- to 8-membered heterocyclic which may be substituted with a substituent selected from the Substituent Group C) amino group; (47') a halogen atom; (48') an azido group; (49') a nitro group; (50') a cyano group; (51') a 5- to 8-membered heterocyclic group which may be substituted with a substituent selected from the Substituent Group C; (52') a 5 - to 8-membered heterocyclic-oxy group which may be substituted with a substituent selected from the Substituent Group C; (53') a 5- to 8-membered heterocyclic-carbonyl group which may be substituted with a substituent selected from the Substituent Group C; (54') a $C_{1-4}$ alkylene; and (55') a $C_{1-4}$ alkylenedioxy group (hereinafter, simply referred to Substituent Group A), (2) a 5- or 6-membered aromatic heterocyclic group which may be substituted with 1 to 5 substituents selected from the Substituent Group A, or (3) a group resulting from condensation of the 5- or 6-membered aromatic heterocyclic group which may be substituted with 1 to 5 substituents selected from the Substituent Group A, with a benzene ring;

$R^2$ is
(1) a hydrogen atom,
(2) an amino group which may be mono- or di-substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a $C_{1-6}$ alkylsulfonyl group which may be substituted with 1 to 5 substituents selected from the Substituent Group A; a $C_{6-10}$ arylsulfonyl group which may be substituted with 1 to 5 substituents selected from the Substituent Group A; a $C_{7-11}$ aralkylsulfonyl group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-carbonyl group which may be substituted with 1 to 5 substituents selected from the Substituent Group A; a 5- to 8-membered heterocyclic oxy-carbonyl group which may be substituted with 1 to 5 substituents selected from the Substituent Group A; and a 5- to 8-membered heterocyclic sulfonyl group which may be substituted with 1 to 5 substituents selected from the Substituent Group A, (3) a hydroxy group which may be substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a $C_{1-6}$ alkylsulfonyl group which may be substituted with 1 to 5 substituents selected from the Substituent Group A; a $C_{6-10}$ arylsulfonyl group which may be substituted with 1 to 5 substituents selected from the Substituent Group A; a $C_{7-11}$ aralkylsulfonyl group which may be substituted with 1 to 5 substituents selected from the Substituent Group A; a $C_{1-6}$ alkylsulfonyloxy group which may be substituted with 1 to 5 substituents selected from the Substituent Group A; a $C_{6-10}$ arylsulfonyloxy group which may be substituted with 1 to 5 substituents selected from the Substituent Group A; a $C_{7-11}$ aralkylsulfonyloxy group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-carbonyl group which may be substituted with 1 to 5 substituents selected from the Substituent Group A; a 5- to 8-membered heterocyclic oxy-carbonyl group which may be substituted with 1 to 5 substituents selected from the Substituent Group A; and a 5- to 8-membered heterocyclic sulfonyl group which may be substituted with 1 to 5 substituents selected from the Substituent Group A, (4) a thiol group which may be substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-oxy group which may be substituted with 1 to 5 substituents selected from the Substituent Group A; a 5- to 8-membered heterocyclic-carbonyl group which may be substituted with 1 to 5 substituents selected from the Substituent Group A; and a 5- to 8-membered heterocyclic oxy-carbonyl group which may be substituted with 1 to 5 substituents selected from the Substituent Group A, (5) a $C_{1-6}$ alkylsulfinyl group which may be substituted with 1 to 5 substituents selected from the Substituent Group A, (6) a $C_{6-10}$ arylsulfinyl group which may be substituted with 1 to 5 substituents selected from the Substituent Group A, (7) a $C_{1-6}$ alkylsulfonyl group which may be substituted with 1 to 5 substituents selected from the Substituent Group A, or (8) a $C_{6-10}$ arylsulfonyl group which may be substituted with 1 to 5 substituents selected from the Substituent Group A;

$R^3$, $R^4$, $R^5$ and $R^6$, which may be identical or different, are each:

(1) a hydrogen atom, (2) a nitro group, (3) a cyano group, (4) a halogen atom, (5) a $C_{1-6}$ alkyl group which may be substituted with 1 to 5 substituents selected from the Substituent Group A, (6) a $C_{2-6}$ alkenyl group which may be substituted with 1 to 5 substituents selected from the Substituent Group A, (7) a $C_{2-6}$ alkynyl group which may be substituted with 1 to 5 substituents selected from the Substituent Group A, (8) a $C_{3-6}$ cycloalkyl group which may be substituted with 1 to 5 substituents selected from the Substituent Group A, (9) a $C_{6-10}$ aryl group which may be substituted with 1 to 5 substituents selected from the Substituent Group A,

(10) a $C_{7-11}$ aralkyl group which may be substituted with 1 to 5 substituents selected from the Substituent Group A,

(11) a $C_{1-6}$ alkyl-carbonyl group which may be substituted with 1 to 5 substituents selected from the Substituent Group A,

(12) a $C_{2-6}$ alkenyl-carbonyl group which may be substituted with 1 to 5 substituents selected from the Substituent Group A,

(13) a $C_{2-6}$ alkynyl-carbonyl group which may be substituted with 1 to 5 substituents selected from the Substituent Group A,

(14) a $C_{3-6}$ cycloalkyl-carbonyl group which may be substituted with 1 to 5 substituents selected from the Substituent Group A,

(15) a $C_{6-10}$ aryl-carbonyl group which may be substituted with 1 to 5 substituents selected from the Substituent Group A,

(16) a $C_{7-11}$ aralkyl-carbonyl group which may be substituted with 1 to 5 substituents selected from the Substituent Group A,

(17) a $C_{1-6}$ alkoxy-carbonyl group which may be substituted with 1 to 5 substituents selected from the Substituent Group A,

(18) a $C_{2-6}$ alkenyloxy-carbonyl group which may be substituted with 1 to 5 substituents selected from the Substituent Group A,

(19) a $C_{2-6}$ alkynyloxy-carbonyl group which may be substituted with 1 to 5 substituents selected from the Substituent Group A,

(20) a $C_{3-6}$ cycloalkyloxy-carbonyl group which may be substituted with 1 to 5 substituents selected from the Substituent Group A,

(21) a $C_{6-10}$ aryloxy-carbonyl group which may be substituted with 1 to 5 substituents selected from the Substituent Group A,

(22) a $C_{7-11}$ aralkyloxy-carbonyl group which may be substituted with 1 to 5 substituents selected from the Substituent Group A,

(23) a carbamoyl group which may be mono- or di-substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a $C_{1-6}$ alkylsulfonyl group which may be substituted with 1 to 5 substituents selected from the Substituent Group A; a $C_{6-10}$ arylsulfonyl group which may be substituted with 1 to 5 substituents selected from the Substituent Group A; a $C_{7-11}$ aralkylsulfonyl group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-carbonyl group which may be substituted with 1 to 5 substituents selected from the Substituent Group A; a 5- to 8-membered heterocyclic oxy-carbonyl group which may be substituted with 1 to 5 substituents selected from the Substituent Group A; and a 5- to 8-membered heterocyclic sulfonyl group which may be substituted with 1 to 5 substituents selected from the Substituent Group A,

(24) a sulfamoyl group which may be mono- or di-substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a $C_{1-6}$ alkylsulfonyl group which may be substituted with 1 to 5 substituents selected from the Substituent Group A; a $C_{6-10}$ arylsulfonyl group which may be substituted with 1 to 5 substituents selected from the Substituent Group A; a $C_{7-11}$ aralkylsulfonyl group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-carbonyl group which may be substituted with 1 to 5 substituents selected from the Substituent Group A; a 5- to 8-membered heterocyclic oxy-carbonyl group which may be substituted with 1 to 5 substituents selected from the Substituent Group A; and a 5- to 8-membered heterocyclic sulfonyl group which may be substituted with 1 to 5 substituents selected from the Substituent Group A,

(25) an amino group which may be mono- or di-substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a $C_{1-6}$ alkylsulfonyl group which may be substituted with 1 to 5 substituents selected from the Substituent Group A; a $C_{6-10}$ arylsulfonyl group which may be substituted with 1 to 5 substituents selected from the Substituent Group A; a $C_{7-11}$ aralkylsulfonyl group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-carbonyl group which may be substituted with 1 to 5 substituents selected from the Substituent Group A; a 5- to 8-membered heterocyclic oxy-carbonyl group which may be substituted with 1 to 5 substituents selected from the Substituent Group A; and a 5- to 8-membered heterocyclic sulfonyl group which may be substituted with 1 to 5 substituents selected from the Substituent Group A,

(26) a hydroxy group which may be substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a $C_{1-6}$ alkylsulfonyl group which may be substituted with 1 to 5 substituents selected from the Substituent Group A; a $C_{6-10}$ arylsulfonyl group which may be substituted with 1 to 5 substituents selected from the Substituent Group A; a $C_{7-11}$ aralkylsulfonyl group which may be substituted with 1 to 5 substituents selected from the Substituent Group A; a $C_{1-6}$ alkylsulfonyloxy group which may be substituted with 1 to 5 substituents selected from the Substituent Group A; a $C_{6-10}$ arylsulfonyloxy group which may be substituted with 1 to 5 substituents selected from the Substituent Group A; a $C_{7-11}$ aralkylsulfonyloxy group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-carbonyl group which may be substituted with 1 to 5 substituents selected from the Substituent Group A; a 5- to 8-membered heterocyclic oxy-carbonyl group which may be substituted with 1 to 5 substituents selected from the Substituent Group A; and a 5- to 8-membered heterocyclic sulfonyl group which may be substituted with 1 to 5 substituents selected from the Substituent Group A,

(27) a thiol group which may be substituted with a substituent selected from: a $C_{1-6}$ alkyl group which may be substituted with 1 to 5 substituents selected from the Substituent Group A; a $C_{2-6}$ alkenyl group which may be substituted with 1 to 5 substituents selected from the Substituent Group A; a $C_{2-6}$ alkynyl group which may be substituted with 1 to 5 substituents selected from the Substituent Group A; a $C_{3-6}$ cycloalkyl group which may be substituted with 1 to 5 substituents selected from the Substituent Group A; a $C_{6-10}$ aryl group which may be substituted with 1 to 5 substituents selected from the Substituent Group A; a $C_{7-11}$ aralkyl group which may be substituted with 1 to 5 substituents selected from the Substituent Group A; a $C_{1-6}$ alkyl-carbonyl group which may be substituted with 1 to 5 substituents selected from the Substituent Group A; a $C_{2-6}$ alkenyl-carbonyl group which may be substituted with 1 to 5 substituents selected from the Substituent Group A; a $C_{2-6}$ alkynyl-carbonyl group which may be substituted with 1 to 5 substituents selected from the Substituent Group A; a $C_{3-6}$ cycloalkyl-carbonyl group which may be substituted with 1 to 5 substituents selected from the Substituent Group A; a $C_{6-10}$ aryl-carbonyl group which may be substituted with 1 to 5 substituents selected from the Substituent Group A; a $C_{7-11}$ aralkyl-carbonyl group which may be substituted with 1 to 5 substituents selected from the Substituent Group A; a $C_{1-6}$ alkoxy-carbonyl group which may be substituted with 1 to 5 substituents selected from the Substituent Group A; a $C_{2-6}$ alkenyloxy-carbonyl group which may be substituted with 1 to 5 substituents selected from the Substituent Group A; a $C_{2-6}$ alkynyloxy-carbonyl group which may be substituted with 1 to 5 substituents selected from the Substituent Group A; a $C_{3-6}$ cycloalkyloxy-carbonyl group which may be substituted with 1 to 5 substituents selected from the Substituent Group A; a $C_{6-10}$ aryloxy-carbonyl group which may be substituted with 1 to 5 substituents selected from the Substituent Group A; a $C_{7-11}$ aralkyloxy-carbonyl group which may be substituted with 1 to 5 substituents selected from the Substituent Group A; a 5- to 8-membered heterocyclic group which may be substituted with 1 to 5 substituents selected from the Substituent Group A; a 5- to 8-membered heterocyclic-oxy group which may be substituted with 1 to 5 substituents selected from the Substituent Group A; a 5- to 8-membered heterocyclic-carbonyl group which may be substituted with 1 to 5 substituents selected from the Substituent Group A; and a 5- to 8-membered heterocyclic oxy-carbonyl group which may be substituted with 1 to 5 substituents selected from the Substituent Group A,

(28) a $C_{1-6}$ alkylsulfinyl group which may be substituted with 1 to 5 substituents selected from the Substituent Group A,

(29) a $C_{6-10}$ arylsulfinyl group which may be substituted with 1 to 5 substituents selected from the Substituent Group A,

(30) a $C_{1-6}$ alkylsulfonyl group which may be substituted with 1 to 5 substituents selected from the Substituent Group A, or

(31) a $C_{6-10}$ arylsulfonyl group which may be substituted with 1 to 5 substituents selected from the Substituent Group A;

or $R^3$ and $R^4$, $R^4$ and $R^5$, and $R^5$ and $R^6$ respectively form, together with the adjacent carbon atom, (1) a 5- to 8-membered homocyclic ring which may be substituted with 1 to 5 substituents selected from the Substituent Group A, or (2) a 5- to 8-membered heterocyclic ring which may be substituted with 1 to 5 substituents selected from the Substituent Group A, and has 1 to 3 heteroatoms selected from a nitrogen atom, an oxygen atom and a sulfur atom.

[3] The compound according to [1] above, wherein $R^1$ is a substituted aryl group, or an aromatic heterocyclic group which may be substituted.

[4] The compound according to [1] above, wherein at least one of $R^3$, $R^4$, $R^5$ and $R^6$ is a nitro group, a cyano group, a hydrocarbon group which may be substituted, an amino group which may be substituted, a hydroxy group which may be substituted, or a thiol group which may be substituted.

[5] The compound according to [1] above, wherein $R^4$ is an amino group which may be substituted, or a hydroxy group which may be substituted.

[6] The compound according to [1] above, wherein $R^1$ is:

(1) a $C_{6-12}$ aryl group (e.g., a phenyl group) which may be substituted with 1 to 3 substituents selected from:

(a) a $C_{1-6}$ alkyl group which may be substituted with 1 to 3 substituents selected from
 (i) a halogen atom,
 (ii) a hydroxy group, and
 (iii) a 5- to 8-membered heterocyclic group (e.g., a piperidyl group, a piperazinyl group, a morpholinyl group, a pyrrolidinyl group) which may be substituted with a substituent selected from a hydroxy group and a $C_{1-6}$ alkyl group, and has 1 to 3 heteroatoms selected from a nitrogen atom, an oxygen atom and a sulfur atom;

(b) a $C_{1-6}$ alkoxy group which may be substituted with a substituent selected from
 (i) a hydroxy group,
 (ii) a $C_{1-6}$ alkoxy group,
 (iii) a carboxy group,
 (iv) a $C_{1-6}$ alkoxy-carbonyl group,
 (v) a carbamoyl group,
 (vi) a carbamoyl group which is mono- or di-substituted with a $C_{1-6}$ alkyl group which may be substituted with a substituent selected from a hydroxy group and a $C_{1-6}$ alkylsulfonyl group,
 (vii) a cyano group, and
 (viii) a 5- to 8-membered heterocyclic group (e.g., a tetrazole group) having 1 to 3 heteroatoms selected from a nitrogen atom, an oxygen atom and a sulfur atom;

(c) a halogen atom;
(d) a hydroxy group;
(e) an amino group;
(f) a nitro group;
(g) a carboxy group;
(h) a $C_{1-6}$ alkoxy-carbonyl group;
(i) a $C_{1-6}$ alkyl-carbonyloxy group;
(j) a $C_{6-12}$ aryloxy group which may be substituted with a substituent selected from a halogen atom, a hydroxy group and a $C_{1-6}$ alkoxy group;
(k) a $C_{6-14}$ aralkyloxy group;
(l) a $C_{3-7}$ cycloalkyloxy group;
(m) a 5- to 8-membered heterocyclic (e.g., pyridyl, pyrimidyl)-oxy group which may be substituted with a $C_{1-6}$ alkyl group, and has 1 to 3 heteroatoms selected from a nitrogen atom, an oxygen atom and a sulfur atom;
(n) a $C_{1-6}$ alkylsulfonyl group; and
(o) a $C_{6-12}$ arylsulfonyl group, or (2) a 5- or 6-membered aromatic heterocyclic group (e.g., a pyridyl group, a pyrazolyl group, a thiazolyl group, a pyrimidyl group) which may be substituted with 1 to 3 substituents selected from:
 (a) a $C_{1-6}$ alkyl group, and
 (b) a $C_{1-6}$ alkoxy group, and has 1 to 3 heteroatoms selected from a nitrogen atom, an oxygen atom and a sulfur atom, or a group resulting from condensation of the 5- or 6-membered aromatic heterocyclic group with a benzene ring;

$R^2$ is:
(1) a hydrogen atom, or
(2) an amino group which may be mono- or di-substituted with a $C_{1-6}$ alkyl group;

$R^3$ is a hydrogen atom;

$R^4$ is:
(1) a hydrogen atom,
(2) a nitro group,
(3) an amino group,
(4) a hydroxy group,
(5) a $C_{1-6}$ alkoxy group which may be substituted with a substituent selected from:
 (a) a hydroxy group,
 (b) a cyano group,
 (c) a $C_{1-6}$ alkoxy group,
 (d) a carboxy group,
 (e) a $C_{1-6}$ alkoxy-carbonyl group,
 (f) a carbamoyl group, (g) a carbamoyl group which is mono- or di-substituted with a $C_{1-6}$ alkyl group, and
(h) an amino group which may be mono- or di-substituted with a $C_{1-6}$ alkyl group, or
(6) a group represented by the formula:

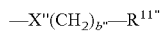

wherein X" is —O—, —NHSO$_2$—, —NHCO— or —NR$^{12"}$— (wherein R$^{12"}$ is a hydrogen atom, or a $C_{1-6}$ alkyl group which may be substituted with a 5- to 8-membered heterocyclic group (e.g., a morpholinyl group) having 1 to 3 heteroatoms selected from a nitrogen atom, an oxygen atom and a sulfur atom),
b" is an integer from 1 to 4, and
R$^{11"}$ is a 5- to 8-membered heterocyclic group (e.g., a piperidyl group, a piperazinyl group, a morpholinyl group, a pyrrolidinyl group) which may be substituted with a substituent selected from
(a) a hydroxy group, and
(b) a $C_{1-6}$ alkyl group, and has 1 to 3 heteroatoms selected from a nitrogen atom, an oxygen atom and a sulfur atom;
R$^5$ is:
(1) a hydrogen atom,
(2) a $C_{1-6}$ alkoxy group, or
(3) a group represented by the formula:

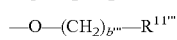

wherein b''' is an integer from 2 to 4, and
R$^{11'''}$ is a 5- to 8-membered heterocyclic group (e.g., a piperazinyl group, a morpholinyl group) which may be substituted with a substituent selected from
(a) a $C_{1-6}$ alkyl group, and
(b) a $C_{6-14}$ aryl group (e.g., a phenyl group) which may be substituted with a halogen atom, and has 1 to 3 heteroatoms selected from a nitrogen atom, an oxygen atom and a sulfur atom;
R$^6$ is:
(1) a hydrogen atom,
(2) a hydroxy group,
(3) a $C_{1-6}$ alkoxy group which may be substituted with a substituent selected from:
(a) a hydroxy group,
(b) a $C_{1-6}$ alkoxy group,
(c) a carboxy group,
(d) a $C_{1-6}$ alkoxy-carbonyl group,
(e) a carbamoyl group,
(f) a carbamoyl group which is mono- or di-substituted with a $C_{1-6}$ alkyl group which may be substituted with an amino group which may be mono- or di-substituted with a $C_{1-6}$ alkyl group,
(g) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom, and
(h) a 5- to 8-membered heterocyclic (e.g., piperazinyl)-carbonyl group which may be substituted with a $C_{1-6}$ alkyl group, and has 1 to 3 heteroatoms selected from a nitrogen atom, an oxygen atom and a sulfur atom,
(4) a $C_{7-14}$ aralkyloxy group, or
(5) a group represented by the formula:

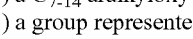

wherein b"" is an integer from 1 to 4, and

R$^{11""}$ is a 5- to 8-membered heterocyclic group (e.g., a morpholinyl group) having 1 to 3 heteroatoms selected from a nitrogen atom, an oxygen atom and a sulfur atom.

[7] The compound according to [1] above, wherein R$^1$ is a $C_{6-12}$ aryl group (e.g., a phenyl group) which may be substituted with 1 to 3 substituents selected from:
(a) a $C_{1-6}$ alkyl group which may be substituted with 1 to 3 substituents selected from:
(i) a halogen atom,
(ii) a hydroxy group, and
(iii) a 5- to 8-membered heterocyclic group (e.g., a piperidyl group, a piperazinyl group, a morpholinyl group, a pyrrolidinyl group) which may be substituted with a substituent selected from a hydroxy group, a halogen atom and a $C_{1-6}$ alkyl group, and has 1 to 3 heteroatoms selected from a nitrogen atom, an oxygen atom and a sulfur atom,
(b) a $C_{1-6}$ alkoxy group which may be substituted with a substituent selected from:
(i) a hydroxy group,
(ii) a $C_{1-6}$ alkoxy group,
(iii) a carboxy group,
(iv) a $C_{1-6}$ alkoxy-carbonyl group,
(v) a carbamoyl group, and
(vi) a carbamoyl group which is mono- or di-substituted with a $C_{1-6}$ alkyl group,
(c) a halogen atom,
(d) a hydroxy group,
(i) a $C_{1-6}$ alkyl-carbonyloxy group,
(j) a $C_{6-12}$ aryloxy group which may be substituted with a halogen atom, and
(m) a 5- to 8-membered heterocyclic (e.g., pyridyl, pyrimidyl)-oxy group which may be substituted with a $C_{1-6}$ alkyl group, and has 1 to 3 heteroatoms selected from a nitrogen atom, an oxygen atom and a sulfur atom;
R$^2$ is:
(1) a hydrogen atom, or
(2) an amino group which may be mono- or di-substituted with a $C_{1-6}$ alkyl group;
R$^3$ is a hydrogen atom;
R$^4$ is:
(1) a hydrogen atom,
(2) a nitro group,
(3) an amino group,
(4) a hydroxy group,
(5) a $C_{1-6}$ alkoxy group which may be substituted with a substituent selected from:
(a) a hydroxy group,
(b) a cyano group,
(c) a $C_{1-6}$ alkoxy group,
(d) a carboxy group,
(e) a $C_{1-6}$ alkoxy-carbonyl group,
(f) a carbamoyl group, and
(g) a carbamoyl group which is mono- or di-substituted with a $C_{1-6}$ alkyl group, or
(6) a group represented by the formula:

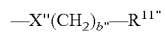

wherein X" is —O—, —NR— (wherein R$^{12"}$ is a hydrogen atom, or a $C_{1-6}$ alkyl group which may be substituted with a 5- to 8-membered heterocyclic group (e.g., a morpholinyl group) having 1 to 3 heteroatoms selected from a nitrogen atom, an oxygen atom and a sulfur atom);

b" is an integer from 1 to 4; and

R$^{11''}$ is a 5- to 8-membered heterocyclic group (e.g., a piperidyl group, a piperazinyl group, a morpholinyl group, a pyrrolidinyl group) which may be substituted with a substituent selected from:
(a) a hydroxy group, and
(b) a C$_{1-6}$ alkyl group, and has 1 to 3 heteroatoms selected from a nitrogen atom, an oxygen atom and a sulfur atom;

R$^5$ is:
(1) a hydrogen atom, or
(2) a C$_{1-6}$ alkoxy group;

R$^6$ is:
(1) a hydrogen atom, or
(2) a C$_{1-6}$ alkoxy group which may be substituted with a substituent selected from:
(a) a hydroxy group,
(b) a C$_{1-6}$ alkoxy group,
(c) a carboxy group,
(d) a C$_{1-6}$ alkoxy-carbonyl group,
(e) a carbamoyl group,
(f) a carbamoyl group which is mono- or di-substituted with a C$_{1-6}$ alkyl group which may be substituted with an amino group which may be mono- or di-substituted with a C$_{1-6}$ alkyl group,
(g) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom, and
(h) a 5- to 8-membered heterocyclic (e.g., piperazinyl)-carbonyl group which may be substituted with a C$_{1-6}$ alkyl group, and has 1 to 3 heteroatoms selected from a nitrogen atom, an oxygen atom and a sulfur atom.

[8] The compound according to [1] above, wherein R$^1$ is (1) a phenyl group which may be substituted with 1 to 3 substituents selected from: (a) a C$_{1-6}$ alkyl group which may be substituted with 1 to 3 halogen atoms or hydroxy groups, (b) a C$_{1-6}$ alkoxy group, (c) a C$_{1-6}$ alkyl-carbonyloxy group, (d) a C$_{1-6}$ alkoxy-carbonyl group, (e) a C$_{1-6}$ alkyl-carbonyl group, (f) a C$_{1-6}$ alkylsulfonyl group, (g) a halogen atom, (h) a hydroxy group, (i) an amino group, (j) a nitro group, (k) a carboxy group, (l) a cyano group, (m) a C$_{6-12}$ aryloxy group, (n) a C$_{7-14}$ aralkyloxy group, (o) a C$_{6-12}$ aryl-carbonyl group, (p) a C$_{7-14}$ aralkyl-carbonyl group, (q) a mono-C$_{1-6}$ alkylamino group, (r) a di-C$_{1-6}$ alkylamino group, (s) a C$_{6-12}$ arylamino group, and (t) a C$_{7-14}$ aralkylamino group (hereinafter, simply referred to as Substituent Group B), (2) a pyridyl group which may be substituted with 1 to 3 substituents selected from the Substituent Group B, (3) a thiazolyl group which may be substituted with 1 to 3 substituents selected from the Substituent Group B, or (4) a pyrimidinyl group which may be substituted with 1 to 3 substituents selected from the Substituent Group B;

R$^2$ is (1) a hydrogen atom, (2) an amino group which may be mono- or di-substituted with (a) a C$_{1-6}$ alkyl group, or (b) a C$_{1-6}$ alkyl-carbonyl group, or (3) a hydroxy group which may be substituted with (a) a C$_{1-6}$ alkyl group, or (b) a C$_{1-6}$ alkyl-carbonyl group;

R$^3$, R$^4$, R$^5$ and R$^6$, which may be identical or different, are each (1) a hydrogen atom, (2) a cyano group, (3) a halogen atom, (4) a C$_{1-6}$ alkyl group, (5) an amino group, (6) a hydroxy group, (7) a C$_{1-6}$ alkoxy group which may be substituted with a C$_{1-6}$ alkoxy group, or (8) a group represented by the formula: —X(CH$_2$)$_b$—R$^{11}$ [wherein X is —O—, —S—, —S(O)—, —S(O)$_2$—, NR$^{12}$—, —OSO$_2$—, —NR$^{12}$CO—, —NR$^{12}$SO$_2$—, —CONR$^{12}$— or —SO$_2$NR$^{12}$— (wherein R$^{12}$ is a hydrogen atom or a C$_{1-6}$ alkyl group); b is an integer from 2 to 4; and R$^{11}$ is (a) a piperidyl group which may be substituted with a hydroxy group or a C$_{1-6}$ alkyl group, (b) a piperazinyl group which may be substituted with a hydroxy group or a C$_{1-6}$ alkyl group, (c) a morpholinyl group which may be substituted with a hydroxy group or a C$_{1-6}$ alkyl group, or (d) a pyrrolidinyl group which may be substituted with a hydroxy group or a C$_{1-6}$ alkyl group]; or R$^3$ and R$^4$, R$^4$ and R$^5$, and R$^5$ and R$^6$ respectively form, together with the adjacent carbon atom, (1) a 5- to 8-membered homocyclic ring, or (2) a 5- to 8-membered heterocyclic ring having 1 to 3 heteroatoms selected from a nitrogen atom, an oxygen atom and a sulfur atom.

[9] The compound according to [1] above, wherein R$^1$ is (1) a phenyl group which may be substituted with 1 to 3 substituents selected from (a) a C$_{1-3}$ alkyl group which may be substituted with 1 to 3 halogen atoms or hydroxy groups, (b) a C$_{1-3}$ alkoxy group, (c) a C$_{1-3}$ alkyl-carbonyloxy group, (d) a halogen atom, (e) a hydroxy group, (f) an amino group, and (g) a cyano group (hereinafter, simply referred to as Substituent Group C), or (2) a pyridyl group which may be substituted with 1 to 3 substituents selected from the Substituent Group C;

R$^2$ is a hydrogen atom or an amino group;

R$^3$ is (1) a hydrogen atom, (2) a cyano group, (3) a halogen atom, (4) a C$_{1-6}$ alkyl group, (5) an amino group, (6) a hydroxy group, or (7) a C$_{1-6}$ alkoxy group;

R$^4$, R$^5$ and R$^6$, which may be identical or different, are each (1) a hydrogen atom, (2) a cyano group, (3) a halogen atom, (4) a C$_{1-6}$ alkyl group, (5) an amino group, (6) a hydroxy group, (7) a C$_{1-6}$ alkoxy group which may be substituted with a C$_{1-6}$ alkoxy group, or (8) a group represented by the formula: —X(CH$_2$)$_b$—R$^{11}$ [wherein X is —O—, —NR$^{12}$—, —OSO$_2$—, —NR$^{12}$CO—, —NR$^{12}$SO$_2$—, —CONR$^{12}$— or —SO$_2$NR$^{12}$— (wherein R$^{12}$ is a hydrogen atom or a C$_{1-6}$ alkyl group); b is an integer from 2 to 4; and R$^{11}$ is (a) a piperidyl group which may be substituted with a hydroxy group or a C$_{1-6}$ alkyl group, (b) a piperazinyl group which may be substituted with a hydroxy group or a C$_{1-6}$ alkyl group, (c) a morpholinyl group which may be substituted with a hydroxy group or a C$_{1-6}$ alkyl group, or (d) a pyrrolidinyl group which may be substituted with a hydroxy group or a C$_{1-6}$ alkyl group]; or R$^3$ and R$^4$, R$^4$ and R$^5$, and R$^5$ and R$^6$ respectively form, together with the adjacent carbon atom, (1) a 5- to 8-membered homocyclic ring, or (2) a 5- to 8-membered heterocyclic ring having 1 to 3 heteroatoms selected from a nitrogen atom, an oxygen atom and a sulfur atom.

[10] The compound according to [1] above, wherein R$^1$ is a phenyl group which may be substituted with 1 to 3 substituents selected from (a) a C$_{1-3}$ alkyl group which may be substituted with 1 to 3 halogen atoms or hydroxy groups, (b) a C$_{1-3}$ alkoxy group, (c) a C$_{1-3}$ alkyl-carbonyloxy group, (d) a halogen atom, (e) a hydroxy group, (f) an amino group, and (g) a cyano group;

R$^2$ is a hydrogen atom or an amino group;

R$^3$ is a hydrogen atom;

R$^4$, R$^5$ and R$^6$, which may be identical or different, are each (1) a hydrogen atom, (2) a cyano group, (3) a halogen atom, (4) a C$_{1-6}$ alkyl group, (5) an amino group, (6) a hydroxy group, (7) a C$_{1-6}$ alkoxy group which may be substituted with a C$_{1-6}$ alkoxy group, or (8) a group represented by the formula: —X(CH$_2$)$_b$—R$^{11}$ [wherein X is —O—, —NR$^{12}$—, —OSO$_2$—, —NR$^2$CO—, —NR$^{12}$SO$_2$— (wherein R$^{12}$ is a hydrogen atom or a C$_{1-6}$ alkyl group); b is an integer from 2 to 4; and R$^{11}$ is (a) a piperidyl group which may be substituted with a hydroxy group or a C$_{1-6}$ alkyl group, (b) a piperazinyl group which may be substituted with a hydroxy group or a $C_{1-6}$ alkyl group, (c) a morpholinyl group which may be substituted with a hydroxy group or a $C_{1-6}$ alkyl group, or (d) a pyrrolidinyl group which may be substituted with a hydroxy group or a $C_{1-6}$ alkyl group]; or $R^3$ and $R^4$, $R^4$ and $R^5$, and $R^5$ and $R^6$ respectively form, together with the adjacent carbon atom, (1) a 5- to 8-membered homocyclic ring, or (2) a 5- to 8-membered heterocyclic ring having 1 to 3 heteroatoms selected from a nitrogen atom, an oxygen atom and a sulfur atom.

[11] The compound according to [1] above, wherein $R^1$ is a phenyl group which may be substituted with 1 to 3 substituents selected from (a) a $C_{1-3}$ alkyl group, (b) a $C_{1-3}$ alkoxy group, (c) a halogen atom, and (d) a hydroxy group.

[12] The compound according to [1] above, wherein $R^2$ is a hydrogen atom or an amino group.

[13] The compound according to [1] above, wherein $R^4$ is (1) a hydrogen atom, (2) a $C_{1-6}$ alkoxy group which may be substituted with a $C_{1-6}$ alkoxy group, or (3) a group represented by the formula: —X'(CH$_2$)$_{b'}$—R$^{11'}$ (wherein X' is —O— or —NH—; b' is an integer from 2 to 4; and R$^{11'}$ is (1') a piperidyl group which may be substituted with a hydroxy group or a $C_{1-6}$ alkyl group, (2') a piperazinyl group which may be substituted with a hydroxy group or a $C_{1-6}$ alkyl group, (3') a morpholinyl group which may be substituted with a hydroxy group or a $C_{1-6}$ alkyl group, or (4') a pyrrolidinyl group which may be substituted with a hydroxy group or a $C_{1-6}$ alkyl group).

[14] The compound according to [1], wherein $R^5$ is (1) a hydrogen atom, (2) a $C_{1-6}$ alkoxy group which may be substituted with a $C_{1-6}$ alkoxy group, or (3) a group represented by the formula: —X'(CH$_2$)$_{b'}$—R$^{11'}$ (wherein X' is —O— or —NH—; b' is an integer from 2 to 4; R$^{11'}$ is (1') a piperidyl group which may be substituted with a hydroxy group or a $C_{1-6}$ alkyl group, (2') a piperazinyl group which may be substituted with a hydroxy group or a $C_{1-6}$ alkyl group, (3') a morpholinyl group which may be substituted with a hydroxy group or a $C_{1-6}$ alkyl group, or (4') a pyrrolidinyl group which may be substituted with a hydroxy group or a $C_{1-6}$ alkyl group).

[15] The compound according to [1] above, wherein $R^6$ is a hydrogen atom, or a $C_{1-6}$ alkoxy group which may be substituted with a $C_{1-6}$ alkoxy group.

[16] The compound according to [1] above, which is 3-amino-7,8-dimethoxy-2-(5-hydroxy-2-methylphenyl)-2,5-dihydro-4 H-pyrazolo[4,3-c]quinolin-4-one, 3-amino-2-(5-hydroxy-2-methylphenyl)-2,5-dihydro-4H-pyrazolo[4,3-c]quinolin-4-one, 3-amino-2 -(2-chloro-5-hydroxyphenyl)-2,5-dihydro-4H-pyrazolo[4,3-c]quinolin-4-one, 3-amino-2-(2-chloro-5-hydroxyphenyl)-7-(3-morpholin-4-ylpropoxy)-2,5-dihydro-4H-pyrazolo[4,3-c]quinolin-4-one, 3-amino-2-(2-chloro-5-hydroxyphenyl)-7-(2-morpholin-4-ylethoxy)-2,5-dihydro-4H-pyrazolo[4,3-c]quinolin-4-one, 3-amino-2-(5-hydroxy-2-methylphenyl)-7-(3-morpholin-4-ylpropoxy)-2,5-dihydro-4H-pyrazolo[4,3-c]quinolin-4-one, 3-amino-2-(5-hydroxy-2-methylphenyl)-7-(2-morpholin-4-ylethoxy)-2,5-dihydro-4H-pyrazolo[4,3-c]quinolin-4-one, 3-amino-2-(5-hydroxy-2-methyl-4 -phenoxyphenyl)-2,5-dihydro-4H-pyrazolo[4,3-c]quinolin-4-one, 3-amino-2-[4-(2,6-difluorophenoxy)-5-hydroxy-2 -methylphenyl]-2,5-dihydro-4H-pyrazolo[4,3-c]quinolin-4-one, 3-amino-7-(2-hydroxyethoxy)-2 -(5-hydroxy-2-methylphenyl)-2,5-dihydro-4H-pyrazolo[4,3-c]quinolin-4-one, 3-amino-2-(5-hydroxy-2,4 -dimethylphenyl)-2,5-dihydro-4H-pyrazolo[4, 3-c]quinolin-4-one, 3-amino-7-(2-hydroxyethoxy)-2-(5-hydroxy-2-methyl-4 -phenoxyphenyl)-2,5-dihydro-4H-pyrazolo[4,3-c]quinolin-4-one, or a salt thereof.

[17] A prodrug of the compound according to [1] above.

[18] A medicine comprising the compound according to [1] above or a prodrug thereof.

[19] The medicine according to [18] above, which is a kinase inhibitor.

[20] The medicine according to [18] above, which is an Src inhibitor.

[21] The medicine according to [18] above, which is an agent for the prophylaxis and/or treatment of cancer.

[22] The medicine according to [18] above, which is an agent for the prophylaxis and/or treatment of breast cancer, renal cancer, urinary bladder cancer, oral cavity cancer, laryngeal cancer, esophageal cancer, stomach cancer, colon cancer, ovarian cancer, lung cancer, pancreatic cancer, liver cancer, prostate cancer or skin cancer.

[23] The medicine according to [18] above, which is an agent for the prophylaxis and/or treatment of osteoporosis.

[24] A method of inhibiting kinase which comprises administrating an effective amount of the compound according to [1] above or a prodrug thereof to a mammal.

[25] A method of preventing and/or treating cancer which comprises administrating an effective amount of the compound according to [1] above or a prodrug thereof to a mammal.

[26] Use of the compound according to [1] above or a prodrug thereof, for the manufacture of a kinase inhibitor.

[27] Use of the compound according to [1] above or a prodrug thereof, for the manufacture of an agent for the prophylaxis and/or treatment of cancer.

[28] A compound represented by the formula:

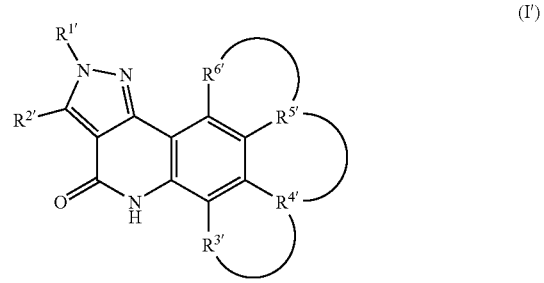

(I')

wherein $R^{1'}$ is a cycloalkyl group which may be substituted; $R^{2'}$ is a hydrogen atom, an amino group which may be substituted, a hydroxy group which may be substituted, or a thiol group which may be substituted; $R^{3'}$, $R^{4'}$, $R^{5'}$ and $R^{6'}$, which may be identical or different, are each (1) a hydrogen atom, (2) a nitro group, (3) a cyano group, (4) a halogen atom, (5) a hydrocarbon group which may be substituted, (6) an amino group which may be substituted, (7) a hydroxy group which may be substituted, or (8) a thiol group which may be substituted; and $R^{3'}$ and $R^{4'}$, $R^{4'}$ and $R^{5'}$, and $R^{5'}$ and $R^{6'}$ may respectively form a ring together with the adjacent carbon atom, or a salt thereof.

BEST MODE FOR CARRYING OUT THE INVENTION

Hereinafter, the present invention will be described in detail.

The "aryl group" of the "aryl group which may be substituted" represented by $R^1$ represents a $C_{6-12}$ aryl group such as a phenyl group, a 1-naphthyl group, a 2-naphthyl group or the like. Among these, a phenyl group is preferred.

The "substituent" for the "aryl group which may be substituted" represented by $R^1$ may be exemplified by substituent selected from:

(1') a $C_{1-6}$ alkyl group which may be substituted with a substituent selected from a $C_{1-6}$ alkyl group, a $C_{2-6}$ alkenyl group, a $C_{2-6}$ alkynyl group, a $C_{6-12}$ aryl group, a $C_{7-14}$ aralkyl group, a hydroxy group, a $C_{1-6}$ alkoxy group, a $C_{6-12}$ aryloxy group, a $C_{7-14}$ aralkyloxy group, a $C_{1-6}$ alkyl-carbonyloxy group, a $C_{2-6}$ alkenyl-carbonyloxy group, a $C_{2-6}$ alkynyl-carbonyloxy group, a $C_{1-6}$ alkylthio group, a $C_{6-12}$ arylthio group, a $C_{7-14}$ aralkylthio group, a carboxy group, a $C_{1-6}$ alkyl-carbonyl group, a $C_{2-6}$ alkenyl-carbonyl group, a $C_{2-6}$ alkynyl-carbonyl group, a $C_{6-12}$ aryl-carbonyl group, a $C_{7-14}$ aralkyl-carbonyl group, a $C_{1-6}$ alkoxy-carbonyl group, a $C_{2-6}$ alkenyloxy-carbonyl group, a $C_{2-6}$ alkynyloxy-carbonyl group, a $C_{6-12}$ aryloxy-carbonyl group, a $C_{7-14}$ aralkyloxy-carbonyl group, a carbamoyl group, a mono-$C_{1-6}$ alkyl-carbamoyl group, a di-$C_{1-6}$ alkyl-carbamoyl group, a $C_{1-6}$ alkyl-sulfonyl group, a $C_{2-6}$ alkenylsulfonyl group, a $C_{2-6}$ alkynylsulfonyl group, an amino group, a mono-$C_{1-6}$ alkylamino group, a di-$C_{1-6}$ alkylamino group, a mono-$C_{2-6}$ alkenylamino group, a di-$C_{2-6}$ alkenylamino group, a mono-$C_{2-6}$ alkynylamino group, a di-$C_{2-6}$ alkynylamino group, a mono-$C_{6-12}$ arylamino group, a di-$C_{6-12}$ arylamino group, a mono-$C_{7-14}$ aralkylamino group, a di-$C_{7-14}$ aralkylamino group, a halogen atom, an azido group, a nitro group, a cyano group, a 5- to 8-membered heterocyclic group (this heterocyclic group may be substituted with a halogen atom, a hydroxy group, or a $C_{1-6}$ alkyl group which may be halogenated), a 5- to 8-membered heterocyclic-oxy group (this heterocyclic moiety may be substituted with a halogen atom, a hydroxy group, or a $C_{1-6}$ alkyl group which may be halogenated), a 5- to 8-membered heterocyclic-carbonyl group (this heterocyclic moiety may be substituted with a halogen atom, a hydroxy group, or a $C_{1-6}$ alkyl group which may be halogenated), a $C_{1-4}$ alkylene group, and a $C_{1-4}$ alkylenedioxy group (hereinafter, simply referred to as Substituent Group C);

(2') a $C_{2-6}$ alkenyl group which may be substituted with a substituent selected from the Substituent Group C, (3') a $C_{2-6}$ alkynyl group which may be substituted with a substituent selected from the Substituent Group C, (4') a $C_{6-12}$ aryl group which may be substituted with a substituent selected from the Substituent Group C, (5') a $C_{7-14}$ aralkyl group which may be substituted with a substituent selected from the Substituent Group C, (6') a hydroxy group, (7') a $C_{1-6}$ alkoxy group which may be substituted with a substituent selected from the Substituent Group C, (8') a $C_{6-12}$ aryloxy group which may be substituted with a substituent selected from the Substituent Group C, (9') a $C_{7-14}$ aralkyloxy group which may be substituted with a substituent selected from the Substituent Group C, (10') a $C_{1-6}$ alkyl-carbonyloxy group which may be substituted with a substituent selected from the Substituent Group C, (11') a $C_{2-6}$ alkenyl-carbonyloxy group which may be substituted with a substituent selected from the Substituent Group C, (12') a $C_{2-6}$ alkynyl-carbonyloxy group which may be substituted with a substituent selected from the Substituent Group C, (13') a $C_{1-6}$ alkylthio group which may be substituted with a substituent selected from the Substituent Group C, (14') a $C_{6-12}$ arylthio group which may be substituted with a substituent selected from the Substituent Group C, (15') a $C_{7-14}$ aralkylthio group which may be substituted with a substituent selected from the Substituent Group C, (16') a carboxy group, (17') a $C_{1-6}$ alkyl-carbonyl group which may be substituted with a substituent selected from the Substituent Group C, (18') a $C_{2-6}$ alkenyl-carbonyl group which may be substituted with a substituent selected from the Substituent Group C, (19') a $C_{2-6}$ alkynyl-carbonyl group which may be substituted with a substituent selected from the Substituent Group C, (20') a $C_{6-12}$ aryl-carbonyl group which may be substituted with a substituent selected from the Substituent Group C, (21') a $C_{7-14}$ aralkyl-carbonyl group which may be substituted with a substituent selected from the Substituent Group C, (22') a $C_{1-6}$ alkoxy-carbonyl group which may be substituted with a substituent selected from the Substituent Group C, (23') a $C_{2-6}$ alkenyloxy-carbonyl group which may be substituted with a substituent selected from the Substituent Group C, (24') a $C_{2-6}$ alkynyloxy-carbonyl group which may be substituted with a substituent selected from the Substituent Group C, (25') a $C_{6-12}$ aryloxy-carbonyl group which may be substituted with a substituent selected from the Substituent Group C, (26') a $C_{7-14}$ aralkyloxy-carbonyl group which may be substituted with a substituent selected from the Substituent Group C, (27') a carbamoyl group, (28') a mono-$C_{1-6}$ alkyl-carbamoyl group which may be substituted with a substituent selected from the Substituent Group C, (29') a di-$C_{1-6}$ alkyl-carbamoyl group which may be substituted with a substituent selected from the Substituent Group C, (30') a $C_{1-6}$ alkylsulfonyl group which may be substituted with a substituent selected from the Substituent Group C, (31') a $C_{2-6}$ alkenylsulfonyl group which may be substituted with a substituent selected from the Substituent Group C, (32') a $C_{2-6}$ alkynylsulfonyl group which may be substituted with a substituent selected from the Substituent Group C, (33') an amino group, (34') a mono-$C_{1-6}$ alkylamino group which may be substituted with a substituent selected from the Substituent Group C, (35') a di-$C_{1-6}$ alkylamino group which may be substituted with a substituent selected from the Substituent Group C, (36') a mono-$C_{2-6}$ alkenylamino group which may be substituted with a substituent selected from the Substituent Group C, (37') a di-$C_{2-6}$ alkenylamino group which may be substituted with a substituent selected from the Substituent Group C, (38') a mono-$C_{2-6}$ alkynylamino group which may be substituted with a substituent selected from the Substituent Group C, (39') a di-$C_{2-6}$ alkynylamino group which may be substituted with a substituent selected from the Substituent Group C, (40') a mono-$C_{6-12}$ arylamino group which may be substituted with a substituent selected from the Substituent Group C, (41') a di-$C_{6-12}$ arylamino group which may be substituted with a substituent selected from the Substituent Group C, (42') a mono-$C_{7-14}$ aralkylamino group which may be substituted with a substituent selected from the Substituent Group C, (43') a di-$C_{7-14}$ aralkylamino group which may be substituted with a substituent selected from the Substituent Group C, (44') a mono-5- to 8-membered heterocyclic amino group which may be substituted with a substituent selected from the Substituent Group C, (45') a di-5- to 8-membered heterocyclic amino group which may be substituted with a substituent selected from the Substituent Group C, (46') a ($C_{1-6}$ alkyl which may be substituted with a substituent selected from the Substituent Group C) (5- to 8-membered heterocyclic which may be substituted with a substituent selected from the Substituent Group C) amino group, (47') a halogen atom, (48') an azido group, (49') a nitro group, (50') a cyano group, (51') a 5- to 8-membered heterocyclic group which may be substituted with a substituent selected from the Substituent Group C, (52') a 5- to 8-membered heterocyclic-oxy group which may be substituted with a substituent selected from the Substituent Group C, (53') a 5- to 8-membered heterocyclic-carbonyl group which may be substituted with a substituent selected from the Substituent Group C, (54') a $C_{1-4}$ alkylene group, (55') a $C_{1-4}$ alkylenedioxy group, and the like (hereinafter, simply referred to as Substituent Group A. Specific examples of the respective substituents include those listed as Substituent Group AA described below), and the like. Among them, a substituent selected from:

(1') a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) which may be substituted with 1 to 3 halogen atoms (e.g., a fluorine atom, a chlorine atom, a bromine atom, an iodine atom) or hydroxy groups, (2') a $C_{2-6}$ alkenyl group (e.g., an ethenyl group, a 1-propenyl group, a 2-propenyl group, etc.), (3') a $C_{2-6}$ alkynyl group (e.g., an ethynyl group, a 1-propynyl group, a 2-propynyl group, etc.), (4') a $C_{6-12}$ aryl group (e.g., a phenyl group, a 1-naphthyl group, a 2-naphthyl group, etc.), (5') a $C_{7-14}$ aralkyl group (e.g., a benzyl group, a phenethyl group, a 1-naphthylmethyl group, a 2-naphthylmethyl group, etc.), (6') a hydroxy group, (7') a $C_{1-6}$ alkoxy group (e.g., a methoxy group, an ethoxy group, a propoxy group, an isopropoxy group, a butoxy group, an isobutoxy group, a sec-butoxy group, a tert-butoxy group, a pentoxy group, a hexyloxy group, etc.), (8') a $C_{6-12}$ aryloxy group (e.g., a phenoxy group, a 1-naphthyloxy group, a 2-naphthyloxy group, etc.), (9') a $C_{7-14}$ aralkyloxy group (e.g., a benzyloxy group, a phenethyloxy group, a 1-naphthylmethoxy group, a 2-naphthylmethoxy group, etc.), (10') a $C_{1-6}$ alkyl-carbonyloxy group (e.g., an acetoxy group, an ethylcarbonyloxy group, a propylcarbonyloxy group, an isopropylcarbonyloxy group, a butylcarbonyloxy group, an isobutylcarbonyloxy group, a sec-butylcarbonyloxy group, a tert-butylcarbonyloxy group, a pentylcarbonyloxy group, a hexylcarbonyloxy group, etc.), (11') a $C_{2-6}$ alkenyl-carbonyloxy group (e.g., an ethenylcarbonyloxy group, a 1-propenylcarbonyloxy group, a 2-propenylcarbonyloxy group, etc.), (12') a $C_{2-6}$ alkynyl-carbonyloxy group (e.g., an ethynylcarbonyloxy group, a 1-propynylcarbonyloxy group, a 2-propynylcarbonyloxy group, etc.), (13') a $C_{1-6}$ alkylthio group (e.g., a methylthio group, an ethylthio group, a propylthio group, an isopropylthio group, a butylthio group, an isobutylthio group, a sec-butylthio group, a tert-butylthio group, a pentylthio group, a hexylthio group, etc.), (14') a $C_{6-12}$ arylthio group (e.g., a phenylthio group, a 1-naphthylthio group, a 2-naphthylthio group, etc.), (15') a $C_{7-14}$ aralkylthio group (e.g., a benzylthio group, a phenethylthio group, a 1-naphthylmethylthio group, a 2-naphthylmethylthio group, etc.), (16') a carboxy group, (17') a $C_{1-6}$ alkyl-carbonyl group (e.g., an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a hexylcarbonyl group, etc.), (18') a $C_{2-6}$ alkenyl-carbonyl group (e.g., an ethenylcarbonyl group, a 1-propenylcarbonyl group, a 2-propenylcarbonyl group, etc.), (19') a $C_{2-6}$ alkynyl-carbonyl group (e.g., ethynylcarbonyl group, a 1-propynylcarbonyl group, a 2-propynylcarbonyl group, etc.), (20') a $C_{6-12}$ arylcarbonyl group (e.g., a benzoyl group, a 1-naphthoyl group, a 2-naphthoyl group, etc.), (21') a $C_{7-14}$ aralkyl-carbonyl group (e.g., a benzylcarbonyl group, a phenethylcarbonyl group, a 1-naphthylmethylcarbonyl group, a 2-naphthylmethylcarbonyl group, etc.), (22') a $C_{1-6}$ alkoxy-carbonyl group (e.g., a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentoxycarbonyl group, a hexyloxycarbonyl group, etc.), (23') a $C_{2-6}$ alkenyloxy-carbonyl group (e.g., an ethenyloxycarbonyl group, a 1-propenyloxycarbonyl group, a 2-propenyloxycarbonyl group, etc.), (24') a $C_{2-6}$ alkynyloxy-carbonyl group (e.g., an ethynyloxycarbonyl group, a 1-propynyloxycarbonyl group, a 2-propynyloxycarbonyl group, etc.), (25') a $C_{6-12}$ aryloxy-carbonyl group (e.g., a phenoxycarbonyl group, a 1-naphthyloxycarbonyl group, a 2-naphthyloxycarbonyl group, etc.), (26') a $C_{7-14}$ aralkyloxy-carbonyl group (e.g., a benzyloxycarbonyl group, a phenethyloxycarbonyl group, a 1-naphthylmethoxycarbonyl group, a 2-naphthylmethoxycarbonyl group, etc.), (27') a carbamoyl group, (28') a mono-$C_{1-6}$ alkyl-carbamoyl group (e.g., a methylcarbamoyl group, an ethylcarbamoyl group, a propylcarbamoyl group, an isopropylcarbamoyl group, a butylcarbamoyl group, an isobutylcarbamoyl group, a sec-butylcarbamoyl group, a tert-butylcarbamoyl group, a pentylcarbamoyl group, a hexylcarbamoyl group, etc.), (29') a di-$C_{1-6}$ alkyl-carbamoyl group (e.g., a dimethylcarbamoyl group, a diethylcarbamoyl group, a dipropylcarbamoyl group, an N-ethyl-N-methylcarbamoyl group, etc.), (30') a $C_{1-6}$ alkylsulfonyl group (e.g., a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, etc.), (31') a $C_{2-6}$ alkenylsulfonyl group (e.g., an ethenylsulfonyl group, a 1-propenylsulfonyl group, a 2-propenylsulfonyl group, etc.), (32') a $C_{2-6}$ alkynylsulfonyl group (e.g., an ethynylsulfonyl group, a 1-propynylsulfonyl group, a 2-propynylsulfonyl group, etc.), (33') an amino group, (34') a mono-$C_{1-6}$ alkylamino group (e.g., a methylamino group, an ethylamino group, a propylamino group, an isopropylamino group, a butylamino group, an isobutylamino group, a sec-butylamino group, a tert-butylamino group, a pentylamino group, a hexylamino group, etc.), (35') a di-$C_{1-6}$ alkylamino group (e.g., a dimethylamino group, a diethylamino group, a dipropylamino group, a diisopropylamino group, an N-ethyl-N-methylamino group, etc.), (36') a mono-$C_{2-6}$ alkenylamino group (e.g., an ethenylamino group, a 1-propenylamino group, a 2-propenylamino group, etc.), (37') a di-$C_{2-6}$ alkenylamino group (e.g., a diethenylamino group, a di(1-propenyl)amino group, a di(2-propenyl)amino group, etc.), (38') a mono-$C_{2-6}$ alkynylamino group (e.g., an ethynylamino group, a 1-propynylamino group, a 2-propynylamino group, etc.), (39') a di-$C_{2-6}$ alkynylamino group (e.g., a diethynylamino group, a di(1-propynyl)amino group, a di(2-propynyl)amino group, etc.), (40') a $C_{6-12}$ arylamino group (e.g., a phenylamino group, an N-phenyl-N-methylamino group, etc.), (41') a $C_{7-14}$ aralkylamino group (e.g., a benzylamino group, an N-benzyl-N-methylamino group, etc.), (42') a halogen atom (e.g., a fluorine atom, a chlorine atom, a bromine atom, an iodine atom), (43') an azido group, (44') a nitro group, (45') a cyano group, (46') a group represented by the formula: —$(CH_2)_n$-Q (wherein n is an integer from 1 to 3; Q is (a) a piperidyl group which may be substituted with (i) a hydroxy group, (ii) a phenyl group which may be substituted with 1 to 3 halogen atoms (e.g., a fluorine atom, a chlorine atom, a bromine atom, an iodine atom), or (iii) a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.), (b) a piperazyl group which may be substituted with (i) a hydroxy group, (ii) a phenyl group which may be substituted with 1 to 3 halogen atoms (e.g., a fluorine atom, a chlorine atom, a bromine atom, an iodine atom), or (iii) a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.), or (c) a morpholinyl group which may be substituted with (i) a hydroxy group, (ii) a phenyl group which may be substituted with 1 to 3 halogen atoms (e.g., a fluorine atom, a chlorine atom, a bromine atom, an iodine atom), or (iii) a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.)), (47') a $C_{1-4}$ alkylene group (e.g., —$CH_2$—, —$CH_2CH_2$—, —$CH_2CH_2CH_2$—, —$CH_2CH_2CH_2CH_2$—, etc.), (48') a $C_{1-4}$ alkylenedioxy group (e.g., —$OCH_2O$—, —$OCH_2CH_2O$—, —$OCH_2CH_2CH_2O$—, —$OCH_2CH_2CH_2CH_2O$—, etc.) (hereinafter, simply referred to as Substituent Group AA) may be mentioned. The number of substituent is 1 to 5, and inter alia, 1 to 3, particularly 1 or 2, is preferred.

The "aromatic heterocyclic group" of the "aromatic heterocyclic group which may be substituted" represented by $R^1$ may be exemplified by a 5- or 6-membered aromatic heterocyclic group (e.g., a 5-membered aromatic heterocyclic group such as a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isooxazolyl group, a 4-isooxazolyl group, a 5-isooxazolyl group, a 2-furyl group, a 3-furyl group, a 2-thienyl group, a 3-thienyl group or the like; a 6-membered aromatic heterocyclic group such as a 2-pyridyl group, a 3-pyridyl group, a 4-pyridyl group, a pyrazinyl group, a 2-pyrimidinyl group, a 4-pyrimidinyl group, a 5-pyrimidinyl group, a 3-pyridazinyl group, a 4-pyridazinyl group or the like, etc.), a group resulting from condensation of the 5- or 6-membered aromatic heterocyclic group and a benzene ring (for example, a 1-indolyl group, a 2-indolyl group, a 3-indolyl group, a 1-benzimidazolyl group, a 2-benzimidazolyl group, a 2-benzothiazolyl group, a 3-benzoisothiazolyl group, a 2-benzoxazolyl group, a 3-benzoisoxazolyl group, a 2-benzofuryl group, a 3-benzofuryl group, a 2-benzothienyl group, a 3-benzothienyl group, etc.), or the like.

The "substituent" for the "aromatic heterocyclic group which may be substituted" represented by $R^1$ may be exemplified by those of the Substituent Group A. The number of substituent is 1 to 5, and inter alia, 1 to 3, particularly 1 or 2, is preferred.

$R^1$ is preferably:

(1) a $C_{6-12}$ aryl group (e.g., a phenyl group) which may be substituted with 1 to 3 substituents selected from:
  (a) a $C_{1-6}$ alkyl group which may be substituted with 1 to 3 substituents selected from
    (i) a halogen atom,
    (ii) a hydroxy group, and
    (iii) a 5- to 8-membered heterocyclic group (e.g., a piperidyl group, a piperazinyl group, a morpholinyl group, and a pyrrolidinyl group) which may be substituted with a substituent selected from a hydroxy group and a $C_{1-6}$ alkyl group, and has 1 to 3 heteroatoms selected from a nitrogen atom, an oxygen atom and a sulfur atom,
  (b) a $C_{1-6}$ alkoxy group which may be substituted with a substituent selected from
    (i) a hydroxy group,
    (ii) a $C_{1-6}$ alkoxy group,
    (iii) a carboxy group,
    (iv) a $C_{1-6}$ alkoxy-carbonyl group,
    (v) a carbamoyl group,
    (vi) a carbamoyl group which is mono- or di-substituted with a $C_{1-6}$ alkyl group which may be substituted with a substituent selected from a hydroxy group and a $C_{1-6}$ alkylsulfonyl group,
    (vii) a cyano group, and
    (viii) a 5- to 8-membered heterocyclic group (e.g., a tetrazole group) having 1 to 3 heteroatoms selected from a nitrogen atom, an oxygen atom and a sulfur atom,
  (c) a halogen atom,
  (d) a hydroxy group,
  (e) an amino group,
  (f) a nitro group,
  (g) a carboxy group,
  (h) a $C_{1-6}$ alkoxy-carbonyl group,
  (i) a $C_{1-6}$ alkyl-carbonyloxy group,
  (j) a $C_{6-12}$ aryloxy group which may be substituted with a substituent selected from a halogen atom, a hydroxy group and a $C_{1-6}$ alkoxy group,
  (k) a $C_{6-14}$ aralkyloxy group,
  (l) a $C_{3-7}$ cycloalkyloxy group,
  (m) a 5- to 8-membered heterocyclic (e.g., pyridyl, pyrimidyl)-oxy group which may be substituted with a $C_{1-6}$ alkyl group, and has 1 to 3 heteroatoms selected from a nitrogen atom, an oxygen atom and a sulfur atom,
  (n) a $C_{1-6}$ alkylsulfonyl group, and
  (o) a $C_{6-12}$ arylsulfonyl group; or (2) a 5- or 6-membered aromatic heterocyclic group (e.g., a pyridyl group, a pyrazolyl group, a thiazolyl group, a pyrimidyl group) which may be substituted with 1 to 3 substituents selected from:
  (a) a $C_{1-6}$ alkyl group and
  (b) a $C_{1-6}$ alkoxy group, and has 1 to 3 heteroatoms selected from a nitrogen atom, an oxygen atom and a sulfur atom, or a group resulting from condensation of the 5- or 6-membered aromatic heterocyclic group with a benzene ring. Inter alia, $R^1$ is preferably:

(a) a $C_{1-6}$ alkyl group which may be substituted with 1 to 3 substituents selected from:
  (i) a halogen atom,
  (ii) a hydroxy group, and
  (iii) a 5- to 8-membered heterocyclic group (e.g., a piperidyl group, a piperazinyl group, a morpholinyl group, and a pyrrolidinyl group) which may be substituted with a substituent selected from a hydroxy group, a halogen atom and a $C_{1-6}$ alkyl group, and has 1 to 3 heteroatoms selected from a nitrogen atom, an oxygen atom and a sulfur atom,
(b) a $C_{1-6}$ alkoxy group which may be substituted with a substituent selected from:
  (i) a hydroxy group,
  (ii) a $C_{1-6}$ alkoxy group,
  (iii) a carboxy group,
  (iv) a $C_{1-6}$ alkoxy-carbonyl group,
  (v) a carbamoyl group, and
  (vi) a carbamoyl group which is mono- or di-substituted with a $C_{1-6}$ alkyl group,
(c) a halogen atom,
(d) a hydroxy group,
(i) a $C_{1-6}$ alkyl-carbonyloxy group,
(j) a $C_{6-12}$ aryloxy group which may be substituted with a halogen atom, and
(m) a 5- to 8-membered heterocyclic (e.g., pyridyl, pyrimidyl)-oxy group which may be substituted with a $C_{1-6}$ alkyl group, and has 1 to 3 heteroatoms selected from a nitrogen atom, an oxygen atom and a sulfur atom.

Further, $R^1$ is preferably: (1) a phenyl group which may be substituted with 1 to 3 substituents selected from (a) a $C_{1-6}$ alkyl group which may be substituted with 1 to 3 halogen atoms or hydroxy groups, (b) a $C_{1-6}$ alkoxy group, (c) a $C_{1-6}$ alkyl-carbonyloxy group, (d) a $C_{1-6}$ alkoxy-carbonyl group, (e) a $C_{1-6}$ alkyl-carbonyl group, (f) a $C_{1-6}$ alkylsulfonyl group, (g) a halogen atom, (h) a hydroxy group, (i) an amino group, (j) a nitro group, (k) a carboxy group, (l) a cyano group, (m) a $C_{6-12}$ aryloxy group, (n) a $C_{7-14}$ aralkyloxy group, (o) a $C_{6-12}$ aryl-carbonyl group, (p) a $C_{7-14}$ aralkyl-carbonyl group, (q) a mono-$C_{1-6}$ alkylamino group, (r) a di-$C_{1-6}$ alkylamino group, (s) a $C_{6-12}$ arylamino group, and (t) a $C_{7-14}$ aralkylamino group (hereinafter, simply referred to Substituent Group B); (2) a pyridyl group which may be substituted with 1 to 3 substituents selected from the Substituent Group B; (3) a thiazolyl group which may be substituted with 1 to 3 substituents selected from the Substituent Group B; or (4) a pyrimidinyl group which may be substituted with 1 to 3 substituents selected from the Substituent Group B; or the like.

Moreover, (1) a phenyl group which may be substituted with 1 to 3 substituents selected from: (a) a $C_{1-3}$ alkyl group which may be substituted with 1 to 3 halogen atoms or hydroxy groups, (b) a $C_{1-3}$ alkoxy group, (c) a $C_{1-3}$ alkyl-carbonyloxy group, (d) a halogen atom, (e) a hydroxy group, (f) an amino group, and (g) a cyano group (hereinafter, simply referred to as Substituent Group C); or (2) a pyridyl group which may be substituted with 1 to 3 substituents selected from the Substituent Group C, and the like are more preferred.

In particular, a phenyl group which may be substituted with 1 to 3 substituents selected from: (a) a $C_{1-3}$ alkyl group which may be substituted with 1 to 3 halogen atoms or hydroxy groups, (b) a $C_{1-3}$ alkoxy group, (c) a $C_{1-3}$ alkyl-carbonyloxy group, (d) a halogen atom, (e) a hydroxy group, (f) an amino group, and (g) a cyano group, is preferred, and in particular, a phenyl group which may be substituted with 1 to 3 substituents selected from: (a) a $C_{1-3}$ alkyl group, (b) a $C_{1-3}$ alkoxy group, (c) a halogen atom, and (d) a hydroxy group, is preferred.

In addition, $R^1$ is preferably an aryl group substituted with a substituent selected from the Substituent Group A, or an aromatic heterocyclic group which may be substituted with a substituent selected from the Substituent Group A.

The "substituent" for the "amino group which may be substituted" represented by $R^2$ may be exemplified by: (1) a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) which may be substituted with 1 to 5 substituents selected from the Substituent Group A, (2) a $C_{2-6}$ alkenyl group (e.g., an ethenyl group, a 1-propenyl group, a 2-propenyl group, etc.) which may be substituted with 1 to 5 substituents selected from the Substituent Group A, (3) a $C_{2-6}$ alkynyl group (e.g., an ethynyl group, a 1-propynyl group, a 2-propynyl group, etc.) which may be substituted with 1 to 5 substituents selected from the Substituent Group A, (4) a $C_{3-6}$ cycloalkyl group (e.g., a cyclopropyl group, a cyclobutyl group, a cyclopentyl group, a cyclohexyl group, etc.) which may be substituted with 1 to 5 substituents selected from the Substituent Group A, (5) a $C_{6-12}$ aryl group (e.g., a phenyl group, a 1-naphthyl group, a 2-naphthyl group, etc.) which may be substituted with 1 to 5 substituents selected from the Substituent Group A, (6) a $C_{7-11}$ aralkyl group (e.g., a benzyl group, a phenethyl group, a 1-naphthylmethyl group, a 2-naphthylmethyl group, etc.) which may be substituted with 1 to 5 substituents selected from the Substituent Group A, (7) a $C_{1-6}$ alkyl-carbonyl group (e.g., an acetyl group, an ethylcarbonyl group, etc.) which may be substituted with 1 to 5 substituents selected from the Substituent Group A, (8) a $C_{2-6}$ alkenyl-carbonyl group (e.g., an ethenylcarbonyl group, a 1-propenylcarbonyl group, a 2-propenylcarbonyl group, etc.) which may be substituted with 1 to 5 substituents selected from the Substituent Group A, (9) a $C_{2-6}$ alkynyl-carbonyl group (e.g., an ethynylcarbonyl group, a 1-propynylcarbonyl group, a 2-propynylcarbonyl group, etc.) which may be substituted with 1 to 5 substituents selected from the Substituent Group A, (10) a $C_{3-6}$ cycloalkyl-carbonyl group (e.g., a cyclopropylcarbonyl group, a cyclobutylcarbonyl group, a cyclopentylcarbonyl group, a cyclohexylcarbonyl group, etc.) which may be substituted with 1 to 5 substituents selected from the Substituent Group A, (11) a $C_{6-10}$ aryl-carbonyl group (e.g., a phenylcarbonyl group, etc.) which may be substituted with 1 to 5 substituents selected from the Substituent Group A, (12) a $C_{7-11}$ aralkyl-carbonyl group (e.g., a benzylcarbonyl group, etc.) which may be substituted with 1 to 5 substituents selected from the Substituent Group A, (13) a $C_{1-6}$ alkoxy-carbonyl group (e.g., a methoxycarbonyl group, an ethoxycarbonyl group, a propoxycarbonyl group, etc.) which may be substituted with 1 to 5 substituents selected from the Substituent Group A, (14) a $C_{2-6}$ alkenyloxy-carbonyl group (e.g., an ethenyloxycarbonyl group, a 1-propenyloxycarbonyl group, a 2-propenyloxycarbonyl group, etc.) which may be substituted with 1 to 5 substituents selected from the Substituent Group A, (15) a $C_{2-6}$ alkynyloxy-carbonyl group (e.g., an ethynyloxycarbonyl group, 1-propynyloxycarbonyl group, a 2-propynyloxycarbonyl group, etc.) which may be substituted with 1 to 5 substituents selected from the Substituent Group A, (16) a $C_{3-6}$ cycloalkyloxy-carbonyl group (e.g., a cyclopropyloxycarbonyl group, a cyclobutyloxycarbonyl group, a cyclopentyloxycarbonyl group, a cyclohexyloxycarbonyl group, etc.) which may be substituted with 1 to 5 substituents selected from the Substituent Group A, (17) a $C_{6-10}$ aryloxy-carbonyl group (e.g., a phenoxycarbonyl group, etc.) which may be substituted with 1 to 5 substituents selected from the Substituent Group A, (18) a $C_{7-11}$ aralkyloxy-carbonyl group (e.g., a benzyloxycarbonyl group, etc.) which may be substituted with 1 to 5 substituents selected from the Substituent Group A, (19) a $C_{1-6}$ alkylsulfonyl group (e.g., a methylsulfonyl group, an ethylsulfonyl group, a propylsulfonyl group, etc.) which may be substituted with 1 to 5 substituents selected from the Substituent Group A, (20) a $C_{6-10}$ arylsulfonyl group (e.g., a phenylsulfonyl group, etc.) which may be substituted with 1 to 5 substituents selected from the Substituent Group A, (21) a $C_{7-11}$ aralkylsulfonyl group (e.g., a benzylsulfonyl group, etc.) which may be substituted with 1 to 5 substituents selected from the Substituent Group A, (22) a 5- to 8-membered heterocyclic group (e.g., a furyl group, a thienyl group, a pyridyl group, a pyrimidyl group, a thiazolyl group, etc.) which may be substituted with 1 to 5 substituents selected from the Substituent Group A, (23) a 5- to 8-membered heterocyclic-carbonyl group (e.g., a furylcarbonyl group, a thienylcarbonyl group, a pyridylcarbonyl group, a pyrimidylcarbonyl group, a thiazolylcarbonyl group, etc.) which may be substituted with 1 to 5 substituents selected from the Substituent Group A, (24) a 5- to 8-membered heterocyclic oxy-carbonyl group (e.g., a furyloxycarbonyl group, a thienyloxycarbonyl group, a pyridyloxycarbonyl group, a pyrimidyloxycarbonyl group, a thiazolyloxycarbonyl group, etc.) which may be substituted with 1 to 5 substituents selected from the Substituent Group A, (25) a 5- to 8-membered heterocyclic sulfonyl group(e.g., a furylsulfonyl group, a thienylsulfonyl group, a pyridylsulfonyl group, a pyrimidylsulfonyl group, a thiazolylsulfonyl group, etc.) which may be substituted with 1 to 5 substituents selected from the Substituent Group A, or the like. The amino group may be mono- or di-substituted with these substituents.

The "substituent" for the "hydroxy group which may be substituted" represented by $R^2$ may be exemplified by: (1) a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) which may be substituted with 1 to 5 substituents selected from the Substituent Group A, (2) a $C_{2-6}$ alkenyl group (e.g., an ethenyl group, a 1-propenyl group, a 2-propenyl group, etc.) which may be substituted with 1 to 5 substituents selected from the Substituent Group A, (3) a $C_{2-6}$ alkynyl group (e.g., an ethynyl group, a 1-propynyl group, a 2-propynyl group, etc.) which may be substituted with 1 to 5 substituents selected from the Substituent Group A, (4) a $C_{3-6}$ cycloalkyl group (e.g., a cyclopropyl group, a cyclobutyl group, a cyclopentyl group, a cyclohexyl group, etc.) which may be substituted with 1 to 5 substituents selected from the Substituent Group A, (5) a $C_{6-12}$ aryl group (e.g., a phenyl group, a 1-naphthyl group, a 2-naphthyl group, etc.) which may be substituted with 1 to 5 substituents selected from the Substituent Group A, and (6) a $C_{7-11}$ aralkyl group (e.g., a benzyl group, a phenethyl group, a 1-naphthylmethyl group, a 2-naphthylmethyl group, etc.) which may be substituted with 1 to 5 substituents selected from the Substituent Group A, (7) a $C_{1-6}$ alkyl-carbonyl group (e.g., an acetyl group, an ethylcarbonyl group, etc.) which may be substituted with 1 to 5 substituents selected from the Substituent Group A, (8) a $C_{2-6}$ alkenyl-carbonyl group (e.g., an ethenylcarbonyl group, a 1-propenylcarbonyl group, a 2-propenylcarbonyl group, etc.) which may be substituted with 1 to 5 substituents selected from the Substituent Group A, (9) a $C_{2-6}$ alkynyl-carbonyl group (e.g., an ethynylcarbonyl group, a 1-propynylcarbonyl group, a 2-propynylcarbonyl group, etc.) which may be substituted with 1 to 5 substituents selected from the Substituent Group A, (10) a $C_{3-6}$ cycloalkyl-carbonyl group (e.g., a cyclopropylcarbonyl group, a cyclobutylcarbonyl group, a cyclopentylcarbonyl group, a cyclohexylcarbonyl group, etc.) which may be substituted with 1 to 5 substituents selected from the Substituent Group A, (11) a $C_{6-10}$ arylcarbonyl group (e.g., a phenylcarbonyl group, etc.) which may be substituted with 1 to 5 substituents selected from the Substituent Group A, (12) a $C_{7-11}$ aralkyl-carbonyl group (e.g., a benzylcarbonyl group, etc.) which may be substituted with 1 to 5 substituents selected from the Substituent Group A, (13) a $C_{1-6}$ alkoxy-carbonyl group (e.g., a methoxycarbonyl group, an ethoxycarbonyl group, a propoxycarbonyl group, etc.) which may be substituted with 1 to 5 substituents selected from the Substituent Group A, (14) a $C_{2-6}$ alkenyloxy-carbonyl group (e.g., an ethenyloxycarbonyl group, a 1-propenyloxycarbonyl group, a 2-propenyloxycarbonyl group, etc.) which may be substituted with 1 to 5 substituents selected from the Substituent Group A, (15) a $C_{2-6}$ alkynyloxy-carbonyl group (e.g., an ethynyloxycarbonyl group, a 1-propynyloxycarbonyl group, a 2-propynyloxycarbonyl group, etc.) which may be substituted with 1 to 5 substituents selected from the Substituent Group A, (16) a $C_{3-6}$ cycloalkyloxy-carbonyl group (e.g., a cyclopropyloxycarbonyl group, a cyclobutyloxycarbonyl group, a cyclopentyloxycarbonyl group, a cyclohexyloxycarbonyl group, etc.) which may be substituted with 1 to 5 substituents selected from the Substituent Group A, (17) a $C_{6-10}$ aryloxy-carbonyl group (e.g., a phenoxycarbonyl group, etc.) which may be substituted with 1 to 5 substituents selected from the Substituent Group A, (18) a $C_{7-11}$ aralkyloxy-carbonyl group (e.g., a benzyloxycarbonyl group, etc.) which may be substituted with 1 to 5 substituents selected from the Substituent Group A, (19) a $C_{1-6}$ alkylsulfonyl group (e.g., a methylsulfonyl group, an ethylsulfonyl group, a propylsulfonyl group, etc.) which may be substituted with 1 to 5 substituents selected from the Substituent Group A, (20) a $C_{6-10}$ arylsulfonyl group (e.g., a phenylsulfonyl group, etc.) which may be substituted with 1 to 5 substituents selected from the Substituent Group A, (21) a $C_{7-11}$ aralkylsulfonyl group (e.g., a benzylsulfonyl group, etc.) which may be substituted with 1 to 5 substituents selected from the Substituent Group A, (22) a $C_{1-6}$ alkylsulfonyloxy group which may be substituted with 1 to 5 substituents selected from the Substituent Group A, (23) a $C_{6-10}$ arylsulfonyloxy group which may be substituted with 1 to 5 substituents selected from the Substituent Group A, (24) a $C_{7-11}$ aralkylsulfonyloxy group which may be substituted with 1 to 5 substituents selected from the Substituent Group A, (25) a 5- to 8-membered heterocyclic group(e.g., a furyl group, a thienyl group, a pyridyl group, a pyrimidyl group, a thiazolyl group, etc.) which may be substituted with 1 to 5 substituents selected from the Substituent Group A, (26) a 5- to 8-membered heterocyclic-carbonyl group (e.g., a furylcarbonyl group, a thienylcarbonyl group, a pyridylcarbonyl group, a pyrimidylcarbonyl group, a thiazolylcarbonyl group, etc.) which may be substituted with 1 to 5 substituents selected from the Substituent Group A, (27) a 5- to 8-membered heterocyclic oxy-carbonyl group (e.g., a furyloxycarbonyl group, a thienyloxycarbonyl group, a pyridyloxycarbonyl group, a pyrimidyloxycarbonyl group, a thiazolyloxycarbonyl group, etc.) which may be substituted with 1 to 5 substituents selected from the Substituent Group A, (28) a 5- to 8-membered heterocyclic sulfonyl group (e.g., a furylsulfonyl group, a thienylsulfonyl group, a pyridylsulfonyl group, a pyrimidylsulfonyl group, a thiazolylsulfonyl group, etc.) which may be substituted with 1 to 5 substituents selected from the Substituent Group A, or the like.

The "thiol group which may be substituted" represented by $R^2$ may be exemplified by:

(1) a thiol group which may be substituted with a substituent selected from: (1') a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) which may be substituted with 1 to 5 substituents selected from the Substituent Group A; (2') a $C_{2-6}$ alkenyl group (e.g., an ethenyl group, a 1-propenyl group, a 2-propenyl group, etc.) which may be substituted with 1 to 5 substituents selected from the Substituent Group A; (3') a $C_{2-6}$ alkynyl group (e.g., an ethynyl group, a 1-propynyl group, a 2-propynyl group, etc.) which may be substituted with 1 to 5 substituents selected from the Substituent Group A; (4') a $C_{3-6}$ cycloalkyl group (e.g., a cyclopropyl group, a cyclobutyl group, a cyclopentyl group, a cyclohexyl group, etc.) which may be substituted with 1 to 5 substituents selected from the Substituent Group A; (5') a $C_{6-12}$ aryl group (e.g., a phenyl group, a 1-naphthyl group, a 2-naphthyl group, etc.) which may be substituted with 1 to 5 substituents selected from the Substituent Group A; (6') a $C_{7-11}$ aralkyl group (e.g., a benzyl group, a phenethyl group, a 1-naphthylmethyl group, a 2-naphthylmethyl group, etc.) which may be substituted with 1 to 5 substituents selected from the Substituent Group A; (7') a $C_{1-6}$ alkyl-carbonyl group (e.g., an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a hexylcarbonyl group, etc.) which may be substituted with 1 to 5 substituents selected from the Substituent Group A; (8') a $C_{2-6}$ alkenyl-carbonyl group (e.g., an ethenylcarbonyl group, a 1-propenylcarbonyl group, a 2-propenylcarbonyl group, etc.) which may be substituted with 1 to 5 substituents selected from the Substituent Group A; (9') a $C_{2-6}$ alkynyl-carbonyl group (e.g., an ethynylcarbonyl group, a 1-propynylcarbonyl group, a 2-propynylcarbonyl group, etc.) which may be substituted with 1 to 5 substituents selected from the Substituent Group A; (10') a $C_{3-6}$ cycloalkyl-carbonyl group (e.g., a cyclopropylcarbonyl group, a cyclobutylcarbonyl group, a cyclopentylcarbonyl group, a cyclohexylcarbonyl group, etc.) which may be substituted with 1 to 5 substituents selected from the Substituent Group A; (11') a $C_{6-12}$ aryl-carbonyl group (e.g., a benzoyl group, a 1-naphthoyl group, a 2-naphthoyl group, etc.) which may be substituted with 1 to 5 substituents selected from the Substituent Group A; (12') a $C_{7-11}$ aralkyl-carbonyl group (e.g., a benzylcarbonyl group, a phenethylcarbonyl group, a 1-naphthylmethylcarbonyl group, a 2-naphthylmethylcarbonyl group, etc.) which may be substituted with 1 to 5 substituents selected from the Substituent Group A; (13') a $C_{1-6}$ alkoxy-carbonyl group (e.g., a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentoxycarbonyl group, a hexyloxycarbonyl group, etc.) which may be substituted with 1 to 5 substituents selected from the Substituent Group A; (14') a $C_{2-6}$ alkenyloxy-carbonyl group (e.g., an ethenyloxycarbonyl group, a 1-propenyloxycarbonyl group, a 2-propenyloxycarbonyl group, etc.) which may be substituted with 1 to 5 substituents selected from the Substituent Group A; (15') a $C_{2-6}$ alkynyloxy-carbonyl group (e.g., an ethynyloxycarbonyl group, a 1-propynyloxycarbonyl group, a 2-propynyloxycarbonyl group, etc.) which may be substituted with 1 to 5 substituents selected from the Substituent Group A; (16') a $C_{3-6}$ cycloalkyloxy-carbonyl group (e.g., a cyclopropyloxycarbonyl group, a cyclobutyloxycarbonyl group, a cyclopentyloxycarbonyl group, a cyclohexyloxycarbonyl group, etc.) which may be substituted with 1 to 5 substituents selected from the Substituent Group A; (17') a $C_{6-12}$ aryloxy-carbonyl group (e.g., a phenoxycarbonyl group, a 1-naphthyloxycarbonyl group, a 2-naphthyloxycarbonyl group, etc.) which may be substituted with 1 to 5 substituents selected from the Substituent Group A; (18') a $C_{7-11}$ aralkyloxy-carbonyl group (e.g., a benzyloxycarbonyl group, a phenethyloxycarbonyl group, a 1-naphthylmethoxycarbonyl group, a 2-naphthylmethoxycarbonyl group, etc.) which may be substituted with 1 to 5 substituents selected from the Substituent Group A; (19') a 5- to 8-membered heterocyclic group (e.g., a furyl group, a thienyl group, a pyridyl group, pyrimidyl group, a thiazolyl group, etc.) which may be substituted with 1 to 5 substituents selected from the Substituent Group A; (20') a 5- to 8-membered heterocyclic-carbonyl group (e.g., a furylcarbonyl group, a thienylcarbonyl group, a pyridylcarbonyl group, a pyrimidylcarbonyl group, a thiazolylcarbonyl group, etc.) which may be substituted with 1 to 5 substituents selected from the Substituent Group A; and (21') a 5- to 8-membered heterocyclic oxycarbonyl group (e.g., a furyloxycarbonyl group, a thienyloxycarbonyl group, a pyridyloxycarbonyl group, a pyrimidyloxycarbonyl group, a thiazolyloxycarbonyl group, etc.) which may be substituted with 1 to 5 substituents selected from the Substituent Group A, (2) a $C_{1-6}$ alkylsulfinyl group (e.g., a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, etc.) which may be substituted with 1 to 5 substituents selected from the Substituent Group A, (3) a $C_{6-10}$ arylsulfinyl group (e.g., a benzenesulfinyl group, a 1-naphthylsulfinyl group, a 2-naphthylsulfinyl group, etc.) which may be substituted with 1 to 5 substituents selected from the Substituent Group A, (4) a $C_{1-6}$ alkylsulfonyl group (e.g., a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, etc.) which may be substituted with 1 to 5 substituents selected from the Substituent Group A, 5 (5) a $C_{6-12}$ arylsulfonyl group (e.g., a benzenesulfonyl group, a 1-naphthylsulfonyl group, a 2-naphthylsulfonyl group, etc.) which may be substituted with 1 to 5 substituents selected from the Substituent Group A, or the like.

$R^2$ is preferably: (1) a hydrogen atom, (2) an amino group which may be mono- or di-substituted with (a) a $C_{1-6}$ alkyl group or (b) a $C_{1-6}$ alkyl-carbonyl group, (3) a hydroxy group which may be substituted with (a) a $C_{1-6}$ alkyl group or (b) a $C_{1-6}$ alkyl-carbonyl group, or the like. Inter alia, (1) a hydrogen atom, or (2) an amino group which may be mono- or di-substituted with a $C_{1-6}$ alkyl group is preferred, and in particular, a hydrogen atom or amino group is preferred.

The "hydrocarbon group which may be substituted" represented by $R^3$, $R^4$, $R^5$ and $R^6$ may be exemplified by:

(1) a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) which may be substituted with 1 to 5 substituents selected from the Substituent Group A, (2) a $C_{2-6}$ alkenyl group (e.g., an ethenyl group, a 1-propenyl group, a 2-propenyl group, etc.) which may be substituted with 1 to 5 substituents selected from the Substituent Group A, (3) a $C_{2-6}$ alkynyl group (e.g., an ethynyl group, a 1-propynyl group, a 2-propynyl group, etc.) which may be substituted with 1 to 5 substituents selected from the Substituent Group A, (4) a $C_{3-6}$ cycloalkyl group (e.g., a cyclopropyl group, a cyclobutyl group, a cyclopentyl group, a cyclohexyl group, etc.) which may be substituted with 1 to 5 substituents selected from the Substituent Group A, (5) a $C_{6-12}$ aryl group (e.g., a phenyl group, a 1-naphthyl group, a 2-naphthyl group, etc.) which may be substituted with 1 to 5 substituents selected from the Substituent Group A, (6) a $C_{7-11}$ aralkyl group (e.g., a benzyl group, a phenethyl group, a 1-naphthylmethyl group, a 2-naphthylmethyl group, etc.) which may be substituted with 1 to 5 substituents selected from the Substituent Group A, (7) a $C_{1-6}$ alkyl-carbonyl group (e.g., an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a hexylcarbonyl group, etc.) which may be substituted with 1 to 5 substituents selected from the Substituent Group A, (8) a $C_{2-6}$ alkenyl-carbonyl group (e.g., an ethenylcarbonyl group, a 1-propenylcarbonyl group, a 2-propenylcarbonyl group, etc.) which may be substituted with 1 to 5 substituents selected from the Substituent Group A, (9) a $C_{2-6}$ alkynyl-carbonyl group (e.g., an ethynylcarbonyl group, a 1-propynylcarbonyl group, a 2-propynylcarbonyl group, etc.) which may be substituted with 1 to 5 substituents selected from the Substituent Group A,

(10) a $C_{3-6}$ cycloalkyl-carbonyl group (e.g., a cyclopropylcarbonyl group, a cyclobutylcarbonyl group, a cyclopentylcarbonyl group, a cyclohexylcarbonyl group, etc.) which may be substituted with 1 to 5 substituents selected from the Substituent Group A,

(11) a $C_{6-12}$ aryl-carbonyl group (e.g., a benzoyl group, a 1-naphthoyl group, a 2-naphthoyl group, etc.) which may be substituted with 1 to 5 substituents selected from the Substituent Group A,

(12) a $C_{7-11}$ aralkyl-carbonyl group (e.g., a benzylcarbonyl group, a phenethylcarbonyl group, a 1-naphthylmethylcarbonyl group, a 2-naphthylmethylcarbonyl group, etc.) which may be substituted with 1 to 5 substituents selected from the Substituent Group A,

(13) a $C_{1-6}$ alkoxy-carbonyl group (e.g., a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentoxycarbonyl group, a hexyloxycarbonyl group, etc.) which may be substituted with 1 to 5 substituents selected from the Substituent Group A,

(14) a $C_{2-6}$ alkenyloxy-carbonyl group (e.g., an ethenyloxycarbonyl group, a 1-propenyloxycarbonyl group, a 2-propenyloxycarbonyl group, etc.) which may be substituted with 1 to 5 substituents selected from the Substituent Group A,

(15) a $C_{2-6}$ alkynyloxy-carbonyl group (e.g., an ethynyloxycarbonyl group, a 1-propynyloxycarbonyl group, a 2-propynyloxycarbonyl group, etc.) which may be substituted with 1 to 5 substituents selected from the Substituent Group A,

(16) a $C_{3-6}$ cycloalkyloxy-carbonyl group (e.g., a cyclopropyloxycarbonyl group, a cyclobutyloxycarbonyl group, a cyclopentyloxycarbonyl group, a cyclohexyloxycarbonyl group, etc.) which may be substituted with 1 to 5 substituents selected from the Substituent Group A,

(17) a $C_{6-12}$ aryloxy-carbonyl group (e.g., a phenoxycarbonyl group, a 1-naphthyloxycarbonyl group, a 2-naphthyloxycarbonyl group, etc.) which may be substituted with 1 to 5 substituents selected from the Substituent Group A,

(18) a $C_{7-11}$ aralkyloxy-carbonyl group (e.g., a benzyloxycarbonyl group, a phenethyloxycarbonyl group, a 1-naphthylmethoxycarbonyl group, a 2-naphthylmethoxycarbonyl group, etc.) which may be substituted with 1 to 5 substituents selected from the Substituent Group A,

(19) a carbamoyl group which may be mono- or di-substituted with a substituent selected from: a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) which may be substituted with 1 to 5 substituents selected from the Substituent Group A; a $C_{2-6}$ alkenyl group (e.g., an ethenyl group, a 1-propenyl group, a 2-propenyl group, etc.) which may be substituted with 1 to 5 substituents selected from the Substituent Group A; a $C_{2-6}$ alkynyl group (e.g., an ethynyl group, a 1-propynyl group, a 2-propynyl group, etc.) which may be substituted with 1 to 5 substituents selected from the Substituent Group A; a $C_{3-6}$ cycloalkyl group (e.g., a cyclopropyl group, a cyclobutyl group, a cyclopentyl group, a cyclohexyl group, etc.) which may be substituted with 1 to 5 substituents selected from the Substituent Group A; a $C_{6-12}$ aryl group (e.g., a phenyl group, a 1-naphthyl group, a 2-naphthyl group, etc.) which may be substituted with 1 to 5 substituents selected from the Substituent Group A; a $C_{7-11}$ aralkyl group (e.g., a benzyl group, a phenethyl group, a 1-naphthylmethyl group, a 2-naphthylmethyl group, etc.) which may be substituted with 1 to 5 substituents selected from the Substituent Group A; a $C_{1-6}$ alkyl-carbonyl group (e.g., an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a hexylcarbonyl group, etc.) which may be substituted with 1 to 5 substituents selected from the Substituent Group A; a $C_{2-6}$ alkenyl-carbonyl group (e.g., an ethenylcarbonyl group, a 1-propenylcarbonyl group, a 2-propenylcarbonyl group, etc.) which may be substituted with 1 to 5 substituents selected from the Substituent Group A; a $C_{2-6}$ alkynyl-carbonyl group (e.g., an ethynylcarbonyl group, a 1-propynylcarbonyl group, a 2-propynylcarbonyl group, etc.) which may be substituted with 1 to 5 substituents selected from the Substituent Group A; a $C_{3-6}$ cycloalkyl-carbonyl group (e.g., a cyclopropylcarbonyl group, a cyclobutylcarbonyl group, a cyclopentylcarbonyl group, a cyclohexylcarbonyl group, etc.) which may be substituted with 1 to 5 substituents selected from the Substituent Group A; a $C_{6-12}$ aryl-carbonyl group (e.g., a benzoyl group, a 1-naphthoyl group, a 2-naphthoyl group, etc.) which may be substituted with 1 to 5 substituents selected from the Substituent Group A; a $C_{7-11}$ aralkyl-carbonyl group (e.g., a benzylcarbonyl group, a phenethylcarbonyl group, a 1-naphthylmethylcarbonyl group, a 2-naphthylmethylcarbonyl group, etc.) which may be substituted with 1 to 5 substituents selected from the Substituent Group A; a $C_{1-6}$ alkoxy-carbonyl group (e.g., a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentoxycarbonyl group, a hexyloxycarbonyl group, etc.) which may be substituted with 1 to 5 substituents selected from the Substituent Group A; a $C_{2-6}$ alkenyloxy-carbonyl group (e.g., an ethenyloxycarbonyl group, a 1-propenyloxycarbonyl group, a 2-propenyloxycarbonyl group, etc.) which may be substituted with 1 to 5 substituents selected from the Substituent Group A; a $C_{2-6}$ alkynyloxy-carbonyl group (e.g., an ethynyloxycarbonyl group, a 1-propynyloxycarbonyl group, a 2-propynyloxycarbonyl group, etc.) which may be substituted with 1 to 5 substituents selected from the Substituent Group A; a $C_{3-6}$ cycloalkyloxy-carbonyl group (e.g., a cyclopropyloxycarbonyl group, a cyclobutyloxycarbonyl group, a cyclopentyloxycarbonyl group, a cyclohexyloxycarbonyl group, etc.) which may be substituted with 1 to 5 substituents selected from the Substituent Group A; a $C_{6-12}$ aryloxy-carbonyl group (e.g., a phenoxycarbonyl group, a 1-naphthyloxycarbonyl group, a 2-naphthyloxycarbonyl group, etc.) which may be substituted with 1 to 5 substituents selected from the Substituent Group A; a $C_{7-11}$ aralkyloxy-carbonyl group (e.g., a benzyloxycarbonyl group, a phenethyloxycarbonyl group, a 1-naphthylmethoxycarbonyl group, a 2-naphthylmethoxycarbonyl group, etc.) which may be substituted with 1 to 5 substituents selected from the Substituent Group A; a $C_{1-6}$ alkylsulfonyl group (e.g., a methylsulfonyl group, an ethylsulfonyl group, a propylsulfonyl group, etc.) which may be substituted with 1 to 5 substituents selected from the Substituent Group A; a $C_{6-10}$ arylsulfonyl group (e.g., a phenylsulfonyl group, etc.) which may be substituted with 1 to 5 substituents selected from the Substituent Group A; a $C_{7-11}$ aralkylsulfonyl group (e.g., a benzylsulfonyl group, etc.) which may be substituted with 1 to 5 substituents selected from the Substituent Group A; a 5- to 8-membered heterocyclic group (e.g., a furyl group, a thienyl group, a pyridyl group, a pyrimidyl group, a thiazolyl group, etc.) which may be substituted with 1 to 5 substituents selected from the Substituent Group A; a 5- to 8-membered heterocyclic-carbonyl group (e.g., a furylcarbonyl group, a thienylcarbonyl group, a pyridylcarbonyl group, a pyrimidylcarbonyl group, a thiazolylcarbonyl group, etc.) which may be substituted with 1 to 5 substituents selected from the Substituent Group A; a 5- to 8-membered heterocyclic oxy-carbonyl group (e.g., a furyloxycarbonyl group, a thienyloxycarbonyl group, a pyridyloxycarbonyl group, a pyrimidyloxycarbonyl group, a thiazolyloxycarbonyl group, etc.) which may be substituted with 1 to 5 substituents selected from the Substituent Group A; and a 5- to 8-membered heterocyclic sulfonyl group (e.g., a furylsulfonyl group, a thienylsulfonyl group, a pyridylsulfonyl group, a pyrimidylsulfonyl group, a thiazolylsulfonyl group, etc.) which may be substituted with 1 to 5 substituents selected from the Substituent Group A,

(20) a sulfamoyl group which may be mono- or di-substituted with a substituent selected from: a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) which may be substituted with 1 to 5 substituents selected from the Substituent Group A; a $C_{2-6}$ alkenyl group (e.g., an ethenyl group, a 1-propenyl group, a 2-propenyl group, etc.) which may be substituted with 1 to 5 substituents selected from the Substituent Group A; a $C_{2-6}$ alkynyl group (e.g., an ethynyl group, a 1-propynyl group, a 2-propynyl group, etc.) which may be substituted with 1 to 5 substituents selected from the Substituent Group A; a $C_{3-6}$ cycloalkyl group (e.g., a cyclopropyl group, a cyclobutyl group, a cyclopentyl group, a cyclohexyl group, etc.) which may be substituted with 1 to 5 substituents selected from the Substituent Group A; a $C_{6-12}$ aryl group (e.g., a phenyl group, a 1-naphthyl group, a 2-naphthyl group, etc.) which may be substituted with 1 to 5 substituents selected from the Substituent Group A; a $C_{7-11}$ aralkyl group (e.g., a benzyl group, a phenethyl group, a 1-naphthylmethyl group, a 2-naphthylmethyl group, etc.) which may be substituted with 1 to 5 substituents selected from the Substituent Group A; a $C_{1-6}$ alkyl-carbonyl group (e.g., an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a hexylcarbonyl group, etc.) which may be substituted with 1 to 5 substituents selected from the Substituent Group A; a $C_{2-6}$ alkenyl-carbonyl group (e.g., an ethenylcarbonyl group, a 1-propenylcarbonyl group, a 2-propenylcarbonyl group, etc.) which may be substituted with 1 to 5 substituents selected from the Substituent Group A; a $C_{2-6}$ alkynyl-carbonyl group (e.g., an ethynylcarbonyl group, a 1-propynylcarbonyl group, a 2-propynylcarbonyl group, etc.) which may be substituted with 1 to 5 substituents selected from the Substituent Group A; a $C_{3-6}$ cycloalkyl-carbonyl group (e.g., a cyclopropylcarbonyl group, a cyclobutylcarbonyl group, a cyclopentylcarbonyl group, a cyclohexylcarbonyl group, etc.) which may be substituted with 1 to 5 substituents selected from the Substituent Group A; a $C_{6-12}$ aryl-carbonyl group (e.g., a benzoyl group, a 1-naphthoyl group, a 2-naphthoyl group, etc.) which may be substituted with 1 to 5 substituents selected from the Substituent Group A; a $C_{7-11}$ aralkyl-carbonyl group (e.g., a benzylcarbonyl group, a phenethylcarbonyl group, a 1-naphthylmethylcarbonyl group, a 2-naphthylmethylcarbonyl group, etc.) which may be substituted with 1 to 5 substituents selected from the Substituent Group A; a $C_{1-6}$ alkoxy-carbonyl group (e.g., a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentoxycarbonyl group, a hexyloxycarbonyl group, etc.) which may be substituted with 1 to 5 substituents selected from the Substituent Group A; a $C_{2-6}$ alkenyloxy-carbonyl group (e.g., an ethenyloxycarbonyl group, a 1-propenyloxycarbonyl group, a 2-propenyloxycarbonyl group, etc.) which may be substituted with 1 to 5 substituents selected from the Substituent Group A; a $C_{2-6}$ alkynyloxy-carbonyl group (e.g., an ethynyloxycarbonyl group, a 1-propynyloxycarbonyl group, a 2-propynyloxycarbonyl group, etc.) which may be substituted with 1 to 5 substituents selected from the Substituent Group A; a $C_{3-6}$ cycloalkyloxy-carbonyl group (e.g., a cyclopropyloxycarbonyl group, a cyclobutyloxycarbonyl group, a cyclopentyloxycarbonyl group, a cyclohexyloxycarbonyl group, etc.) which may be substituted with 1 to 5 substituents selected from the Substituent Group A; a $C_{6-12}$ aryloxy-carbonyl group (e.g., a phenoxycarbonyl group, a 1-naphthyloxycarbonyl group, a 2-naphthyloxycarbonyl group, etc.) which may be substituted with 1 to 5 substituents selected from the Substituent Group A; a $C_{7-11}$ aralkyloxy-carbonyl group (e.g., a benzyloxycarbonyl group, a phenethyloxycarbonyl group, a 1-naphthylmethoxycarbonyl group, a 2-naphthylmethoxycarbonyl group, etc.) which may be substituted with 1 to 5 substituents selected from the Substituent Group A; a $C_{1-6}$ alkylsulfonyl group (e.g., a methylsulfonyl group, an ethylsulfonyl group, a propylsulfonyl group, etc.) which may be substituted with 1 to 5 substituents selected from the Substituent Group A; a $C_{6-10}$ arylsulfonyl group (e.g., a phenylsulfonyl group, etc.) which may be substituted with 1 to 5 substituents selected from the Substituent Group A; a $C_{7-11}$ aralkylsulfonyl group (e.g., a benzylsulfonyl group, etc.) which may be substituted with 1 to 5 substituents selected from the Substituent Group A; a 5- to 8-membered heterocyclic group (e.g., a furyl group, a thienyl group, a pyridyl group, a pyrimidyl group, a thiazolyl group, etc.) which may be substituted with 1 to 5 substituents selected from the Substituent Group A; a 5- to 8-membered heterocyclic-carbonyl group (e.g., a furylcarbonyl group, a thienylcarbonyl group, a pyridylcarbonyl group, a pyrimidylcarbonyl group, a thiazolylcarbonyl group, etc.) which may be substituted with 1 to 5 substituents selected from the Substituent Group A; a 5- to 8-membered heterocyclic oxy-carbonyl group (e.g., a furyloxycarbonyl group, a thienyloxycarbonyl group, a pyridyloxycarbonyl group, a pyrimidyloxycarbonyl group, a thiazolyloxycarbonyl group, etc.) which may be substituted with 1 to 5 substituents selected from the Substituent Group A; a 5- to 8-membered heterocyclic sulfonyl group (e.g., a furylsulfonyl group, a thienylsulfonyl group, a pyridylsulfonyl group, a pyrimidylsulfonyl group, a thiazolylsulfonyl group, etc.) which may be substituted with 1 to 5 substituents selected from the Substituent Group A, or the like.

The "substituent" for the "amino group which may be substituted" represented by $R^3$, $R^4$, $R^5$ and $R^6$ may be exemplified by the same substituent as the above-mentioned "substituent" for the "amino group which may be substituted" represented by $R^2$, and the amino group may be mono- or di-substituted with those substituents.

The "substituent" for the "hydroxy group which may be substituted" represented by $R^2$, $R^3$, $R^4$, $R^5$ and $R^6$ may be exemplfieid by the same substituent as the above-mentioned "substituent" for the "hydroxy group which may be substituted" represented by $R^2$.

The "substituent" for the "thiol group which may be substituted" represented by $R^3$, $R^4$, $R^5$ and $R^6$ may be exemplified by the same substituent as the above-mentioned "substituent" for the "thiol group which may be substituted" represented by $R^2$.

The ring formed by $R^3$ and $R^4$, $R^4$ and $R^5$, and $R^5$ and $R^6$, respectively, together with the adjacent carbon atom, may be exemplified by (1) a 5- to 8-membered homocyclic ring which may be substituted with 1 to 5 substituents selected from the Substituent Group A, or (2) a 5- to 8-membered heterocyclic ring which may be substituted with 1 to 5 substituents selected from the Substituent Group A, and has 1 to 3 heteroatoms selected from a nitrogen atom, an oxygen atom and a sulfur atom. Thus, a ring in which a moiety structure represented by the formula:

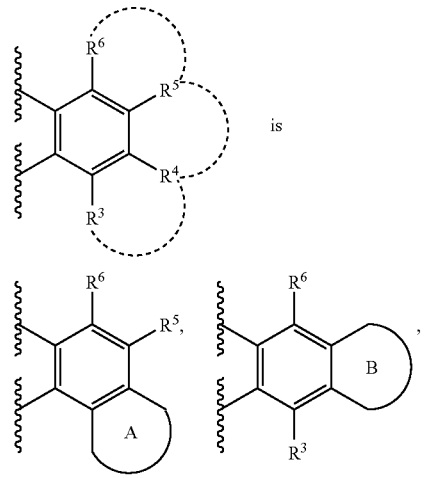

-continued

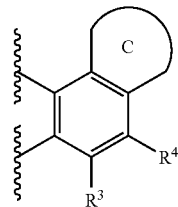

wherein $R^3$, $R^4$ and $R^5$ have the same meaning as defined above; ring A, ring B and ring C are each (1) a 5- to 8-membered homocyclic ring which may be substituted with 1 to 5 substituents selected from the Substituent Group A, or (2) a 5- to 8-membered heterocyclic ring which may be substituted with 1 to 5 substituents selected from the Substituent Group A, and has 1 to 3 heteroatoms selected from a nitrogen atom, an oxygen atom and a sulfur atom, may be mentioned.

Here, the "5- to 8-membered homocyclic ring" of the "5- to 8-membered homocyclic ring which may be substituted with 1 to 5 substituents selected from the Substituent Group A" represented by ring A, ring B and ring C, may be exemplified by $C_{5-8}$ cycloalkane (e.g., cyclopentane, cyclohexane, cycloheptane, and cyclooctane), $C_{5-8}$ cycloalkene (e.g., cyclopentene, cyclohexene, cycloheptene, and cyclooctene), $C_{6-10}$ arene (e.g., benzene), or the like.

The "5- to 8-membered heterocyclic ring which has 1 to 3 heteroatoms selected from a nitrogen atom, an oxygen atom and a sulfur atom" of the "5- to 8-membered heterocyclic ring which may be substituted with 1 to 5 substituents selected from the Substituent Group A, and has 1 to 3 heteroatoms selected from a nitrogen atom, an oxygen atom and a sulfur atom" represented by ring A, ring B and ring C, may be exemplified by pyrrole, pyrazole, imidazole, furan, thiophene, oxazole, thiazole, pyridine, pyrimidine, pyridazine, [1,3]-dioxole, [2,3]-dihydro-1,4-dioxine, [1,4]-oxazepam, [1,4]-thiazepam, or the like.

$R^3$, $R^4$, $R^5$ and $R^6$, which may be identical or different, is preferably (1) a hydrogen atom, (2) a cyano group, (3) a halogen atom, (4) a $C_{1-6}$ alkyl group, (5) an amino group, (6) a hydroxy group, (7) a $C_{1-6}$ alkoxy group which may be substituted with a $C_{1-6}$ alkoxy group, or (8) a group represented by the formula: —X(CH$_2$)$_b$—R$^{11}$ (wherein, X is —O—, —S—, —S(O)—, —S(O)$_2$—, —NR$^{12}$—, —OSO$_2$—, —NR$^{12}$CO—, —NR$^{12}$SO$_2$—, —CONR$^{12}$— or —SO$_2$NR$^{12}$— [wherein R$^{12}$ is a hydrogen atom, or a $C_{1-6}$ alkyl group (e.g., a methyl group, an ethyl group, a propyl group, an isopropyl group, a butyl group, an isobutyl group, a sec-butyl group, a tert-butyl group, etc.)]; b is an integer from 2 to 4; and R$^{11}$ is (a) a piperidyl group which may be substituted with a hydroxy group or a $C_{1-6}$ alkyl group (e.g., a methyl group, an ethyl group, etc.), (b) a piperazinyl group which may be substituted with a hydroxy group or a $C_{1-6}$ alkyl group (e.g., a methyl group, an ethyl group, etc.), (c) a morpholinyl group which may be substituted with a hydroxy group or a $C_{1-6}$ alkyl group (e.g., a methyl group, an ethyl group, etc.), or (d) a pyrrolidinyl group which may be substituted with a hydroxy group or a $C_{1-6}$ alkyl group (e.g., a methyl group, an ethyl group, etc.). Alternatively, (1) a 5- to 8-membered homocyclic ring, or (2) a 5- to 8-membered heterocyclic ring having 1 to 3 heteroatoms selected from a nitrogen atom, an oxygen atom and a sulfur atom, each being formed by $R^3$ and $R^4$, $R^4$ and $R^5$, and $R^5$ and $R^6$, respectively, together with the adjacent carbon atom, is also preferred.

Further, $R^3$, $R^4$, $R^5$ and $R^6$, which may be identical or different, are each preferably:

(1) a hydrogen atom,
(2) a nitro group,
(3) an amino group,
(4) a hydroxy group,
(5) a $C_{1-6}$ alkoxy group which may be substituted with a substituent selected from:
   (a) a hydroxy group,
   (b) a cyano group,
   (c) a $C_{1-6}$ alkoxy group,
   (d) a carboxy group,
   (e) a $C_{1-6}$ alkoxy-carbonyl group,
   (f) a carbamoyl group,
   (g) a carbamoyl group which is mono- or di-substituted with a $C_{1-6}$ alkyl group which may be substituted with an amino group which may be mono- or di-substituted with a $C_{1-6}$ alkyl group,
   (h) an amino group which may be mono- or di-substituted with a $C_{1-6}$ alkyl group,
   (i) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom, and
   (j) a 5- to 8-membered heterocyclic (e.g., piperazinyl)-carbonyl group which may be substituted with a $C_{1-6}$ alkyl group, and has 1 to 3 heteroatoms selected from a nitrogen atom, an oxygen atom and a sulfur atom,
(6) a $C_{7-14}$ aralkyloxy group, or
(7) a group represented by the formula:

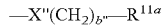

wherein X" is —O—, —NHSO$_2$—, —NHCO— or —NR$^{12"}$— (wherein R$^{12"}$ is a hydrogen atom, or a $C_{1-6}$ alkyl group which may be substituted with a 5- to 8-membered heterocyclic group (e.g., a morpholinyl group) which has 1 to 3 heteroatoms selected from a nitrogen atom, an oxygen atom and a sulfur atom);

b" is an integer from 1 to 4; and $R^{11a}$ is a 5- or 8-membered heterocyclic group (e.g., a piperidyl group, a piperazinyl group, a morpholinyl group, a pyrrolidinyl group) which may be substituted with a substituent selected from:

(a) a hydroxy group,
(b) a $C_{1-6}$ alkyl group, and
(C) a $C_{6-14}$ aryl group (e.g., a phenyl group) which may be substituted with a halogen atom, and has 1 to 3 heteroatoms selected from a nitrogen atom, an oxygen atom and a sulfur atom. In particular, (1) a hydrogen atom,
(2) a nitro group,
(3) an amino group,
(4) a hydroxy group,
(5) a $C_{1-6}$ alkoxy group which may be substituted with a substituent selected from:
   (a) a hydroxy group,
   (b) a cyano group,
   (c) a $C_{1-6}$ alkoxy group,
   (d) a carboxy group,
   (e) a $C_{1-6}$ alkoxy-carbonyl group,
   (f) a carbamoyl group,
   (g) a carbamoyl group which is mono- or di-substituted with a $C_{1-6}$ alkyl group which may be substituted with an amino group which may be mono- or di-substituted with a $C_{1-6}$ alkyl group,
   (h) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom, and
   (i) a 5- to 8-membered heterocyclic (e.g., piperazinyl)-carbonyl group which may be substituted with a $C_{1-6}$ alkyl group, and has 1 to 3 heteroatoms selected from a nitrogen atom, an oxygen atom and a sulfur atom, or
(6) a group represented by the formula:

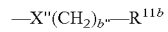

wherein X" is —O—, —NR$^{12"}$— (wherein R$^{12"}$ is a hydrogen atom, or a $C_{1-6}$ alkyl group which may be substituted with a 5- to 8-membered heterocyclic group (e.g., a morpholinyl group) having 1 to 3 heteroatoms selected from a nitrogen atom, an oxygen atom and a sulfur atom);

b" is an integer from 1 to 4; and $R^{11b}$ is a 5- to 8-membered heterocyclic group (e.g., a piperidyl group, a piperazinyl group, a morpholinyl group, a pyrrolidinyl group) which may be substituted with a substituent selected from:

(a) a hydroxy group, and
(b) a $C_{1-6}$ alkyl group and has 1 to 3 heteroatoms selected from a nitrogen atom, an oxygen atom and a sulfur atom, or the like is preferred.

In particular, $R^3$ is preferably: (1) a hydrogen atom, (2) a cyano group, (3) a halogen atom, (4) a $C_{1-6}$ alkyl group, (5) an amino group, (6) a hydroxy group, (7) a $C_{1-6}$ alkoxy group, or the like, and particularly preferably a hydrogen atom.

In particular, $R^4$ is preferably: (1) a hydrogen atom, (2) a cyano group, (3) a halogen atom, (4) a $C_{1-6}$ alkyl group, (5) an amino group, (6) a hydroxy group, (7) a $C_{1-6}$ alkoxy group which may be substituted with a $C_{1-6}$ alkoxy group, or (8) a group represented by the formula: —X(CH$_2$)$_b$—R$^{11}$ [wherein X is —O—, —NR$^{12}$—, —OSO$_2$—, —NR$^{12}$CO—, or —NR$^{12}$SO$_2$— (wherein R$^{12}$ is a hydrogen atom, or a $C_{1-6}$ alkyl group); b is an integer from 2 to 4; and R$^{11}$ is (a) a piperidyl group which may be substituted with a hydroxy group or a $C_{1-6}$ alkyl group, (b) a piperazinyl group which may be substituted with a hydroxy group or a $C_{1-6}$ alkyl group, (c) a morpholinyl group which may be substituted with a hydroxy group or a $C_{1-6}$ alkyl group, or (d) a pyrrolidinyl group which may be substituted with a hydroxy group or a $C_{1-6}$ alkyl group]. In particular, (1) a hydrogen atom, (2) a $C_{1-6}$ alkoxy group which may be substituted with a $C_{1-6}$ alkoxy group, or (3) a group represented by the formula: —X'(CH$_2$)$_{b'}$—R$^{11'}$ (wherein X' is —O— or —NH—; b' is an integer from 2 to 4; and R$^{11'}$ is (1) a piperidyl group which may be substituted with a hydroxy group or a $C_{1-6}$ alkyl group, (2) a piperazyl group which may be substituted with a hydroxy group or a $C_{1-6}$ alkyl group, (3) a morpholinyl group which may be substituted with a hydroxy group or a $C_{1-6}$ alkyl group, or (4) a pyrrolidinyl group which may be substituted with a hydroxy group or a $C_{1-6}$ alkyl group), or the like is preferred.

Further, $R^4$ is preferably:

(1) a hydrogen atom,
(2) a nitro group,
(3) an amino group,
(4) a hydroxy group,
(5) a $C_{1-6}$ alkoxy group which may be substituted with a substituent selected from:
   (a) a hydroxy group,
   (b) a cyano group,
   (c) a $C_{1-6}$ alkoxy group, (d) a carboxy group,
(e) a $C_{1-6}$ alkoxy-carbonyl group,
(f) a carbamoyl group,
(g) a carbamoyl group which is mono- or di-substituted with a $C_{1-6}$ alkyl group, and
(h) an amino group which may be mono- or di-substituted with a $C_{1-6}$ alkyl group,
(6) a group represented by the formula:

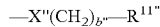

wherein X" is —O—, —NHSO$_2$—, —NHCO— or —NR$^{12''}$— (wherein R$^{12''}$ is a hydrogen atom, or a $C_{1-6}$ alkyl group which may be substituted with a 5- to 8-membered heterocyclic group (e.g., a morpholinyl group) having 1 to 3 heteroatoms selected from a nitrogen atom, an oxygen atom and a sulfur atom;

b" is an integer from 1 to 4;

R$^{11''}$ is a 5- to 8-membered heterocyclic group (e.g., a piperidyl group, a piperazinyl group, a morpholinyl group, a pyrrolidinyl group) which may be substituted with a substituent selected from:

(a) a hydroxy group, and
(b) a $C_{1-6}$ alkyl group, and has 1 to 3 heteroatoms selected from a nitrogen atom, an oxygen atom and a sulfur atom, or the like.

In particular, $R^5$ is preferably: (1) a hydrogen atom, (2) a cyano group, (3) a halogen atom, (4) a $C_{1-6}$ alkyl group, (5) an amino group, (6) a hydroxy group, (7) a $C_{1-6}$ alkoxy group which may be substituted with a $C_{1-6}$ alkoxy group or (8) a group represented by the formula: —X(CH$_2$)$_b$—R$^{11}$ [wherein X is —O—, —NR$^{12}$—, —OSO$_2$—, —NR$^{12}$CO—, —NR$^{12}$SO$_2$— (wherein R$^{12}$ is a hydrogen atom or a $C_{1-6}$ alkyl group); b is an integer from 2 to 4; R$^{11}$ is (a) a piperidyl group which may be substituted with a hydroxy group or a $C_{1-6}$ alkyl group, (b) a piperazinyl group which may be substituted with a hydroxy group or a $C_{1-6}$ alkyl group, (c) a morpholinyl group which may be substituted with a hydroxy group or a $C_{1-6}$ alkyl group or (d) a pyrrolidinyl group which may be substituted with a hydroxy group or a $C_{1-6}$ alkyl group], or the like is preferred. In particular, (1) a hydrogen atom, (2) a $C_{1-6}$ alkoxy group which may be substituted with a $C_{1-6}$ alkoxy group or (3) a group represented by the formula: —X'(CH$_2$)$_{b'}$—R$^{11'}$ (wherein X' is —O— or —NH—; b' is an integer from 2 to 4; and R$^{11'}$ is (1) a piperidyl group which may be substituted with a hydroxy group or a $C_{1-6}$ alkyl group, (2) a piperazyl group which may be substituted with a hydroxy group or a $C_{1-6}$ alkyl group, (3) a morpholinyl group which may be substituted with a hydroxy group or a $C_{1-6}$ alkyl group, or (4) a pyrrolidinyl group which may be substituted with a hydroxy group or a $C_{1-6}$ alkyl group), or the like is preferred.

Further, $R^5$ is preferably:
(1) a hydrogen atom,
(2) a $C_{1-6}$ alkoxy group, or
(3) a group represented by the formula:

wherein b''' is an integer from 2 to 4;

R$^{11'''}$ is a 5- to 8-membered heterocyclic group (e.g., a piperazinyl group, a morpholinyl group) which may be substituted with a substituent selected from:

(a) a $C_{1-6}$ alkyl group, and
(b) a $C_{6-14}$ aryl group (e.g., a phenyl group) which may be substituted with a halogen atom, and has 1 to 3 heteroatoms selected from a nitrogen atom, an oxygen atom and a sulfur atom, or the like. Inter alia, (1) a hydrogen atom, or
(2) a $C_{1-6}$ alkoxy group is preferred.

In particular, $R^6$ is preferably: (1) a hydrogen atom, (2) a cyano group, (3) a halogen atom, (4) a $C_{1-6}$ alkyl group, (5) an amino group, (6) a hydroxy group, (7) a $C_{1-6}$ alkoxy group which may be substituted with a $C_{1-6}$ alkoxy group, or (8) a group represented by the formula: —X(CH$_2$)$_b$—R$^{11}$ [wherein X is —O—, —NR$^{12}$—, —OSO$_2$—, —NR$^{12}$CO— or —NR$^{12}$SO$_2$— (wherein R$^{12}$ is a hydrogen atom or a $C_{1-6}$ alkyl group); b is an integer from 2 to 4; and R$^{11}$ is (a) a piperidyl group which may be substituted with a hydroxy group or a $C_{1-6}$ alkyl group, (b) a piperazinyl group which may be substituted with a hydroxy group or a $C_{1-6}$ alkyl group, (c) a morpholinyl group which may be substituted with a hydroxy group or a $C_{1-6}$ alkyl group, or (d) a pyrrolidinyl group which may be substituted with a hydroxy group or a $C_{1-6}$ alkyl group], or the like. In particular, a hydrogen atom or a $C_{1-6}$ alkoxy group which may be substituted with a $C_{1-6}$ alkoxy group is preferred.

Further, $R^6$ is preferably:
(1) a hydrogen atom,
(2) a hydroxy group,
(3) a $C_{1-6}$ alkoxy group which may be substituted with a substituent selected from:
(a) a hydroxy group,
(b) a $C_{1-6}$ alkoxy group,
(c) a carboxy group,
(d) a $C_{1-6}$ alkoxy-carbonyl group,
(e) a carbamoyl group,
(f) a carbamoyl group which is mono- or di-substituted with a $C_{1-6}$ alkyl group which may be substituted with an amino group which may be mono- or di-substituted with a $C_{1-6}$ alkyl group,
(g) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom, and
(h) a 5- to 8-membered heterocyclic (e.g., piperazinyl)-carbonyl group which may be substituted with a $C_{1-6}$ alkyl group, and has 1 to 3 heteroatoms selected from a nitrogen atom, an oxygen atom and a sulfur atom,
(4) a $C_{7-14}$ aralkyloxy group,
(5) a group represented by the formula:

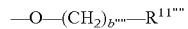

wherein b'''' is an integer from 1 to 4; and

R$^{11''''}$ is a 5- to 8-membered heterocyclic group (e.g., a morpholinyl group) having 1 to 3 heteroatoms selected from a nitrogen atom, an oxygen atom and a sulfur atom, or the like. Inter alia, $R^6$ is preferably:

(1) a hydrogen atom, or
(2) a $C_{1-6}$ alkoxy group which may be substituted with a substituent selected from:
(a) a hydroxy group,
(b) a $C_{1-6}$ alkoxy group,
(c) a carboxy group,
(d) a $C_{1-6}$ alkoxy-carbonyl group,
(e) a carbamoyl group,
(f) a carbamoyl group which is mono- or di-substituted with a $C_{1-6}$ alkyl group which may be substituted with an amino group which may be mono- or di-substituted with a $C_{1-6}$ alkyl group, (g) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom, and
(h) a 5- to 8-membered heterocyclic (e.g., piperazinyl)-carbonyl group which may be substituted with a $C_{1-6}$ alkyl group, and has 1 to 3 heteroatoms selected from a nitrogen atom, an oxygen atom and a sulfur atom, or the like.

It is also preferred that at least one of $R^3$, $R^4$, $R^5$ and $R^6$ is a nitro group, a cyano group, a hydrocarbon group which may be substituted, an amino group which may be substituted, a hydroxy group which may be substituted, or a thiol group which may be substituted.

Further, it is also preferred that $R^4$ is an amino group which may be substituted, or a hydroxy group which may be substituted.

Compound (I) is preferably exemplified by the following compounds.

[Compound (I-1)]
Compound (I) wherein:
$R^1$ is a phenyl group which may be substituted with 1 to 3 substituents selected from: (a) a $C_{1-3}$ alkyl group which may be substituted with 1 to 3 halogen atoms or hydroxy groups, (b) a $C_{1-3}$ alkoxy group, (c) a $C_{1-3}$ alkyl-carbonyloxy group, (d) a halogen atom, (e) a hydroxy group, (f) an amino group, and (g) a cyano group;
$R^2$ is a hydrogen atom or an amino group;
$R^3$ is a hydrogen atom;
$R^4$, $R^5$ and $R^6$, which may be identical or different, are each (1) a hydrogen atom, (2) a cyano group, (3) a halogen atom, (4) a $C_{1-6}$ alkyl group, (5) an amino group, (6) a hydroxy group, (7) a $C_{1-6}$ alkoxy group which may be substituted with a $C_{1-6}$ alkoxy group, or (8) a group represented by the formula: —X(CH$_2$)$_b$—R$^{11}$ [wherein X is —O—, —NR$^{12}$—, —OSO$_2$—, —NR$^{12}$CO—, or —NR$^{12}$SO$_2$— (wherein R$^{12}$ is a hydrogen atom or a $C_{1-6}$ alkyl group); b is an integer from 2 to 4; and R$^{11}$ is (a) a piperidyl group which may be substituted with a hydroxy group or a $C_{1-6}$ alkyl group, (b) a piperazinyl group which may be substituted with a hydroxy group or a $C_{1-6}$ alkyl group, (c) a morpholinyl group which may be substituted with a hydroxy group or a $C_{1-6}$ alkyl group, or (d) a pyrrolidinyl group which may be substituted with a hydroxy group or a $C_{1-6}$ alkyl group];
or $R^3$ and $R^4$, $R^4$ and $R^5$, and $R^5$ and $R^6$ respectively form, together with the adjacent carbon atom, (1) a 5- to 8-membered homocyclic ring, or (2) a 5- to 8-membered heterocyclic ring having 1 to 3 heteroatoms selected from a nitrogen atom, an oxygen atom and a sulfur atom.

[Compound (I-2)]
Compound (I) wherein:
$R^1$ is:
(1) a $C_{6-12}$ aryl group (e.g., a phenyl group) which may be substituted with 1 to 3 substituents selected from:
(a) a $C_{1-6}$ alkyl group which may be substituted with 1 to 3 substituents selected from:
(i) a halogen atom,
(ii) a hydroxy group, and
(iii) a 5- to 8-membered heterocyclic group (e.g., a piperidyl group, a piperazinyl group, a morpholinyl group, a pyrrolidinyl group) which may be substituted with a substituent selected from a hydroxy group and a $C_{1-6}$ alkyl group, and has 1 to 3 heteroatoms selected from a nitrogen atom, an oxygen atom and a sulfur atom;
(b) a $C_{1-6}$ alkoxy group which may be substituted with a substituent selected from:
(i) a hydroxy group,
(ii) a $C_{1-6}$ alkoxy group,
(iii) a carboxy group,
(iv) a $C_{1-6}$ alkoxy-carbonyl group,
(v) a carbamoyl group,
(vi) a carbamoyl group which is mono- or di-substituted with a $C_{1-6}$ alkyl group which may be substituted with a substituent selected from a hydroxy group and a $C_{1-6}$ alkylsulfonyl group,
(vii) a cyano group, and
(viii) a 5- to 8-membered heterocyclic group (e.g., a tetrazole group) having 1 to 3 heteroatoms selected from a nitrogen atom, an oxygen atom and a sulfur atom;
(c) a halogen atom;
(d) a hydroxy group;
(e) an amino group;
(f) a nitro group;
(g) a carboxy group;
(h) a $C_{1-6}$ alkoxy-carbonyl group;
(i) a $C_{1-6}$ alkyl-carbonyloxy group;
(j) a $C_{6-12}$ aryloxy group which may be substituted with a substituent selected from a halogen atom, a hydroxy group and a $C_{1-6}$ alkoxy group;
(k) a $C_{6-14}$ aralkyloxy group;
(l) a $C_{3-7}$ cycloalkyloxy group;
(m) a 5- to 8-membered heterocyclic (e.g., pyridyl, py1rimidyl)-oxy group which may be substituted with a $C_{1-6}$ alkyl group, and has 1 to 3 heteroatoms selected from a nitrogen atom, an oxygen atom and a sulfur atom;
(n) a $C_{1-6}$ alkylsulfonyl group; and
(o) a $C_{6-12}$ arylsulfonyl group, or
(2) a 5- or 6-membered aromatic heterocyclic group (e.g., a pyridyl group, a pyrazolyl group, a thiazolyl group, a pyrimidyl group) which may be substituted with 1 to 3 substituents selected from:
(a) a $C_{1-6}$ alkyl group, and
(b) a $C_{1-6}$ alkoxy group, and has 1 to 3 heteroatoms selected from a nitrogen atom, an oxygen atom and a sulfur atom, or a group resulting from condensation of the 5- or 6-membered aromatic heterocyclic group with a benzene ring;
$R^2$ is:
(1) a hydrogen atom, or
(2) an amino group which may be mono- or di-substituted with a $C_{1-6}$ alkyl group;
$R^3$ is a hydrogen atom;
$R^4$ is:
(1) a hydrogen atom,
(2) a nitro group,
(3) an amino group,
(4) a hydroxy group,
(5) a $C_{1-6}$ alkoxy group which may be substituted with a substituent selected from:
(a) a hydroxy group,
(b) a cyano group,
(c) a $C_{1-6}$ alkoxy group,
(d) a carboxy group,
(e) a $C_{1-6}$ alkoxy-carbonyl group,
(f) a carbamoyl group,
(g) a carbamoyl group which is mono- or di-substituted with a $C_{1-6}$ alkyl group, and
(h) an amino group which may be mono- or di-substituted with a $C_{1-6}$ alkyl group, or (6) a group represented by the formula:

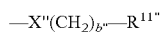

wherein X″ is —O—, —NHSO$_2$—, —NHCO— or —NR$^{12″}$— (wherein R$^{12″}$ is a hydrogen atom, or a C$_{1-6}$ alkyl group which may be substituted with a 5- to 8-membered heterocyclic group (e.g., a morpholinyl group) having 1 to 3 heteroatoms selected from a nitrogen atom, an oxygen atom and a sulfur atom;

b″ is an integer from 1 to 4;

R$^{11″}$ is a 5- to 8-membered heterocyclic group (e.g., a piperidyl group, a piperazinyl group, a morpholinyl group, a pyrrolidinyl group) which may be substituted with a substituent selected from:

(a) a hydroxy group, and
(b) a C$_{1-6}$ alkyl group, and has 1 to 3 heteroatoms selected from a nitrogen atom, an oxygen atom and a sulfur atom;

R$^5$ is:
(1) a hydrogen atom,
(2) a C$_{1-6}$ alkoxy group, or
(3) a group represented by the formula:

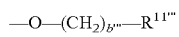

wherein b‴ is an integer from 2 to 4;

R$^{11‴}$ is a 5- to 8-membered heterocyclic group (e.g., a piperazinyl group, a morpholinyl group) which may be substituted with a substituent selected from:

(a) a C$_{1-6}$ alkyl group, and
(b) a C$_{6-14}$ aryl group (e.g., a phenyl group) which may be substituted with a halogen atom, and has 1 to 3 heteroatoms selected from a nitrogen atom, an oxygen atom and a sulfur atom;

R$^6$ is:
(1) a hydrogen atom,
(2) a hydroxy group,
(3) a C$_{1-6}$ alkoxy group which may be substituted with a substituent selected from:
  (a) a hydroxy group;
  (b) a C$_{1-6}$ alkoxy group;
  (c) a carboxy group;
  (d) a C$_{1-6}$ alkoxy-carbonyl group;
  (e) a carbamoyl group;
  (f) a carbamoyl group which is mono- or di-substituted with a C$_{1-6}$ alkyl group which may be substituted with an amino group which may be mono- or di-substituted with a C$_{1-6}$ alkyl group;
  (g) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom; and
  (h) a 5- to 8-membered heterocyclic (e.g., piperazinyl)- carbonyl group which may be substituted with a C$_{1-6}$ alkyl group, and has 1 to 3 heteroatoms selected from a nitrogen atom, an oxygen atom and a sulfur atom,
(4) a C$_{7-14}$ aralkyloxy group, or
(5) a group represented by the formula:

wherein b″″ is an integer from 1 to 4; and

R$^{11″″}$ is a 5- to 8-membered heterocyclic group (e.g., a morpholinyl group) having 1 to 3 heteroatoms selected from a nitrogen atom, an oxygen atom and a sulfur atom.

[Compound (I-3)]

Compound (I), wherein:

R$^1$ is a C$_{6-12}$ aryl group (e.g., a phenyl group) which may be substituted with 1 to 3 substituents selected from:
(a) a C$_{1-6}$ alkyl group which may be substituted with 1 to 3 substituents selected from:
  (i) a halogen atom,
  (ii) a hydroxy group, and
  (iii) a 5- to 8-membered heterocyclic group (e.g., a piperidyl group, a piperazinyl group, a morpholinyl group, a pyrrolidinyl group) which may be substituted with a substituent selected from a hydroxy group, a halogen atom and a C$_{1-6}$ alkyl group, and has 1 to 3 heteroatoms selected from a nitrogen atom, an oxygen atom and a sulfur atom,
(b) a C$_{1-6}$ alkoxy group which may be substituted with a substituent selected from:
  (i) a hydroxy group,
  (ii) a C$_{1-6}$ alkoxy group,
  (iii) a carboxy group,
  (iv) a C$_{1-6}$ alkoxy-carbonyl group,
  (v) a carbamoyl group, and
  (vi) a carbamoyl group which is mono- or di-substituted with a C$_{1-6}$ alkyl group,
(c) a halogen atom,
(d) a hydroxy group,
(i) a C$_{1-6}$ alkyl-carbonyloxy group,
(j) a C$_{6-12}$ aryloxy group which may be substituted with a halogen atom, and
(m) a 5- to 8-membered heterocyclic (e.g., pyridyl, pyrimidyl)-oxy group which may be substituted with a C$_{1-6}$ alkyl group, and has 1 to 3 heteroatoms selected from a nitrogen atom, an oxygen atom and a sulfur atom;

R$^2$ is:
(1) a hydrogen atom, or
(2) an amino group which may be mono- or di-substituted with a C$_{1-6}$ alkyl group;

R$^3$ is a hydrogen atom;

R$^4$ is:
(1) a hydrogen atom,
(2) a nitro group,
(3) an amino group,
(4) a hydroxy group,
(5) a C$_{1-6}$ alkoxy group which may be substituted with a substituent selected from:
  (a) a hydroxy group,
  (b) a cyano group,
  (c) a C$_{1-6}$ alkoxy group,
  (d) a carboxy group,
  (e) a C$_{1-6}$ alkoxy-carbonyl group,
  (f) a carbamoyl group, and
  (g) a carbamoyl group which is mono- or di-substituted with a C$_{1-6}$ alkyl group, or
(6) a group represented by the formula:

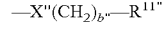

wherein X″ is —O—, —NR$^{12″}$— (wherein R$^{12″}$ is a hydrogen atom, or a C$_{1-6}$ alkyl group which may be substituted with a 5- to 8-membered heterocyclic group (e.g., a morpholinyl group) having 1 to 3 heteroatoms selected from a nitrogen atom, an oxygen atom and a sulfur atom;

b″ is an integer from 1 to 4;

R$^{11″}$ is a 5- to 8-membered heterocyclic group (e.g., a piperidyl group, a piperazinyl group, a morpholinyl group, a pyrrolidinyl group) which may be substituted with a substituent selected from:

(a) a hydroxy group, and
(b) a $C_{1-6}$ alkyl group, and has 1 to 3 heteroatoms selected from a nitrogen atom, an oxygen atom and a sulfur atom;

$R^5$ is:
(1) a hydrogen atom, or
(2) a $C_{1-6}$ alkoxy group;

$R^6$ is:
(1) a hydrogen atom, or
(2) a $C_{1-6}$ alkoxy group which may be substituted with a substituent selected from:
(a) a hydroxy group,
(b) a $C_{1-6}$ alkoxy group,
(c) a carboxy group,
(d) a $C_{1-6}$ alkoxy-carbonyl group,
(e) a carbamoyl group,
(f) a carbamoyl group which is mono- or di-substituted with a $C_{1-6}$ alkyl group which may be substituted with an amino group which may be mono- or di-substituted with a $C_{1-6}$ alkyl group,
(g) a carbamoyl group which is mono- or di-substituted with a 5- to 8-membered heterocyclic group (e.g., a pyrazolyl group) having 1 to 3 heteroatoms selected from a nitrogen atom, an oxygen atom and a sulfur atom, and
(h) a 5- to 8-membered heterocyclic (e.g., piperazinyl)-carbonyl group which may be substituted with a $C_{1-6}$ alkyl group, and has 1 to 3 heteroatoms selected from a nitrogen atom, an oxygen atom and a sulfur atom.

Moreover, preferred examples of Compound (I) include, specifically, 3-amino-7,8-dimethoxy-2-(5-hydroxy-2-methylphenyl)-2,5-dihydro-4H-pyrazolo[4,3-c]quinolin-4-one, 3-amino-2-(5-hydroxy-2-methylphenyl)-2,5-dihydro-4H-pyrazolo[4,3-c]quinolin-4-one, 3-amino-2-(2-chloro-5-hydroxy phenyl)-2,5-dihydro-4H-pyrazolo[4,3-c]quinolin-4-one, 3-amino-2-(2-chloro-5-hydroxyphenyl)-7-(3-morpholin-4-ylpropoxy)-2,5-dihydro-4H-pyrazolo[4,3-c]quinolin-4-one, 3-amino-2-(2-chloro-5-hydroxyphenyl)-7-(2-morpholin-4-ylethoxy)-2,5-dihydro-4H-pyrazolo[4,3-c]quinolin-4-one, 3-amino-2-(5-hydroxy-2-methylphenyl)-7-(3-morpholin-4-ylpropoxy)-2,5-dihydro-4H-pyrazolo[4,3-c]quinolin-4-one, 3-amino-2-(5-hydroxy-2-methylphenyl)-7-(2-morpholin-4-ylethoxy)-2,5-dihydro-4H-pyrazolo[4,3-c]quinolin-4-one, 3-amino-2-(5-hydroxy-2-methyl-4-phenoxyphenyl)-2,5-dihydro-4H-pyrazolo[4,3-c]quinolin-4-one, 3-amino-2-[4-(2,6-difluorophenoxy)-5-hydroxy-2-methylphenyl]-2,5-dihydro-4H-pyrazolo[4,3-c]quinolin-4-one, 3-amino-7-(2-hydroxyethoxy)-2-(5-hydroxy-2-methylphenyl)-2,5-dihydro-4H-pyrazolo[4,3-c]quinolin-4-one, 3-amino-2-(5-hydroxy-2,4-dimethylphenyl)-2,5-dihydro-4H-pyrazolo[4,3-c]quinolin-4-one, 3-amino-7-(2-hydroxyethoxy)-2-(5-hydroxy-2-methyl-4-phenoxyphenyl)-2,5-dihydro-4H-pyrazolo[4,3-c]quinolin-4-one, and the like.

For the "cycloalkyl group" of the "cycloalkyl group which may be substituted" represented by $R^{1'}$, a $C_{3-8}$ cycloalkyl group such as a cyclopropyl group, a cyclobutyl group, a cyclopentyl group, a cyclohexyl group or the like, preferably a $C_{3-6}$ cycloalkyl group or the like, is used, and among these, a cyclohexyl group is preferred.

The substituent for the "cycloalkyl group" is exemplified by the substituents selected from the Substituent Group A. The number of substituent is 1 to 5, and inter alia, is preferably 1 to 3, and particularly preferably 1 or 2.

The "amino group which may be substituted", "hydroxy group which may be substituted", or "thiol group which may be substituted" represented by $R^2$, may be respectively exemplified by the same one as the "amino group which may be substituted", "hydroxy group which may be substituted", or "thiol group which may be substituted" represented by $R^2$. Inter alia, the "amion group which may be substituted" is preferred, and particularly, an amino group is preferred.

The "halogen atom", "hydrocarbon group which may be substituted", "amino group which may be substituted", "hydroxy group which may be substituted", and "thiol group which may be substituted" represented by $R^{3'}$, $R^{4'}$, $R^{5'}$ or $R^{6'}$, may be respectively exemplified by the same one as the "halogen atom", "hydrocarbon group which may be substituted", "amino group which may be substituted", "hydroxy group which may be substituted", and "thiol group which may be substituted" represented by $R^3$, $R^4$, $R^5$ or $R^6$.

For the ring formed by $R^{3'}$ and $R^{4'}$, $R^{4'}$ and $R^{5'}$, and $R^{5'}$ and $R^{6'}$, respectively, together with the adjacent carbon atom, the same ones as the rings formed by $R^3$ and $R^4$, $R^4$ and $R^5$, and $R^5$ and $R^6$, respectively, together with the adjacent carbon atom, are used.

$R^{3'}$, $R^{4'}$, $R^{5'}$ and $R^{6'}$ are each preferably a hydrogen atom.

The salt of Compound (I) or Compound (I') may be exemplified by metal salts, ammonium salts, salts with organic bases, salts with inorganic acids, salts with organic acids, salts with basic or acidic amino acids, and the like. Suitable examples of the metal salt include, for example, alkali metal salts such as sodium salt, potassium salt and the like; alkaline earth metal salts such as calcium salt, magnesium salt, barium salt and the like; aluminum salt; and the like. Suitable examples of the salt with organic base include, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Suitable examples of the salt with inorganic acid include, for example, salts with hydrochloric acid, hydrobromic acid, nitric acid, sulfuric acid, phosphoric acid and the like. Suitable examples of salt with organic acid include, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with basic amino acid include, for example, salts with arginine, lysine, ornithine and the like, while suitable examples of the salt with acidic amino acid include, for example, salts with aspartic acid, glutamic acid and the like.

Among these, pharmaceutically acceptable salts are preferred. For example, when an acidic functional group is present in the compound, inorganic salts such as alkali metal salts (e.g., sodium salt, potassium salt, etc.), alkaline earth metal salts (e.g., calcium salt, magnesium salt, barium salt, etc.) and the like, ammonium salts, and the like may be mentioned. Also, when a basic functional group is present in the compound, for example, salts with inorganic acids such as hydrobromic acid, nitric acid, sulfuric acid, phosphoric acid and the like, or salts with organic acids such as acetic acid, phthalic acid, fumaric acid, oxalic acid, tartaric acid, maleic acid, citric acid, succinic acid, methanesulfonic acid, p-toluenesulfonic acid and the like, may be mentioned.

Compound (I) or compound (I') may be a hydrate or nonhydrate. Examples of the hydrate include 0.5 hydrate, 1 hydrate, 1.5 hydrate and 2 hydrate.

In addition, when $R^2$ of compound (I) or compound (I') is a hydroxy group, tautomers thereof are also encompassed in the compound (I) or the compound (I').

When compound (I) or compound (I') is provided as a mixture (racemate) of optically active substance, it can be resolved into aimed (R) form and (S) form by generally known optical resolution means.

Compound (I) or compound (I') may be labeled with an isotope (for example, $^3H$, $^{14}C$, $^{35}S$ etc.).

A prodrug for a compound (I) or compound (I') is a compound which is converted into a compound (I) or compound (I') under a physiological condition in vivo as a result of a reaction with an enzyme or gastric acid, thus a compound undergoing an enzymatic oxidation, reduction or hydrolysis to form a compound (I) or compound (I') and a compound hydrolyzed by gastric acid to form a compound (I) or compound (I'). A prodrug for a compound (I) or compound (I') may, for example, be a compound obtained by subjecting an amino group in a compound (I) or compound (I') to an acylation, alkylation or phosphorylation (e.g., a compound obtained by subjecting an amino group in a compound (I) or compound (I') to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation); a compound obtained by subjecting a hydroxy group in a compound (I) to an acylation, alkylation, phosphorylation and boration (e.g., a compound obtained by subjecting a hydroxy group in a compound (I) or compound (I') to an acetylation, palmitoylation, propanoylation, pivaloylation, succinylation, fumarylation, alanylation and dimethylaminomethylcarbonylation); a compound obtained by subjecting a carboxy group in a compound (I) or compound (I') to an esterification or amidation (e.g, a compound obtained by subjecting a carboxy group in a compound (I) or compound (I') to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification and methylamidation) and the like. These compounds can be prepared from the compound (I) or compound (I') according to a method known per se.

Also, a prodrug for a compound (I) or compound (I') may also be one which is converted into a compound (I) or compound (I') under a physiological condition, such as those described in "IYAKUHIN no KAIHATSU (Development of Pharmaceuticals)", Vol.7, Design of Molecules, p. 163-198, Published by HIROKAWA SHOTEN (1990).

A method of preparing the compound (I) will be described below. The compounds in Reaction Scheme include salts thereof, and the salts are, for example, ones as defined in the compound (I).

For example, for alcohol, ether, hydrocarbon, and halogen solvents which are used in the manufacturing process, the following solvent can be used.

Alcohol solvents: methanol, ethanol, etc.
Ether solvents: diethyl ether, the tetrahydrofuran, etc.
Hydrocarbon solvents: toluene, hexane, etc.
Halogen solvents: dichloromethane, dichloroethane, etc.

The compound (I) of the present invention and pharmaceutically acceptable salts thereof can be prepared by a method known per se or a method analogous thereto, for example, by scheme 1.

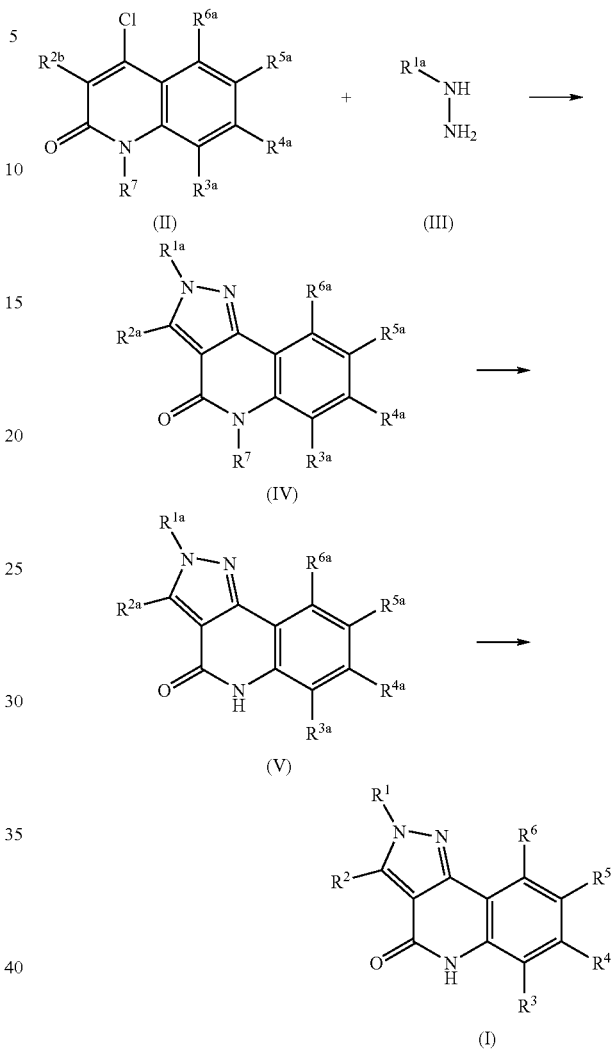

[Wherein, $R^1$, $R^2$, $R^3$, $R^4$, $R^5$ and $R^6$ are the same as described above. $R^{1a}$, $R^{2a}$, $R^{3a}$, $R^{4a}$, $R^{5a}$ and $R^{6a}$ are groups converted into $R^1$, $R^2$, $R^3$, $R^4$, $R^5$ and $R^6$ in order, or $R^1$, $R^2$, $R^3$, $R^4$, $R^5$ and $R^6$ with an appropriate reaction in order, $R^{2b}$ represents an alkoxy-carbonyl group, an alkoxythiocarbonyl group or a cyano group, $R^7$ represents a protective group such as a benzyl group, a 4-methoxybenzyl group, or the like.]

An "alkoxy-carbonyl group" represented as $R^{2b}$, for example, includes a $C_{1-6}$ alkoxy-carbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl, and the like.

An "alkoxythiocarbonyl group" represented as $R^{2b}$, for example, includes a $C_{1-6}$ alkoxy-carbonyl group such as a methoxythiocarbonyl group, an ethoxythiocarbonyl group, a propoxythiocarbonyl group, an isopropoxythiocarbonyl group, a butoxythiocarbonyl group, an isobutoxythiocarbonyl group, a sec-butoxythiocarbonyl group, a tert-butoxythiocarbonyl group, and the like.

The compound (I) can be prepared by subjecting a compound (IV) obtained by a reaction of compound (II) with compound (III) to a deprotection reaction, and further subjecting an obtained compound (V) therefor with an appropriate reaction.

Preparation of compound (IV) obtained by a reaction of compound (II) with compound (III) or with salt thereof, can be processed by using a base in an appropriate solvent. The solvent for use, for example, includes alcohol solvents, ether solvents, hydrocarbon solvents, halogen solvents, acetonitrile, N,N-dimethylformamide, and the like. The base for use includes an organic base such as triethylamine, 4-dimethylaminopyridine, N,N-diisopropylethylamine, 4-methylmorpholine, and the like, and an inorganic base such as potassium carbonate, sodium hydrogencarbonate, sodium hydroxide, and the like. The compound (III) or salts thereof are used in an amount of 0.5 to 10 moles equivalent and preferably 1 to 5 moles equivalent, the base is used in an amount of 0.5 to 10 moles equivalent and preferably 1 to 5 moles equivalent, to 1 mole of compound (II). The reaction temperature is −50 to 200° C. and preferably −20 to 100° C., and the reaction time is 0.5 to 96 hours, preferably 0.5 to 72 hours, and more preferably 1 to 24 hours.

Preparation of compound (V) obtained by subjecting the compound (IV) to the deprotection reaction can be processed by treating with an appropriate reagent for deprotection in an appropriate solvent. For example, in the case of compound (IV) that $R^7$ is a 4-methoxybenzyl group, the compound (V) can be prepared by treating with a mixture of trifluoromethanesulfonic acid, anisole, and trifluoroacetic acid. Trifluoromethanesulfonic acid is used in an amount of 0.1 to 1 times volume and anisole is used in an amount of 0.1 to 1 times volume, of trifluoroacetic acid. The reaction temperature is −50 to 200° C. and preferably −20 to 100° C., and the reaction time is 0.5 to 96 hours and preferably 0.5 to 72 hours. In the case of compound (IV) that $R^7$ is a benzyl group, the compound (V) can be prepared by treating with a mixture of hydrobromic acid and acetic acid. The concentration of hydrogen bromide is 5 to 50%, the reaction temperature is −20 to 200° C. and preferably 0 to 100° C., and the reaction time is 0.5 to 96 hours and preferably 0.5 to 72 hours.

Preparation of compound (I) from compound (V) can be processed by carrying out generally known methods, for example, alkylation, acylation, hydrolysis, oxidation, reduction, reductive alkylation and the like reactions, in an appropriate combination according to its need. When $R^{1a}$, $R^{2a}$, $R^{3a}$, $R^{4a}$, $R^{5a}$ and $R^{6a}$ are respectively $R^1$, $R^2$, $R^3$, $R^4$, $R^5$ and $R^6$, compound (V) is included by compound (I).

The compound (V) of above scheme 1, for example, can be prepared by following scheme 2.

Scheme 2

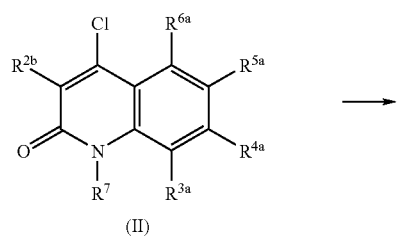

(II)

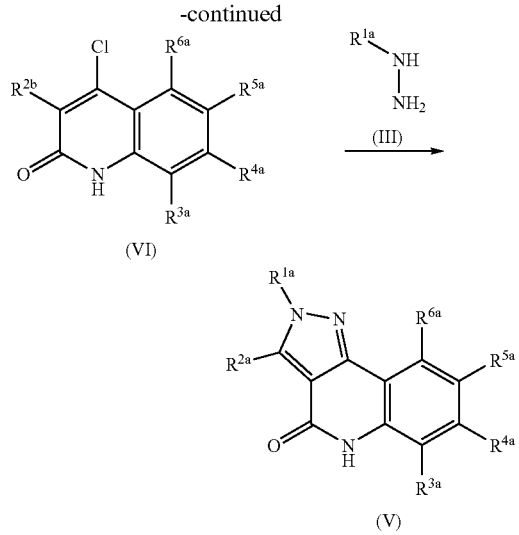

[Wherein, $R^{1a}$, $R^{2a}$, $R^{3a}$, $R^{4a}$, $R^{5a}$, $R^{6a}$, $R^{2b}$ and $R^7$ are the same as described above.]

The compound (V) can be prepared by a reaction of the compound (III) with (VI) obtained by a deprotection reaction of $R^7$ group in the compound (II).

Preparation of compound (VI) obtained by subjecting the compound (II) to the deprotection reaction can be processed by treating with an appropriate reagent for deprotection in an appropriate solvent. For example, in the case of compound (II) that $R^7$ is a 4-methoxybenzyl group, the compound (VI) can be prepared by treating with a mixture of trifluoromethanesulfonic acid, anisole, and trifluoroacetic acid. Trifluoromethanesulfonic acid is used in an amount of 0.1 to 1 times volume and anisole is used in an amount of 0.1 to 1 times volume, of trifluoroacetic acid. The reaction temperature is −50 to 200° C. and preferably −20 to 100° C., and the reaction time is 0.5 to 96 hours and preferably 0.5 to 72 hours.

Preparation of compound (V) obtained by a reaction of compound (VI) with compound (III) or with salt thereof, can be processed by using a base in an appropriate solvent. The solvent for use, for example, includes alcohol solvents, ether solvents, hydrocarbon solvents, halogen solvents, acetonitrile, N,N-dimethylformamide, and the like. The base for use includes an organic base such as triethylamine, 4-dimethylaminopyridine, N,N-diisopropylethylamine, 4-methylmorpholine, and the like, and an inorganic base such as potassium carbonate, sodium hydrogencarbonate, sodium hydroxide, and the like. The compound (III) or salts thereof are used in an amount of 0.5 to 10 moles equivalent and preferably 1 to 5 moles equivalent, the base is used in an amount of 0.5 to 10 moles equivalent and preferably 1 to 5 moles equivalent, to 1 mole of compound (VI). The reaction temperature is −50 to 200° C. and preferably −20 to 100° C., and the reaction time is 0.5 to 96 hours, preferably 0.5 to 72 hours, and more preferably 1 to 24 hours.

The compound (II) which is the raw material for above scheme 1 and scheme 2, for example, can be prepared by following scheme 3.

Scheme 3

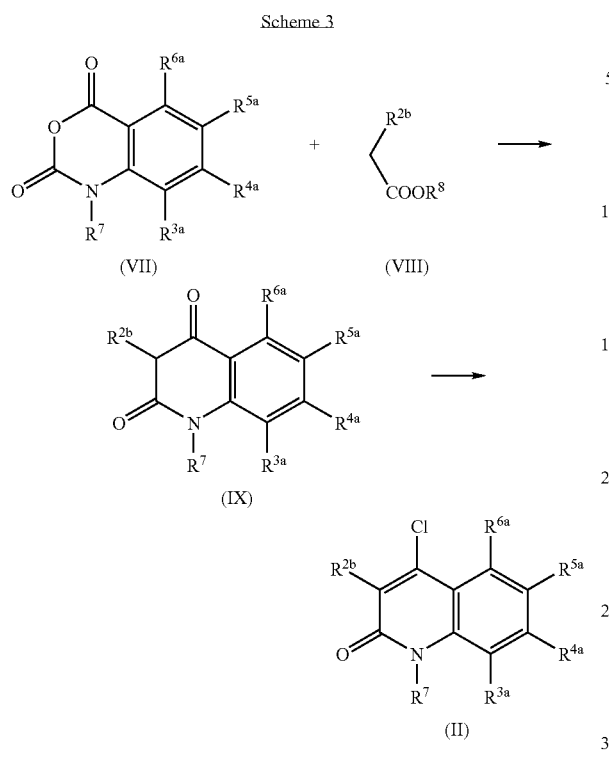

[Wherein, $R^{3a}$, $R^{4a}$, $R^{5a}$, $R^{6a}$, $R^{2b}$ and $R^7$ are the same as described above, and $R^8$ represents a lower alkyl group.]

A "lower alkyl group" represented as $R^8$, for example, includes a $C_{1-6}$ alkyl group such as a methyl group, an ethyl group, a propyl group, an isopropyl group, a butyl group, an isobutyl group, a sec-butyl group, a tert-butyl group, a pentyl group, a hexyl group, and the like.

Compound (II) can be prepared by chlorination of compound (IX) prepared by compound (VII) and compound (VIII).

Preparation of compound (IX) obtained by compound (VII) and compound (VIII), can be processed by using a base in an appropriate solvent. The solvent for use, for example, includes ether solvents, acetonitrile, N,N-dimethylacetamide, N,N-dimethylformamide, and the like. The base for use includes an inorganic base such as sodium hydride, potassium tert-butoxide, and the like. The compound (VIII) is used in an amount of 0.5 to 5 moles equivalent and preferably 1 to 3 moles equivalent, the base is used in an amount of 0.5 to 5 moles equivalent and preferably 1 to 3 moles equivalent, to 1 mole of compound (VII). The reaction temperature is 0 to 200° C. and preferably 50 to 150° C., and the reaction time is 1 to 96 hours, preferably 1 to 72 hours, and more preferably 1 to 24 hours.

Preparation of compound (II) obtained by chlorination of compound (IX), can be processed by treating with a chlorinating agent in absence of solvent or in an appropriate solvent. In addition, tertiary amines or the like can be added to it. The solvent for use, for example, includes ether solvents, hydrocarbon solvents, halogen solvents and the like. The chlorinating agent for use includes phosphorus oxychloride, phosphorous pentachloride, thionyl chloride and the like. Tertiary amines to be added include N,N-diethylaniline, N,N-dimethylaniline, tripropylamine, ethylene carbonate, maleic anhydride and the like. The chlorinating agent is used in an amount of 1 to 50 moles equivalent and preferably 3 to 10 moles equivalent, and the tertiary amines to be added is used in an amount of 1 to 10 moles equivalent and preferably 3 to 5 moles equivalent, to 1 mole of compound (IX). The reaction temperature is 0 to 200° C. and preferably 0 to 150° C., and the reaction time is 0.5 to 96 hours, referably 0.5 to 72 hours, and more preferably 1 to 24 hours.

The compound (VII) which is the starting material for above scheme 3, for example, can be prepared by following scheme 4.

Scheme 4

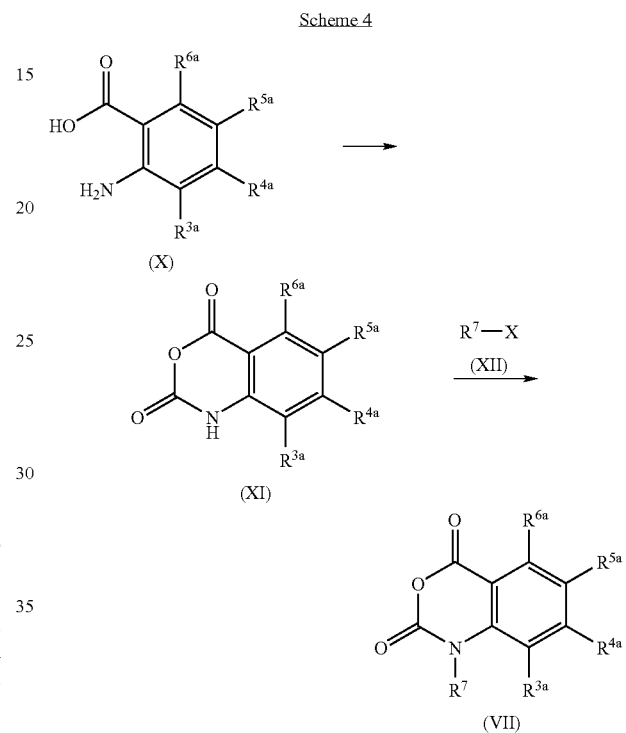

[Wherein, $R^{3a}$, $R^{4a}$, $R^{5a}$, $R^{6a}$ and $R^7$ are the same as described above. X represents a leaving group such as a halogen atom such as a chlorine atom, a bromine atom or the like, and a methanesulfonyloxy group, a benzenesulfonyloxy group, a p-toluenesulfonyloxy group, or the like.]

The compound (VII) can be prepared by treating the compound (XI) obtained from the compound (X) that is prepared by a method known per se or a method analogous thereto, with the compound (XII).

A reaction starting from compound (X) to compound (XI) can be processed by treating with an appropriate carbonylation agent in an appropriate solvent under the presence or non-presence of bases. The solvent for use, for example, includes ether solvents, hydrocarbon solvents, halogen solvents, acetonitrile, N,N-dimethylformamide, and the like. The base for use includes an organic base such as triethylamine, 4-dimethylaminopyridine, N,N-diisopropylethylamine, 4-methylmorpholine, and the like, and an inorganic base such as potassium carbonate, sodium hydrogencarbonate, sodium carbonate, and the like. The carbonylation agent for use includes triphosgene, phosgene and the like. The carbonylation agent is used in an amount of 0.5 to 10 moles equivalent and preferably 1 to 5 moles equivalent, and the base is used in an amount of 0 to 10 moles equivalent and preferably 0 to 5 moles equivalent, to 1 mole of compound (X). The reaction temperature is −50 to 200° C. and preferably −20 to 100° C., and the reaction time is 0.5 to 96 hours, preferably 0.5 to 72 hours, and more preferably 1 to 24 hours.

Compound (VII) can be prepared by reacting compound (XI) with compound (XII) in a solvent under the presence of base. The solvent for use, for example, includes ether solvents, hydrocarbon solvents, halogen solvents, acetonitrile, N,N-dimethylformamide, and the like. The base for use includes sodium hydride, potassium tert-butoxide, and the like. The compound (XII) is used in an amount of 0.5 to 10 moles equivalent and preferably 1 to 5 moles equivalent, and the base is used in an amount of 0.5 to 10 moles equivalent and preferably 1 to 5 moles equivalent, to 1 mole of compound (XI). The reaction temperature is −50 to 200° C. and preferably −20 to 100° C., and the reaction time is 0.5 to 96 hours, preferably 0.5 to 72 hours, and more preferably 1 to 24 hours.

The compound (VII) which is the raw material for above scheme 3, for example, can also be prepared by following scheme 5.

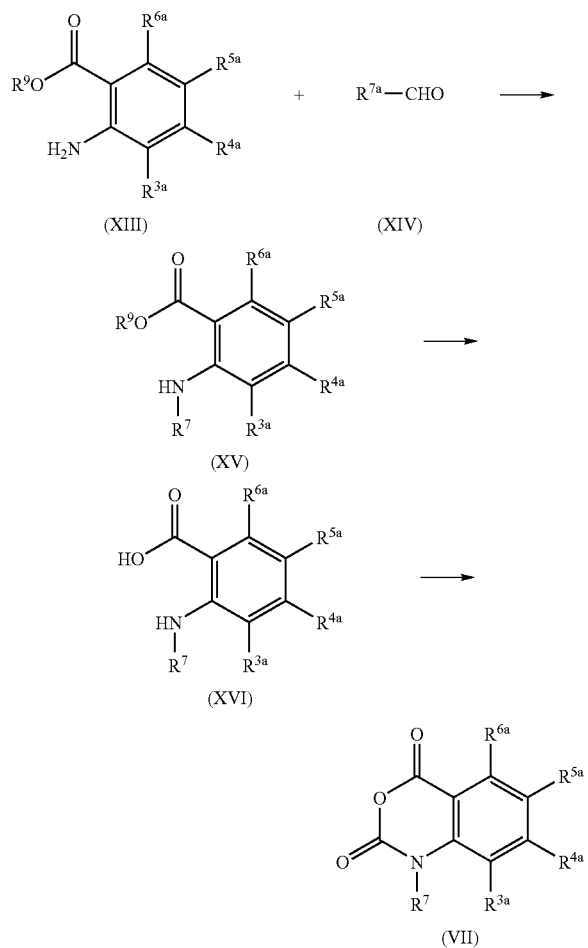

[Wherein, $R^{3a}$, $R^{4a}$, $R^{5a}$, $R^{6a}$ and $R^7$ are the same as described above. $R^9$ represents a hydrogen atom, a lower alkyl group, or a benzyl group, and $R^{7a}$ represents a phenyl group, or a 4-methoxyphenyl group.]

A "lower alkyl group" represented as $R^9$, for example, represents a $C_{1-6}$ alkyl group such as a methyl group, an ethyl group, a propyl group, an isopropyl group, a butyl group, an isobutyl group, a sec-butyl group, a tert-butyl group, a pentyl group, a hexyl group, and the like.

The compound (VII) can be prepared by carbonylation of compound (XVI) prepared from the compound (XV) obtained by compound (XIII) and compound (XIV).

The compound (XV) can be prepared by using the compound (XIV) and the compound (XIII) prepared according to a method generally known or is known per se, under a reductive amination condition. Reductive amination reaction is carried out in the solvents such as ether solvents, hydrocarbon solvents, halogen solvents, acetonitrile, N,N-dimethylformamide, acetic acid and the like, or mixtures thereof, by reacting the compound (XIII) with the compound (XIV) under the presence of metal-hydrogen complex compound (e.g., sodium borohydride, sodium cyanoborohydride, sodium triacetoxyborohydride and the like). The compound (XIV) is used in an amount of 0.5 to 10 moles equivalent and preferably 1 to 5 moles equivalent, and the metal-hydrogen complex compound is used in an amount of 0.5 to 10 moles equivalent and, preferably 1 to 5 moles equivalent, to 1 mole of compound (XIII). The reaction temperature is 0 to 200° C. and preferably 20 to 100° C., and the reaction time is 0.5 to 96 hours and preferably 1 to 24 hours.

In the case where $R^9$ of the compound (XV) is a hydrogen atom, the compound (XV) is a compound (XVI). In the case where $R^9$ of the compound (XV) is not a hydrogen atom, the compound (XVI) can be prepared from the compound (XV) according to a generally known method, for example, an alkaline hydrolysis reaction, an acid hydrolysis reaction, a catalytic hydrogenation reaction or the like.

A reaction starting from compound (XVI) to compound (VII) can be processed by treating with an appropriate carbonylation agent in an appropriate solvent under the presence or non-presence of bases. The solvent for use, for example, includes ether solvents, hydrocarbon solvents, halogen solvents, acetonitrile, N,N-dimethylformamide, and the like. The base for use includes an organic base such as triethylamine, 4-dimethylaminopyridine, N,N-diisopropylethylamine, 4-methylmorpholine, and the like, and an inorganic base such as potassium carbonate, sodium hydrogencarbonate, sodium carbonate, and the like. The carbonylation agent for use includes triphosgene, phosgene and the like. The carbonylation agent is used in an amount of 0.5 to 10 moles equivalent and preferably 1 to 5 moles equivalent, and the base is used in an amount of 0 to 10 moles equivalent and preferably 0 to 5 moles equivalent, to 1 mole of compound (XVI). The reaction temperature is −50 to 200° C. and preferably −20 to 100° C., and the reaction time is 0.5 to 96 hours, preferably 0.5 to 72 hours, and more preferably 1 to 24 hours.

A compound (Ia) in which $R^2$ of the present invention is a hydrogen atom and pharmaceutically acceptable salts thereof can be prepared by a method generally known or a method analogous thereto, for example, by scheme 6.

Scheme 6

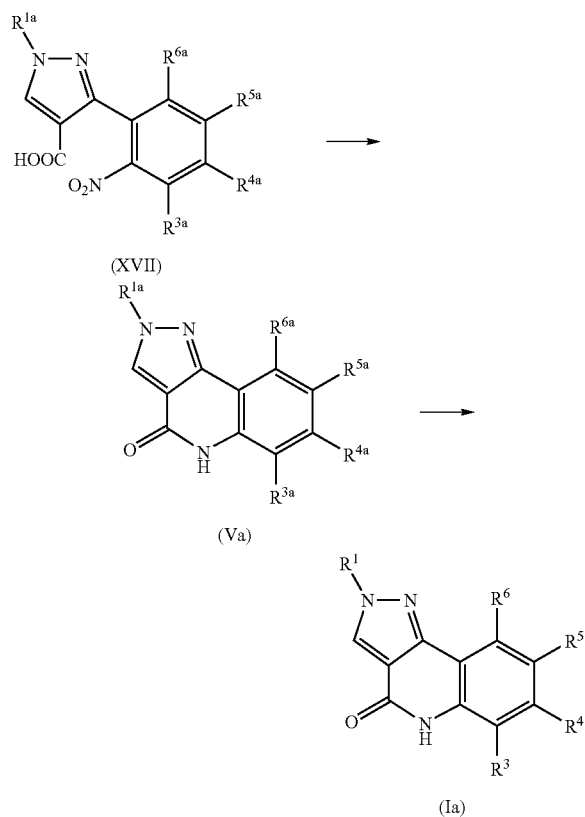

[Wherein, $R^1$, $R^3$, $R^4$, $R^5$, $R^6$, $R^{1a}$, $R^{3a}$, $R^{4a}$, $R^{5a}$ and $R^{6a}$ are the same as described above.]

The compound (Ia) can be prepared by appropriately reacting a compound (Va) prepared from a compound (XVII).

The compound (Va) can be prepared by a reaction of an amino group generated by reducing a nitro group in the compound (XVII) with a carboxyl group. Reduction of the compound (XVII), for example, can be carried out by a generally known method such as a catalytic hydrogenation. For the catalytic hydrogenation to be carried out, the compound (XVII) should be in a solvent under the presence of catalyst and under a hydrogen atmosphere. The solvent for use, for example, includes an alcohol-based solvent, ether solvents, hydrocarbon solvents, acetonitrile, N,N-dimethylformamide, and the like. The catalyst for use includes palladium/active carbon and the like. The reaction temperature is −50 to 200° C. and preferably 0 to 100° C., and the reaction time is 0.5 to 96 hours, preferably 0.5 to 72 hours, and more preferably 1 to 24 hours.

Preparation of compound (Ia) from compound (Va) can be processed by carrying out generally known methods, for example, alkylation, reduction, reductive alkylation, oxidation, acylation, hydrolysis and the like reactions, in an appropriate combination according to its need. When $R^{1a}$, $R^{2a}$, $R^{3a}$, $R^{4a}$, $R^{5a}$ and $R^{6a}$ are respectively $R^1$, $R^2$, $R^3$, $R^4$, $R^5$ and $R^6$, compound (Va) is included by compound (Ia).

The compound (XVII) which is the raw material for above scheme 6, for example, can be prepared by following scheme 7.

Scheme 7

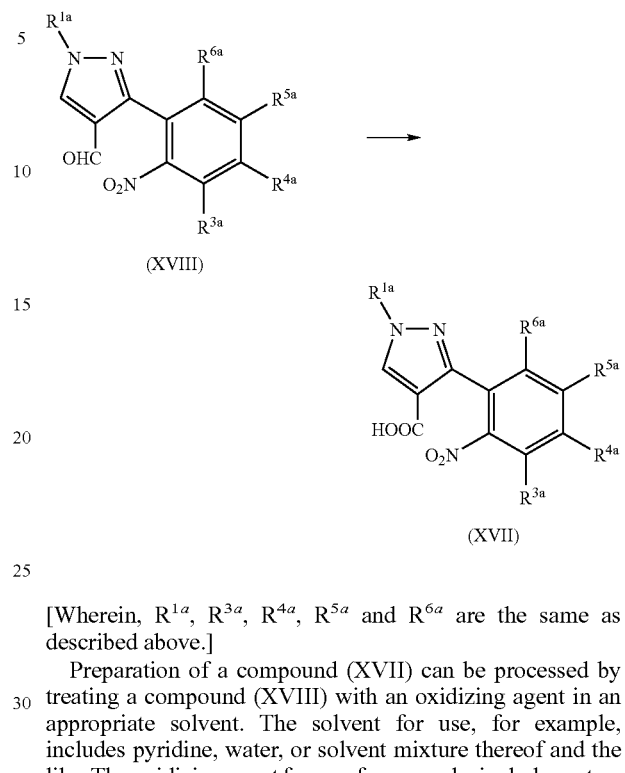

[Wherein, $R^{1a}$, $R^{3a}$, $R^{4a}$, $R^{5a}$ and $R^{6a}$ are the same as described above.]

Preparation of a compound (XVII) can be processed by treating a compound (XVIII) with an oxidizing agent in an appropriate solvent. The solvent for use, for example, includes pyridine, water, or solvent mixture thereof and the like. The oxidizing agent for use, for example, includes potassium permanganate, chromic acid, potassium dichromate, and the like. The oxidizing agent is used in an amount of 0.5 to 10 moles equivalent and preferably 1 to 5 moles equivalent, to 1 mole of compound (XVIII). The reaction temperature is −50 to 200° C. and preferably −20 to 100° C., and the reaction time is 0.5 to 96 hours, preferably 0.5 to 72 hours, and more preferably 1 to 24 hours.

The compound (XVIII) which is the raw material for above scheme 7, for example, can be prepared by following scheme 8.

Scheme 8

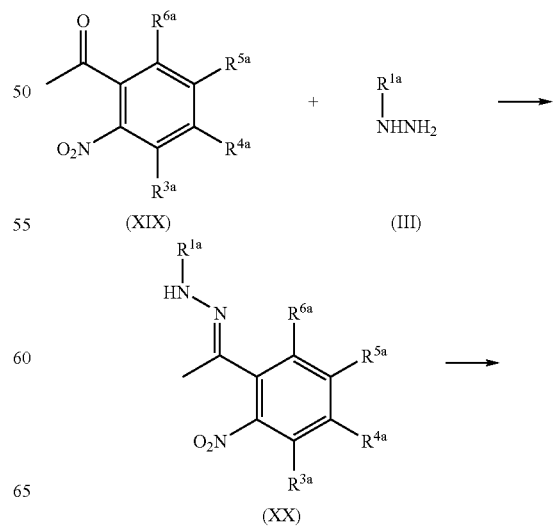

-continued

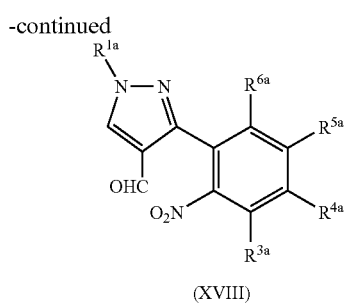

(XVIII)

[Wherein, $R^{1a}$, $R^3$, $R^{4a}$, $R^{5a}$ and $R^{6a}$ are the same as described above.]

Preparation of a compound (XVIII) can be processed by using a compound (XX) as a raw material prepared from a compound (XIX) and a compound (III) which are prepared by a method known per se or a method analogous thereto.

A reaction starting from compound (XIX) and compound (III) to compound (XX) can be processed by mixing in an appropriate solvent. The solvent for use, for example, includes acetic acid, formic acid, and the like. The reaction temperature is −50 to 200° C. and preferably 0 to 100° C., and the reaction time is 0.5 to 96 hours, preferably 0.5 to 72 hours, and more preferably 1 to 24 hours.

A reaction starting from compound (XX) to compound (XVIII) can be processed by treating with a formylation agent in an appropriate solvent. The solvent for use includes phosphorus oxychloride, N,N-dimethylformamide, 1,2-dichloroethane, and the like, and the formylation agent includes (chloromethylene)dimethylammonia hydrochloride (Vilsmeier' reagent) prepared from phosphorus oxychloride and N,N-dimethylformamide. The formylation agent is used in an amount of 1 to 10 moles equivalent and preferably 2 to 5 moles equivalent, to 1 mole of compound (XX). The reaction temperature is −50 to 200° C. and preferably 0 to 100° C., and the reaction time is 0.5 to 96 hours, preferably 0.5 to 72 hours, and more preferably 1 to 24 hours.

In the above described reaction, when the starting compound has an amino group, a carboxy group or a hydroxy group as the substituent, protective groups that are generally used in peptide chemistry or the like may be introduced in these groups. The target compound can be obtained by removing the protective group, if necessary, after the reaction. Introduction or removal of these protective groups may be favorably carried out according to a method known per se, for example, the method disclosed in Theodora W. Greene and Peter G. M. Wuts, "Protective Groups in Organic Synthesis, 3$^{rd}$ Ed.", Wiley-Interscience (1999), or the like.

In any case, further if necessary, compound (I) can be synthesized by using generally known deprotection reactions, acylation reactions, alkylation reactions, hydrogenation reactions, oxidation reactions, reduction reactions, carbon chain extension reactions, substituent exchange reactions, each alone or in combination of two or more of them. As these reactions, for example, methods described in SHINJIKKEN KAGAKU KOUZA 14, Vol. 15, 1977 (Maruzen Press), etc. are adopted.

When the desired product is obtained in the free form by the above mentioned reaction, it may be converted into a salt according to an ordinary method, while when obtained in the form of a salt, it can also be converted into a free form or other salt according to an ordinary method. Thus obtained compound (I) can be isolated and purified from a reaction solution by known methods, for example, partition, concentration, solvent extraction, fractionation, crystallization, recrystallization, chromatography and the like.

When the compound (I) is present as a configurational isomer, diastereomer, conformer and the like, it can be separately isolated by a separation or purification means as described above, if desired. When the compound (I) is present as a racemate, it can be resolved into S form and R form by an ordinary optical resolution method.

The compound (I') can also be prepared according to the above-mentioned preparation method.

When the compound (I) or the compound (I') has its stereoisomers, individual isomers or a mixture thereof may also be encompassed in the invention.

When the compound (I) has its tautomers, for example, it may exists as

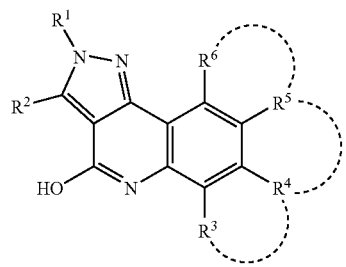

[Wherein, each symbol is the same as described above.], and especially when $R^2$ is a hydroxy group, the compound (I) may exists as

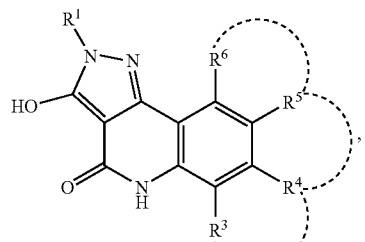

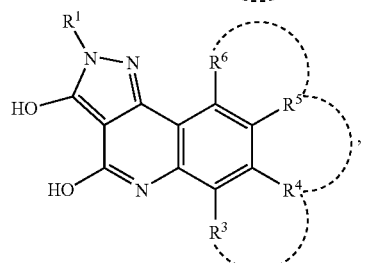

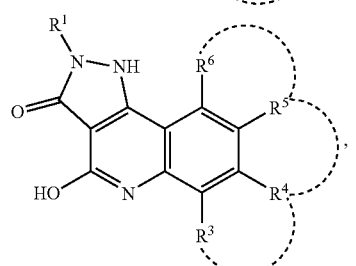

-continued

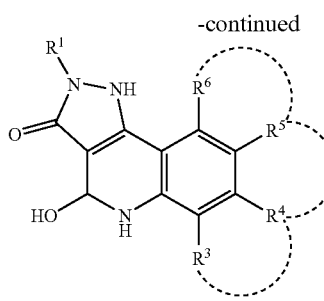

[Wherein, each symbol is the same as described above.]. These tautomers are also encompassed in the compound (I) of the present invention. It is the same for the compound (I').

The compound (I), compound (I'), and salts thereof (hereinafter, abbreviated as compound of the present invention) have excellent kinase inhibitory activity, e.g., Src inhibitory activity, Abl inhibitory activity, raf inhibitory activity, EGF-R inhibitory activity, MAPK inhibitory activity, Lck inhibitory activity, c-Yes inhibitory activity, c-Fyn inhibitory activity, VEGF inhibitory activity, particularly excellent Src inhibitory activity, against animals, especially mammals (e.g., human, monkey, dog, cat, rabbit, guinea pig, rat, mouse, etc.), and lower toxicity (e.g., acute toxicity, chronic toxicity, genetic toxicity, reproductive toxicity, cardiac toxicity, drug interaction, carcinogenicity, etc.). Therefore, the compound of the present invention can be used as a safe agent for the prevention or treatment of diseases due to an abnormal cellular proliferation such as various cancers (particularly, breast cancer, prostatic cancer, pancreatic carcinoma, gastric cancer, lung cancer, colon cancer, rectal cancer, esophageal cancer, duodenal cancer, tongue cancer, pharyngeal cancer, cerebral tumor, neurilemma, non-small cell lung cancer, small cell lung cancer, liver cancer, kidney cancer, bile duct cancer, uterine cancer, cancer of uterine cervix, ovarian cancer, bladder cancer, cutaneous cancer, hemangioma, malignant lymphoma, malignant melanoma, thyroid cancer, bone tumor, angiofibroma, retina sarcoma, penile cancer, infant solid cancer, Kaposi's sarcoma, Kaposi's sarcoma due to AIDS, maxillary antrum tumour, fibrous histiocytoma, leiomyosarcoma, rhabdomyosarcoma, leucaemia, or the like), atherosclerosis, neoangiogenesis (e.g., neoangiogenesis with growth of solid cancer and sarcoma, neoangiogenesis with metastasis of neoplasm, and neoangiogenesis with diabetic retinopathy), viral illness (HIV infection etc.), or the like.

The compound of the present invention is effective as an antitumor agent for the prevention or treatment of cancers, in particular, breast cancer, prostatic cancer, pancreatic carcinoma, gastric cancer, lung cancer, colon cancer, large bowel cancer or the like.

Also, the compound of the present invention can be used as an agent for the prophylaxis and/or treatment of bone/joint diseases (e.g., an arthrosis, chronic articular rheumatism, osteoporosis, etc.), on the basis of its Src inhibitory activity.

Other active component, for example, following hormone therapy agents, antitumor agents (e.g., chemotherapy agents, immunotherapy agents, or agents for inhibiting actions of cell growth factors and receptors thereof, etc.), or the like may be included in pharmaceutical composition together with the compound of the present invention.

For administering the compound of the present invention as a drug to mammals such as human, there are ways of administering e.g., oral preparations such as a tablet, a capsule (including a soft capsule and a microcapsule), powder, a granule and the like; and parenteral preparations such as an injectable preparation, a suppository, a pellet and the like. The 'Parenteral preparations' include administrations by intravenous, intramuscular, subcutaneous, intraorgan route, intranasal, intracutaneous, ocular instillation, intracerebral, intrarectal, intravaginal and interperitoneal, intratumor, intratumor-nearby and the like, or administration directly to the lesion.

The amount of administration of the compound of the present invention may vary depending on the administration route, subject disease or the like; however, in the case of administering orally to a patient (from 40 to 80 kg weight) suffering from breast cancer, prostatic cancer as an antitumor agent, for example, the amount of administration is about 0.5 to 100 mg/kg of body weight per a day, preferably about 1 to 50 mg/kg of body weight per a day, and more preferably about 1 to 25 mg/kg of body weight per a day. It can be administered once or two to three times a day.

The compound of the present invention can be orally or parenterally administered as solid medications such as a tablet, a capsule, a granule, powder and the like; or liquid medications such as syrup, injectable preparation and the like, by mixing with a pharmaceutically acceptable carrier.

The pharmaceutically acceptable carrier may be exemplified by various organic or inorganic carrier materials that are conventionally used as preparation materials, for example, excipient, gliding agent, binding agent and disintegrant for solid medications; or solvent, solution aid, suspending agent, isotonic agent, buffering agent, soothing agent and the like for liquid medications. Further, if necessary, preparation additives such as preservative, antioxidant, colorant, sweetening agent and the like can be also used.

The pharmaceutical composition varies depending on the dosage form, administration route, carriers or the like; however, it can be prepared according to a common procedure by including the compound of the present invention in an amount of generally 0.1 to 95% (w/w) to a total preparation amount.

In addition, cancer can be further effectively prevented and/or treated by (1) administration of effective amount of the compound of the present invention, and (2)(a) administration of effective amount of other antitumor agents, (b) administration of effective amount of a hormone therapy agent, and (c) combination of 1 to 3 kinds selected from groups consisting of non-drug therapy. The non-drug therapy includes surgery, radiotherapy, gene therapy, hyperthermia therapy, freeze therapy, an optical laser burning therapy and the like, and two or more of these can be used in combination.

For example, the compound of the present invention can be used in combination with other hormone therapy agents, antitumor agents (e.g., chemotherapy agents, immunotherapy agents, or agents for inhibiting actions of cell growth factors and receptors thereof) etc., (hereinafter, abbreviated as combined drug).

The compound of the present invention exhibits an excellent antitumor action when used as a single agent, and the effect can be increased further by concomitantly using (multiple drug combination) one or some of above-mentioned combined drugs.

Examples of the 'hormone therapy agents' include fosfestrol, diethylstilbestrol, chlorotrianisene, medroxyprogesterone acetate, megestrol acetate, chlormadinone acetate, cyproterone acetate, danazol, allylestrenol, gestrinone, mepartricine, raloxifene, ormeloxifene, levormeloxifene, antiestrogen (e.g., tamoxifen citrate, toremifene citrate, etc.), pill, mepitiostane, testololactone, aminoglutethimide, LH-RH agonist (e.g., goserelin acetate, buserelin, leu-proréline, etc.), droloxifene, epitiostanol, ethinylestradiol sulfonate, aromatase inhibitor (e.g., fadrozole hydrochloride, anastrozole, letrozole, exemestane, volozole, formestane, etc.), antiandrogen (e.g., flutamide, bicalutamide, nilutamide, etc.), 5α-reductase inhibitor (e.g., finasteride, epristeride, etc.), adrenocorticotropic hormone (e.g., dexamethasone, prednisolone, betamethasone, triamcinolone, etc.), androgen synthesis inhibitor (e.g., abiraterone, etc.), and drugs to delay retinoid and metabolism of retinoid (e.g., Liarozole, etc.), and among them, LH-RH agonist (e.g., goserelin acetate, buserelin, leu-proréline, etc.) is preferable.

Examples of the 'chemotherapy agents' include alkylating agents, antimetabolites, antitumor antibiotics, plant-derived antitumor agents, and the like.

Examples of the 'alkylating agents' include nitrogen mustard, nitrogen mustard-N-oxide hydrochloride, chlorambucil, cychlophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylene melamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, threosulfan, trophosphamide, zinostatin stimalamer, adozelesin, cystemustine, bizelesin, and the like.

Examples of the 'antimetabolites' include mercaptopurine, 6-mercaptopurine riboside, Thioinosine, methotrexate, enocitabine, cytarabine, cytarabine ocphosphate, ancitabine hydrochloride, 5-FU agents (e.g., fluorouracil, tegafur, UFT, doxifluridine, carmofur, Galocitabine, emitefur), aminopterin, leucovorin calcium, Tabloid, butosine, calcium folinate, levofolinate calcium, cladribine, emitefur, fludarabine, gemicitabine, hydroxycarbamide, pentostatin, piritrexim, idoxuridine, mitoguazone, tiazofurin, ambamustine, and the like.

Examples of the 'antitumor antibiotics' include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, xorubicin hydrochloride, mitoxantrone hydrochloride, idarubicin hydrochloride, and the like.

Examples of the 'plant-derived antitumor agents' include etoposide, etoposide phosphate, vinblastine sulfate, vincristine sulfate, vindesine sulfate, teniposide, paclitaxel, docetaxel, vinorelbine, and the like.

Examples of the 'immunotherapy agents (BRM)' include picibanil, krestin, schizophyllan, lentinan, ubenimex, interferon, interleukin, macrophage colony-stimulating factor, granulocyte colony-stimulating factor, erythropoietin, lymphotoxin, BCG vaccine, corynebacterium parvum, levamisole, polysaccharide K, procodazol, and the like.

Examples of 'cell growth factors' in the 'drugs inhibiting the actions of cell growth factors and receptors thereof' may be any substance promoting cellular propagation, and in general, factors that of the peptide's molecular weight is 20,000 or less, and that exhibit action when bound to a receptor at a low concentration are used. General examples include (1) EGF (epidermal growth factor) or a substance having substantially the same activity [e.g., EGF, heregulin (HER2 ligand) etc.], (2) insulin or a substance having substantially the same activity [e.g., insulin, IGF (insulin-like growth factor)-1, IGF-2, etc.], (3) FGF (fibroblast growth factor) or a substance having substantially the same activity [e.g., acidic FGF, basic FGF, KGF (keratinocyte growth factor), FGF-10, etc.], (4) other cell growth factors [e.g., CSF (colony stimulating factor), EPO (erythropoietin), IL-2 (interleukin-2), NGF (nerve growth factor), PDGF (platelet-derived growth factor), TGF β (transforming growth factor β), HGF (hepatocyte growth factor), VEGF (vascular endothelial growth factor), etc.], and the like.

The 'receptor of cell growth factor' may be any receptors having binding capacity with the above-mentioned cell growth factors. General examples include EGF receptor, heregulin receptor (HER2), insulin receptor, IGF receptor, FGF-1 receptor or FGF-2 receptor, and the like.

The 'drug for inhibiting the action of cell growth factor' include trastuzumab (horceptin (trade name); HER2 antibody, imatinib mesylate, ZD1839 or cetuximab, and the like.

Other than the above-mentioned drugs, L-asparaginase, aceglatone, procarbazine hydrochloride, cobalt-protoporphyrin complex, mercury-Hematoporphyrin-sodium, topoisomerase I inhibitor (e.g., irinotecan, topotecan, etc.), topoisomerase II inhibitor (e.g., sobuzoxane, etc.), inducer of differentiation (e.g., retinoid, vitamin D, etc.), arterialization inhibitor, α-blocker (e.g., tamsulosin hydrochloride, etc.) or the like can also be used.

Among the above-mentioned drugs, LH-RH agonist (e.g., goserelin acetate, buserelin, leu-proréline, etc.), trastuzumab (HER2 antibody) or the like are preferable as a concomitant drug.

With regard to the concomitant use of the compound of the present invention and a concomitant drug, the compound of the present invention and the concomitant drug are free of any limitation on the timing of the administration, or the compound of the present invention and the concomitant drug may be simultaneously administered to the administration object, or may be administered with time difference. The dose of the concomitant drug follows a clinical dose and can be appropriately determined depending on the administration object, administration route, disease, combination and the like.

The mode of administration of the compound of the present invention and the concomitant drug is not particularly limited, as long as the compound of the present invention and the concomitant drug are combined for administration. The administration mode may be exemplified by (1) administration of a single preparation obtained by simultaneously formulating the compound of the present invention and the concomitant drug, (2) simultaneous administration through the same administration route of two preparations obtained by separately formulating the compound of the present invention and the concomitant drug, (3) administration with a time interval through the same administration route of two preparations obtained by separately formulating the compound of the present invention and the concomitant drug, (4) simultaneous administration through different administration routes of two preparations obtained by separately formulating the compound of the present invention and the concomitant drug, (5) administration with a time interval through different administration routes of two preparations obtained by separately formulating the compound of the present invention and the concomitant drug (for example, administration in order of the compound of the present invention and then the concomitant drug, or administration in the reverse order), or the like. Hereinafter, these administration modes are together abbreviated as a 'concomitant agent of the present invention'.

The concomitant agent of the present invention has low toxicity and can be administered safely by admixing the compound of the present invention or (and) above-mentioned concomitant drug with, for example, a pharmacologically acceptable carrier according to a method known per se to give a pharmaceutical composition, such as tablets (inclusive of sugar-coated tablets and film-coated tablets), powders, granules, capsules, (inclusive of soft capsules), liquids, injections, suppositories, sustained release agents and the like, for oral or parenteral (e.g., topical, rectal or intravenous administration, etc.) administration. An injection can be administered intravenously, intramuscularly, subcutaneously, intraorgan routely, intranasally, intracutaneously, ocular instillationary, intracerebrally, intrarectally, intravaginally and interperitoneally, intratumorly, administration nearby-intratumorly, or administration directly to the lesion.

As the pharmacologically acceptable carrier usable for the production of the concomitant agents of the present invention, same substance usable for above-mentioned pharmaceutical composition of the present invention can be used.

The mixing ratio of the compound of the present invention and the concomitant drug, for the concomitant agents of the present invention, can be appropriately selected in accordance with the subject of administration, administration route, disease and the like.

For example, the content of the compound of the present invention in the concomitant agent of the present invention differs depending on the form of a preparation, and usually from about 0.01 to 100% by weight, preferably from about 0.1 to 50% by weight, and further preferably from about 0.5 to 20% by weight, based on the total amount of the preparation.

The content of the concomitant drug in the concomitant agent of the present invention differs depending on the form of a preparation, and usually from about 0.01 to 100% by weight, preferably from about 0.1 to 50% by weight, and further preferably from about 0.5 to 20% by weight, based on the total amount of the preparation.

The content of additives such as a carrier in the concomitant agent of the present invention differs depending on the form of a preparation, and usually from about 1 to 99.99% by weight, preferably from about 10 to 90% by weight, based on the total amount of the preparation.

In the case when the compound of the present invention and the concomitant drug are separately prepared respectively, the same contents may be adopted.

While the dose of the concomitant agent of the present invention varies depending on the kind of the compound of the present invention, the patient's age, body weight and condition, the dosage form, the mode and the period of the administration, etc., the amount of the compound of the present invention and the concomitant drug may respectively, for example, be generally about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg per day in a patient with breast cancer (adult weighing about 60 kg), said daily dose being given intravenously all at once or in several portions during a day. It is a matter of course that a lower daily dose may be sufficient or an excessive dose may be required since the dose may vary depending on various factors as discussed above.

The concomitant drug may be contained in any amount as long as a side effect does not pose a problem. While the daily dose of the concomitant drug may vary depending on the disease state, the age, sex, body weight and difference in sensitivity of the administration object, timing and interval of administration, characteristics, dispensing and kind of the pharmaceutical preparation, the kind of active ingredient and the like and is not particularly limited, the amount of the drug is generally about 0.001 to 2000 mg, preferably about 0.01 to 500 mg, more preferably about 0.1 to 100 mg, per 1 kg body weight of mammal by oral administration, which is generally administered all at once or in 2 to 4 portions during a day.

The concomitant agent of the present invention may be administered at the same time, or the concomitant drug may be administered first, and then the compound of the present invention may be administered. Alternatively, the compound of the present invention may be administered first, and then the concomitant drug may be administered. For time stagger administration, the time difference varies depending on the active ingredient to be administered, dosage form and administration route. For example, when the concomitant drug is to be administered first, the compound of the present invention is administered within 1 min to 3 days, preferably 10 min to 1 day, more preferably 15 min to 1 hour, after the administration of the concomitant drug. When the compound of the present invention is to be administered first, the concomitant drug is administered within 1 min to 1 day, preferably 10 min to 6 hours, more preferably 15 min to 1 hour, after the administration of the compound of the present invention.

In a preferable administration method, for example, the concomitant drug which has been formed into an oral administration preparation is administered orally at a daily dose of about 0.001 to 200 mg/kg, and about 15 minutes after, the compound of the invention which has been formed into an oral administration preparation is administered orally at a daily dose of about 0.005 to 100 mg/kg.

In addition, pharmaceutical composition of the present invention or a concomitant agent of the present invention can be used in combination with non-drug therapy, for example, (1) surgery, (2) vasopressor chemotherapy using angiotensin II and the like, (3) gene therapy, (4) hyperthermia therapy, (5) freeze therapy, (6) an optical laser burning therapy, (7) radiotherapy, and the like.

For example, by using the pharmaceutical composition of the present invention or the concomitant agent of the present invention before or after a surgery etc., or otherwise before or after a treatment of two or three kinds of those therapies, effects on the prevention of resistance development, elongation of disease-free survival, inhibition of cancer matastasis and recurrence, life lengthening, and the like are obtained.

In addition, a therapy with the pharmaceutical composition of the present invention or a concomitant drug of the present invention, and a support therapy [(i) administration of antibiotics (e.g., β-lactam such as panspoprin, macrolides such as clarithromycin, etc.) against complication of various infections, (ii) administration of intravenous hyperalimentation, amino acid preparation, multivitamin preparation, for improvement in nutritional disorder, (iii) administration of morphine for pain-relief (iv) administration of drugs for improving side effects such as nausea, vomiting, anorexia, diarrhea, leukopenia, thrombocytopia, reduced haemoglobin concentration, depilation, hepatic disorder, renal disturbance, DIC, and pyrexia, (v) administration of drugs for inhibiting multidrug-resistance in carcinoma, and the like] can also be in combination.

Before or after the above-mentioned treatment, the pharmaceutical composition of the present invention or the concomitant agent of the present invention is preferable to be administered by an oral administration (including sustained-release), an intravenous administration (including bolus, infusion, and clathrate), subcutaneous and intramuscular (including bolus, infusion, and sustained-release), percutaneous, intratumor and intratumor-nearby administration.

Before the surgery and the like, the pharmaceutical composition of the present invention or the concomitant agents of the present invention is administered, for example, about 30 min to 24 hours before the surgery and the like all at once, or is administered about 3 to 6 months before the surgery and the like all at once or in 2 to 3 cycle portions. As such, surgery and the like become easier by administering the pharmaceutical composition of the present invention or the concomitant agent of the present invention before the surgery and the like which for example reduces the carcinoma tissue.

After the surgery and the like, the pharmaceutical composition of the present invention or the concomitant agents of the present invention is administered, for example, about 30 min to 24 hours after the surgery and the like, or for example is administered repeatedly for about several weeks to 3 months term. As such, effects on surgery and the like are increased by administering the pharmaceutical composition of the present invention or the concomitant agents of the present invention after the surgery and the like.

EXAMPLES

The present invention will be further explained in detail below by way of Reference Examples, Examples, Preparation Examples and Test Examples. However, the present invention is not limited thereto.

Elution in column chromatography of Reference Examples and Examples were performed under an observation by UV detector or TLC (Thin Layer Chromatography). For TLC observation, Kieselgel 60F$_{254}$ plate, manufactured by Merck Co., Ltd. was used as a TLC plate. For the column, silica gel or propylaminated silica gel, manufactured by Fuji Silysia Co., Ltd., were used. NMR spectra represents proton NMR, recorded on a VARIAN Gemini-200 (200 MHz spectrometer), a VARIAN Mercury-300 (300 MHz spectrometer) or a Bruker AVANCE 300 (300 MHz spectrometer) using tetramethylsilane as an internal standard, and the δ values were represented in ppm.

Symbols used in the Reference Examples and the Examples indicate the following meanings.

Bzl: benzyl
PMB: 4-methoxybenzyl
s: singlet
d: doublet
t: triplet
q: quartet
dd: double doublet
dt: double triplet
sept: septet
br: broad (wide)
br s: broad (wide) singlet
br q: broad (wide) quartet
m: multiplet
J: coupling constant
Hz: Hertz
CDCl$_3$: deuterated chloroform
DMSO-d$_6$: deuterated dimethylsulfoxide
$^1$H NMR: proton nuclear magnetic resonance Also, for $^1$H NMR, extremely broad peaks in protons such as hydroxy group or amino group are not mentioned.

In the Reference Examples and the Examples described below, HPLC-mass spectra (LC-MS) were measured under following conditions.

Measuring instrument: Micromass ZQ-Alliance Ht, manufactured by Waters, Co.
Column: CAPCELL PAK C18UG120, S-3 μm, 1.5×35 mm
Solvent: liquid A; 0.05% trifluoroacetic acid/water
liquid B; 0.04% trifluoroacetic acid/acetonitrile Gradient cycle: 0.00 min (liquid A/liquid B=90/10), 2.00 min (liquid A/liquid B=5/95), 2.75 min (liquid A/liquid B=5/95), 2.76 min (liquid A/liquid B=90/10), 3.45 min (liquid A/liquid B=90/10)
Injection amount: 2 μl, flow rate: 0.5 ml/min,
Detection method: UV 220 nm
Ionization method: electron-impact ionization (Electron Spray Ionization: ESI)

Reference Example 1

7-nitro-2H-3,1-benzoxazine-2,4(1H)-dione

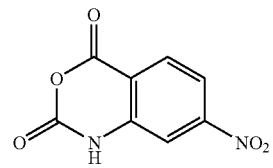

A mixture of 4-nitroanthranilic acid (9.11 g), triphosgene (4.92 g) and tetrahydrofuran (240 ml) was stirred for 10 hours at 45° C. The precipitated solids were collected by filtration, washed with tetrahydrofuran, and then dried to obtain the target product (700 g).

$^1$H-NMR (DMSO-d$_6$, 300 MHz): δ 7.85 (1H, d, J=2.3 Hz), 7.95 (1H, dd, J=8.6, 2.3 Hz), 8.15 (1H, d, J=8.6 Hz), 12.07 (1H, br).

Reference Example 2

7-isopropoxy-2H-3,1-benzoxazine-2,4(1H)-dione

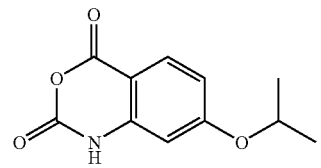

In the same manner as shown in Reference Example 1, the target compound was obtained.

$^1$H-NMR (CDCl$_3$, 300 MHz) δ 1.40 (6H, d, J=6.0 Hz), 4.69 (1H, sept, J=6.0 Hz), 6.53 (1H, d, J=2.4 Hz), 6.77 (1H, dd, J=8.7, 2.4 Hz), 7.97 (1H, d, J=8.7 Hz).

Reference Example 3

6,7-dimethoxy-2H-3,1-benzoxazine-2,4(1H)-dione

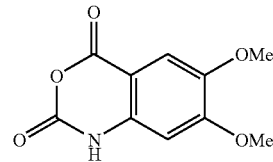

In the same manner as shown in Reference Example 1, the target compound was obtained.

¹H-NMR (CDCl₃, 300 MHz): δ 3.80 (3H, s), 3.86 (3H, s), 6.63 (1H, s), 7.24 (1H, s), 11.56 (1H, s).

Reference Example 4 methyl 4-isopropoxy-5-methoxy-2-(4-methoxybenzyl)aminobenzoate

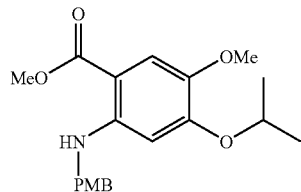

A mixture of methyl 2-amino-4-isopropoxy-5-methoxybenzoate (12.67 g), 4-methoxybenzaldehyde (7.90 g), N,N-dimethylformamide (150 ml) and acetic acid (3 ml) was stirred for 8 hours. After stirring, the sodium triacetoxyborohydride (13.4 g) was added thereto. The reaction mixture was stirred for 1 night. To the reaction mixture was added 4-methoxybenzaldehyde (1.98 g) and sodium triacetoxyborohydride (3.35 g) and stirred for 1 day. The reaction mixture was concentrated under reduced pressure until the amount was concentrated to a half, adjusted to pH 8~9 by adding 5% sodium carbonate. Water was added thereto, the precipitated solid was collected by filtration, washed with water and dried to obtain the target compound (18.9 g).

¹H-NMR (CDCl₃, 300 MHz): δ 1.27 (6H, d, J=6.0 Hz), 3.78 (6H, s), 3.83 (3H, s), 4.34-4.47 (3H, m), 6.09 (1H, s), 6.85 (2H, d, J=8.7 Hz), 7.26 (2H, d, J=8.7 Hz), 7.37 (1H, s), 7.99 (1H, br).

Reference Example 5

4-isopropoxy-5-methoxy-2-(4-methoxybenzyl)aminobenzoic acid

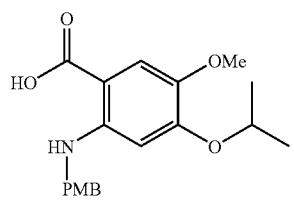

A mixture of methyl 4-isopropoxy-5-methoxy-2-(4-methoxybenzyl)aminobenzoate (18.9 g), methanol (50 ml), tetrahydrofuran (150 ml) and a 1N aqueous sodium hydroxide solution (80 ml) was stirred at room temperature for 1 night, heated under reflux for 12 hours. The solvent was distilled off under reduced pressure, the reaction mixture was adjusted to about pH 6 by adding 1N hydrochloric acid and 5% citric acid. The precipitated solid was collected by filtration, washed and dried to obtain the target compound (18.0 g).

¹H-NMR (CDCl₃, 300 MHz): δ 1.26 (6H, d, J=6.0 Hz), 3.78 (3H, s), 3.79 (3H, s), 4.38-4.48 (3H, m), 6.07 (1H, s), 6.87 (2H, d, J=8.7 Hz), 7.26 (2H, d, J=8.7 Hz), 7.41 (1H, s).

Reference Example 6

1-(4-methoxybenzyl)-2H-3,1-benzoxazine-2,4(1H)-dione

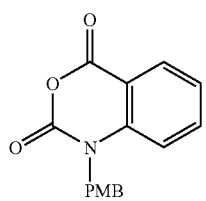

To a mixture of 2H-3,1-benzoxazine-2,4(1H)-dione (18.7 g), sodium hydride (an oily, about 66%, 4.8 g) and N,N-dimethylformamide (70 ml) was added dropwise 4-methoxybenzyl chloride (17.6 ml), stirred at room temperature for 1 night. To the reaction mixture was added water and extracted with ethyl acetate. The extract was washed with water and a saturated brine, dried over anhydrous magnesium sulfate, and then concentrated under reduced pressure. The residue was recrystallized from ethyl acetate-hexane to obtain the target compound (26.1 g).

¹H-NMR (CDCl₃, 200 MHz) δ 3.79 (3H, s), 5.25 (2H, s), 6.83-6.91 (2H, m), 7.14-7.30 (4H, m), 7.61-7.67 (1H, m), 8.14-8.20 (1H, m).

Reference Example 7

1-benzyl-2H-3,1-benzoxazine-2,4(1H)-dione

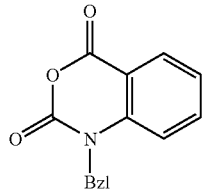

In the same manner as shown in Reference Example 6, the target compound was obtained.

¹H-NMR (CDCl₃, 200 MHz): δ 5.31 (2H, s), 7.08-7.14 (1H, m), 7.24-7.41 (6H, m), 7.60-7.67 (1H, m), 8.15-8.22 (1H, m).

Reference Example 8

1-(4-methoxybenzyl)-7-nitro-2H-3,1-benzoxazine-2,4(1H)-dione

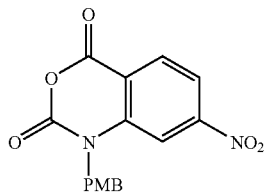

In the same manner as shown in Reference Example 6, the target compound was obtained.

$^1$H-NMR (DMSO-d$_6$, 300 MHz): δ 3.72 (3H, s), 5.31 (2H, s), 6.89-6.94 (2H, m), 7.38-7.42 (2H, m), 7.95 (1H, d, J=2.0 Hz), 8.01 (1H, dd, J=8.6, 2.0 Hz), 8.24 (1H, d, J=8.6 Hz).

Reference Example 9

7-isopropoxy-1-(4-methoxybenzyl)-2H-3,1-benzoxazine-2,4(1H)-dione

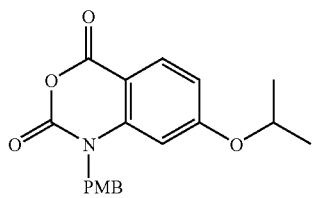

In the same manner as shown in Reference Example 6, the target compound was obtained.

$^1$H-NMR (CDCl$_3$, 300 MHz) δ 1.30 (6H, d, J=6.0 Hz), 3.79 (3H, s), 4.54 (1H, sept, J=6.0 Hz), 5.19 (2H, s), 6.53 (1H, d, J=2.1 Hz), 6.72 (1H, dd, J=8.7, 2.1 Hz), 6.89 (2H, d, J=8.7 Hz), 7.26 (2H, d, J=8.7 Hz), 8.04 (1H, d, J=8.7 Hz).

Reference Example 10

6,7-dimethoxy-1-(4-methoxybenzyl)-2H-3,1-benzoxazine-2,4(1H)-dione

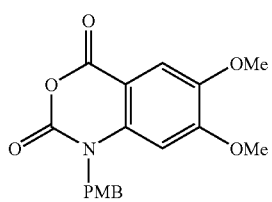

In the same manner as shown in Reference Example 6, the target compound was obtained.

$^1$H-NMR (DMSO-d$_6$, 300 MHz): δ 3.71 (3H, s), 3.79 (3H, s), 3.80 (3H, s), 5.26 (2H, s), 6.80 (1H, s), 6.90 (2H, d, J=8.3 Hz), 7.34 (1H, s), 7.37 (2H, d, J=8.3 Hz).

Reference Example 11

7-isopropoxy-6-methoxy-1-(4-methoxybenzyl)-2H-3,1-benzoxazine-2,4(1H)-dione

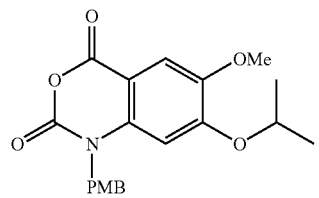

In the same manner as shown in Reference Example 1, the target compound was obtained.

$^1$H-NMR (CDCl$_3$, 300 MHz): δ 1.28 (6H, d, J=6.0 Hz), 3.78 (3H, s), 3.87 (3H, s), 4.43 (1H, sept, J=6.0 Hz), 5.21 (2H, s), 6.52 (1H, s), 6.87 (2H, d, J=8.7 Hz), 7.23 (2H, d, J=8.7 Hz), 7.44 (1H, s).

Reference Example 12

1-(4-methoxybenzyl)-2,4-dioxo-1,2,3,4-tetrahydro-quinoline-3-carbonitrile

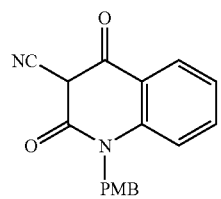

To a solution of ethyl cyanoacetate (7.9 ml) in N,N-dimethylacetamide (150 ml) was added sodium hydride (an oily, about 66%, 3.0 g), and added a solution of 1-(4-methoxybenzyl)2H-3,1-benzoxazine-2,4(1H)-dione (21.0 g) in N,N-dimethylacetamide (50 ml), stirred at 120° C. for 19 hours. After cooling, the reaction mixture was concentrated under reduced pressure. Water was added to the residue and the mixture was washed with ether. The aqueous layer was acidified by adding 1N hydrochloric acid. The precipitated solid was collected by filtration, washed with water, and dried to obtain the target compound (8.1 g).

$^1$H-NMR (DMSO-d$_6$, 200 MHz): δ 3.70 (3H, s), 5.37 (2H, s), 6.82-8.12 (8H, m).

Reference Example 13

1-benzyl-2,4-dioxo-1,2,3,4-tetrahydroquinoline-3-carbonitrile

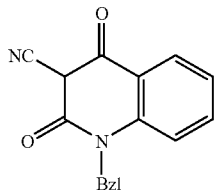

In the same manner as shown in Reference Example 12, the target compound was obtained.

$^1$H-NMR (DMSO-$d_6$, 200 MHz): δ 5.45 (2H, s), 7.16-7.37 (7H, m), 7.55-7.64 (1H, m), 8.05-8.13 (1H, m).

Reference Example 14

1-(4-methoxybenzyl)-7-nitro-2,4-dioxo-1,2,3,4-tetrahydroquinoline-3-carbonitrile

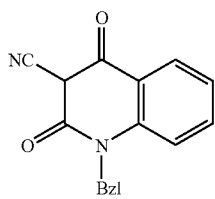

In the same manner as shown in Reference Example 12, the target compound was obtained.

$^1$H-NMR (DMSO-$d_6$, 300 MHz): δ 3.71 (3H, s), 5.41 (2H, br), 6.85 (1H, br), 6.90 (2H, d, J=8.9 Hz), 7.20 (2H, d, J=8.9 Hz), 7.93 (1H, dd, J=8.7, 2.1 Hz), 8.05 (1H, d, J=2.1 Hz), 8.24 (1H, d, J=8.7 Hz).

Reference Example 15

7-isopropoxy-1-(4-methoxybenzyl)-2,4-dioxo-1,2,3,4-tetrahydroquinoline-3-carbonitrile

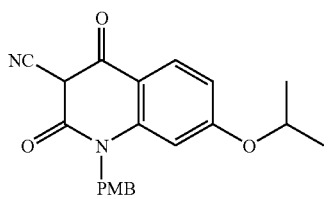

In the same manner as shown in Reference Example 12, the target compound was obtained.

$^1$H-NMR (DMSO-$d_6$, 300 MHz): δ 1.18 (6H, d, J=6.0 Hz), 3.69 (3H, s), 4.72 (1H, sept, J=6.0 Hz), 5.37 (2H, s), 6.73 (1H, d, J=2.1 Hz), 6.83-6.90 (3H, m), 7.15-7.19 (2H, m), 7.99 (1H, d, J=9.3 Hz).

Reference Example 16

6,7-dimethoxy-1-(4-methoxybenzyl)-2,4-dioxo-1,2,3,4-tetrahydroquinoline-3-carbonitrile

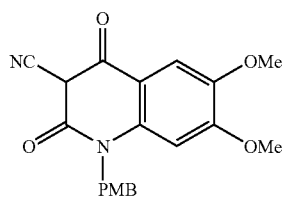

In the same manner as shown in Reference Example 12, the target compound was obtained.

$^1$H-NMR (DMSO-$d_6$, 200 MHz): δ 3.70 (3H, s), 3.78 (3H, s), 3.79 (3H, s), 4.80 (1H, br), 5.44 (2H, br), 6.86-6.90 (3H, m), 7.23 (2H, d, J=8.4 Hz), 7.54 (1H, s).

Reference Example 17

7-isopropoxy-6-methoxy-1-(4-methoxybenzyl)-2,4-dioxo-1,2,3,4-tetrahydroquinoline-3-carbonitrile

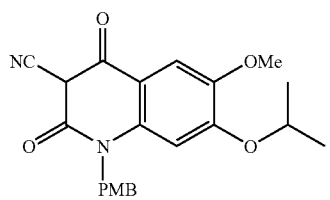

In the same manner as shown in Reference Example 12, the target compound was obtained.

$^1$H-NMR (DMSO-$d_6$, 300 MHz): δ 1.24 (6H, d, J=6.0 Hz), 3.44 (1H, br), 3.72 (3H, s), 3.85 (3H, s), 4.42 (1H, sept, J=6.0 Hz), 5.39 (2H, br), 6.64 (1H, s), 6.80 (2H, d, J=8.7 Hz), 7.14 (2H, d, J=8.7 Hz), 7.41 (1H, s).

Reference Example 18

4-chloro-1-(4-methoxybenzyl)-2-oxo-1,2-dihydroquinoline-3-carbonitrile

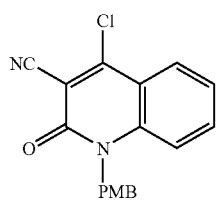

A mixture of 1-(4-methoybenzyl)-2,4-dioxo-1,2,3,4-tetrahydroquinoline-3-carbonitrile (9.52 g), N,N-diethylaniline (12.5 ml) and phosphorus oxychloride (58.7 g) was stirred at 90° C. for 2 hours. After cooling, the reaction mixture was poured into ice water. The precipitated solid was collected by filtration, washed with water, and dried to obtain the target compound (9.71 g).

$^1$H-NMR (DMSO-$d_6$, 200 MHz): δ 3.70 (3H, s), 5.48 (2H, s), 6.83-6.90 (2H, m), 7.18-7.24 (2H, m), 7.41-7.49 (1H, m), 7.56-7.62 (1H, m), 7.74-7.83 (1H, m), 8.04-8.12 (1H, m).

Reference Example 19

1-benzyl-4-chloro-2-oxo-1,2-dihydroquinoline-3-carbonitrile

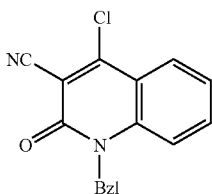

In the same manner as shown in Reference Example 18, the target compound was obtained.

$^1$H-NMR (DMSO-$d_6$, 200 MHz): δ 5.56 (2H, s), 7.20-7.36 (5H, m), 7.42-7.58 (2H, m), 7.74-7.83 (1H, m), 8.06-8.13 (1H, m).

Reference Example 20

4-chloro-1-(4-methoxybenzyl)-7-nitro-2-oxo-1,2-dihydroquinoline-3-carbonitrile

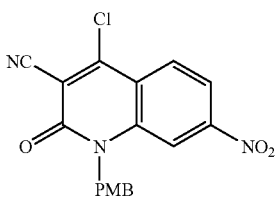

In the same manner as shown in Reference Example 18, the target compound was obtained.

$^1$H-NMR (DMSO-$d_6$, 300 MHz): δ 3.71 (3H, s), 5.57 (2H, br), 6.87-6.92 (2H, m), 7.27-7.31 (2H, m), 8.15 (1H, dd, J=8.9, 1.9 Hz), 8.28 (1H, d, J=1.9 Hz), 8.34 (1H, d, J=8.9 Hz).

Reference Example 21

4-chloro-7-isopropoxy-1-(4-methoxybenzyl)-2-oxo-1,2-dihydroquinoline-3-carbonitrile

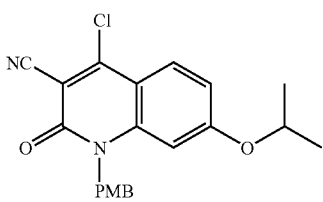

In the same manner as shown in Reference Example 18, the target compound was obtained.

$^1$H-NMR (DMSO-$d_6$, 300 MHz): δ 1.19 (6H, d, J=6.0 Hz), 3.70 (3H, s), 4.82 (1H, sept, J=6.0 Hz), 5.49 (2H, s), 6.85-6.95 (3H, m), 7.05 (1H, dd, J=9.0, 2.1 Hz), 7.23 (2H, d, J=8.7 Hz), 7.98 (1H, d, J=9.0 Hz).

Reference Example 22

4-chloro-6,7-dimethoxy-1-(4-methoxybenzyl)-2-oxo-1,2-dihydroquinoline-3-carbonitrile

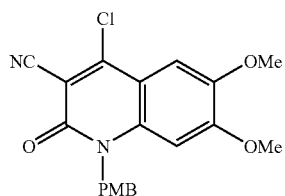

In the same manner as shown in Reference Example 18, the target compound was obtained.

$^1$H-NMR (DMSO-$d_6$, 200 MHz): δ 3.70 (3H, s), 3.85 (3H, s), 3.87 (3H, s), 5.55 (2H, br), 6.89 (2H, d, J=8.6 Hz), 7.04 (1H, s), 7.29 (2H, d, J=8.6 Hz), 7.33 (1H, s).

Reference Example 23

4-chloro-7-isopropoxy-6-methoxy-1-(4-methoxybenzyl)-2-oxo-1,2-dihydroquinoline-3-carbonitrile

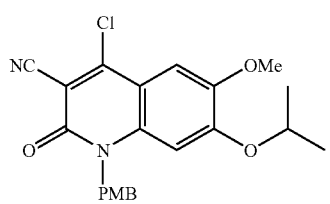

In the same manner as shown in Reference Example 18, the target compound was obtained.

$^1$H-NMR (CDCl$_3$, 200 MHz): δ 1.29 (6H, d, J=6.2 Hz), 3.77 (3H, s), 3.93 (3H, s), 4.49 (1H, sept, J=6.2 Hz), 5.47 (2H, br), 6.77 (1H, s), 6.85 (2H, d, J=8.8 Hz), 7.18 (2H, d, J=8.8 Hz), 7.33 (1H, s).

Reference Example 24

4-chloro-6,7-dimethoxy-2-oxo-1,2-dihydroquinoline-3-carbonitrile

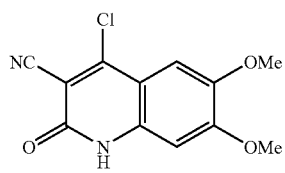

A mixture of 4-chloro-6,7-dimethoxy-1-(4-methoxybenzyl)2-oxo-1,2-dihydroquinoline-3-carbonitrile (300 mg), trifluoroacetic acid (5 ml), anisole (2 ml) and trifluoromethanesulfonic acid (1 ml) was stirred at room temperature for 1 day. After concentoration, the residue was cooled to 0° C. and ethyl acetate was added. The pH was adjusted to about 9 by adding 5% sodium carbonate, and the mixture was extracted with ethyl acetate. The extract was washed with water and brine, dried over anhydrous magnesium sulfate. The concentrated residue was purified with silica gel column chromatography to obtain the target compound (125 mg).

$^1$H-NMR (DMSO-$d_6$, 300 MHz): δ 3.86 (3H, s), 3.89 (3H, s), 6.90 (1H, s), 7.20 (1H, s), 12.54 (1H, br).

Reference Example 25

3-amino-5-(4-methoxybenzyl)-2-(2-methoxyphenyl)-2,5-dihydro-4H-pyrazolo[4,3-c]quinolin-4-one

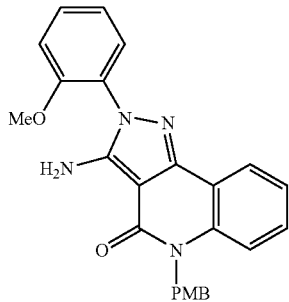

A mixture of 4-chloro-1-(4-methoxybenzyl)-2-oxo-1,2-dihydroquinoline-3-carbonitrile (500 mg), 2-methoxyphenylhydrazine hydrochloride (321 mg), triethylamine (627 μl) and ethanol (5 ml) was stirred at room temperature for 1 hour and at 90° C. for 2 hours. After cooling, water was added to the mixture and the precipitated solid was collected by filtration, washed with water-ethanol and dried to obtain the target compound (421 mg).

$^1$H-NMR (DMSO-$d_6$, 300 MHz): δ 3.70 (3H, s), 3.84 (3H, s), 5.39 (2H, br), 6.24 (2H, br), 6.88 (2H, d, J=8.7 Hz), 7.10-7.21 (4H, m), 7.26-7.40 (3H, m), 7.46 (1H, dd, J=7.9, 1.7 Hz), 7.51-7.57 (1H, m), 7.94-7.97 (1H, m).

LC/MS (ESI): m/z 427.1 (M+1).

Reference Example 26

3-amino-5-(4-methoxybenzyl)-2-(3-methoxyphenyl)-2,5-dihydro-4H-pyrazolo[4,3-c]quinolin-4-one

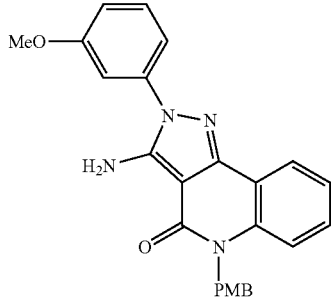

In the same manner as shown in Reference Example 25, the target compound was obtained.

$^1$H-NMR (DMSO-$d_6$, 200 MHz): δ 3.69 (3H, s), 3.85 (3H, s), 5.39 (2H, br), 6.58 (2H, br), 6.85-6.89 (2H, m), 7.02-7.05 (1H, m), 7.16-7.41 (7H, m), 7.46-7.52 (1H, m), 8.01 (1H, dd, J=7.8, 1.5 Hz)

LC/MS (ESI): m/z 427.2 (M+1).

Reference Example 27

3-amino-5-(4-methoxybenzyl)-2-(4-methoxyphenyl)-2,5-dihydro-4H-pyrazolo[4,3-c]quinolin-4-one

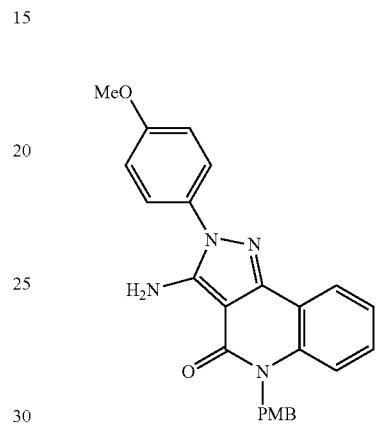

In the same manner as shown in Reference Example 25, the target compound was obtained.

$^1$H-NMR (CDCl$_3$, 200 MHz): δ 3.76 (3H, s), 3.87 (3H, s), 5.28 (2H, s), 5.44 (2H, s), 6.80-6.86 (2H, m), 7.03-7.08 (2H, m), 7.13-7.30 (4H, m), 7.30-7.38 (1H, m), 7.51-7.61 (2H, m), 8.17-8.22 (1H, m).

Reference Example 28

3-amino-5-benzyl-2-phenyl-2,5-dihydro-4H-pyrazolo[4,3-c]quinolin-4-one

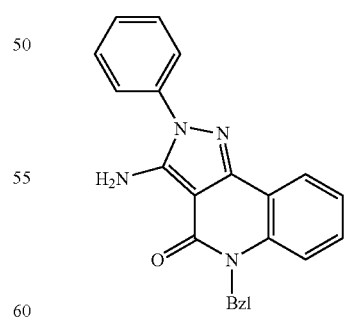

In the same manner as shown in Reference Example 25, the target compound was obtained.

$^1$H-NMR (DMSO-$d_6$, 200 MHz): δ 5.47 (2H, br), 6.56 (2H, br), 7.15-7.51 (9H, m), 7.52-7.64 (2H, m), 7.64-7.76 (2H, m), 7.97-8.06 (1H, m).

Reference Example 29

3-amino-5-(4-methoxybenzyl)-2-[3-(trifluoromethyl)phenyl]-2,5-dihydro-4H-pyrazolo[4,3-c]quinolin-4-one

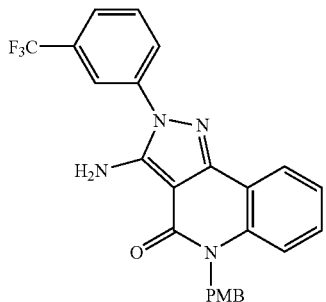

In the same manner as shown in Reference Example 25, the target compound was obtained.

$^1$H-NMR (DMSO-$d_6$, 200 MHz): δ 3.70 (3H, s), 5.41 (2H, br), 6.80 (2H, br), 6.88 (2H, d, J=8.8 Hz), 7.16-7.20 (3H, m), 7.31-7.46 (2H, m), 7.82-7.85 (2H, m), 8.02-8.06 (3H, m).

LC/MS (ESI): m/z 465.1 (M+1).

Reference Example 30

3-amino-5-(4-methoxybenzyl)-2-(3-nitrophenyl)-2,5-dihydro-4H-pyrazolo[4,3-c]quinolin-4-one

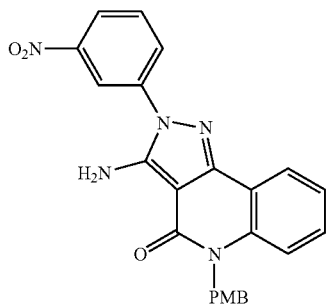

In the same manner as shown in Reference Example 25, the target compound was obtained.

$^1$H-NMR (DMSO-$d_6$, 200 MHz): δ 3.70 (3H, s), 5.41 (2H, br), 6.88 (2H, d, J=8.8 Hz), 6.93 (2H, br), 7.17-7.22 (3H, m), 7.32-7.46 (2H, m), 7.83-7.92 (1H, m), 8.02-8.06 (1H, m), 8.17-8.22 (1H, m), 8.27-8.32 (1H, m), 8.49-8.51 (1H, m).

LC/MS (ESI): m/z 442.2 (M+1).

Reference Example 31

3-amino-2-(3-fluorophenyl)-5-(4-methoxybenzyl)-2,5-dihydro-4H-pyrazolo[4,3-c]quinolin-4-one

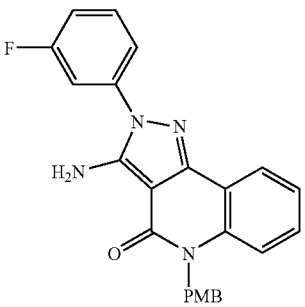

In the same manner as shown in Reference Example 25, the target compound was obtained.

$^1$H-NMR (DMSO-$d_6$, 300 MHz): δ 3.69 (3H, s), 5.39 (2H, br), 6.72 (2H, br), 6.83-6.89 (2H, m), 7.15-7.20 (3H, m), 7.28-7.43 (3H, m), 7.54-7.66 (3H, m), 8.01 (1H, dd, J=7.6, 1.7 Hz).

LC/MS (ESI): m/z 415.2 (M+1).

Reference Example 32 methyl 3-[3-amino-5-(4-methoxybenzyl)-4-oxo-4,5-dihydro-2H-pyrazolo[4,3-c]quinolin-2-yl]benzoate

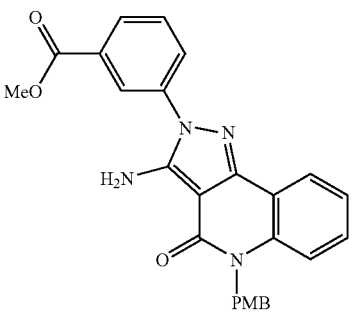

In the same manner as shown in Reference Example 25, the target compound was obtained.

$^1$H-NMR (DMSO-$d_6$, 200 MHz): δ 3.70 (3H, s), 3.92 (3H, s), 5.41 (2H, br), 6.75 (2H, br), 6.88 (2H, d, J=8.8 Hz), 7.16-7.22 (3H, m), 7.31-7.46 (2H, m), 7.71-7.79 (1H, m), 7.98-8.02 (3H, m), 8.23-8.25 (1H, m).

LC/MS (ESI): m/z 455.1 (M+1).

Reference Example 33

3-amino-5-(4-methoxybenzyl)-2-(6-methoxypyridin-2-yl)-2,5-dihydro-4H-pyrazolo[4,3-c]quinolin-4-one

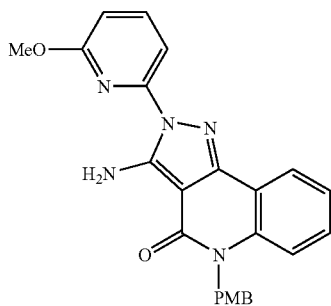

In the same manner as shown in Reference Example 25, the target compound was obtained.

¹H-NMR (DMSO-d₆, 300 MHz): δ 3.69 (3H, s), 3.97 (3H, s), 5.38 (2H, br), 6.80-6.88 (3H, m), 7.18-7.23 (3H, m), 7.32 (1H, d, J=8.4 Hz), 7.40-7.45 (1H, m), 7.58 (2H, br), 7.63 (1H, d, J=7.8 Hz), 7.94-7.99 (1H, m), 8.07 (1H, d, J=7.8 Hz).

LC/MS (ESI): m/z 428.2 (M+1).

Reference Example 34

3-amino-2-(4-chlorophenyl)-5-(4-methoxybenzyl)-2,5-dihydro-4H-pyrazolo[4,3-c]quinolin-4-one

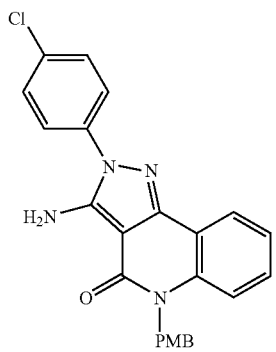

In the same manner as shown in Reference Example 25, the target compound was obtained.

¹H-NMR (CDCl₃, 200 MHz): δ 3.75 (3H, s), 5.38 (2H, br), 5.43 (2H, br), 6.80-6.83 (2H, m), 7.15-7.24 (3H, m), 7.32-7.39 (2H, m), 7.48-7.56 (2H, m), 7.61-7.68 (2H, m), 8.16-8.20 (1H, m).

Reference Example 35

4-[3-amino-5-(4-methoxybenzyl)-4-oxo-4,5-dihydro-2H-pyrazolo[4,3-c]quinolin-2-yl]benzenesulfonamide

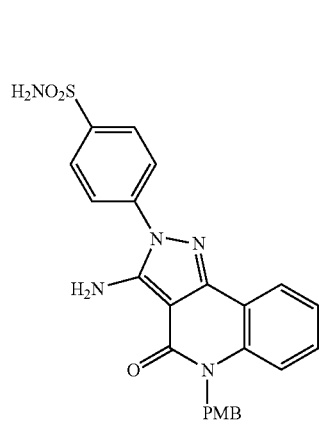

In the same manner as shown in Reference Example 25, the target compound was obtained.

¹H-NMR (DMSO-d₆, 200 MHz): δ 3.72 (3H, s), 5.40 (2H, br), 6.75 (2H, br), 6.80-6.86 (2H, m), 7.12-7.42 (4H, m), 7.46 (2H, br), 7.89-7.96 (1H, m), 8.00-8.07 (2H, m), 8.16-8.22 (1H, m).

Reference Example 36

3-amino-2-(2,5-difluorophenyl)-5-(4-methoxybenzyl)-2,5-dihydro-4H-pyrazolo[4,3-c]quinolin-4-one

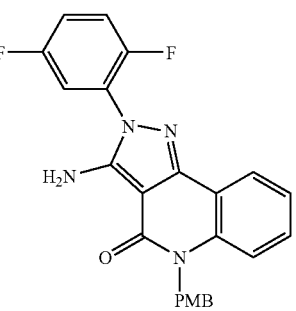

In the same manner as shown in Reference Example 25, the target compound was obtained.

¹H-NMR (DMSO-d₆, 300 MHz): δ 3.69 (3H, s), 5.39 (2H, br), 6.77 (2H, br), 6.84-6.89 (2H, m), 7.13-7.20 (3H, m), 7.31 (1H, d, J=7.8 Hz), 7.36-7.67 (4H, m), 7.95 (1H, dd, J=7.6, 1.7 Hz).

LC/MS (ESI): m/z 433.2 (M+1).

Reference Example 37

3-amino-2-(2,5-dimethylphenyl)-5-(4-methoxybenzyl)-2,5-dihydro-4H-pyrazolo[4,3-c]quinolin-4-one

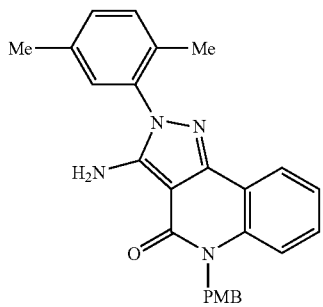

In the same manner as shown in Reference Example 25, the target compound was obtained.

$^1$H-NMR (CDCl$_3$, 300 MHz): δ 2.18 (3H, s), 2.39 (3H, s), 3.77 (3H, s), 5.07 (2H, s), 5.46 (2H, s), 6.82-6.89 (2H, m), 7.14-7.38 (8H, m), 8.20 (1H, dd, J=7.8, 1.5 Hz).

LC/MS (ESI): m/z 425.2 (M+1).

Reference Example 38

3-amino-2-(2,5-dichlorophenyl)-5-(4-methoxybenzyl)-2,5-dihydro-4H-pyrazolo[4,3-c]quinolin-4-one

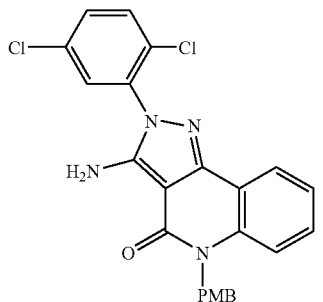

In the same manner as shown in Reference Example 25, the target compound was obtained.

$^1$H-NMR (CDCl$_3$, 300 MHz): δ 3.77 (3H, s), 5.26 (2H, s), 5.45 (2H, s), 6.81-6.88 (2H, m), 7.16-7.25 (4H, m), 7.34-7.40 (1H, m), 7.46-7.50 (1H, m), 7.54-7.58 (1H, m), 7.64 (1H, d, J=2.4 Hz), 8.17 (1H, dd, J=7.8, 1.5 Hz).

LC/MS (ESI): m/z 465.1 (M+1)

Reference Example 39

3-amino-2-(2,5-dimethoxyphenyl)-5-(4-methoxybenzyl)-2,5-dihydro-4H-pyrazolo[4,3-c]quinolin-4-one

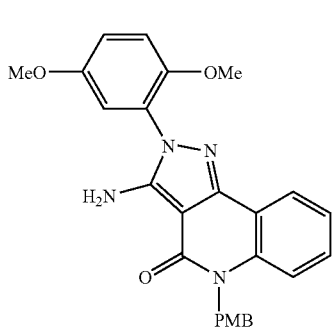

In the same manner as shown in Reference Example 25, the target compound was obtained.

$^1$H-NMR (DMSO-d$_6$, 300 MHz): δ 3.67 (3H, s), 3.71 (3H, s), 3.72 (3H, s), 4.96 (2H, s), 5.37 (2H, s), 6.41 (1H, s), 6.73 (1H, s), 6.87 (2H, d, J=8.7 Hz), 7.16 (2H, d, J=8.7 Hz), 7.25 (1H, t, J=7.2 Hz), 7.37 (1H, d, J=8.4 Hz), 7.59 (1H, t, J=7.2 Hz), 8.36 (1H, d, J=8.4 Hz), 9.34 (1H, s).

LC/MS (ESI): m/z 457.0 (M+1).

Reference Example 40

3-amino-5-(4-methoxybenzyl)-2-(5-methoxy-2-methylphenyl)-2,5-dihydro-4H-pyrazolo[4,3-c]quinolin-4-one

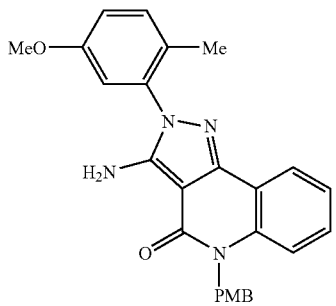

In the same manner as shown in Reference Example 25, the target compound was obtained.

$^1$H-NMR (CDCl$_3$, 300 MHz): δ 2.15 (3H, s), 3.77 (3H, s), 3.83 (3H, s), 5.11 (2H, s), 5.46 (2H, s), 6.81-6.88 (2H, m), 6.95-7.03 (2H, m), 7.14-7.40 (6H, m), 8.20 (1H, d, J=7.8 Hz).

LC/MS (ESI): m/z 441.2 (M+1).

Reference Example 41

3-amino-2-(2-chloro-5-methoxyphenyl)-5-(4-methoxybenzyl)-2,5-dihydro-4H-pyrazolo[4,3-c]quinolin-4-one

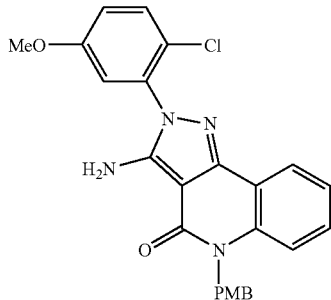

In the same manner as shown in Reference Example 25, the target compound was obtained.

$^1$H-NMR (DMSO-d$_6$, 300 MHz): δ 3.71 (3H, s), 3.84 (3H, s), 5.40 (2H, s), 6.53 (2H, s), 6.84-6.91 (2H, m), 7.13-7.25 (5H, m), 7.31 (1H, d, J=8.1 Hz), 7.35-7.42 (1H, m), 7.61 (1H, d, J=8.9 Hz), 8.00 (1H, dd, J=7.5, 1.5 Hz).

LC/MS (ESI): m/z 461.2 (M+1).

Reference Example 42

3-amino-2-(2,4-dichloro-5-methoxyphenyl)-5-(4-methoxybenzyl)-2,5-dihydro-4H-pyrazolo[4,3-c]quinolin-4-one

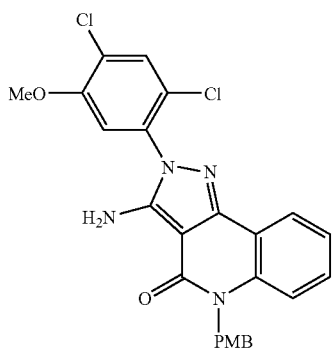

In the same manner as shown in Reference Example 25, the target compound was obtained.

$^1$H-NMR (CDCl$_3$, 300 MHz): δ 3.77 (3H, s), 3.95 (3H, s), 5.27 (2H, s), 5.45 (2H, s), 6.82-6.87 (2H, m), 7.12-7.28 (5H, m), 7.34-7.40 (1H, m), 7.62 (1H, s), 8.18 (1H, dd, J=7.8, 1.8 Hz).

LC/MS (ESI): m/z 495.0 (M+1).

Reference Example 43

3-amino-5-(4-methoxybenzyl)-7-nitro-2-phenyl-2,5-dihydro-4H-pyrazolo[4,3-c]quinolin-4-one

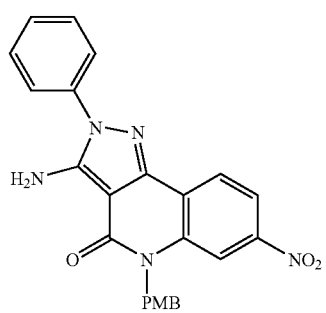

In the same manner as shown in Reference Example 25, the target compound was obtained.

$^1$H-NMR (DMSO-d$_6$, 300 MHz): δ 3.70 (3H, s), 5.47 (2H, br), 6.72 (2H, br), 6.90 (2H, d, J=8.7 Hz), 7.23 (2H, d, J=8.7 Hz), 7.48-7.72 (5H, m), 8.00 (1H, dd, J=8.7, 2.2 Hz), 8.10 (1H, d, J=2.2 Hz), 8.21 (1H, d, J=8.7 Hz).

LC/MS (ESI): m/z 442.2 (M+1).

Reference Example 44

3-amino-5-(4-methoxybenzyl)-2-(3-methoxyphenyl)-7-nitro-2,5-dihydro-4H-pyrazolo[4,3-c]quinolin-4-one

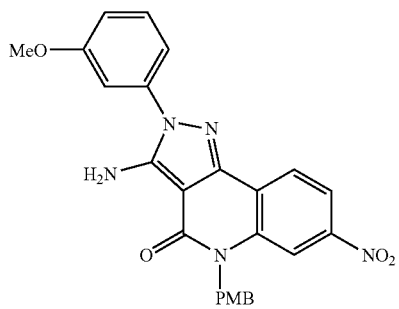

In the same manner as shown in Reference Example 25, the target compound was obtained.

$^1$H-NMR (DMSO-d$_6$, 300 MHz): δ 3.70 (3H, s), 3.85 (3H, s), 5.46 (2H, br), 6.74 (2H, br), 6.90 (2H, d, J=8.4 Hz), 7.05-7.08 (1H, m), 7.20-7.27 (4H, m), 7.48-7.53 (1H, m), 7.99 (1H, dd, J=8.6, 2.0 Hz), 8.09 (1H, d, J=2.0 Hz), 8.20 (1H, d, J=8.6 Hz).

LC/MS (ESI): m/z 471.9 (M+1).

Reference Example 45

3-amino-2-(2-chloro-5-methoxyphenyl)-5-(4-methoxybenzyl)-7-nitro-2,5-dihydro-4H-pyrazolo[4,3-c]quinolin-4-one

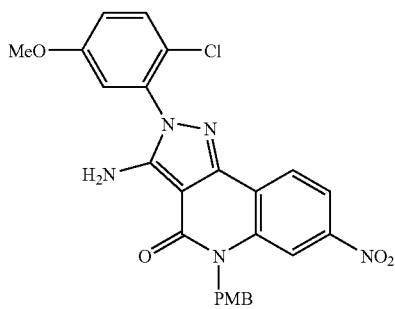

In the same manner as shown in Reference Example 25, the target compound was obtained.

$^1$H-NMR (CDCl$_3$, 300 MHz): δ 3.78 (3H, s), 3.87 (3H, s), 5.29 (2H, s), 5.55 (2H, br), 6.83-6.92 (2H, m), 7.04-7.10 (2H, m), 7.28-7.33 (2H, m), 7.48-7.54 (1H, m), 8.02 (1H, dd, J=8.7, 1.8 Hz), 8.23 (1H, d, J=1.8 Hz), 8.30 (1H, d, J=8.7 Hz).

LC/MS (ESI): m/z 506.0 (M+1).

Reference Example 46

3-amino-8-methoxy-5-(4-methoxybenzyl)-2-phenyl-2,5-dihydro-4H-pyrazolo[4,3-c]quinolin-4-one

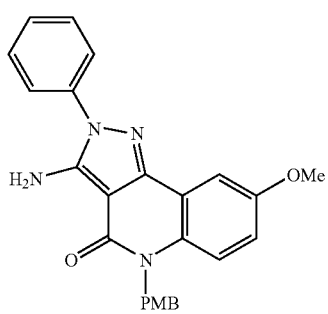

In the same manner as shown in Reference Example 25, the target compound was obtained.

$^1$H-NMR (DMSO-d$_6$, 200 MHz): δ 3.69 (3H, s), 3.78 (3H, s), 5.37 (2H, br), 6.54 (2H, br), 6.83-7.03 (3H, m), 7.12-7.19 (2H, m), 7.22-7.27 (1H, m), 7.43-7.49 (2H, m), 7.54-7.63 (2H, m), 7.64-7.72 (2H, m).

Reference Example 47

3-amino-7-isopropoxy-5-(4-methoxybenzyl)-2-(5-methoxy-2-methylphenyl)-2,5-dihydro-4H-pyrazolo[4,3-c]quinolin-4-one

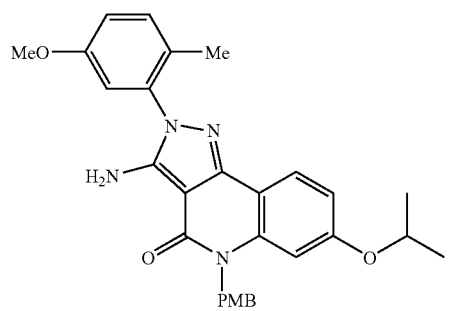

In the same manner as shown in Reference Example 25, the target compound was obtained.

$^1$H-NMR (DMSO-d$_6$, 200 MHz): δ 1.17 (6H, d, J=6.0 Hz), 2.04 (3H, s), 3.70 (3H, s), 3.79 (3H, s), 4.61 (1H, sept, J=6.0 Hz), 5.38 (2H, br), 6.28 (2H, s), 6.71 (1H, d, J=2.1 Hz), 6.75 (1H, dd, J=8.4, 2.1 Hz), 6.89 (2H, d, J=8.7 Hz), 6.98 (1H, d, J=2.7 Hz), 7.05 (1H, dd, J=8.4, 2.7 Hz), 7.19 (2H, d, J=8.7 Hz), 7.35 (1H, d, J=8.4 Hz), 7.83 (1H, d, J=8.4 Hz)

LC/MS (ESI): m/z 499.2 (M+1).

Reference Example 48

3-amino-7,8-dimethoxy-5-(4-methoxybenzyl)-2-(5-methoxy-2-methylphenyl)-2,5-dihydro-4H-pyrazolo[4,3-c]quinolin-4-one

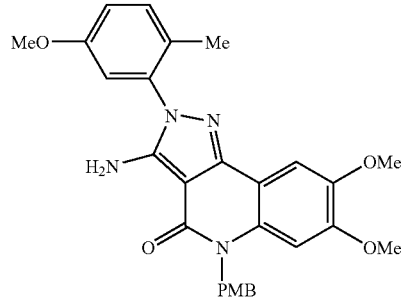

In the same manner as shown in Reference Example 25, the target compound was obtained.

$^1$H-NMR (DMSO-d$_6$, 300 MHz): δ 2.04 (3H, s), 3.70 (6H, s), 3.76 (3H, s), 3.79 (3H, s), 5.42 (2H, br), 6.28 (2H, s), 6.88-6.91 (3H, m), 6.99 (1H, d, J=2.4 Hz), 7.06 (1H, d, J=8.7, 2.4 Hz), 7.26 (2H, d, J=8.4 Hz), 7.34-7.36 (2H, m).

LC/MS (ESI): m/z 501.1 (M+1).

Reference Example 49

3-amino-7,8-dimethoxy-5-(4-methoxybenzyl)-2-(4-phenoxyphenyl)-2,5-dihydro-4H-pyrazolo[4,3-c]quinolin-4-one

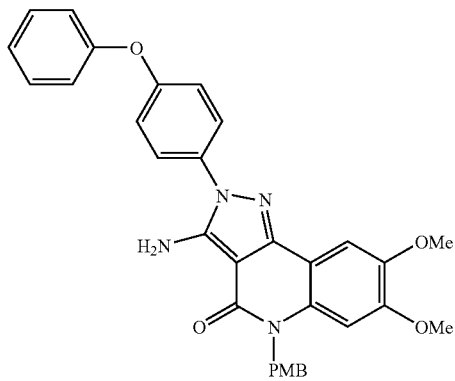

In the same manner as shown in Reference Example 25, the target compound was obtained.

$^1$H-NMR (DMSO-d$_6$, 300 MHz): δ 3.69 (3H, s), 3.70 (3H, s), 3.78 (3H, s), 5.42 (2H, br), 6.28 (2H, s), 6.86-6.89 (2H, m), 7.08-7.25 (8H, m), 7.30 (1H, s), 7.41-7.47 (2H, m), 7.66 (2H, d, J=9.0 Hz).

LC/MS (ESI): m/z 549.1 (M+1).

Reference Example 50

3-amino-7-isopropoxy-8-methoxy-5-(4-methoxybenzyl)-2-(5-methoxy-2-methylphenyl)-2,5-dihydro-4H-pyrazolo[4,3-c]quinolin-4-one

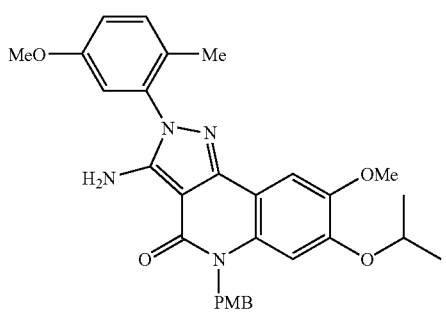

In the same manner as shown in Reference Example 25, the target compound was obtained.

$^1$H-NMR (CDCl$_3$, 300 MHz): δ 1.22 (6H, d, J=6.0 Hz), 2.15 (3H, s), 3.76 (3H, s), 3.83 (3H, s), 3.88 (3H, s), 4.36 (1H, sept, J=6.0 Hz), 5.11 (2H, s), 5.43 (2H, br), 6.79 (1H, s), 6.84 (2H, d, J=8.7 Hz), 6.97-7.01 (2H, m), 7.21 (2H, d, J=8.7 Hz), 7.30 (1H, d, J=8.7 Hz), 7.58 (1H, s).

LC/MS (ESI): m/z 529.2 (M+1).

Reference Example 51

3-amino-2-(2-chloro-5-methoxyphenyl)-7-isopropoxy-8-methoxy-5-(4-methoxybenzyl)-2,5-dihydro-4H-pyrazolo[4,3-c]quinolin-4-one

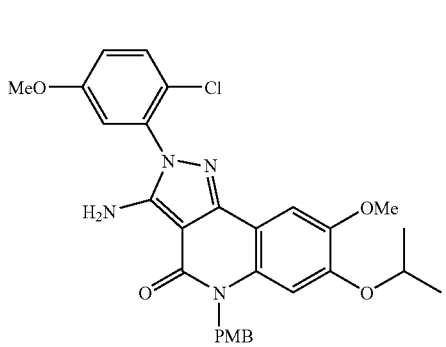

In the same manner as shown in Reference Example 25, the target compound was obtained.

$^1$H-NMR (CDCl$_3$, 300 MHz): δ 1.23 (6H, d, J=6.3 Hz), 3.77 (3H, s), 3.86 (3H, s), 3.88 (3H, s), 4.38 (1H, sept, J=6.0 Hz), 5.24 (2H, br), 5.42 (2H, br), 6.78 (1H, s), 6.85 (2H, d, J=8.5 Hz), 7.04 (1H, dd, J=9.0, 3.0 Hz), 7.12 (1H, d, J=3.0 Hz), 7.21 (2H, d, J=8.5 Hz), 7.48 (1H, d, J=9.0 Hz), 7.58 (1H, s).

LC/MS (ESI): m/z 549.0 (M+1).

Reference Example 52

3-[3-amino-7,8-dimethoxy-5-(4-methoxybenzyl)-4-oxo-4,5-dihydro-2H-pyrazolo[4,3-c]quinolin-2-yl]-4-methylbenzonitrile

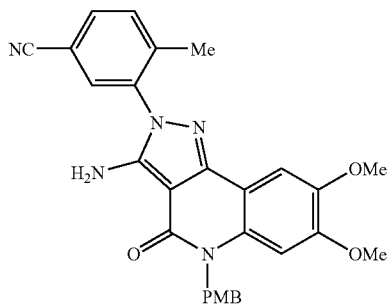

In the same manner as shown in Reference Example 25, the target compound was obtained.

$^1$H-NMR (DMSO-d$_6$, 300 MHz): δ 2.21 (3H, s), 3.69 (6H, s), 3.76 (3H, s), 5.42 (2H, br), 6.54 (2H, br), 6.85-6.90 (3H, m), 7.25 (2H, d, J=8.7 Hz), 7.34 (1H, s), 7.66 (1H, d, J=8.2 Hz), 7.93 (1H, d, J=8.2 Hz), 7.99 (1H, s).

LC/MS (ESI): m/z 496.0 (M+1).

Reference Example 53

3-amino-7,8-dimethoxy-5-(4-methoxybenzyl)-2-(4-methylpyridin-3-yl)-2,5-dihydro-4H-pyrazolo[4,3-c]quinolin-4-one

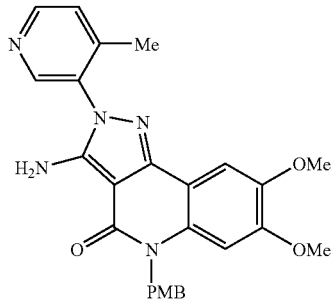

In the same manner as shown in Reference Example 25, the target compound was obtained.

$^1$H-NMR (CDCl$_3$, 300 MHz): δ 2.32 (3H, s), 3.77 (3H, s), 3.78 (3H, s), 3.92 (3H, s), 5.20 (2H, br), 5.45 (2H, br), 6.79 (1H, s), 6.86 (2H, d, J=8.5 Hz), 7.24 (2H, d, J=8.5 Hz), 7.37-7.39 (1H, m), 7.54 (1H, s), 8.63 (1H, d, J=4.8 Hz), 8.09 (1H, s).

LC/MS (ESI): m/z 472.1 (M+1).

Reference Example 54

2-(2-chloro-5-methoxyphenyl)-3-(dimethylamino)-5-(4-methoxybenzyl)-2,5-dihydro-4H-pyrazolo[4,3-c]quinolin-4-one

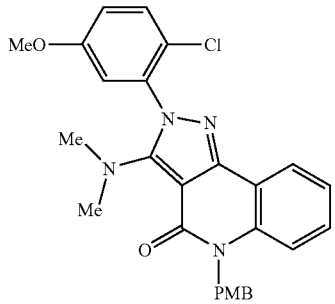

A mixture of 3-amino-2-(2-chloro-5-methoxyphenyl)-5-(4-methoxybenzyl)-2,5-dihydro-4H-pyrazolo[4,3-c]quinolin-4-one (50 mg), sodium hydride (an oily, about 66%, 20 mg), tetrahydrofuran (0.8 ml) and N,N-dimethylformamide (0.8 ml) was stirred at room temperature for 2 hours, added methyl iodide thereto and stirred for 12 hours. The reaction mixture was concentrated under reduced pressure, ethyl acetate was added thereto, and washed with 5% sodium hydrogen carbonate and saturated brine, dried over anhydrous magnesium sulfate and then concentrated under reduced pressure. The concentrated residue was recrystallized from ethyl acetate-hexane-diisopropyl ether to obtain the target compound (35 mg).

$^1$H-NMR (CDCl$_3$, 300 MHz): δ 2.97 (6H, s), 3.77 (3H, s), 3.86 (3H, s), 5.50 (2H, br), 6.80-6.88 (2H, m), 7.00 (1H, dd, J=9.0, 3.0 Hz), 7.11 (1H, d, J=3.0 Hz), 7.15-7.25 (4H, m), 7.34 (1H, dt, J=1.5, 7.8 Hz), 7.44 (1H, d, J=9.0 Hz), 8.23 (1H, dd, J=7.8, 1.5 Hz).

LC/MS (ESI): m/z 489.1 (M+1).

Reference Example 55

3-amino-2-[4-(2-hydroxyethyl)phenyl]-5-(4-methoxybenzyl)-2,5-dihydro-4H-pyrazolo[4,3-c]quinolin-4-one

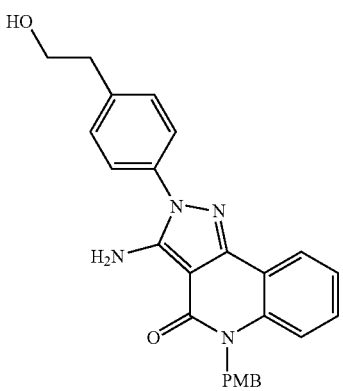

A mixture of 4-chloro-1-benzyl-2-oxo-1,2-dihydroquinoline-3-carbonitrile (0.6 g), 4-(2-hydroxyethyl)phenylhydrazine (0.24 g), triethylamine (0.27 ml) and ethanol (40 ml) was heated under reflux for 12 hours. The solvent was distilled off under reduced pressure, and an aqueous sodium hydrogen carbonate solution was added thereto and extracted with ethyl acetate. The extract was washed with water and brine, dried and concentrated. The residue was purified with silica gel column chromatography to obtain the target compound (0.47 g).

$^1$H-NMR (CDCl$_3$, 200 MHz): δ 1.54 (1H, m), 2.96 (2H, t, J=4 Hz), 3.76 (3H, s), 3.84-3.96 (2H, m), 5.38 (2H, br), 5.44 (2H, br), 6.78-6.84 (2H, m), 7.14-7.68 (9H, m), 8.06-8.24 (1H, m).

Reference Example 56

N-{2-[4-(2-hydroxyethyl)phenyl]-5-(4-methoxybenzyl)-4-oxo-4,5-dihydro-2H-pyrazolo[4,3-c]quinolin-3-yl}acetamide

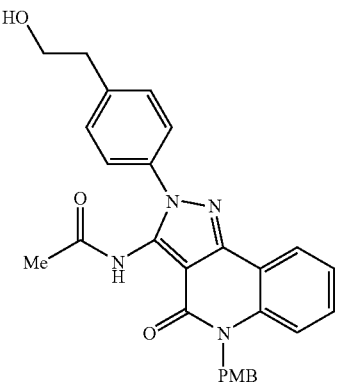

A mixture of 3-amino-2-[4-(2-hydroxyethyl)phenyl]-5-(4-methoxybenzyl)-2,5-dihydro-4H-pyrazolo[4,3-c]quinolin- 4-one (0.2 g) and acetic anhydride (2 ml) was heated under reflux for 5 hours. The reaction mixture was concentrated under reduced pressure, an aqueous sodium hydrogen carbonate solution was added thereto, and extracted with ethyl acetate. The extract was washed with water and saturated brine, and concentrated after drying. To the obtained crystal was added methanol (20 ml) and an 1N aqueous sodium hydroxide solution (0.5 ml), and the mixture was stirred at room temperature for 1 hour. The solvent was distilled off under reduced pressure, a 1N hydrochloric acid (0.5 ml) was added to the residue and the mixture was extracted with ethyl acetate. The extract was washed with an aqueous sodium hydrogen carbonate solution, water and saturated brine, dried and concentrated to obtain the target compound (0.2 g).

$^1$H-NMR (CDCl$_3$, 200 MHz): δ 1.54 (1H, br), 2.16 (3H, s), 2.95 (2H, t, J=4 Hz), 3.76 (3H, s), 3.88-3.94 (2H, m), 5.48 (2H, br), 6.82-6.86 (2H, m), 7.16-7.62 (10H, m), 8.26-8.32 (1H, m).

Reference Example 57

2-{4-[3-(acetylamino)-5-(4-methoxybenzyl)-4-oxo-4,5-dihydro-2H-pyrazolo[4,3-c]quinolin-2-yl]phenyl}ethyl methanesulfonate

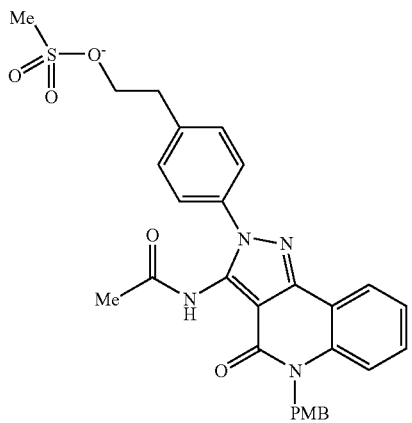

To a solution of N-{2-[4-(2-hydroxyethyl)phenyl]-5-(4-methoxybenzyl)-4-oxo-4,5-dihydro-2H-pyrazolo[4,3-c]quinolin-3-yl}acetamide (3.2 g) and triethylamine (1.85 ml) in tetrahydrofuran (400 ml) was added dropwise methanesulfonyl chloride (0.77 ml) at 0° C. The mixture was stirred at room temperature for 5 hours, triethylamine (0.46 ml) and methanesulfonyl chloride (0.19 ml) were added thereto, and stirred again for 3 hours. The mixture was concentrated under reduced pressure, and to the residue was added ethyl acetate, washed with an aqueous sodium hydrogen carbonate solution, water, saturated brine, dried and concentrated under reduced pressure to obtain the target compound (3.5 g).

$^1$H-NMR (CDCl$_3$, 200 MHz): δ 2.15 (3H, s), 2.90 (3H, s), 3.13 (2H, t, J=4.4 Hz), 3.75 (3H, s), 4.46 (2H, t, J=4.4 Hz), 5.46 (2H, br), 6.79-6.84 (2H, m), 7.15-7.43 (7H, m), 7.57-7.63 (2H, m), 8.24-8.30 (1H, m), 8.50 (1H, br).

Reference Example 58

N-{5-(4-methoxybenzyl)-4-oxo-2-[4-(2-piperidin-1-ylethyl)phenyl]-4,5-dihydro-2H-pyrazolo[4,3-c]quinolin-3-yl}acetamide

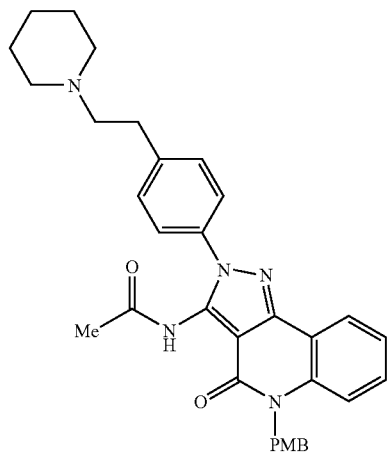

To a solution of N-{2-[4-(2-hydroxyethyl)phenyl]-5-(4-methoxybenzyl)-4-oxo-4,5-dihydro-2H-pyrazolo[4,3-c]quinolin-3-yl}acetamide (0.2 g) and triethylamine (0.12 ml) in tetrahydrofuran (25 ml) was added dropwise methanesulfonyl chloride (0.048 ml) at 0° C. The solution was stirred at 0° C. for 2 hours and at room temperature for 15 minutes, an aqueous sodium hydrogen carbonate solution was added thereto, and extracted with ethyl acetate. The extract was washed with water and saturated brine, dried and concentrated under reduced pressure. To the residue was added ethanol (30 ml), triethylamine (0.087 ml), piperidine (0.045 ml) and the mixture was refluxed with heating. After 2 hours, piperidine (0.1 ml) was added thereto, and the mixture was stirred with heating for 6 hours. The solvent was distilled off under reduced pressure, ethyl acetate was added thereto, and extracted with 1N hydrochloric acid. The aqueous layer was washed ether, basified by adding a 2N aqueous sodium hydroxide solution, and extracted with ethyl acetate. The extract was washed with saturated brine, dried and concentrated under reduced pressure to obtain the target compound (0.13 g).

$^1$H-NMR (CDCl$_3$, 200 MHz): δ 1.43-1.52 (2H, m), 1.60-1.72 (4H, m), 2.14 (3H, s), 2.40-2.64 (6H, m), 2.84-2.97 (2H, m), 3.75 (3H, s), 5.46 (2H, br), 6.78-6.84 (2H, m), 7.12-7.56 (9H, m), 8.24-8.30 (1H, m).

Reference Example 59

N-(3-methoxyphenyl)-N'-[1-(2-nitrophenyl)ethylidene]hydrazine

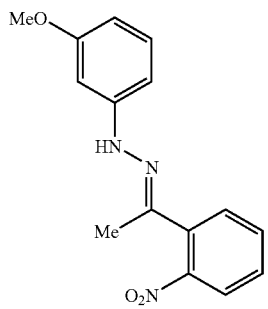

A mixture of 3-methoxyphenylhydrazine hydrochloride (1.75 g), 2-nitroacetophenone (1.65 g), sodium acetate (0.82 g) and acetic acid (10 ml) was stirred at room temperature for 4 days. To the reaction mixture was added water, extracted with ethyl acetate. The extract was washed with water, brine, dried over anhydrous magnesium sulfate. The solvent was distilled off under reduced pressure to obtain the target compound (2.72 g).

$^1$H-NMR (DMSO-$d_6$, 300 MHz): δ 2.25 (3H, s), 3.72 (3H, s), 6.33 (1H, dd, J=8.4, 2.4 Hz), 6.64 (1H, dd, J=8.1, 1.8 Hz), 6.67-6.69 (1H, m), 7.04-7.09 (1H, m), 7.47-7.52 (1H, m), 7.63-7.78 (3H, m), 9.41 (1H, br).

Reference Example 60

N-(2-chloro-5-methoxyphenyl)-N'-[1-(2,4-dinitrophenyl)ethylidene]hydrazine

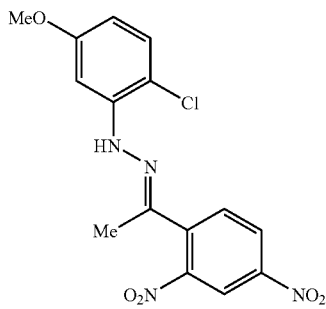

A mixture of 2-chloro-5-methoxyphenylhydrazine (2.85 g), 2,4-dinitroacetophenone (3.47 g) and acetic acid (15 ml) was stirred at room temperature for one night. The reaction mixture was concentrated, to the residue was added toluene, and concentrated again. To the residue was added toluene, concentrated to obtain the target compound (6.02 g).

$^1$H-NMR (DMSO-$d_6$, 300 MHz): δ 2.40 (3H, s), 3.78 (3H, s), 6.50 (1H, dd, J=8.7, 2.9 Hz), 6.85 (1H, d, J=2.9 Hz), 7.27 (1H, d, J=8.7 Hz), 8.02 (1H, d, J=8.7 Hz), 8.47 (1H, dd, J=8.7, 2.5 Hz), 8.61 (1H, br), 8.68 (1H, d, J=2.5 Hz).

Reference Example 61

1-(3-methoxyphenyl)-3-(2-nitrophenyl)-1H-pyrazole-4-carbaldehyde

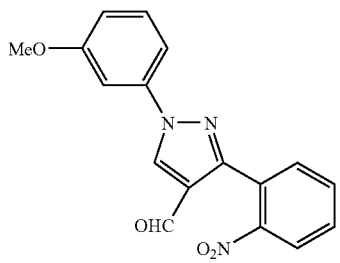

To an N,N-dimethylformamide (15 ml) cooled to 0° C. was added phosphorus oxychloride (1.96 ml). The solution was stirred at 0° C. for 30 minutes, a solution of N-(3-methoxyphenyl)-N'-[1-(2-nitrophenyl)ethylidene]hydrazine (2.72 g) in N,N-dimethylformamide (5 ml) was added thereto, stirred at room temperature for one night. Water (100 ml) was added thereto, stirred for 1 day, and extracted with ethyl acetate. The extract was washed with water and brine, and dried over anhydrous magnesium sulfate. The solvent was distilled off under reduced pressure, the residue was solidified by adding ethyl acetate-diisopropyl ether. The solid was collected by filtration and washed with ethyl acetate-diisopropyl ether to obtain the target compound (1.08 g).

$^1$H-NMR (CDCl$_3$, 300 MHz): δ 3.87 (3H, s), 6.90-6.94 (1H, m), 7.25-7.45 (3H, m), 7.60-7.73 (3H, m), 8.11-8.14 (1H, m), 8.48 (1H, s), 9.84 (1H, s).

Reference Example 62

1-(2-chloro-5-methoxyphenyl)-3-(2,4-dinitrophenyl)-1H-pyrazole-4-carbaldehyde

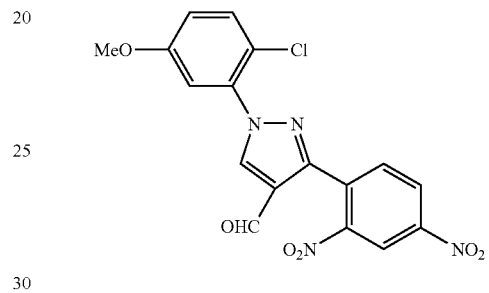

In the same manner as shown in Reference Example 61, the target compound was obtained.

$^1$H-NMR (DMSO-$d_6$, 300 MHz): δ 3.84 (3H, s), 7.19 (1H, dd, J=9.2, 3.1 Hz), 7.35 (1H, d, J=3.1 Hz), 7.65 (1H, d, J=9.2 Hz), 8.05 (1H, d, J=8.7 Hz), 8.62 (1H, dd, J=8.7, 2.6 Hz), 8.84 (1H, d, J=2.6 Hz), 9.14 (1H, s), 9.88 (1H, s).

Reference Example 63

1-(3-methoxyphenyl)-3-(2-nitrophenyl)-1H-pyrazole-4-carboxylic acid

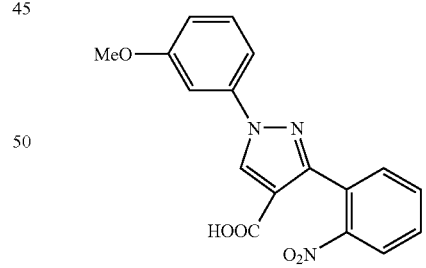

To a mixture of 1-(3-methoxyphenyl)-3-(2-nitrophenyl)-1H-pyrazole-4-carbaldehyde (1.00 g), water (2 ml) and pyridine (2 ml) was added portionwise potassium permanganate (538 mg). After stirring for 1 hour, the precipitated manganese oxide was filtered off through Celite, the Celite layer was washed with 1N aqueous sodium hydroxide solution. The filtrate and washings were combined, washed with ethyl acetate. The aqueous layer was acidified with 6N hydrochloric acid, extracted with ethyl acetate. The extract was washed with water and brine, and dried over anhydrous magnesium sulfate. The solvent was distilled off under reduced pressure, the residue was solidified by adding hexane. The solid was collected by filtration and washed with hexane to obtain the target compound (676 mg).

$^1$H-NMR (DMSO-d$_6$, 300 MHz): δ 3.89 (3H, s), 6.87-6.93 (1H, m), 7.30-7.46 (3H, m), 7.55-7.72 (3H, m), 8.10 (1H, d, J=7.6 Hz), 8.55 (1H, s).

Reference Example 64

1-(2-chloro-5-methoxyphenyl)-3-(2,4-dinitrophenyl)-1H-pyrazole-4-carboxylic acid

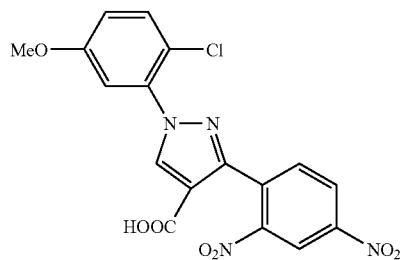

In the same manner as shown in Reference Example 63, the target compound was obtained.

$^1$H-NMR (DMSO-d$_6$, 300 MHz): δ 3.84 (3H, s), 7.16 (1H, dd, J=8.8, 2.9 Hz), 7.32 (1H, d, J=2.9 Hz), 7.62 (1H, d, J=8.8 Hz), 8.00 (1H, d, J=8.7 Hz), 8.60 (1H, dd, J=8.7, 2.4 Hz), 8.79 (1H, s), 8.81 (1H, d, J=2.4 Hz), 12.87 (1H, br).

Reference Example 65

3-amino-9-hydroxy-7-methoxy-5-(4-methoxybenzyl)-2-(4-phenoxyphenyl)-2,5-dihydro-4H-pyrazolo[4,3-c]quinolin-4-one

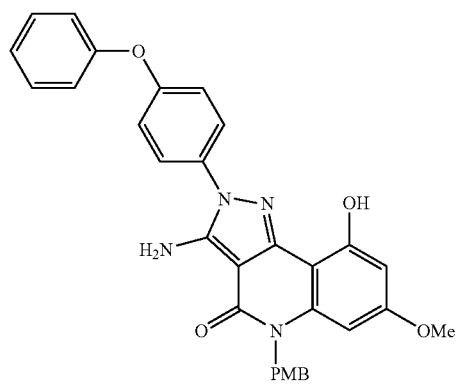

A mixture of 3-amino-7,9-dimethoxy-5-(4-methoxybenzyl)-2-(4-phenoxyphenyl)-2,5-dihydro-4H-pyrazolo[4,3-c]quinolin-4-one (500 mg), magnesium bromide (168 mg) and pyridine (10 ml) was heated under reflux for 2 days, added water thereto after cooling. The precipitated solid was collected by filtration, washed with water, and purified with silica gel column chromatography to obtain the target compound (360 mg).

$^1$H-NMR (DMSO-d6, 300 MHz): δ 3.69 (6H, s), 5.31 (2H, br s), 6.33 (2H, s), 6.70 (2H, br s), 6.86 (2H, d, J=8.4 Hz), 7.11 (2H, d, J=8.7 Hz), 7.16-7.22 (5H, m), 7.44 (2H, t, J=8.7 Hz), 7.66 (2H, d, J=8.7 Hz), 9.21 (1H, br s).

LC/MS (ESI): m/z 535.2 (M+1).

Reference Example 66

3-amino-9-hydroxy-7-methoxy-5-(4-methoxybenzyl)-2-(2-methyl-4-phenoxyphenyl)-2,5-dihydro-4H-pyrazolo[4,3-c]quinolin-4-one

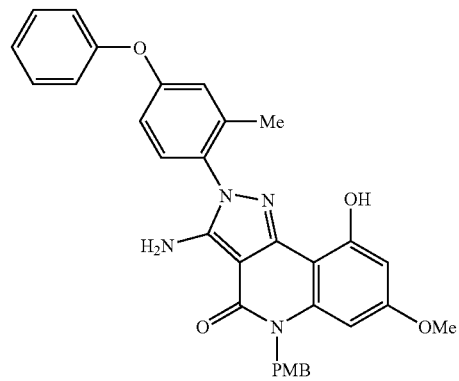

In the same manner as shown in Reference Example 65, the target compound was obtained.

$^1$H-NMR (DMSO-d6, 300 MHz): δ 2.07 (3H, s), 3.67 (3H, s), 3.68 (3H, s), 5.30 (2H, br s), 6.30 (2H, br s), 6.55-6.56 (2H, m), 6.84-6.97 (3H, m), 7.08-7.19 (6H, m), 7.40-7.44 (3H, m), 9.25 (1H, br s).

LC/MS (ESI): m/z 549.4 (M+1).

Reference Example 67

3-amino-9-hydroxy-7-methoxy-5-(4-methoxybenzyl)-2-(5-methoxy-2-methylphenyl)-2,5-dihydro-4H-pyrazolo[4,3-c]quinolin-4-one

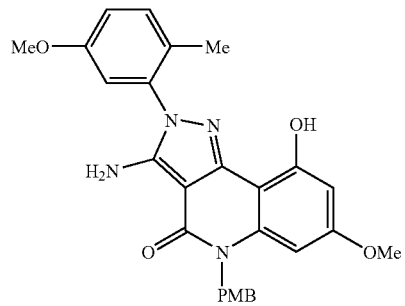

In the same manner as shown in Reference Example 65, the target compound was obtained.

$^1$H-NMR (DMSO-d6, 300 MHz): δ 1.98 (3H, s), 3.70 (3H, s), 3.77 (3H, s), 3.84 (3H, s), 6.08 (2H, br s), 6.16 (1H, d, J=2.3 Hz), 6.35 (2H, br s), 6.45 (1H, d, J=2.3 Hz), 6.75-6.89 (3H, m), 6.94 (1H, dd, J=8.4, 2.4 Hz), 7.12 (2H, d, J=8.1 Hz), 7.28 (1H, d, J=8.4 Hz), 8.88 (1H, br s).

LC/MS (ESI): m/z 487.2 (M+1).

Reference Example 68

3-amino-9-hydroxy-7-methoxy-5-(4-methoxybenzyl)-2-(2-methylphenyl)-2,5-dihydro-4H-pyrazolo[4,3-c]quinolin-4-one

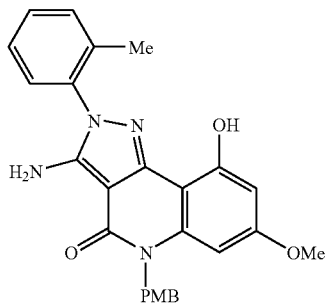

In the same manner as shown in Reference Example 65, the target compound was obtained.
$^1$H-NMR (DMSO-d6, 300 MHz): δ 2.11 (3H, s), 3.69 (3H, s), 3.72 (3H, s), 5.31 (2H, br s), 5.91 (2H, br s), 6.33 (1H, s), 6.70 (1H, s), 6.80 (2H, d, J=8.4 Hz), 7.14 (2H, d, J=8.4 Hz), 7.33-7.40 (4H, m), 9.03 (1H, br s).
LC/MS (ESI): m/z 457.2 (M+1).

Reference Example 69

5,7-dimethoxy-2H-3,1-benzoxazine-2,4(1H)-dione

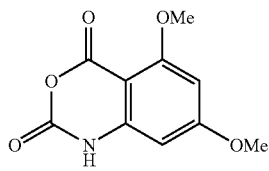

In the same manner as shown in Reference Example 1, the target compound was obtained.
$^1$H-NMR (DMSO-d6, 300 MHz): δ 3.84 (3H, s), 3.86 (3H, s), 6.20 (1H, d, J=2.3 Hz), 6.36 (1H, d, J=2.3 Hz), 11.50 (1H, br s).
LC/MS (ESI): m/z 224.2 (M+1).

Reference Example 70

5,7-dimethoxy-1-(4-methoxybenzyl)-2H-3,1-benzoxazine-2,4(1H)-dione

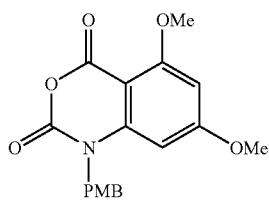

In the same manner as shown in Reference Example 6, the target compound was obtained.
$^1$H-NMR (DMSO-d6, 300 MHz): δ 3.72 (3H, s), 3.80 (3H, s), 3.88 (3H, s), 5.18 (2H, br s), 6.28 (1H, d, J=2.3 Hz), 6.45 (1H, d, J=2.3 Hz), 6.89 (2H, d, J=8.8 Hz), 7.32 (2H, d, J=8.8 Hz).
LC/MS (ESI): m/z 344.2 (M+1).

Reference Example 71

5,7-dimethoxy-1-(4-methoxybenzyl)-2,4-dioxo-1,2,3,4-tetrahydroquinoline-3-carbonitrile

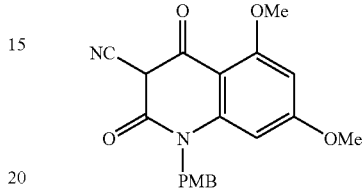

In the same manner as shown in Reference Example 12, the target compound was obtained.
$^1$H-NMR (DMSO-d6, 300 MHz): δ 3.69 (3H, s), 3.79 (3H, s), 4.00 (3H, s), 5.37 (2H, br s), 6.49 (1H, s), 6.54 (1H, s), 6.87 (2H, d, J=8.3 Hz), 7.18 (2H, d, J=8.3 Hz).
LC/MS (ESI): m/z 367.1 (M+1).

Reference Example 72

4-chloro-5,7-dimethoxy-1-(4-methoxybenzyl)-2-oxo-1,2-dihydroquinoline-3-carbonitrile

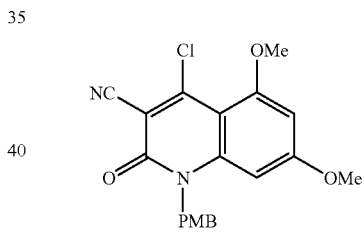

In the same manner as shown in Reference Example 18, the target compound was obtained.
$^1$H-NMR (DMSO-d6, 300 MHz): δ 3.69 (3H, s), 3.80 (3H, s), 3.90 (3H, s), 5.43 (2H, br s), 6.52 (1H, s), 6.55 (1H, s), 6.85 (2H, d, J=7.8 Hz), 7.21 (2H, d, J=7.8 Hz).
LC/MS (ESI): m/z 385.0 (M+1).

Reference Example 73

Ethyl 1-(4-methoxybenzyl)-2,4-dioxo-1,2,3,4-tetrahydroquinoline-3-carboxylate

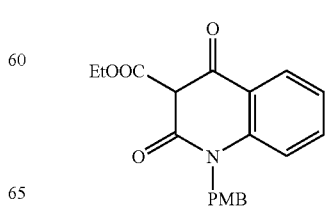

In the same manner as shown in Reference Example 12, the target compound was obtained.

¹H-NMR (DMSO-d6, 300 MHz): δ 1.32 (3H, t, J=7.2 Hz), 3.69 (3H, s), 4.35 (2H, q, J=7.2 Hz), 5.38 (2H, br s), 6.85 (2H, d, J=8.5 Hz), 7.14 (2H, d, J=8.5 Hz), 7.23-7.29 (1H, m), 7.39 (1H, d, J=8.4 Hz), 7.60-7.65 (1H, m), 8.06 (1H, dd, J=8.1, 1.5 Hz).

Reference Example 74

Ethyl 4-chloro-1-(4-methoxybenzyl)-2-oxo-1,2-dihydroquinoline-3-carboxylate

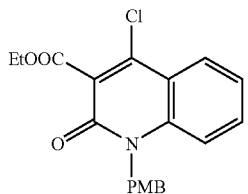

In the same manner as shown in Reference Example 18, the target compound was obtained.

¹H-NMR (DMSO-d6, 300 MHz): δ 1.33 (3H, t, J=7.2 Hz), 3.70 (3H, s), 4.39 (2H, q, J=7.2 Hz), 5.47 (2H, br s), 6.88 (2H, d, J=8.7 Hz), 7.17 (2H, d, J=8.7 Hz), 7.39-7.44 (1H, m), 7.60 (1H, d, J=8.7 Hz), 7.69-7.74 (1H, m), 8.04 (1H, dd, J=7.9, 1.4 Hz).

LC/MS (ESI): m/z 372.0 (M+1).

Reference Example 75

4-chloro-2-oxo-1,2-dihydroquinoline-3-carbonitrile

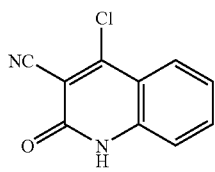

In the same manner as shown in Reference Example 24, the target compound was obtained.

¹H-NMR (DMSO-d6, 300 MHz): δ 7.37-7.43 (2H, m), 7.75-7.81 (1H, m), 7.94-7.97 (1H, m)., 12.70 (1H, br s).

LC/MS (ESI): m/z 205.1 (M+1).

Reference Example 76

4-chloro-7-hydroxy-2-oxo-1,2-dihydroquinoline-3-carbonitrile

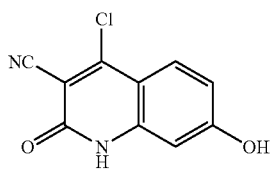

In the same manner as shown in Reference Example 24, the target compound was obtained.

¹H-NMR (DMSO-d6, 300 MHz): δ 6.65 (1H, d, J=2.5 Hz), 6.77 (1H, dd, J=9.1, 2.5 Hz), 7.72 (1H, d, J=9.1 Hz), 12.24 (1H, br s).

LC/MS (ESI): m/z 221.0 (M+1).

Reference Example 77

3-amino-7,8-dimethoxy-5-(4-methoxybenzyl)-2-(2-methylphenyl)-2,5-dihydro-4H-pyrazolo[4,3-c]quinolin-4-one

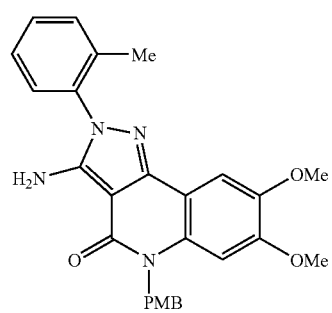

In the same manner as shown in Reference Example 25, the target compound was obtained.

¹H-NMR (DMSO-d6, 300 MHz): δ 2.13 (3H, s), 3.70 (6H, s), 3.75 (3H, s), 5.41 (2H, br s), 6.26 (2H, br s), 6.87-6.89 (3H, m), 7.58 (2H, d, J=7.8 Hz), 7.34 (1H, s), 7.38-7.47 (4H, m).

LC/MS (ESI): m/z 471.0 (M+1).

Reference Example 78

3-amino-7-isopropoxy-8-methoxy-5-(4-methoxybenzyl)-2-(4-phenoxyphenyl)-2,5-dihydro-4H-pyrazolo[4,3-c]quinolin-4-one

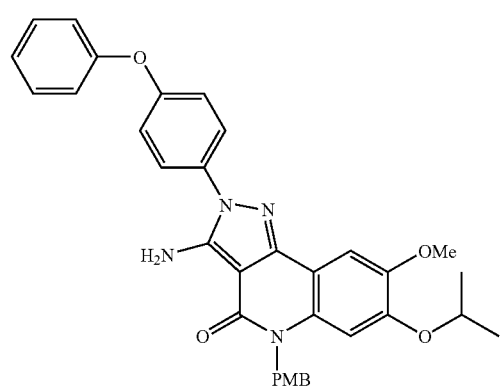

In the same manner as shown in Reference Example 25, the target compound was obtained.

¹H-NMR (DMSO-d6, 300 MHz): δ 1.10 (6H, d, J=6.0 Hz), 3.74 (3H, s), 3.77 (3H, s), 4.52 (1H, sept, J=6.0 Hz), 5.40 (2H, br s), 6.49 (2H, br s), 6.80 (1H, s), 6.86 (2H, d, J=8.4 Hz), 7.10 (2H, d, J=8.7 Hz), 7.17-7.21 (5H, m), 7.37 (1H, s), 7.41-7.47 (2H, m), 7.66 (2H, d, J=9.0 Hz).

LC/MS (ESI): m/z 577.2 (M+1).

Reference Example 79

3-amino-7-isopropoxy-5-(4-methoxybenzyl)-2-(4-methoxyphenyl)-2,5-dihydro-4H-pyrazolo[4,3-c]quinolin-4-one

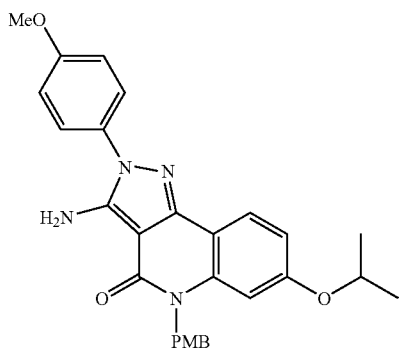

In the same manner as shown in Reference Example 25, the target compound was obtained ¹H-NMR (DMSO-d6, 300 MHz): δ 1.18 (6H, d, J=5.9 Hz), 3.70 (3H, s), 3.84 (3H, s), 4.61 (1H, sept, J=5.9 Hz), 5.38 (2H, br s), 6.39 (2H, br s), 6.72-6.78 (2H, m), 6.88 (2H, d, J=9.0 Hz), 7.12 (2H, d, J=9.0 Hz), 7.18 (2H, d, J=9.0 Hz), 7.57 (2H, d, J=9.0 Hz), 7.86 (1H, d, J=8.4 Hz).

LC/MS (ESI): m/z 485.1 (M+1).

Reference Example 80

3-amino-7-isopropoxy-5-(4-methoxybenzyl)-2-(2-methoxy-5-methylpyrimidin-4-yl)-2,5-dihydro-4H-pyrazolo[4,3-c]quinolin-4-one

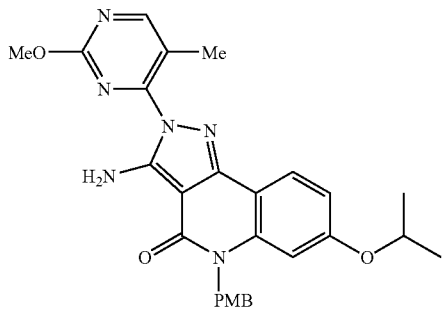

In the same manner as shown in Reference Example 25, the target compound was obtained ¹H-NMR (DMSO-d6, 300 MHz): δ 1.18 (6H, d, J=5.7 Hz), 2.53 (3H, s), 3.70 (3H, s), 3.98 (3H, s), 4.63 (1H, sept, J=5.7 Hz), 5.38 (2H, br s), 6.72 (1H, s), 6.80 (1H, d, J=8.7 Hz), 6.89 (2H, d, J=8.5 Hz), 7.20 (2H, d, J=8.5 Hz), 7.43 (2H, br s), 7.90 (1H, d, J=8.7 Hz), 8.64 (1H, s).

LC/MS (ESI): m/z 501.1 (M+1).

Reference Example 81

3-amino-8-methoxy-5-(4-methoxybenzyl)-2-(4-phenoxyphenyl)-2,5-dihydro-4H-pyrazolo[4,3-c]quinolin-4-one

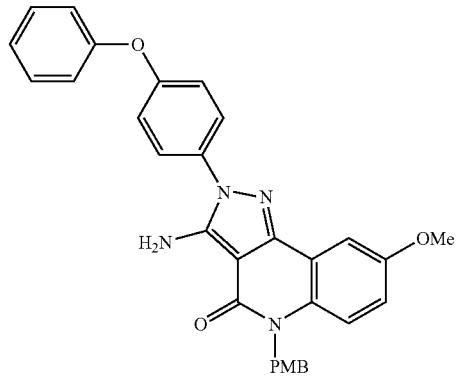

In the same manner as shown in Reference Example 25, the target compound was obtained.

¹H-NMR (DMSO-d6, 300 MHz): δ 3.69 (3H, s), 3.78 (3H, s), 5.37 (2H, br s), 6.53 (2H, br s), 6.86 (2H, d, J=8.4 Hz), 6.97-7.01 (2H, m), 7.09-7.26 (6H, m), 7.36-7.47 (4H, m), 7.67 (2H, d, J=8.7 Hz).

LC/MS (ESI): m/z 519.1 (M+1).

Reference Example 82

3-amino-7-isopropoxy-5-(4-methoxybenzyl)-2-(4-phenoxyphenyl)-2,5-dihydro-4H-pyrazolo[4,3-c]quinolin-4-one

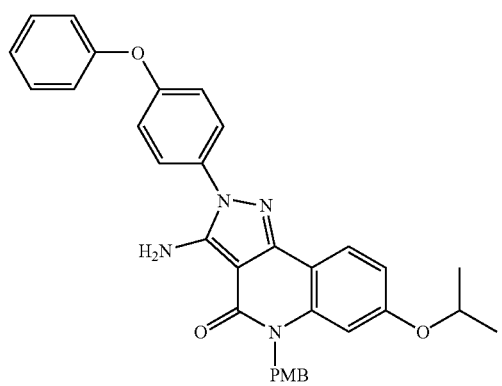

In the same manner as shown in Reference Example 25, the target compound was obtained.

¹H-NMR (DMSO-d6, 300 MHz): δ 1.18 (6H, d, J=6.0 Hz), 3.70 (3H, s), 4.61 (1H, sept, J=6.0 Hz), 5.39 (2H, br s), 6.52 (2H, br s), 6.73-6.79 (2H, m), 6.89 (2H, d, J=8.9 Hz), 7.10-7.23 (7H, m), 7.43-7.48 (2H, m), 7.67 (2H, d, J=8.9 Hz), 7.87 (1H, d, J=8.7 Hz).

LC/MS (ESI): m/z 547.2 (M+1).

Reference Example 83

3-amino-7-isopropoxy-5-(4-methoxybenzyl)-2-(2-methyl-4-phenoxyphenyl)-2,5-dihydro-4H-pyrazolo[4,3-c]quinolin-4-one

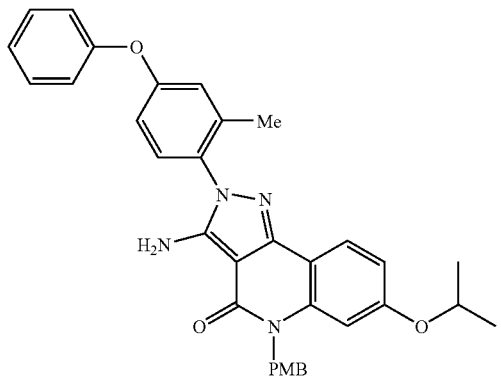

In the same manner as shown in Reference Example 25, the target compound was obtained.

¹H-NMR (DMSO-d6, 300 MHz): δ 1.17 (6H, d, J=5.7 Hz), 2.09 (3H, s), 3.70 (3H, s), 4.61 (1H, sept, J=5.7 Hz), 5.38 (2H, br s), 6.34 (2H, br s), 6.72 (1H, s), 6.75 (1H, d, J=8.4 Hz), 6.89 (2H, d, J=7.5 Hz), 6.97 (1H, dd, J=8.4, 2.4 Hz), 7.09-7.14 (3H, m), 7.17-7.22 (3H, m), 7.40-7.47 (3H, m), 7.83 (1H, dd, J=8.7, 1.2 Hz).

LC/MS (ESI): m/z 561.2 (M+1).

Reference Example 84

3-amino-7-isopropoxy-5-(4-methoxybenzyl)-2-(3-methoxy-4-phenoxyphenyl)-2,5-dihydro-4H-pyrazolo[4,3-c]quinolin-4-one

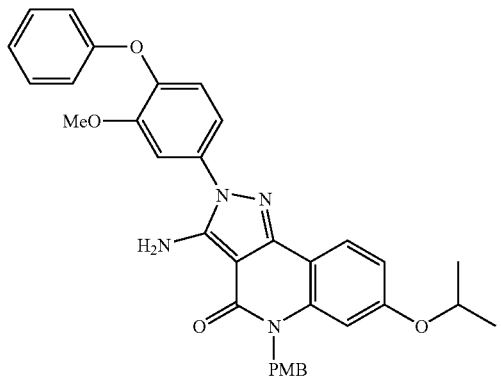

In the same manner as shown in Reference Example 25, the target compound was obtained.

¹H-NMR (DMSO-d6, 300 MHz): δ 1.18 (6H, d, J=5.7 Hz), 3.70 (3H, s), 3.84 (3H, s), 4.62 (1H, sept, J=5.7 Hz), 5.39 (2H, br s), 6.61 (2H, br s), 6.73 (1H, s), 6.78 (1H, d, J=9.0 Hz), 6.89 (2H, d, J=7.8 Hz), 6.95 (2H, d, J=7.5 Hz), 7.05-7.10 (1H, m), 7.17-7.27 (4H, m), 7.33-7.42 (3H, m), 7.89 (1H, d, J=8.4 Hz).

LC/MS (ESI): m/z 577.2 (M+1).

Reference Example 85

3-amino-5-(4-methoxybenzyl)-2-(3-methoxy-4-phenoxyphenyl)-2,5-dihydro-4H-pyrazolo[4,3-c]quinolin-4-one

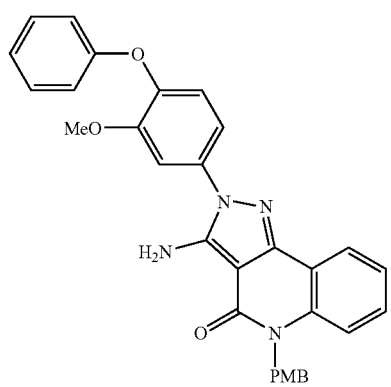

In the same manner as shown in Reference Example 25, the target compound was obtained.

¹H-NMR (DMSO-d6, 300 MHz): δ 3.70 (3H, s), 3.84 (3H, s), 5.41 (2H, br s), 6.65 (2H, br s), 6.80-7.43 (15H, m), 8.02 (1H, d, J=7.8 Hz).

LC/MS (ESI): m/z 518.6 (M+1).

Reference Example 86

3-amino-5-(4-methoxybenzyl)-2-[4-(phenylsulfonyl)phenyl]-2,5-dihydro-4H-pyrazolo[4,3-c]quinolin-4-one

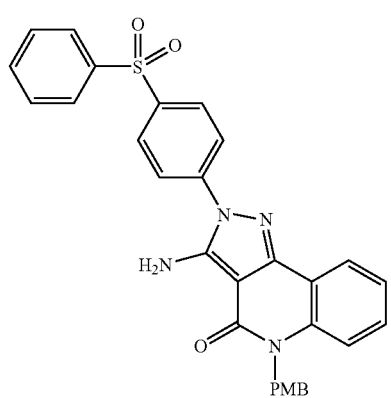

In the same manner as shown in Reference Example 25, the target compound was obtained.

¹H-NMR (DMSO-d6, 300 MHz): δ 3.69 (3H, s), 5.39 (2H, br s), 6.85-6.88 (4H, m), 7.17-7.31 (3H, m), 7.33 (1H, d, J=8.4 Hz), 7.39-7.58 (1H, m), 7.61-7.76 (3H, m), 7.97-8.05 (5H, m), 8.16 (2H, d, J=8.4 Hz).

LC/MS (ESI): m/z 537.2 (M+1).

Reference Example 87

3-amino-5-(4-methoxybenzyl)-2-(5-methoxy-2-methyl-4-phenoxyphenyl)-2,5-dihydro-4H-pyrazolo[4,3-c]quinolin-4-one

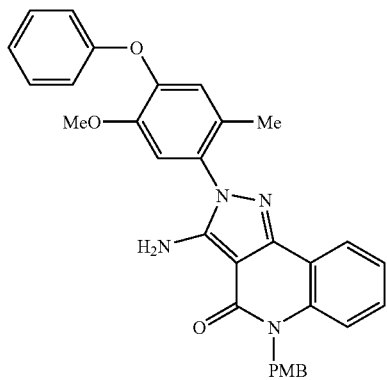

In the same manner as shown in Reference Example 25, the target compound was obtained.

$^1$H-NMR (DMSO-d6, 300 MHz): δ 2.02 (3H, s), 3.70 (3H, s), 3.76 (3H, s), 5.40 (2H, br s), 6.46 (2H, br s), 6.88 (2H, d, J=7.8 Hz), 6.97 (2H, d, J=8.7 Hz), 7.04-7.09 (1H, m), 7.11 (1H, s), 7.14-7.21 (3H, m), 7.22 (1H, s), 7.30-7.41 (4H, m), 7.97 (1H, d, J=7.8 Hz).

LC/MS (ESI): m/z 533.2 (M+1).

Reference Example 88

5-(4-methoxybenzyl)-2-(5-methoxy-2-methylphenyl)-1,2-dihydro-5H-pyrazolo[4,3-c]quinoline-3,4-dione

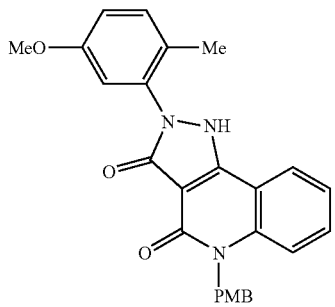

In the same manner as shown in Reference Example 25, the target compound was obtained.

$^1$H-NMR (DMSO-d6, 300 MHz): δ 2.08 (3H, br s), 3.70 (3H, s), 3.78 (3H, s), 5.42 (2H, br s), 6.87 (2H, d, J=8.4 Hz), 7.00-7.05 (2H, m), 7.18-7.20 (3H, m), 7.31-7.36 (2H, m), 7.42 (1H, br s), 8.00 (1H, d, J=7.8 Hz).

LC/MS (ESI): m/z 442.1 (M+1).

Reference Example 89

3-amino-7-isopropoxy-8-methoxy-5-(4-methoxybenzyl)-2-(2-methylphenyl)-2,5-dihydro-4H-pyrazolo[4,3-c]quinolin-4-one

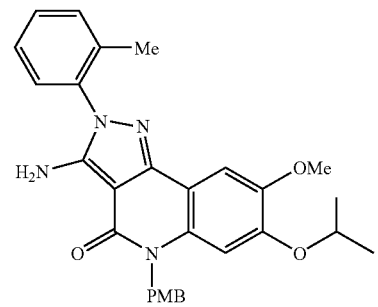

In the same manner as shown in Reference Example 25, the target compound was obtained.

$^1$H-NMR (DMSO-d6, 300 MHz): δ 1.10 (6H, d, J=6.0 Hz), 2.13 (3H, s), 3.69 (3H, s), 3.75 (3H, s), 5.01 (1H, sept, J=6.0 Hz), 5.39 (2H, br s), 6.25 (2H, br s), 6.80 (1H, s), 6.87 (2H, d, J=8.5 Hz), 7.20 (2H, d, J=8.5 Hz), 7.35 (1H, s), 7.38-7.47 (4H, m).

LC/MS (ESI): m/z 499.1 (M+1).

Reference Example 90

3-amino-7-isopropoxy-5-(4-methoxybenzyl)-2-(5-methoxy-2-methyl-4-phenoxyphenyl)-2,5-dihydro-4H-pyrazolo[4,3-c]quinolin-4-one

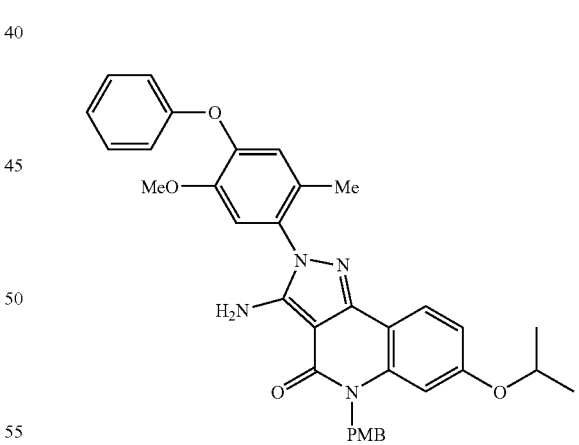

In the same manner as shown in Reference Example 25, the target compound was obtained.

$^1$H-NMR (DMSO-d6, 300 MHz): δ 1.18 (6H, d, J=6.0 Hz), 2.01 (3H, s), 3.70 (3H, s), 3.75 (3H, s), 4.61 (1H, sept, J=6.0 Hz), 5.38 (2H, br s), 6.42 (2H, br s), 6.70-6.73 (1H, m), 6.76 (1H, d, J=2.4 Hz), 6.89 (2H, d, J=8.4 Hz), 6.96 (2H, d, J=7.8 Hz), 7.02-7.08 (1H, m), 7.09 (1H, s), 7.17-7.20 (3H, m), 7.32-7.37 (2H, m), 7.83 (1H, d, J=8.7 Hz).

LC/MS (ESI): m/z 591.2 (M+1).

Reference Example 91

3-amino-2-(5-fluoro-2-methylphenyl)-7-isopropoxy-5-(4-methoxybenzyl)-2,5-dihydro-4H-pyrazolo[4,3-c]quinolin-4-one

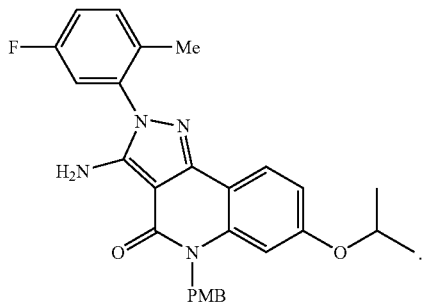

In the same manner as shown in Reference Example 25, the target compound was obtained.

$^1$H-NMR (DMSO-d6, 300 M Hz): δ 1.17 (6H, d, J=6.0 Hz), 2.10 (3H, s), 3.70 (3H, s), 4.61 (1H, sept, J=6.0 Hz), 5.38 (2H, br s), 6.43 (2H, br s), 6.72 (1H, d, J=2.1 Hz), 6.76 (1H, dd, J=8.7, 2.1 Hz), 6.90 (2H, d, J=8.7 Hz), 7.20 (2H, d, J=8.7 Hz), 7.30-7.39 (2H, m), 7.49 (1H, d, t=7.2 Hz), 7.82 (1H, d, J=8.7 Hz).

LC/MS (ESI): m/z 486.5 (M+1).

Reference Example 92

3-amino-2-(5-chloro-2-methylphenyl)-7-isopropoxy-5-(4-methoxybenzyl)-2,5-dihydro-4H-pyrazolo[4,3-c]quinolin-4-one

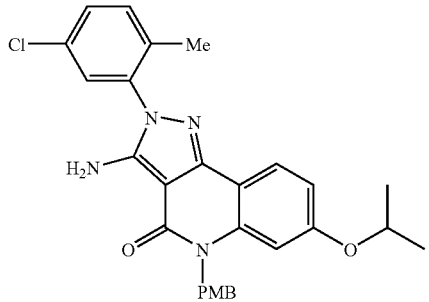

In the same manner as shown in Reference Example 25, the target compound was obtained.

$^1$H-NMR (DMSO-d6, 300 MHz): δ 1.17 (6H, d, J=6.0 Hz), 2.11 (3H, s), 3.70 (3H, s), 4.61 (1H, sept, J=6.0 Hz), 5.38 (2H, br s), 6.47 (2H, br s), 6.72 (1H, d, J=2.1 Hz), 6.76 (1H, dd, J=8.4, 2.1 Hz), 6.86-6.93 (2H, m), 7.16-7.33 (2H, m), 7.46-7.57 (3H, m), 7.82 (1H, d, J=8.4 Hz).

LC/MS (ESI): m/z 503.0 (M+1).

Reference Example 93

3-amino-7-isopropoxy-2-(2-isopropylphenyl)-5-(4-methoxybenzyl)-2,5-dihydro-4H-pyrazolo[4,3-c]quinolin-4-one

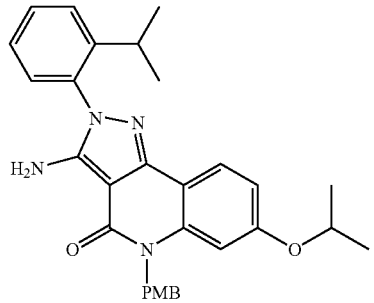

In the same manner as shown in Reference Example 25, the target compound was obtained.

$^1$H-NMR (DMSO-d6, 300 MHz): δ 1.14-1.19 (12H, m), 2.68-2.82 (1H, m), 3.71 (3H, s), 4.61 (1H, sept, J=6.0 Hz), 5.38 (2H, br s), 6.24 (2H, br s), 6.72 (1H, d, J=1.8 Hz), 6.75 (1H, dd, J=8.7, 1.8 Hz), 6.86-6.93 (2H, m), 7.17-7.23 (2H, m), 7.34-7.44 (2H, m), 7.52-7.58 (2H, m), 7.81 (1H, d, J=8.7 Hz).

LC/MS (ESI): m/z 497.2 (M+1).

Reference Example 94

3-amino-7-isopropoxy-5-(4-methoxybenzyl)-2-{4-[(6-methylpyridin-3-yl)oxy]phenyl}-2,5-dihydro-4H-pyrazolo[4,3-c]quinolin-4-one

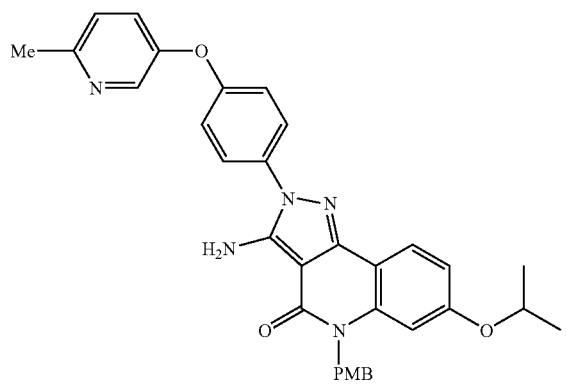

In the same manner as shown in Reference Example 25, the target compound was obtained.

$^1$H-NMR (DMSO-d6, 300 MHz): δ 1.18 (6H, d, J=6.0 Hz), 2.49 (3H, s), 3.70 (3H, s), 4.61 (1H, sept, J=6.0 Hz), 5.38 (2H, br s), 6.53 (2H, br s), 6.72 (1H, d, J=2.1 Hz), 6.77 (1H, dd, J=8.7, 2.1 Hz), 6.85-6.94 (2H, m), 7.15-7.24 (4H, m), 7.34 (1H, d, J=8.4 Hz), 7.46 (1H, dd, J=8.4, 3.0 Hz), 7.64-7.70 (2H, m), 7.86 (1H, d, J=8.7 Hz), 8.33 (1H, d, J=3.0 Hz).

LC/MS (ESI): m/z 562.2 (M+1).

Reference Example 95

3-amino-5-(4-methoxybenzyl)-2-(5-methyl-1H-benzoimidazol-4-yl)-2,5-dihydro-4H-pyrazolo[4,3-c]quinolin-4-one and 3-amino-5-(4-methoxybenzyl)-2-(6-methyl-1H-benzoimidazol-7-yl)-2,5-dihydro-4H-pyrazolo[4,3-c]quinolin-4-one

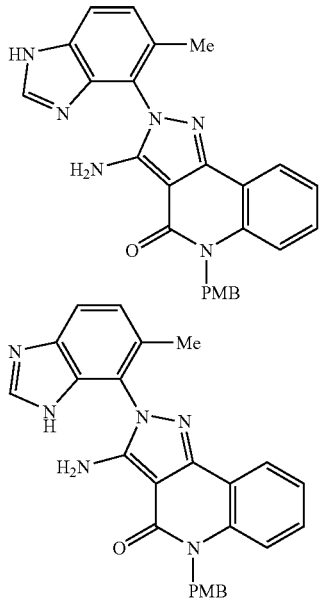

In the same manner as shown in Reference Example 25, the target compound was obtained.

$^1$H-NMR (DMSO-d6, 300 MHz): δ 2.20 (1.5H, s,), 2.23 (1.5H, s), 3.71 (3H, s), 5.43 (2H, br s), 6.08 (1H, br s), 6.36 (1H, br s), 6.87-6.92 (2H, m), 7.14-7.45 (6H, m), 7.64 (0.5H, d, J=8.1 Hz), 7.75 (0.5H, d, J=8.1 Hz), 7.93-7.98 (1H, m), 8.16 (0.5H, s), 8.22 (0.5H, s), 12.5 (0.5H, br s), 12.7 (0.5H, br s).

LC/MS (ESI): m/z 451.1 (M+1).

Reference Example 96

3-amino-2-(1,3-benzothiazol-2-yl)-5-(4-methoxybenzyl)-2,5-dihydro-4H-pyrazolo[4,3-c]quinolin-4-one

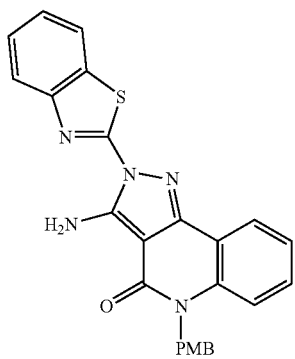

In the same manner as shown in Reference Example 25, the target compound was obtained.

$^1$H-NMR (DMSO-d6, 300 MHz): δ 3.70 (3H, s), 5.40 (2H, br s), 6.88 (2H, d, J=8.7 Hz), 7.20-7.28 (3H, m), 7.34-7.61 (4H, m), 8.00-8.17 (5H, m).

LC/MS (ESI): m/z 454.0 (M+1).

Reference Example 97

3-amino-7-isopropoxy-5-(4-methoxybenzyl)-2-(5-methoxy-2,4-dimethylphenyl)-2,5-dihydro-4H-pyrazolo[4,3-c]quinolin-4-one

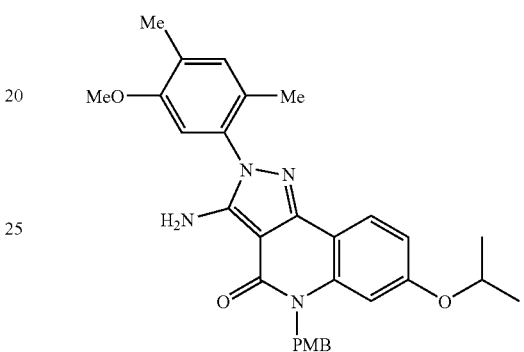

In the same manner as shown in Reference Example 25, the target compound was obtained.

$^1$H-NMR (DMSO-d6, 300 MHz): δ 1.18 (6H, d, J=5.7 Hz), 2.01 (3H, s), 2.21 (3H, s), 3.70 (3H, s), 3.80 (3H, s), 4.61 (1H, sept, J=5.7 Hz), 5.38 (2H, br s), 6.23 (2H, br s), 6.72 (1H, d, J=2.1 Hz), 6.75 (1H, dd, J=8.4, 2.1 Hz), 6.87-6.95 (3H, m), 7.16-7.22 (3H, m), 7.83 (1H, d, J=8.4 Hz).

LC/MS (ESI): m/z 513.2 (M+1).

Reference Example 98

3-amino-5-(4-methoxybenzyl)-2-[4-(2-methoxyphenoxy)-2-methylphenyl]-2,5-dihydro-4H-pyrazolo[4,3-c]quinolin-4-one

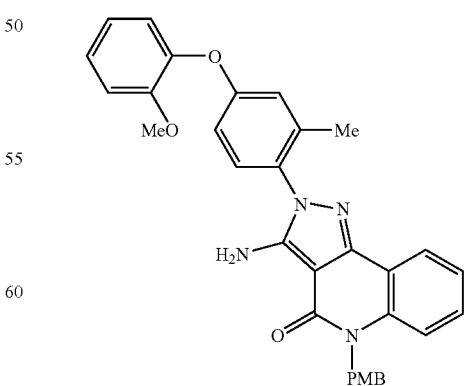

In the same manner as shown in Reference Example 25, the target compound was obtained.

¹H-NMR (DMSO-d6, 300 MHz): δ 2.06 (3H, s), 3.70 (3H, s), 3.79 (3H, s), 5.38 (2H, br s), 6.32 (2H, br s), 6.74-7.38 (14H, m), 7.94 (1H, d, J=7.2 Hz).

LC/MS (ESI): m/z 533.2 (M+1).

Reference Example 99

3-amino-5-(4-methoxybenzyl)-2-(2-methyl-4-phenoxyphenyl)-2,5-dihydro-4H-pyrazolo[4,3-c]quinolin-4-one

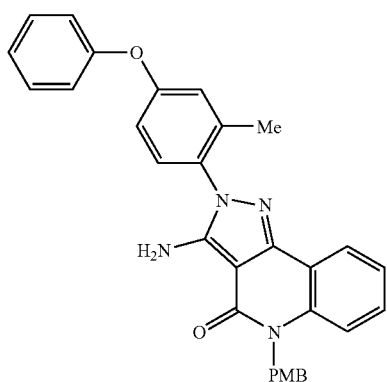

In the same manner as shown in Reference Example 25, the target compound was obtained.

¹H-NMR (DMSO-d6, 300 MHz): δ 2.07 (3H, s), 3.68 (3H, s), 5.37 (2H, br s), 6.36 (2H, br s), 6.84-6.88 (2H, m), 6.95 (1H, dd, J=8.7, 2.7 Hz), 7.07-7.20 (7H, m), 7.27-7.45 (5H, m), 7.93 (1H, d, J=8.4 Hz).

LC/MS (ESI): m/z 503.2 (M+1).

Reference Example 100

3-amino-7,9-dimethoxy-5-(4-methoxybenzyl)-2-(5-methoxy-2-methylphenyl)-2,5-dihydro-4H-pyrazolo[4,3-c]quinolin-4-one

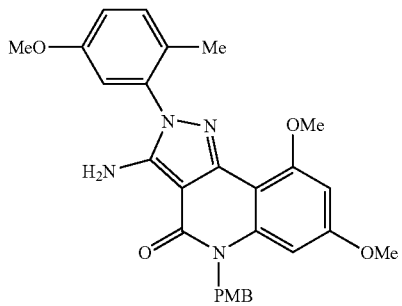

In the same manner as shown in Reference Example 25, the target compound was obtained.

¹H-NMR (DMSO-d6, 300 MHz): δ 2.01 (3H, s), 3.70 (3H, s), 3.72 (3H, s), 3.78 (3H, s), 3.81 (3H, s), 5.34 (2H, br s), 6.21 (2H, br s), 6.41 (2H, br s), 6.87 (2H, d, J=8.4 Hz), 6.95 (1H, d, J=2.7 Hz), 7.04 (1H, dd, J=8.4, 2.7 Hz), 7.19 (2H, d, J=8.4 Hz), 7.34 (1H, d, J=8.4 Hz).

LC/MS (ESI): m/z 501.1 (M+1).

Reference Example 101

3-amino-7,9-dimethoxy-5-(4-methoxybenzyl)-2-(4-phenoxyphenyl)-2,5-dihydro-4H-pyrazolo[4,3-c]quinolin-4-one

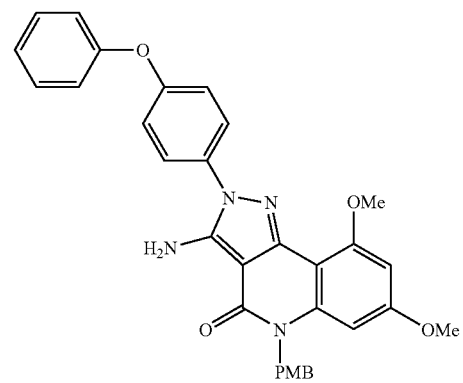

In the same manner as shown in Reference Example 25, the target compound was obtained.

¹H-NMR (DMSO-d6, 300 MHz): δ 3.69 (3H, s), 3.72 (3H, s), 3.84 (3H, s), 5.37 (2H, br s), 6.42-6.44 (4H, m), 6.86 (2H, d, J=8.4 Hz), 7.10 (2H, d, J=8.7 Hz), 7.16-7.21 (5H, m), 7.44 (2H, t, J=7.8 Hz), 7.63 (2H, d, J=8.7 Hz).

LC/MS (ESI): m/z 549.2 (M+1).

Reference Example 102

3-amino-7,9-dimethoxy-5-(4-methoxybenzyl)-2-(2-methylphenyl)-2,5-dihydro-4H-pyrazolo[4,3-c]quinolin-4-one

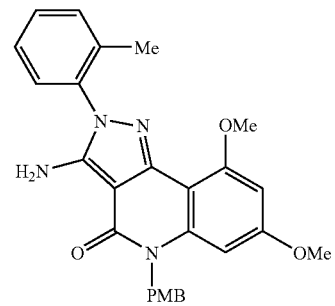

In the same manner as shown in Reference Example 25, the target compound was obtained.

¹H-NMR (DMSO-d6, 300 MHz): δ 2.10 (3H, s), 3.69 (3H, s), 3.71 (3H, s), 3.79 (3H, s), 5.34 (2H, br s), 6.18 (2H, br s), 6.28 (1H, s), 6.40 (1H, s), 6.86 (2H, d, J=8.4 Hz), 7.18 (2H, d, J=8.4 Hz), 7.38-7.45 (4H, m).

LC/MS (ESI): m/z 471.2 (M+1).

Example 1

3-amino-2-phenyl-2,5-dihydro-4H-pyrazolo[4,3-c]quinolin-4-one

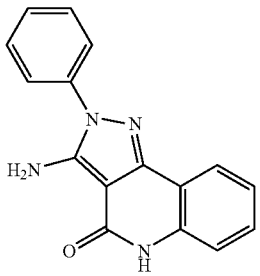

A mixture of 3-amino-5-benzyl-2-phenyl-2,5-dihydro-4H-pyrazolo[4,3-c]quinolin-4-one (0.26 g), 48% aqueous hydrobromic acid (8 ml) and acetic acid (1.3 ml) was heated at 100° C. for 36 hours. After cooling, ice was added thereto, and basified by adding an 11N aqueous sodium hydroxide solution. The precipitated crystal was collected by filtration, washed with water and dried. Methanol and ethyl acetate were added to the crystal, and the mixture was heated under reflux for 10 minutes. After cooling, the precipitated crystal was collected by filtration to obtain the target compound (47 mg).

$^1$H-NMR (DMSO-d$_6$, 200 MHz): δ 6.41 (2H, br), 7.11-7.17 (1H, m), 7.23-7.32 (1H, m), 7.36-7.51 (2H, m), 7.50-7.76 (4H, m), 7.87-7.93 (1H, m), 10.79 (1H, br).

Example 2

3-amino-2-(2-methoxyphenyl)-2,5-dihydro-4H-pyrazolo[4,3-c]quinolin-4-one

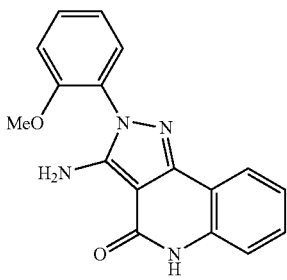

A mixture of 3-amino-5-(4-methoxybenzyl)-2-(2-methoxyphenyl)-2,5-dihydro-4H-pyrazolo[4,3-c]quinolin-4-one (370 mg), anisole (2 ml), trifluoroacetic acid (5 ml) and trifluoromethanesulfonic acid (1 ml) was stirred at room temperature for 3.5 hours. The mixture was concentrated under reduced pressure. To the mixture was added 5% sodium carbonate to adjust pH to about 9. Ethyl acetate was added to the mixture. An insoluble solid was collected by filtration, washed with water and ethyl acetate, and dried to obtain the target compound (250 mg).

$^1$H-NMR (DMSO-d$_6$, 200 MHz): δ 3.82 (3H, s), 6.06 (2H, br), 7.07-7.15 (2H, m), 7.26 (2H, d, J=7.8 Hz), 7.34-7.57 (3H, m), 7.84 (1H, d, J=7.0 Hz), 10.69 (1H, br).

LC/MS (ESI): m/z 307.0 (M+1).

Example 3

3-amino-2-(3-methoxyphenyl)-2,5-dihydro-4H-pyrazolo[4,3-c]quinolin-4-one

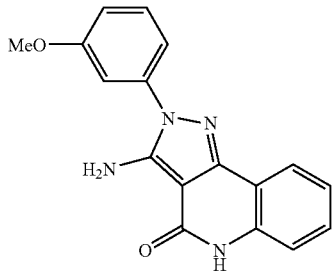

In the same manner as shown in Example 2, the target compound was obtained.

$^1$H-NMR (DMSO-d$_6$, 300 MHz): δ 3.84 (3H, s), 6.42 (2H, br), 7.00-7.03 (1H, m), 7.10-7.16 (1H, m), 7.20-7.27 (3H, m), 7.36-7.39 (1H, m), 7.41-7.50 (1H, m), 7.90 (1H, dd, J=7.8, 1.5 Hz), 10.76 (1H, br).

LC/MS (ESI): m/z 307.1 (M+1).

Example 4

3-amino-2-(4-methoxyphenyl)-2,5-dihydro-4H-pyrazolo[4,3-c]quinolin-4-one

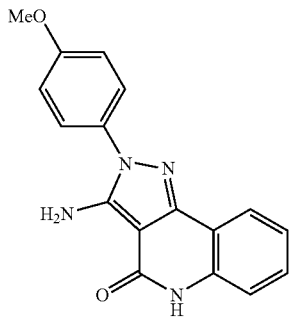

In the same manner as shown in Example 2, the target compound was obtained.

$^1$H-NMR (DMSO-d$_6$, 200 MHz): δ 3.84 (3H, s), 6.28 (2H, br), 7.10-7.60 (7H, m), 7.87-7.92 (1H, m), 10.77 (1H, br).

Example 5

3-amino-2-(3-fluorophenyl)-2,5-dihydro-4H-pyrazolo[4,3-c]quinolin-4-one

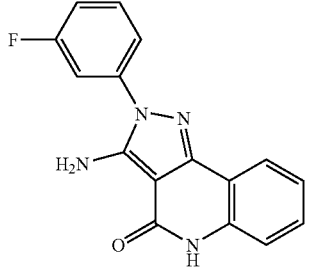

In the same manner as shown in Example 2, the target compound was obtained.

¹H-NMR (DMSO-d$_6$, 300 MHz): δ 6.56 (2H, br), 7.11-7.16 (1H, m), 7.25-7.32 (2H, m), 7.37-7.43 (1H, m), 7.52-7.64 (3H, m), 7.90 (1H, dd, J=7.8, 1.5 Hz), 10.79 (1H, br).

LC/MS (ESI): m/z 295.1 (M+1).

Example 6

3-amino-2-[3-(trifluoromethyl)phenyl]-2,5-dihydro-4H-pyrazolo[4,3-c]quinolin-4-one

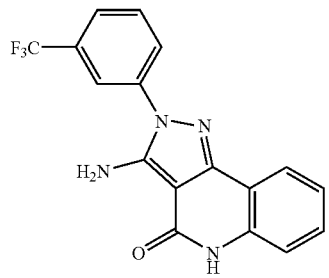

In the same manner as shown in Example 2, the target compound was obtained.

¹H-NMR (DMSO-d$_6$, 300 MHz): δ 6.64 (2H, br), 7.12-7.17 (1H, m), 7.27 (1H, d, J=7.8 Hz), 7.39-7.44 (1H, m), 7.81-7.82 (2H, m), 7.93 (1H, d, J=6.9 Hz), 8.00-8.02 (2H, m), 10.83 (1H, br).

LC/MS (ESI): m/z 345.0 (M+1).

Example 7

3-amino-2-(3-nitrophenyl)-2,5-dihydro-4H-pyrazolo[4,3-c]quinolin-4-one

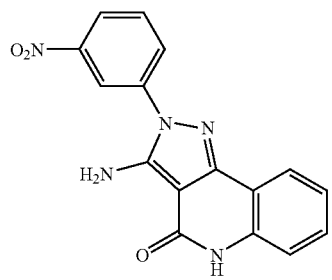

In the same manner as shown in Example 2, the target compound was obtained.

¹H-NMR (DMSO-d$_6$, 200 MHz): δ 6.78 (2H, br), 7.12-7.19 (1H, m), 7.28 (1H, d, J=7.6 Hz), 7.39-7.46 (1H, m), 7.82-7.95 (2H, m), 8.15-8.19 (1H, m), 8.26-8.30 (1H, m), 8.46-8.48 (1H, m), 10.85 (1H, br).

LC/MS (ESI): m/z 322.1 (M+1).

Example 8

3-amino-2-(4-chlorophenyl)-2,5-dihydro-4H-pyrazolo[4,3-c]quinolin-4-one

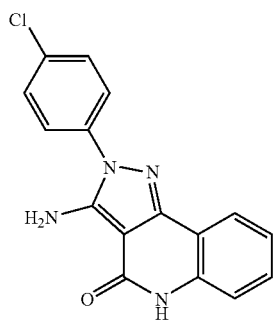

In the same manner as shown in Example 2, the target compound was obtained.

¹H-NMR (DMSO-d$_6$, 200 MHz): δ 6.53 (2H, br), 7.10-7.18 (1H, m), 7.23-7.30 (1H, m), 7.37-7.44 (1H, m), 7.60-7.73 (4H, m), 7.89-7.93 (1H, m), 10.82 (1H, br).

Example 9

3-amino-2-(6-methoxypyridin-2-yl)-2,5-dihydro-4H-pyrazolo[4,3-c]quinolin-4-one

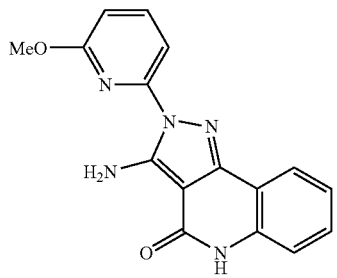

In the same manner as shown in Example 2, the target compound was obtained.

¹H-NMR (DMSO-d$_6$, 300 MHz): δ 3.95 (3H, s), 6.80 (1H, d, J=8.4 Hz), 7.13-7.18 (1H, m), 7.26 (1H, d, J=7.8 Hz), 7.40-7.45 (3H, m), 7.60 (1H, d, J=7.8 Hz), 7.92-7.98 (2H, m), 10.78 (1H, br).

LC/MS (ESI): m/z 308.1 (M+1).

Example 10

3-amino-2-(2,5-difluorophenyl)-2,5-dihydro-4H-pyrazolo[4,3-c]quinolin-4-one

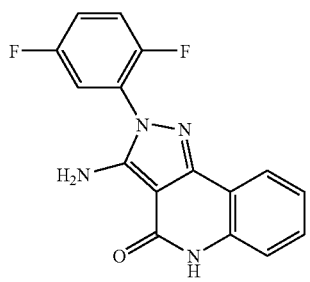

In the same manner as shown in Example 2, the target compound was obtained.

¹H-NMR (DMSO-d₆, 200 MHz): δ 6.62 (2H, br), 7.08-7.16 (1H, m), 7.26 (1H, d, J=7.2 Hz), 7.36-7.65 (4H, m), 7.85 (1H, dd, J=7.6, 1.0 Hz), 10.75 (1H, br).

LC/MS (ESI): m/z 313.1 (M+1).

Example 11

3-amino-2-(2,5-dimethylphenyl)-2,5-dihydro-4H-pyrazolo[4,3-c]quinolin-4-one

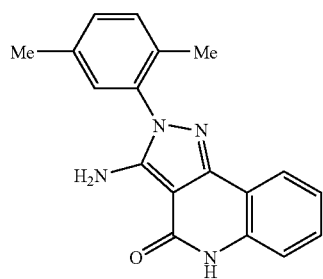

In the same manner as shown in Example 2, the target compound was obtained.

¹H-NMR (DMSO-d₆, 300 MHz): δ 2.07 (3H, s), 2.36 (3H, s), 6.09 (2H, s), 7.06-7.13 (1H, m), 7.21-7.40 (5H, m), 7.83-7.86 (1H, m), 10.70 (1H, br).

LC/MS (ESI): m/z 305.1 (M+1).

Example 12

3-amino-2-(2,5-dichlorophenyl)-2,5-dihydro-4H-pyrazolo[4,3-c]quinolin-4-one

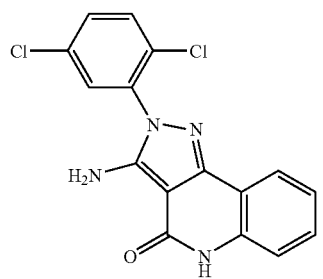

In the same manner as shown in Example 2, the target compound was obtained.

¹H-NMR (DMSO-d₆, 300 MHz): δ 6.57 (2H, s), 7.08-7.14 (1H, m), 7.24-7.27 (1H, m), 7.35-7.42 (1H, m), 7.68 (1H, dd, J=8.4, 2.4 Hz), 7.75 (1H, d, J=8.4 Hz), 7.80-7.85 (2H, m), 10.75 (1H, s).

LC/MS (ESI): m/z 344.9 (M+1).

Example 13

3-amino-2-(2,5-dimethoxyphenyl)-2,5-dihydro-4H-pyrazolo[4,3-c]quinolin-4-one

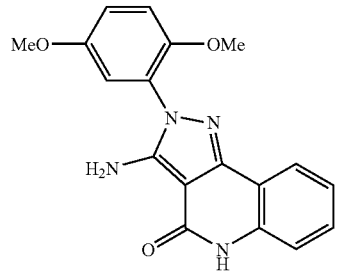

In the same manner as shown in Example 2, the target compound was obtained.

¹H-NMR (DMSO-d₆, 300 MHz): δ 3.65 (3H, s), 3.71 (3H, s), 4.94 (2H, s), 6.39 (1H, s), 6.70 (1H, s), 7.15-7.28 (2H, m), 7.57 (1H, d, J=7.8 Hz), 8.26 (1H, d, J=7.8 Hz), 9.23 (1H, s), 11.27 (1H, s).

LC/MS (ESI): m/z 337.0 (M+1).

Example 14

3-amino-2-(2-chloro-5-methoxyphenyl)-2,5-dihydro-4H-pyrazolo[4,3-c]quinolin-4-one

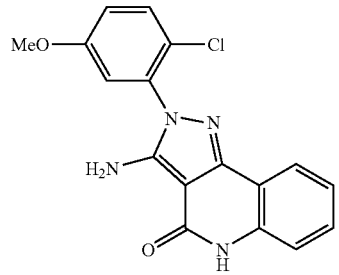

In the same manner as shown in Example 2, the target compound was obtained.

¹H-NMR (DMSO-d₆, 300 MHz): δ 3.81 (3H, s), 6.37 (2H, s), 7.07-7.40 (5H, m), 7.58 (1H, d, J=8.7 Hz), 7.83 (1H, dd, J=7.8, 1.2 Hz), 10.71 (1H, br).

LC/MS (ESI): m/z 341.1 (M+1).

Example 15

3-amino-2-(5-methoxy-2-methylphenyl)-2,5-dihydro-4H-pyrazolo[4,3-c]quinolin-4-one

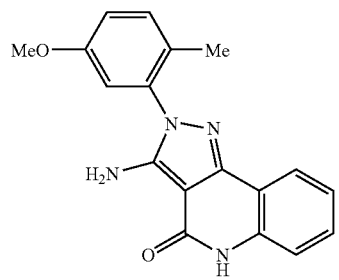

In the same manner as shown in Example 2, the target compound was obtained.

¹H-NMR (DMSO-d₆, 300 MHz): δ 2.02 (3H, s), 3.79 (3H, s), 6.12 (2H, s), 6.96 (1H, d, J=2.7 Hz), 7.04 (1H, dd, J=8.4, 2.7 Hz), 7.07-7.14 (1H, m), 7.26 (1H d, J=7.5 Hz), 7.32-7.42 (2H, m), 7.85 (1H, d, J=8.4 Hz), 10.71 (1H br).

LC/MS (ESI): m/z 321.2 (M+1).

Example 16

3-amino-2-(2,4-dichloro-5-methoxyphenyl)-2,5-dihydro-4H-pyrazolo[4,3-c]quinolin-4-one

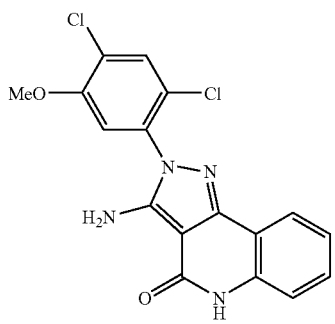

In the same manner as shown in Example 2, the target compound was obtained.

¹H-NMR (DMSO-d₆, 300 MHz): δ 3.92 (3H, s), 6.46 (2H, s), 7.07-7.14 (1H, m), 7.25 (1H, d, J=7.8 Hz), 7.34-7.41 (1H, m), 7.43 (1H, s), 7.83-7.87 (2H, m), 10.70 (1H, s).

LC/MS (ESI): m/z 375.0 (M+1).

Example 17 methyl 3-(3-amino-4-oxo-4,5-dihydro-2H-pyrazolo[4,3-c]quinolin-2-yl)benzoate

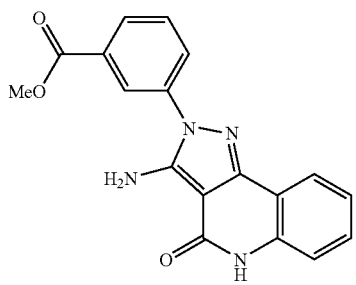

In the same manner as shown in Example 2, the target compound was obtained.

¹H-NMR (DMSO-d₆, 200 MHz): δ 3.91 (3H, s), 6.58 (2H, br), 7.11-7.18 (1H, m), 7.27 (1H, d, J=8.4 Hz), 7.38-7.45 (1H, m), 7.69-7.77 (1H, m), 7.91-8.03 (3H, m), 8.21 (1H, s), 10.88 (1H, br).

LC/MS (ESI): m/z 335.0 (M+1).

Example 18

4-(3-amino-4-oxo-4,5-dihydro-2H-pyrazolo[4,3-c]quinolin-2-yl)benzenesulfonamide

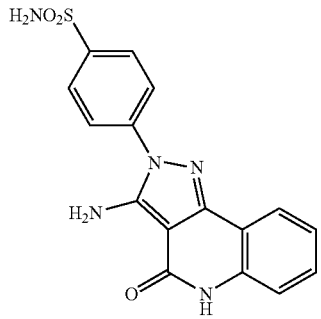

In the same manner as shown in Example 2, the target compound was obtained.

¹H-NMR (DMSO-d₆, 200 MHz): δ 6.45 (2H, br), 7.10-7.18 (1H, m), 7.23-7.28 (1H, m), 7.37-7.46 (1H, m), 7.51 (2H, br), 7.86-8.02 (5H, m), 10.82 (1H, br).

Example 19

3-amino-8-methoxy-2-phenyl-2,5-dihydro-4H-pyrazolo[4,3-c]quinolin-4-one

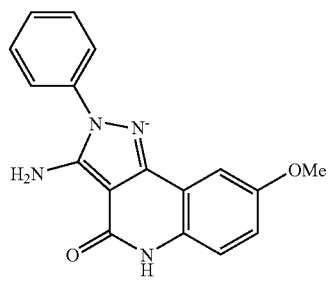

In the same manner as shown in Example 2, the target compound was obtained.

¹H-NMR (DMSO-d₆, 200 MHz): δ 3.80 (3H, s), 6.40 (2H, br), 7.01-7.06 (1H, m), 7.19-7.24 (1H, m), 7.36-7.39 (1H, m), 7.43-7.50 (1H, m), 7.55-7.64 (2H, m), 7.66-7.72 (2H, m), 10.70 (1H, br).

Example 20

3-amino-7,8-dimethoxy-2-(5-methoxy-2-methylphenyl)-2,5-dihydro-4H-pyrazolo[4,3-c]quinolin-4-one

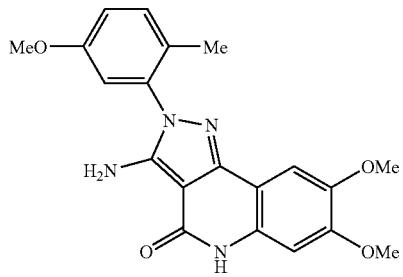

In the same manner as shown in Example 2, the target compound was obtained.

¹H-NMR (DMSO-d₆, 300 MHz): δ 2.01 (3H, s), 3.34 (3H, s), 3.78 (6H, s), 6.10 (2H, br), 6.86 (1H, s), 6.94 (1H, s), 7.02 (1H, d, J=8.6 Hz), 7.27 (1H, s), 7.32 (1H, d, J=8.6 Hz), 10.51 (1H, s).

LC/MS (ESI): m/z 381.0 (M+1).

Example 21

3-amino-2-(2-chloro-5-methoxyphenyl)-7-hydroxy-8-methoxy-2,5-dihydro-4H-pyrazolo[4,3-c]quinolin-4-one

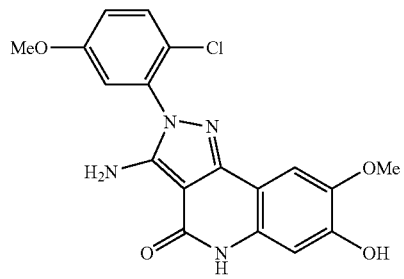

In the same manner as shown in Example 2, the target compound was obtained.

¹H-NMR (DMSO-d₆, 200 MHz): δ 3.78 (3H, s), 3.82 (3H, s), 6.27 (2H, br), 6.74 (1H, s), 7.13-7.18 (2H, m), 7.23 (1H, s), 7.56-7.60 (1H, m), 9.51 (1H, s), 10.45 (1H, br).

LC/MS (ESI): m/z 387.0 (M+1).

Example 22

3-amino-7-hydroxy-8-methoxy-2-(5-methoxy-2-methylphenyl)-2,5-dihydro-4H-pyrazolo[4,3-c]quinolin-4-one

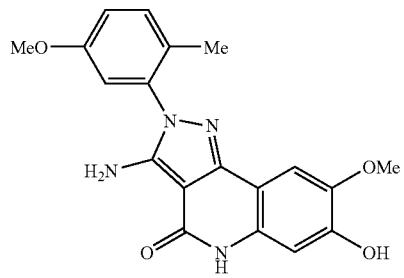

In the same manner as shown in Example 2, the target compound was obtained.

¹H-NMR (CDCl₃ 200 MHz): δ 2.13 (3H, s), 3.83 (3H, s), 3.93 (3H, s), 5.07 (2H, br), 6.06 (1H, s), 6.77 (1H, s), 6.96 (1H, d, J=2.8 Hz), 7.00 (1H, dd, J=8.4, 2.8 Hz), 7.30 (1H, d, J=8.4 Hz), 7.53 (1H, s), 8.96 (1H, br).

LC/MS (ESI): m/z 367.0 (M+1).

Example 23

3-amino-2-(2-chloro-5-methoxyphenyl)-7-nitro-2,5-dihydro-4H-pyrazolo[4,3-c]quinolin-4-one

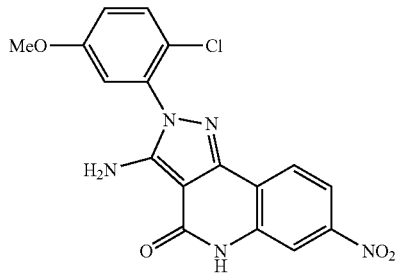

In the same manner as shown in Example 2, the target compound was obtained.

¹H-NMR (DMSO-d₆, 300 MHz): δ 3.83 (3H, s), 6.58 (2H, br), 7.15-7.25 (2H, m), 7.60 (1H, d, J=9.0 Hz), 7.94 (1H, dd, J=8.7, 2.1 Hz), 8.08 (1H, d, J=8.7 Hz), 8.14 (1H, d, J=2.1. Hz), 11.1 (1H, br)

LC/MS (ESI): m/z 385.9 (M+1).

Example 24

3-amino-7-nitro-2-phenyl-2,5-dihydro-4H-pyrazolo[4,3-c]quinolin-4-one

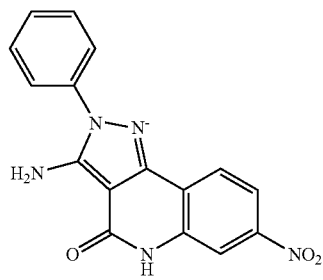

In the same manner as shown in Example 2, the target compound was obtained.

¹H-NMR (DMSO-d₆, 300 MHz): δ 6.55 (2H, br), 7.46-7.50 (1H, m), 7.56-7.61 (2H, m), 7.66-7.69 (2H, m), 7.94 (1H, dd, J=8.5, 2.3 Hz), 8.09-8.13 (2H, m), 11.17 (1H, br).

LC/MS (ESI): m/z 322.1 (M+1).

Example 25

3-amino-2-(3-methoxyphenyl)-7-nitro-2,5-dihydro-4H-pyrazolo[4,3-c]quinolin-4-one

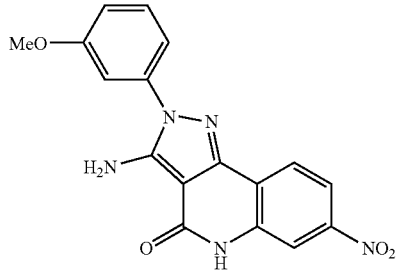

In the same manner as shown in Example 2, the target compound was obtained.

¹H-NMR (DMSO-d₆, 200 MHz): δ 3.85 (3H, s), 6.57 (2H, br), 7.04-7.12 (1H, m), 7.22-7.26 (2H, m), 7.46-7.54 (1H, m), 7.96 (1H, dd, J=8.4, 2.2 Hz), 8.11-8.15 (2H, m), 11.17 (1H. br).

LC/MS (ESI): m/z 352.0 (M+1).

Example 26

3-amino-7,8-dimethoxy-2-(4-phenoxyphenyl)-2,5-dihydro-4H-pyrazolo[4,3-c]quinolin-4-one

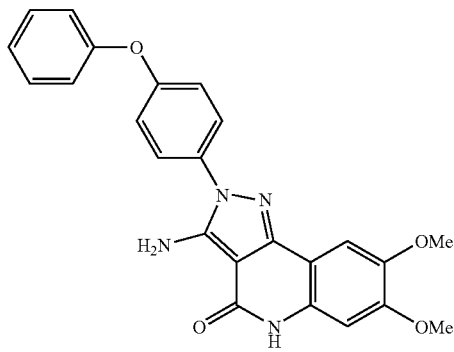

In the same manner as shown in Example 2, the target compound was obtained.

¹H-NMR (DMSO-d₆, 300 MHz): δ 3.77 (6H, s), 6.33 (2H, br), 6.85 (1H, s), 7.07-7.20 (5H, m), 7.28 (1H, s), 7.40-7.45 (2H, m), 7.63 (2H, d, J=9.0 Hz), 10.55 (1H, br).

LC/MS (ESI): m/z 429.0 (M+1).

Example 27

3-(3-amino-7,8-dimethoxy-4-oxo-4,5-dihydro-2H-pyrazolo[4,3-c]quinolin-2-yl)-4-methylbenzonitrile

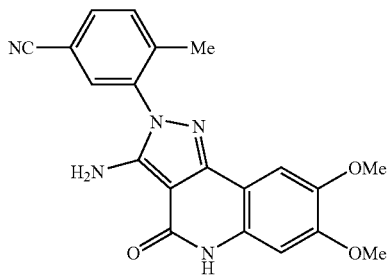

In the same manner as shown in Example 2, the target compound was obtained.

¹H-NMR (DMSO-d₆, 300 MHz): δ 2.17 (3H, s), 3.76 (3H, s), 3.78 (3H, s), 6.37 (2H, br), 6.85 (1H, s), 7.25 (1H, s), 7.64 (1H, d, J=8.1 Hz), 7.89-7.94 (2H, m), 10.54 (1H, br).

LC/MS (ESI): m/z 376.0 (M+1).

Example 28

3-amino-7,8-dimethoxy-2-(4-methylpyridin-3-yl)-2,5-dihydro-4H-pyrazolo[4,3-c]quinolin-4-one

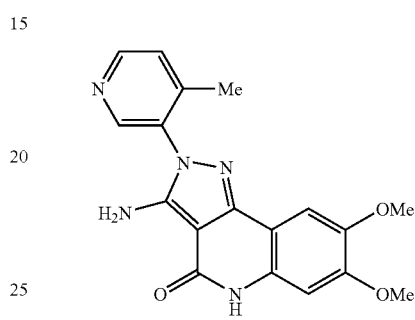

In the same manner as shown in Example 2, the target compound was obtained.

¹H-NMR (DMSO-d₆, 300 MHz): δ 2.14 (3H, s), 3.77 (3H, s), 3.78 (3H, s), 6.37 (2H, br), 6.86 (1H, s), 7.26 (1H, s), 7.49 (1H, d, J=4.9 Hz), 8.53 (1H, s), 8.57 (1H, d, J=4.9 Hz), 10.55 (1H, br).

LC/MS (ESI): m/z 352.0 (M+1).

Example 29

3-amino-7-hydroxy-2-(5-methoxy-2-methylphenyl)-2,5-dihydro-4H-pyrazolo[4,3-c]quinolin-4-one

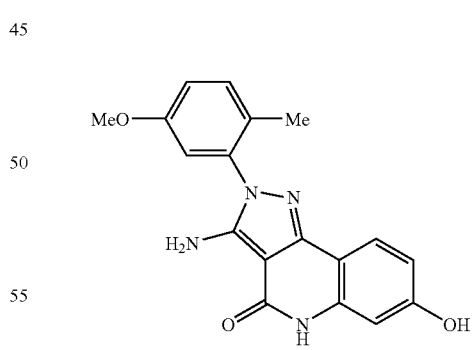

In the same manner as shown in Example 2, the target compound was obtained.

¹H-NMR (DMSO-d₆, 300 MHz): δ 2.01 (3H, s), 3.78 (3H, s), 6.08 (2H, s), 6.55 (1H, dd, J=8.7, 2.4 Hz), 6.67 (1H, d, J=2.4 Hz), 6.91-6.95 (1H, m), 7.03 (1H, dd, J=8.4, 2.7 Hz), 7.33 (1H, d, J=8.7 Hz), 7.63 (1H, d, J=8.4 Hz), 9.95 (1H, br), 10.55 (1H, s).

LC/MS (ESI): m/z 337.0 (M+1).

Example 30

2-(2-chloro-5-methoxyphenyl)-3-(dimethylamino)-2,5-dihydro-4H-pyrazolo[4,3-c]quinolin-4-one

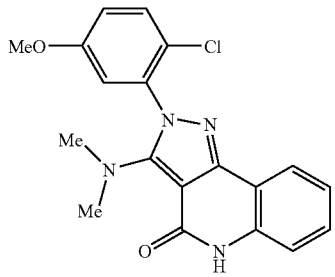

In the same manner as shown in Example 2, the target compound was obtained.

¹H-NMR (CDCl₃, 300 MHz): δ 2.97 (6H, s), 3.86 (3H, s), 7.00 (1H, dd, J=9.0, 3.0 Hz), 7.04-7.12 (2H, m), 7.13-7.21 (1H, m), 7.36-7.46 (2H, m), 8.15 (1H, d, J=7.8 Hz), 8.28 (1H, s).

LC/MS (ESI): m/z 369.0 (M+1).

Example 31

3-amino-2-(5-benzyloxy-2-methylphenyl)-7,8-dimethoxy-2,5-dihydro-4H-pyrazolo[4,3-c]quinolin-4-one

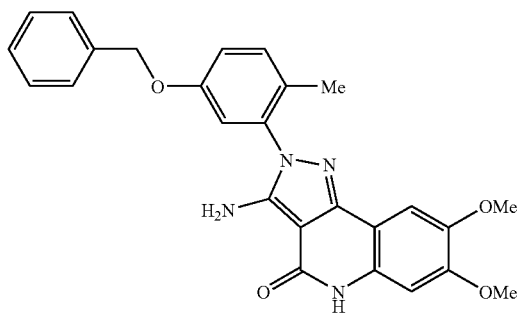

A mixture of 4-chloro-6,7-dimethoxy-2-oxo-1,2-dihydroquinoline-3-carbonitrile (53 mg), 5-benzyloxy-2-methylphenylhydrazine hydrochloride (53 mg), triethylamine (84 μl) and ethanol (5 ml) was stirred at 80° C. for 24 hours. After cooling, 10% citric acid was added thereto, extracted with ethyl acetate. The extract was washed with water and brine, dried over anhydrous magnesium sulfate, and then the solvent was distilled off under reduced pressure. The residue was purified with silica gel column chromatography to obtain the target compound (68 mg).

¹H-NMR (CDCl₃, 300 MHz): δ 2.14 (3H, s), 3.92 (3H, s), 3.94 (3H, s), 5.04 (2H, br), 5.07 (2H, s), 6.69 (1H, s), 7.03-7.07 (2H, m), 7.27-7.43 (6H, m), 7.51 (1H, s), 9.29 (1H, br).

LC/MS (ESI): m/z 457.1 (M+1).

Example 32

3-amino-7,8-dimethoxy-2-(5-hydroxy-2-methylphenyl)-2,5-dihydro-4H-pyrazolo[4,3-c]quinolin-4-one

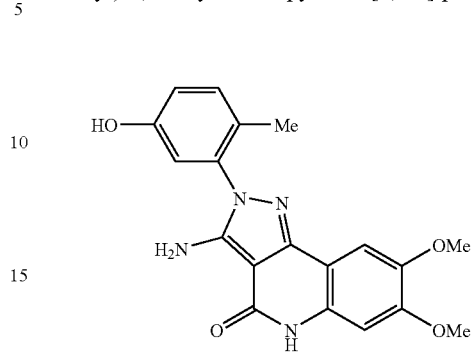

A mixture of 3-amino-7,8-dimethoxy-2-(5-benzyloxy-2-methylphenyl)-2,5-dihydro-4H-pyrazolo[4,3-c]quinolin-4-one (50 mg), 10% palladium/active carbon (50% water, 25 mg), methanol (20 ml) and ethyl acetate (20 ml) was stirred under the hydrogen atmosphere for 1 day. The reaction mixture was filtered, and the filtrate was concentrated under reduced pressure. The residue was solidified by adding ethyl acetate-hexane. The solid was collected by filtration, washed with ethyl acetate-hexane, and then dried to obtain the target compound (25 mg).

¹H-NMR (DMSO-d₆, 300 MHz): δ 1.97 (3H, s), 3.77 (3H, s), 3.78 (3H, s), 6.04 (2H, br), 6.73 (1H, d, J=2.4 Hz), 6.68-6.86 (2H, m), 7.20 (1H, d, J=8.4 Hz), 7.26 (1H, s), 9.62 (1H, s), 10.50 (1H, br).

LC/MS (ESI): m/z 367.0 (M+1).

Example 33

3-amino-2-(4-hyroxyphenyl)-2,5-dihydro-4H-pyrazolo[4,3-c]quinolin-4-one

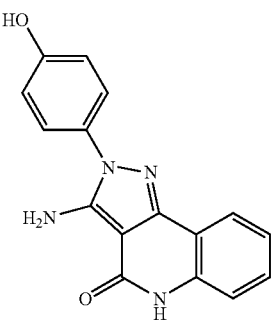

A mixture of 3-amino-2-(4-methoxyphenyl)-2,5-dihydro-4H-pyrazolo[4,3-c]quinolin-4-one (150 mg), DL-methionine (371 mg) and methanesulfonic acid (3 ml) was stirred at 100° C. for 3 hours. The reaction mixture was cooled, pH of the reaction mixture was adjusted to about 8 by adding an aqueous 20% sodium hydroxide solution and a 10% aqueous citric acid solution. The precipitated solid was collected by filtration, washed with water and then dried to obtain the target compound (132 mg).

¹H-NMR (DMSO-d₆, 200 MHz): δ 6.17 (2H, br), 6.92 (2H, d, J=8.8 Hz), 7.09-7.16 (1H, m), 7.26 (1H, d, J=7.8 Hz), 7.35-7.44 (3H, m), 7.87 (1H, d, J=7.8 Hz), 9.83 (1H, br), 10.72 (1H, br).

LC/MS (ESI): m/z 293.0 (M+1).

Example 34

3-amino-2-(3-hyroxyphenyl)-2,5-dihydro-4H-pyrazolo[4,3-c]quinolin-4-one

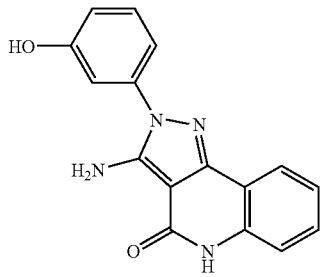

In the same manner as shown in Example 33, the target compound was obtained.

¹H-NMR (DMSO-d₆, 300 MHz): δ 6.35 (2H, br), 6.81-6.85 (1H, m), 7.07-7.15 (3H, m), 7.26 (1H, d, J=8.1 Hz), 7.32-7.41 (2H, m), 7.87-7.90 (1H, m), 9.87 (1H, s), 10.76 (1H, br).

LC/MS (ESI): m/z 293.1 (M+1).

Example 35

3-amino-2-(2-hyroxyphenyl)-2,5-dihydro-4H-pyrazolo[4,3-c]quinolin-4-one

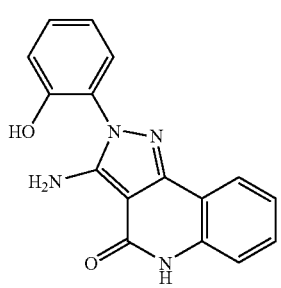

In the same manner as shown in Example 33, the target compound was obtained.

¹H-NMR (DMSO-d₆, 300 MHz): δ 5.96 (2H, br), 6.94-6.99 (1H, m), 7.06-7.13 (2H, m), 7.24-7.39 (4H, m), 7.85 (1H, dd, J=7.7, 1.4 Hz), 10.29 (1H, br), 10.69 (1H, br).

LC/MS (ESI): m/z 293.0 (M+1).

Example 36

3-amino-2-(6-oxo-1,6-dihydropyridin-2-yl)-2,5-dihydro-4H-pyrazolo[4,3-c]quinolin-4-one

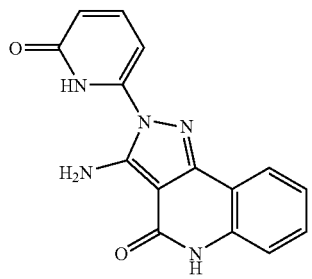

In the same manner as shown in Example 33, the target compound was obtained.

¹H-NMR (DMSO-d₆, 300 MHz): δ 6.56 (1H, d, J=9.0 Hz), 7.14-7.19 (1H, m), 7.26 (1H, d, J=8.1 Hz), 7.40-7.49 (2H, m), 7.83 (2H, br), 7.85-7.88 (1H, m), 7.96 (1H, d, J=7.7 Hz), 10.77 (1H, br), 11.23 (1H, br).

LC/MS (ESI): m/z 294.1 (M+1).

Example 37

3-amino-2-(5-hydroxy-2-methylphenyl)-2,5-dihydro-4H-pyrazolo[4,3-c]quinolin-4-one

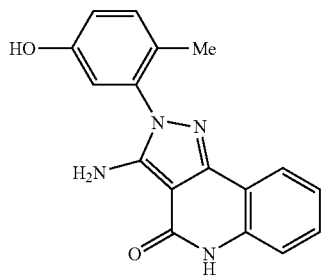

In the same manner as shown in Example 33, the target compound was obtained.

¹H-NMR (CDCl₃, 300 MHz): δ 1.99 (3H, s), 4.08 (1H, br), 6.08 (2H, br), 6.75 (1H, d, J=2.4 Hz), 6.86 (1H, dd, J=8.4, 2.4 Hz), 7.04-7.16 (1H, m), 7.17-7.30 (2H, m), 7.32-7.42 (1H, m), 7.85 (1H, d, J=8.4 Hz), 10.70 (1H, br)

LC/MS (ESI): m/z 307.2 (M+1).

Example 38

3-amino-2-(2-chloro-5-hydroxyphenyl)-2,5-dihydro-4H-pyrazolo[4,3-c]quinolin-4-one

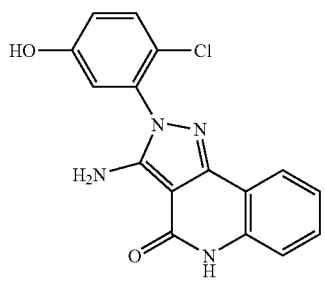

In the same manner as shown in Example 33, the target compound was obtained.

¹H-NMR (DMSO-d₆, 300 MHz): δ 6.21 (2H, s), 6.93-6.99 (2H, m), 7.05-7.45 (4H, m), 7.86 (1H, d, J=7.5 Hz), 10.66 (1H, br).

LC/MS (ESI): m/z 327.1 (M+1).

Example 39

3-amino-2-(2,4-dichloro-5-hydroxyphenyl)-2,5-dihydro-4H-pyrazolo[4,3-c]quinolin-4-one

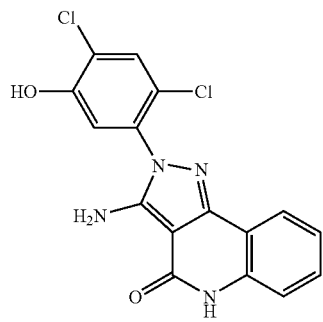

In the same manner as shown in Example 33, the target compound was obtained.

¹H-NMR (DMSO-d₆, 300 MHz): δ 6.50 (2H, s), 7.09 (1H, s), 7.10-7.14 (1H, m), 7.23-7.27 (1H, m), 7.35-7.42 (1H, m), 7.77 (1H, s), 7.80-7.85 (1H, m), 10.99 (1H, br).

LC/MS (ESI): m/z 360.9 (M+1).

Example 40

3-amino-2-(3-hydroxyphenyl)-7-nitro-2,5-dihydro-4H-pyrazolo[4,3-c]quinolin-4-one

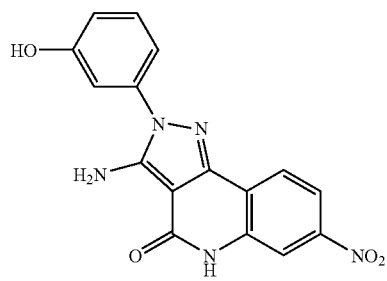

In the same manner as shown in Example 33, the target compound was obtained.

¹H-NMR (DMSO-d₆, 300 MHz): δ 6.50 (2H, br), 6.84-6.88 (1H, m), 7.05-7.10 (2H, m), 7.34-7.39 (1H, m), 7.94 (1H, dd, J=8.7, 2.4 Hz), 8.09-8.13 (2H, m), 9.92 (1H, br), 11.16 (1H, br).

LC/MS (ESI): m/z 338.0 (M+1).

Example 41

2-(3-hydroxyphenyl)-2,5-dihydro-4H-pyrazolo[4,3-c]quinolin-4-one

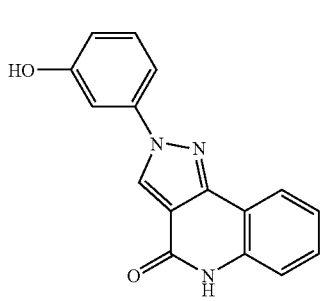

In the same manner as shown in Example 33, the target compound was obtained.

¹H-NMR (DMSO-d₆, 200 MHz): δ 6.82-6.87 (1H, m), 7.22-7.40 (3H, m), 7.46-7.53 (3H, m), 8.11 (1H, d, J=7.0 Hz), 9.28 (1H, s), 9.96 (1H, br), 11.24 (1H, br).

LC/MS (ESI): m/z 278.0 (M+1).

Example 42

2-(2-chloro-5-hydroxyphenyl)-7-[(3-morpholin-4-ylpropyl)amino]-2,5-dihydro-4H-pyrazolo[4,3-c]quinolin-4-one

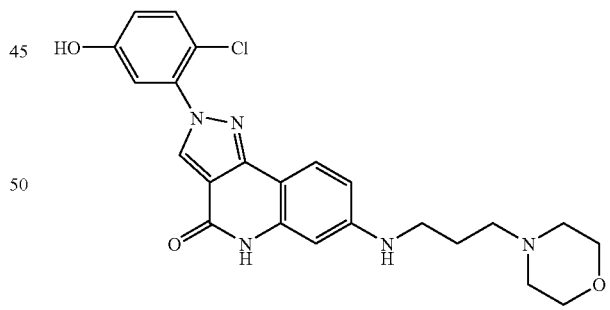

In the same manner as shown in Example 33, the target compound was obtained.

¹H-NMR (DMSO-d₆, 300 MHz): δ 1.68-1.78 (2H, m), 2.30-2.45 (6H, m), 3.06-3.14 (2H, m), 3.55-3.65 (4H, m), 6.18-6.24 (1H, m), 6.44 (1H, s), 6.50 (1H, d, J=8.5 Hz), 6.95 (1H, dd, J=8.8, 2.4 Hz), 7.08 (1H, d, J=2.4 Hz), 7.48 (1H, d, J=8.8 Hz), 7.69 (1H, d, J=8.5 Hz), 8.74 (1H, s), 10.24 (1H, br), 10.88 (1H, br).

LC/MS (ESI): m/z 454.0 (M+1).

Example 43

3-amino-2-(3-hydroxyphenyl)-7-[2-(4-morpholinyl)ethoxy]-2,5-dihydro-4H-pyrazolo[4,3-c]quinolin-4-one

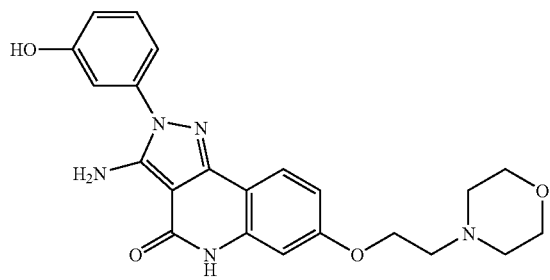

In the same manner as shown in Example 33, the target compound was obtained.

$^1$H-NMR (DMSO-d$_6$, 300 MHz): δ 2.46-2.51 (4H, m), 2.71 (2H, t, J=5.8 Hz), 3.56-3.60 (4H, m), 4.10 (2H, t, J=5.8 Hz), 6.31 (2H, br), 6.74-6.83 (3H, m), 7.05-7.08 (2H, m), 7.30-7.36 (1H, m), 7.77 (1H, d, J=8.4 Hz), 9.85 (1H, br), 10.64 (1H, br).

LC/MS (ESI): m/z 422.0 (M+1).

Example 44

3-amino-2-(3-hydroxyphenyl)-7-{[3-(4-methyl-1-piperazinyl)propyl]amino}-2,5-dihydro-4H-pyrazolo[4,3-c]quinolin-4-one

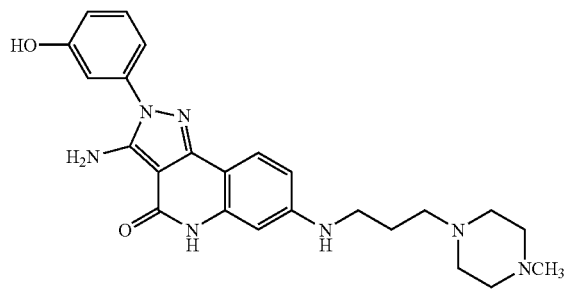

In the same manner as shown in Example 33, the target compound was obtained.

$^1$H-NMR (DMSO-d$_6$, 300 MHz): δ 1.66-1.75 (2H, m), 2.15 (3H, s), 2.20-2.40 (10H, m), 2.91-3.06 (2H, m), 6.10 (1H, t, J=5.4;Hz), 6.22 (2H, br), 6.34 (1H, d, J=1.9 Hz), 6.41 (1H, dd, J=8.4, 1.9 Hz), 6.76-6.80 (1H, m), 7.05-7.07 (2H, m), 7.29-7.34 (1H, m), 7.55 (1H, d, J=8.4 Hz), 9.83 (1H, br), 10.40 (1H, br).

LC/MS (ESI): m/z 448.1 (M+1).

Example 45

3-amino-2-(2-chloro-5-hydroxyphenyl)-7-[(3-morpholin-4-ylpropyl)amino]-2,5-dihydro-4H-pyrazolo[4,3-c]quinolin-4-one

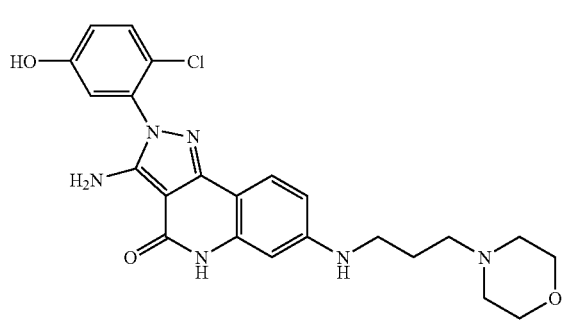

In the same manner as shown in Example 33, the target compound was obtained.

$^1$H-NMR (DMSO-d$_6$, 300 MHz): δ 1.66-1.77 (2H, m), 2.32-2.41 (6H, m), 3.00-3.08 (2H, m), 3.55-3.62 (4H, m), 6.03-6.07 (1H, m), 6.16 (2H, s), 6.35 (1H, d, J=1.8 Hz), 6.40 (1H, dd, J=8.7, 2.1 Hz), 6.88 (1H, d, J=2.7 Hz), 6.94 (1H, dd, J=8.7, 2.7 Hz), 7.43 (1H, d, J=8.7 Hz), 7.49 (1H, d, J=8.4 Hz), 10.35 (1H, s).

LC/MS (ESI): m/z 469.0 (M+1).

Example 46

3-amino-2-(2-chloro-5-hydroxyphenyl)-7-(3-morpholin-4-ylpropoxy)-2,5-dihydro-4H-pyrazolo[4,3-c]quinolin-4-one

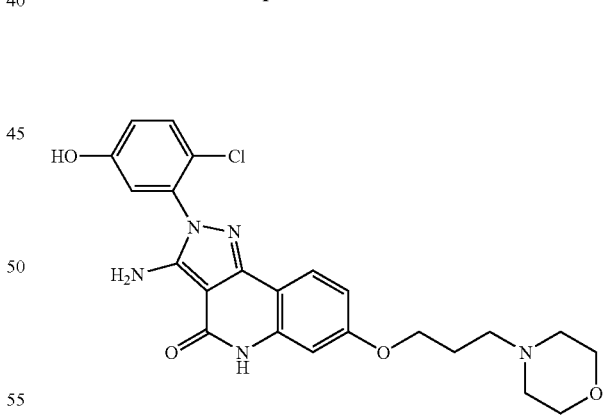

In the same manner as shown in Example 33, the target compound was obtained.

$^1$H-NMR (DMSO-d$_6$, 300 MHz): δ 1.90 (2H, m), 2.33-2.40 (4H, m), 2.43 (2H, t, J=7.2 Hz), 3.56-3.60 (4H, m), 4.03 (2H, t, J=6.3 Hz), 6.28 (2H, s), 6.72 (1H, dd, J=8.7, 2.4 Hz), 6.79 (1H, d, J=2.4 Hz), 6.90 (1H, d, J=2.7 Hz), 6.93-6.98 (1H, m), 7.45 (1H, d, J=8.7 Hz), 7.71 (1H, d, J=8.7 Hz), 10.58 (1H, s).

LC/MS (ESI): m/z 470.0 (M+1).

Example 47

3-amino-2-(2-chloro-5-hydroxyphenyl)-7-(2-morpholin-4-ylethoxy)-2,5-dihydro-4H-pyrazolo[4,3-c]quinolin-4-one

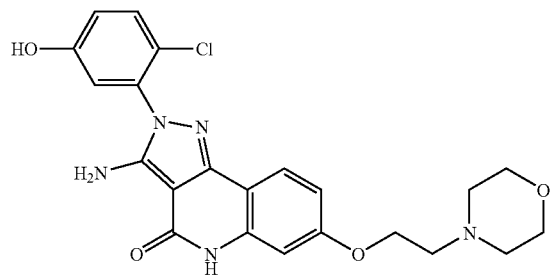

In the same manner as shown in Example 33, the target compound was obtained.

$^1$H-NMR (DMSO-d$_6$, 300 MHz): δ 2.54-2.49 (4H, m), 2.71 (2H, t, J=5.7 Hz), 3.59 (4H, t, J=4.2 Hz), 4.10 (2H, t, J=5.7 Hz), 6.30 (2H, s), 6.74 (1H, dd, J=8.7, 1.8 Hz), 6.79 (1H, d, J=1.8 Hz), 6.91 (1H, d, J=2.4 Hz), 6.96 (1H, dd, J=8.7, 2.4 Hz), 7.46 (1H, d, J=8.7 Hz), 7.72 (1H, d, J=8.7 Hz), 10.14 (1H, s), 10.59 (1H, s).

LC/MS (ESI): m/z 456.0 (M+1).

Example 48

3-amino-2-(5-hydroxy-2-methylphenyl)-7-(3-morpholin-4-ylpropoxy)-2,5-dihydro-4H-pyrazolo[4,3-c]quinolin-4-one

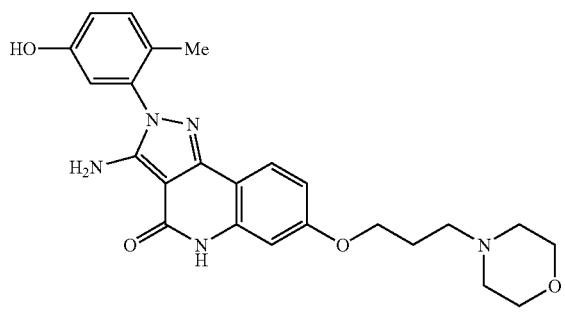

In the same manner as shown in Example 33, the target compound was obtained.

$^1$H-NMR (DMSO-d$_6$, 300 MHz): δ 1.84-1.98 (5H, m), 2.32-2.47 (6H, m), 3.55-3.60 (4H, m), 4.02 (2H, t, J=6.3 Hz), 6.08 (2H, s), 6.70-6.75 (2H, m), 6.79 (1H, d, J=2.4 Hz), 6.85 (1H, dd, J=8.4, 2.4 Hz), 7.21 (1H, d, J=8.4 Hz), 7.72 (1H, d, J=8.4 Hz), 9.67 (1H, br), 10.60 (1H, s).

LC/MS (ESI): m/z 450.0 (M+1).

Example 49

3-amino-2-(5-hydroxy-2-methylphenyl)-7-(2-morpholin-4-ylethoxy)-2,5-dihydro-4H-pyrazolo[4,3-c]quinolin-4-one

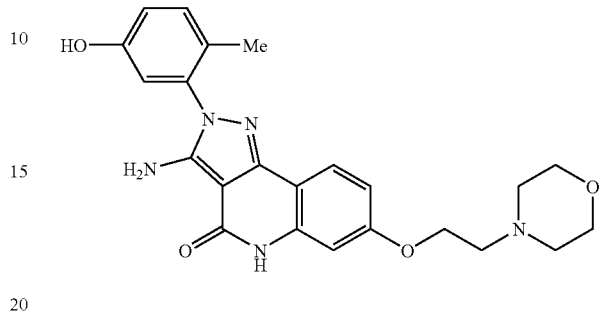

In the same manner as shown in Example 33, the target compound was obtained.

$^1$H-NMR (DMSO-d$_6$, 300 MHz): δ 1.97 (3H, s), 2.46-2.52 (4H, m), 2.71 (2H, t, J=5.7 Hz), 3.57-3.61 (4H, m), 4.10 (2H, t, J=5.7 Hz), 6.08 (2H, br), 6.70-6.77 (2H, m), 6.80 (1H, d, J=2.4 Hz), 6.85 (1H, d, J=2.4 Hz), 7.21 (1H, d, J=8.4 Hz), 7.73 (1H, d, J=8.7 Hz), 9.66 (1H, br), 10.61 (1H, s).

LC/MS (ESI): m/z 436.0 (M+1).

Example 50

3-amino-2-(3-hydroxyphenyl)-7-[3-(4-methyl-1-piperazinyl)propoxy]-2,5-dihydro-4H-pyrazolo[4,3-c]quinolin-4-one

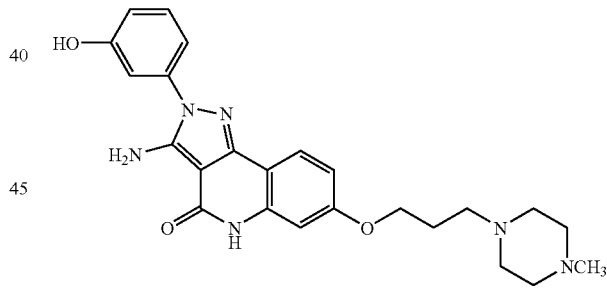

A mixture of 3-amino-2-(2-chloro-5-methoxyphenyl)-7-hydroxy-2,5-dihydro-4H-pyrazolo[4,3-c]quinolin-4-one (75 mg), 1-(3-chloropropyl)-4-methylpiperazine dihydrochloride (70 mg), potassium carbonate (112 mg), potassium iodide (5 mg) and N,N-dimethylformamide (3 ml) was stirred at 80° C. for 4 hours. To the reaction mixture was added water, extracted with ethyl acetate. The extract was washed with brine, dried over anhydrous magnesium sulfate and the solvent was distilled off under reduced pressure. To the concentrated residue (53 mg) was added DL-methilonine (265 mg) and methanesulfonic acid (3 ml), and the mixture was stirred at 90° C. for one night. The reaction mixture was cooled and then pH of the reaction mixture was adjusted to about 9 by adding an aqueous 20% sodium hydroxide and 5% sodium hydrogen carbonate, and extracted with ethyl acetate. The extract was washed with brine, dried over anhydrous sodium sulfate and the solvent was distilled off under reduced pressure. The residue was purified with propylaminated silica gel column chromatography to obtain the target compound (13 mg).

¹H-NMR (DMSO-d₆, 300 MHz): δ 1.86-1.92 (2H, m), 2.14 (3H, s), 2.20-2.50 (10H, m), 4.01 (2H, t, J=7.0 Hz), 6.31 (2H, br), 6.71-6.83 (3H, m), 7.05-7.08 (2H, m), 7.31-7.36 (1H, m), 7.77 (1H, d, J=8.4 Hz), 9.86 (1H, br), 10.63 (1H, br).

LC/MS (ESI): m/z 449.1 (M+1).

Example 51

3-amino-2-(3-aminophenyl)-2,5-dihydro-4H-pyrazolo[4,3-c]quinolin-4-one

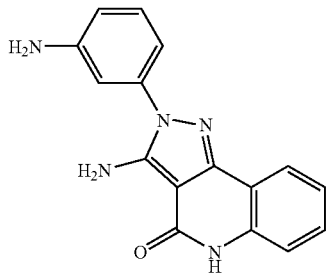

A mixture of 3-amino-2-(3-nitrophenyl)-2,5-dihydro-4H-pyrazolo[4,3-c]quinolin-4-one (150 mg), 10% palladium/active carbon (50% water, 40 mg), tetrahydrofuran (10 ml) and methanol (30 ml) was stirred under hydrogen atmosphere, at room temperature for 3 hours. The reaction mixture was filtered and the filtrate was concentrated under reduced pressure. To the residue was added methanol, and the precipitated solid was collected by filtration, washed with methanol, and dried to obtain the target compound (120 mg).

¹H-NMR (DMSO-d₆, 200 MHz): δ 5.44 (2H, br), 6.24 (2H, br), 6.60-6.64 (1H, m), 6.74-6.78 (1H, m), 6.85-6.87 (1H, m), 7.10-7.28 (3H, m), 7.36-7.43 (1H, m), 7.89 (1H, d, J=6.6 Hz), 10.76 (1H, br).

LC/MS (ESI): m/z 292.1 (M+1).

Example 52

3,7-diamino-2-phenyl-2,5-dihydro-4H-pyrazolo[4,3-c]quinolin-4-one

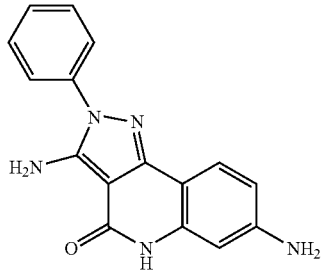

In the same manner as shown in Example 51, the target compound was obtained.

¹H-NMR (DMSO-d₆, 200 MHz): δ 5.49 (2H, br), 6.27 (2H, br), 6.37-6.41 (2H, m), 7.37-7.44 (1H, m), 7.52-7.68 (5H, m), 10.44 (1H, br).

LC/MS (ESI): m/z 292.2 (M+1).

Example 53

3,7-diamino-2-(3-methoxyphenyl)-2,5-dihydro-4H-pyrazolo[4,3-c]quinolin-4-one

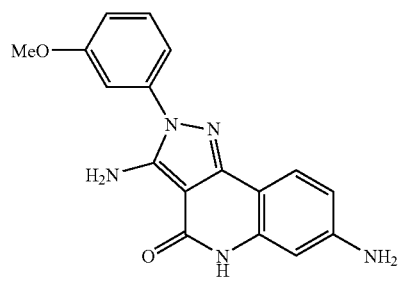

In the same manner as shown in Example 51, the target compound was obtained.

¹H-NMR (DMSO-d₆, 300 MHz): δ 3.83 (3H, s), 5.50 (2H, br), 6.29 (2H, br), 6.37-6.40 (2H, m), 6.94-6.98 (1H, m), 7.17-7.23 (2H, m), 7.41-7.46 (1H, m), 7.53 (1H, d, J=9.0 Hz), 10.43 (1H, br).

LC/MS (ESI): m/z 322.1 (M+1).

Example 54

2-(3-methoxyphenyl)-7-(3-morpholin-4-ylpropoxy)-2,5-dihydro-4H-pyrazolo[4,3-c]quinolin-4-one hydrochloride

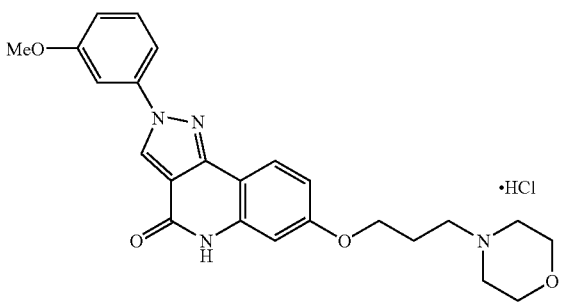

In the same manner as shown in Example 51, the target compound was obtained.

¹H-NMR (DMSO-d₆, 300 MHz): δ 2.10-2.30 (2H, m), 3.00-4.20 (15H, m), 6.85-6.92 (2H, m), 6.97-7.01 (1H, m), 7.44-7.49 (1H, m), 7.64-7.67 (2H, m), 8.03 (1H, d, J=8.7 Hz), 9.36 (1H, s), 10.84 (1H, br), 11.17 (1H, br).

Example 55

3,7-diamino-2-(2-chloro-5-methoxyphenyl)-2,5-dihydro-4H-pyrazolo[4,3-c]quinolin-4-one

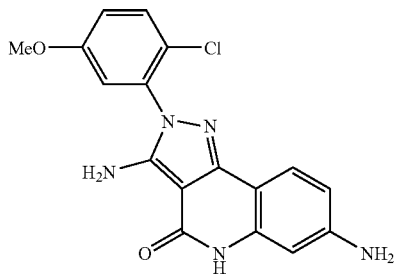

A mixture of 3-amino-2-(2-chloro-5-methoxyphenyl)-7-nitro-2,5-dihydro-4H-pyrazolo[4,3-c]quinolin-4-one (0.50 g), 90% calcium chloride (0.40 g), reduced iron (1.0 g) and 90% ethanol (30 ml) was heated under reflux for 3 hours, and 90% calcium chloride (0.10 g) and reduced iron (0.27 g) was added thereto. The reaction mixture was heated under reflux for additional 8 hours. The reaction mixture was cooled and the insoluble materials were filtered off through Celite, and the filtrate was extracted with ethyl acetate. The extract was washed with a 5% sodium hydrogen carbonate and brine, dried over anhydrous sodium sulfate and then concentrated under reduced pressure. The residual solid was washed with diisopropyl ether, and dried to obtain the target compound (0.30 g).

$^1$H-NMR (DMSO-$d_6$, 300 MHz): δ 3.82 (3H, s), 5.44 (2H, s), 6.19 (2H, s), 6.35-6.40 (2H, m), 7.10-7.16 (2H, m), 7.47 (1H, d, J=8.7 Hz), 7.53-7.58 (1H, m), 10.37 (1H, s).

LC/MS (ESI): m/z 356.0 (M+1).

Example 56

3-amino-2-[3-(hydroxymethyl)phenyl]-2,5-dihydro-4H-pyrazolo[4,3-c]quinolin-4-one

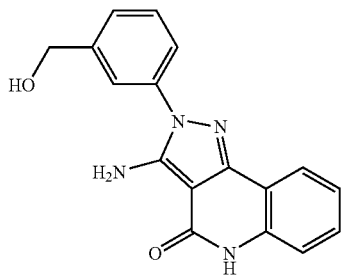

A mixture of methyl 3-(3-amino-4-oxo-4,5-dihydro-2H-pyrazolo[4,3-c]quinolin-2-yl)benzoate (80 mg), lithium aluminum hydride (12 mg) and tetrahydrofuran (5 ml) was stirred at room temperature for 3 hours. Diethyl ether and then saturated aqueous sodium sulfate solution were added to the reaction mixture, and the organic layer was separated by decantation. The organic layer was dried over anhydrous magnesium sulfate and the solvent was distilled off under reduced pressure. Diisopropy ether was added to the residue. The precipitated solid was collected by filtration, washed with diisopropyl ether, and dried to obtain the target compound (60 mg).

$^1$H-NMR (DMSO-$d_6$, 200 MHz): δ 4.61 (2H, d, J=5.7 Hz), 5.33 (1H, t, J=5.7 Hz), 6.39 (2H, br), 7.10-7.18 (1H, m), 7.27 (1H, d, J=7.0 Hz), 7.36-7.44 (2H, m), 7.51-7.54 (2H, m), 7.62 (1H, s), 7.91 (1H, d, J=6.8, Hz), 10.77 (1H, br).

LC/MS (ESI): m/z 307.0 (M+1).

Example 57

2-(3-methoxyphenyl)-2,5-dihydro-4H-pyrazolo[4,3-c]quinolin-4-one

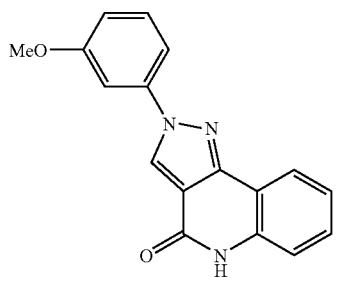

A mixture of 1-(3-methoxyphenyl)-3-(2-nitrophenyl)-1H-pyrazole-4-carboxylic acid (500 mg), 10% palladium/active carbon (50% water, 50 mg), tetrahydrofuran (30 ml) and methanol (50 ml) was stirred under hydrogen atmosphere, at room temperature for one night. To the reaction mixture was added tetrahydrofuran to dissolve the precipitated solid and the reaction mixture was filtered. The filtrate was concentrated under reduced pressure. To the residue was added ethanol-ethyl acetate, and the solid was collected by filtration. The solid was washed with ethyl acetate and dried to obtain the target compound (353 mg).

$^1$H-NMR (DMSO-$d_6$, 300 MHz): δ 3.89 (3H, s), 7.00-7.03 (1H, m), 7.23-7.28 (1H, m), 7.38 (1H, d, J=7.2 Hz), 7.47-7.52 (2H, m), 7.68-7.71 (2H, m), 8.14 (1H, dd, J=7.8, 1.5 Hz), 9.42 (1H, s), 11.24 (1H, br).

LC/MS (ESI): m/z 292.1 (M+1).

Example 58

7-amino-2-(2-chloro-5-methoxyphenyl)-2,5-dihydro-4H-pyrazolo[4,3-c]quinolin-4-one

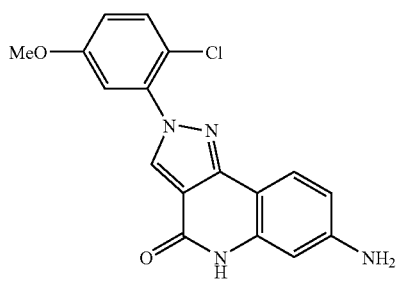

A mixture of 1-(2-chloro-5-methoxyphenyl)-3-(2,4-dinitrophenyl)-1H-pyrazole-4-carboxylic acid (3.20 g), 90% calcium chloride (200 mg) and 90% ethanol (150 ml) was stirred at 90° C. for 10 minutes, reduced iron (5.12 g) was added thereto, and then was stirred at 90° C. for 4 hours. The reaction mixture was cooled, filtered through Celite, the Celite layer was washed ethyl acetate. The filtrate and washings were combined, added water thereto and then extracted with ethyl acetate. The extract was washed with water and brine, dried over anhydrous magnesium sulfate. The solvent was distilled off under reduced pressure to obtain the target compound (1.20 g).

$^1$H-NMR (DMSO-$d_6$, 300 MHz): δ 3.84 (3H, s), 5.62 (2H, br), 6.46-6.48 (2H, m), 7.16 (1H, dd, J=9.0, 1.7 Hz), 7.32 (1H, d, J=1.7 Hz), 7.62 (1H, dd, J=9.0, 1.3 Hz), 7.68 (1H, d, J=8.4 Hz), 8.77 (1H, d, J=1.3 Hz), 10.92 (1H, s).

LC/MS (ESI): m/z 341.1 (M+1).

Example 59

3-amino-7-{[3-(4-methyl-1-piperazinyl)propyl]amino}-2-phenyl-2,5-dihydro-4H-pyrazolo[4,3-c]quinolin-4-one

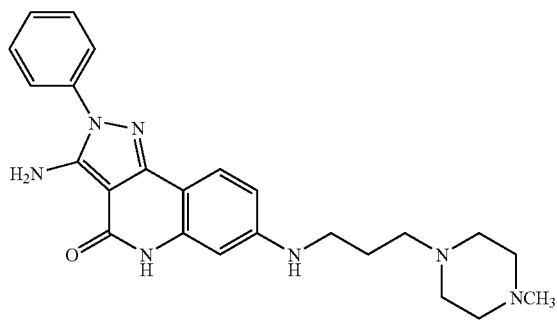

A mixture of 1-methylpiperazine (86 µl), 1,8-diazabicyclo[5.4.0]undec-7-ene (0.8 µl) and tetrahydrofuran (6 ml), was cooled to −20° C., acrolein (51.7 µl) was added thereto, and was stirred for 1 hour from −20° C. to −10° C. To the reaction mixture was added 3,7-diamino-2-phenyl-2,5-dihydro-4H-pyrazolo[4,3-c]quinolin-4-one (100 mg), stirred at 0° C. for 30 minutes, sodium triacetoxyborohydride (268 mg) was added thereto, and stirred at room temperature for 3 hours. The reaction mixture was basified by adding 5% sodium hydrogen carbonate, brine were added thereto and then extracted with ethyl acetate. The extract was washed with brine, dried over anhydrous magnesium sulfate, and the solvent was distilled off under reduced pressure. The residue was purified with aminopropylated silica gel column chromatography. To the concentrated residue of fraction was solidified by adding diisopropyl ether-hexane. The solid was collected by filtration, washed with hexane, and dried to obtain the target compound (45 mg).

$^1$H-NMR (DMSO-$d_6$, 300 MHz): δ 1.65-1.74 (2H, m), 2.14 (3H, s), 2.15-2.50 (10H, m), 2.99-3.05 (2H, m), 6.09 (1H, t, J=5.7 Hz), 6.26 (2H, s), 6.34 (1H, s), 6.40 (1H, d, J=8.4 Hz), 7.36-7.41 (1H, m), 7.50-7.65 (5H, m), 10.39 (1H, br).

LC/MS (ESI): m/z 432.2 (M+1).

Example 60

3-amino-2-(3-methoxyphenyl)-7-{[3-(4-methyl-1-piperazinyl)propyl]amino}-2,5-dihydro-4H-pyrazolo[4,3-c]quinolin-4-one

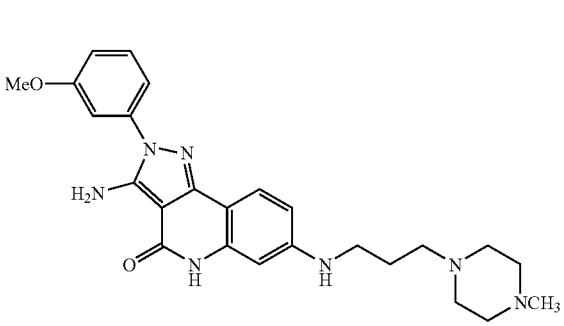

In the same manner as shown in Example 59, the target compound was obtained.

$^1$H-NMR (DMSO-$d_6$, 300 MHz): δ 1.66-1.75 (2H, m), 2.15 (3H, s), 2.15-2.60 (10H, m), 3.00-3.05 (2H, m), 3.83 (3H, s), 6.10 (1H, t, J=5.1 Hz), 6.29-6.42 (4H, m), 6.97 (1H, d, J=7.5 Hz), 7.17-7.22 (2H, m), 7.41-7.46 (1H, m), 7.56 (1H, d, J=8.7Hz), 10.40 (1H, br).

LC/MS (ESI): m/z 462.2 (M+1).

Example 61

3-amino-2-(3-hydroxyphenyl)-7-{[3-(4-hydroxy-1-piperidinyl)propyl]amino}-2,5-dihydro-4H-pyrazolo[4,3-c]quinolin-4-one

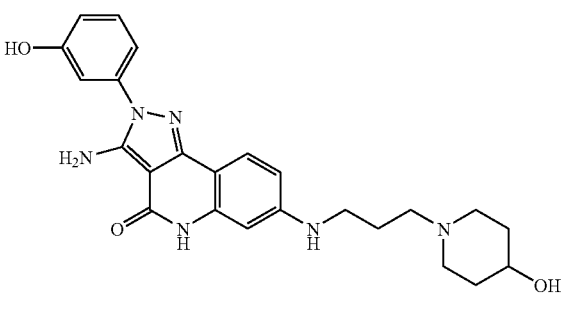

In the same manner as shown in Example 59, the target compound was obtained.

$^1$H-NMR (DMSO-$d_6$, 300 MHz): δ 1.37-1.41 (2H, m), 1.66-1.80 (4H, m), 1.90-2.05 (2H, m), 2.35 (2H, t, J=7.0 Hz), 2.65-2.75 (2H, m), 3.00-3.05 (2H, m), 3.43 (1H, br), 4.53-4.54 (1H, m), 6.12 (1H, t, J=5.1 Hz), 6.22 (2H, br), 6.35 (1H, s), 6.42 (1H, d, J=8.4 Hz), 6.79 (1H, d, J=7.2 Hz), 7.07-7.08 (2H, m), 7.30-7.36 (1H, m), 7.56 (1H, d, J=9.0 Hz), 9.82 (1H, br), 10.41 (1H, br).

LC/MS (ESI): m/z 449.2 (M+1).

Example 62

3-amino-2-(3-hydroxyphenyl)-7-{[3-(4-morpholinyl)propyl]amino}-2,5-dihydro-4H-pyrazolo[4,3-c]quinolin-4-one

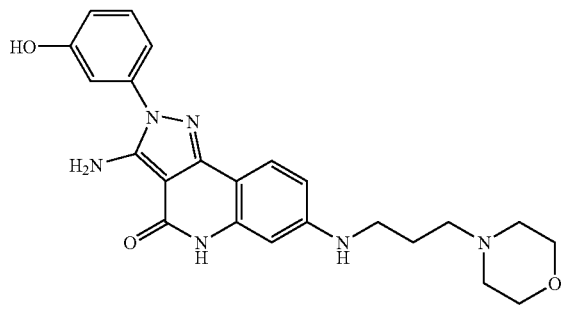

In the same manner as shown in Example 59, the target compound was obtained.

$^1$H-NMR (DMSO-d$_6$, 300 MHz): δ 1.68-1.77 (2H, m), 2.25-2.45 (6H, m), 3.01-3.09 (2H, m), 3.59 (4H, br), 6.10 (1H, br), 6.24 (2H, br), 6.37 (1H, s), 6.44 (1H, d, J=8.7 Hz), 6.80 (1H, d, J=8.4 Hz), 7.07-7.08 (2H, m), 7.31-7.36 (1H, m), 7.57 (1H, d, J=8.4 Hz), 9.83 (1H, br), 10.42 (1H, br).

LC/MS (ESI): m/z 435.2 (M+1).

Example 63

3-amino-2-(2-chloro-5-methoxyphenyl)-7-[(3-morpholin-4-ylpropyl)amino]-2,5-dihydro-4H-pyrazolo[4,3-c]quinolin-4-one

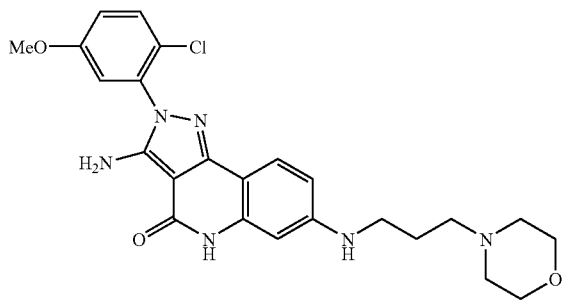

In the same manner as shown in Example 59, the target compound was obtained.

$^1$H-NMR (CDCl$_3$, 300 MHz): δ 1.79-1.89 (2H, m), 2.45-2.57 (6H, m), 3.21-3.29 (2H, m), 3.72-3.79 (4H, m), 3.84 (3H, s), 5.09 (2H, s), 6.14 (1H, d, J=2.1 Hz), 6.46 (1H, dd, J=8.6, 2.1 Hz), 7.02 (1H, dd, J=9.0, 3.0 Hz), 7.10 (1H, d, J=3.0 Hz), 7.46 (1H, d, J=9.0 Hz), 7.73 (1H, s), 7.87 (1H, d, J=8.6 Hz).

LC/MS (ESI): m/z 483.1 (M+1).

Example 64

3-amino-7-[bis(3-morpholin-4-ylpropyl)amino]-2-(2-chloro-5-methoxyphenyl)-2,5-dihydro-4H-pyrazolo[4,3-c]quinolin-4-one

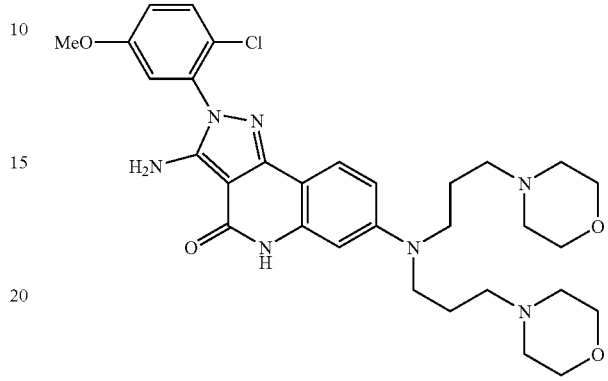

In the same manner as shown in Example 59, the target compound was obtained.

$^1$H-NMR (CDCl$_3$, 300 MHz): δ 1.73-1.87 (4H, m), 2.37 (4H, t, J=6.9 Hz), 2.41-2.48 (8H, m), 3.41 (4H, t, J=6.9 Hz), 3.70-3.76 (8H, m), 3.84 (3H, s), 5.09 (2H, s), 6.23 (1H, d, J=2.1 Hz), 6.65 (1H, dd, J=8.9, 2.1 Hz), 7.02 (1H, dd, J=9.0, 3.0 Hz), 7.10 (1H, d, J=3.0 Hz), 7.46 (1H, d, J=9.0 Hz), 7.81 (1H, s), 7.88 (1H, d, J=8.9 Hz).

LC/MS (ESI): m/z 610.1 (M+1).

Example 65

2-(2-chloro-5-methoxyphenyl)-7-[(3-morpholin-4-ylpropyl)amino]-2,5-dihydro-4H-pyrazolo[4,3-c]quinolin-4-one

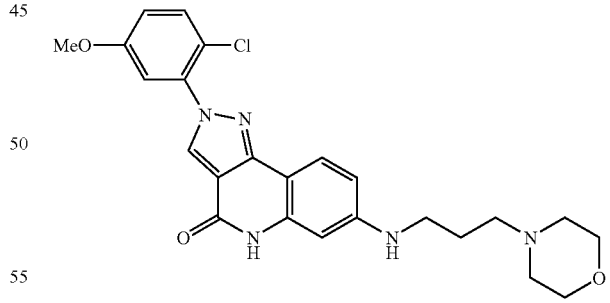

In the same manner as shown in Example 59, the target compound was obtained.

$^1$H-NMR (DMSO-d$_6$, 300 MHz): δ 1.69-1.99 (2H, m), 2.30-2.49 (6H, m), 3.04-3.10 (2H, m), 3.57-3.60 (4H, m), 3.83 (3H, s), 6.20 (1H, t, J=5.3 Hz), 6.44 (1H, d, J=2.1 Hz), 6.50 (1H dd, J=8.6, 2.1 Hz), 7.15 (1H, dd, J=9.0, 3.0 Hz), 7.31 (1H, d, J=3.0 Hz), 7.61 (1H, d, J=9.0 Hz), 7.69 (1H, d, J=8.6 Hz), 8.76 (1H, s), 10.87 (1H, br).

LC/MS (ESI): m/z 468.1 (M+1).

Example 66

3-amino-7-{[2-(4-methyl-1-piperazinyl)ethyl]amino}-2-phenyl-2,5-dihydro-4H-pyrazolo[4,3-c]quinolin-4-one

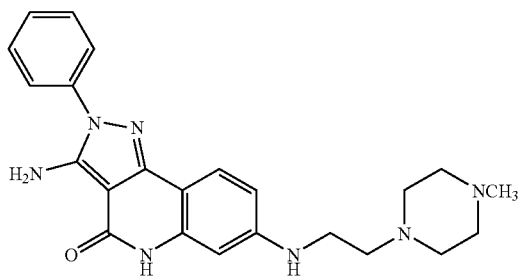

A mixture of 3,7-diamino-2-phenyl-2,5-dihydro-4H-pyrazolo[4,3-c]quinolin-4-one (150 mg), 40% chloroacetaldehyde (151 μl), Molecular Sieves 4A, acetic acid (60 μl) and N,N-dimethylformaldehyde (3 ml) was stirred at room temperature for 1 hour, sodium triacetoxyborohydride (218 mg) was added thereto, and stirred at room temperature for 6 hours. To the reaction mixture were added 40% chloroacetaldehyde (75 μl) and sodium triacetoxyborohydride (218 mg), stirred at room temperature for one night. After stirring, to the reaction mixture was added water, and extracted with ethyl acetate. The extract was washed with water and brine, dried over anhydrous magnesium sulfate, and the solvent was distilled off under reduced pressure. To the residue were added 1-methylpiperazine (257 μl) and tetrahydrofuran (5 ml), and stirred at room temperature for 3 days and at 70° C. for 3 hours. To the mixture was added 1-methylpiperazine (1028 μl) and the mixture was stirred with distilling off tetrahydrofuran at 90° C. for 4 hours. To the reaction mixture was added water, and the insoluble materials were filtered off. To the filtrate was added sodium chloride, and the mixture was extracted with ethyl acetate. The extract was washed with brine, dried over anhydrous magnesium sulfate, and the solvent was distilled off under reduced pressure. The residue was purified with aminopropylated silica gel column chromatography. The concentrated residue of fraction was solidified by adding ethyl acetate-diisopropyl ether-hexane. The solid was collected by filtration, washed with diisopropyl ether, and dried to obtain the target compound (29 mg).

$^1$H-NMR (DMSO-$d_6$, 200 MHz): δ 2.16 (3H, s), 2.25-2.55 (10H, m), 3.07-3.18 (2H, m), 5.88 (1H, br), 6.28 (2H, br), 6.38 (1H, s), 6.44 (1H, d, J=8.4 Hz), 7.36-7.44 (1H, m), 7.51-7.68 (5H, m), 10.42 (1H, br).

LC/MS (ESI): m/z 418.3 (M+1).

Example 67

3-amino-2-(3-hydroxyphenyl)-7-{[2-(4-methyl-1-piperazinyl)ethyl]amino}-2,5-dihydro-4H-pyrazolo[4,3-c]quinolin-4-one

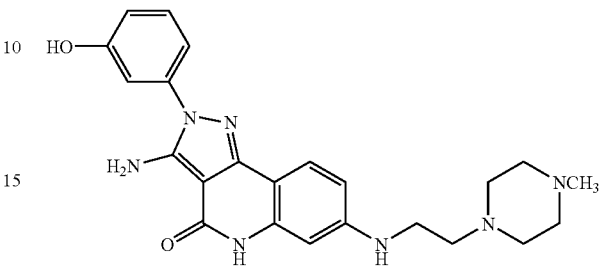

In the same manner as shown in Example 66, the target compound was obtained.

$^1$H-NMR (DMSO-$d_6$, 300 MHz): δ 2.16 (3H, s), 2.20-2.53 (10H, m), 3.10-3.16 (2H, m), 5.88 (1H, t, J=5.4 Hz), 6.23 (2H, br), 6.38 (1H, d, J=1.9 Hz), 6.45 (1H, dd, J=8.6, 1.9 Hz), 6.78-6.81 (1H, m), 7.01-7.08 (2H, m), 7.30-7.35 (1H, m), 7.57 (1H, d, J=8.6 Hz), 9.85 (1H, br), 10.42 (1H, br).

LC/MS (ESI): m/z 434.2 (M+1).

Example 68

3-amino-7-hydroxy-2-phenyl-2,5-dihydro-4H-pyrazolo[4,3-c]quinolin-4-one

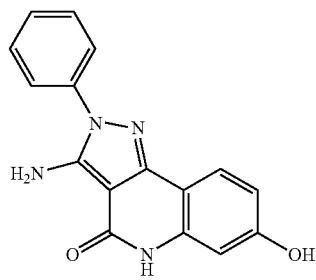

A mixture, which is cooled to 0° C., of 3,7-diamino-2-phenyl-2,5-dihydro-4H-pyrazolo[4,3-c]quinolin-4-one (100 mg), concentrated sulfuric acid (0.7 ml) and water (4 ml) was added dropwise a solution of sodium nitrite (46 mg) in water (1 ml), stirred at 0° C. for 30 minutes, at 90° C. for 1 hour and at room temperature for one night. The reaction mixture was neturalized by adding 5% sodium hydrogen carbonate, and ethyl acetate and methanol were added thereto. The insoluble materials were filtered off. The filtrate was extracted with ethyl acetate. The extract was washed with water and brine, dried over anhydrous magnesium sulfate and then the solvent was distilled off under reduced pressure. The residue was purified with silica gel column chromatography to obtain the target compound (18 mg).

$^1$H-NMR (DMSO-$d_6$, 300 MHz): δ 6.32 (2H, br), 6.57 (1H, dd, J=8.6, 2.2 Hz), 6.67 (1H, d, J=2.2 Hz), 7.39-7.44 (1H, m), 7.52-7.58 (2H, m), 7.63-7.70 (3H, m), 9.80 (1H, s), 10.59 (1H, br).

LC/MS (ESI): m/z 293.1 (M+1)

Example 69

3-amino-2-(3-methoxyphenyl)-7-hydroxy-2,5-dihydro-4H-pyrazolo[4,3-c]quinolin-4-one

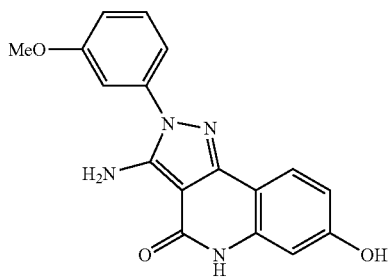

In the same manner as shown in Example 68, the target compound was obtained.

$^1$H-NMR (DMSO-d$_6$, 300 MHz): δ 3.83 (3H, s), 6.35 (2H, br), 6.57 (1H, dd, J=8.6, 2.5 Hz), 6.67 (1H, d, J=2.5 Hz), 6.97-7.00 (1H, m), 7.17-7.23 (2H, m), 7.42-7.48 (1H, m), 7.68 (1H, d, J=8.6 Hz), 9.80 (1H, s), 10.59 (1H. br).

LC/MS (ESI): m/z 323.0 (M+1).

Example 70

3-amino-2-(2-chloro-5-methoxyphenyl)-7-hydroxy-2,5-dihydro-4H-pyrazolo[4,3-c]quinolin-4-one

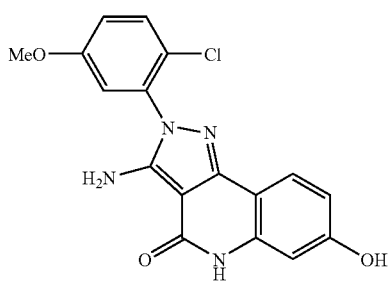

In the same manner as shown in Example 68, the target compound was obtained.

$^1$H-NMR (DMSO-d$_6$, 300 MHz): δ 3.82 (3H, s), 6.29 (2H, s), 6.56 (1H, dd, J=8.4, 2.1 Hz), 6.67 (1H, d, J=1.8 Hz), 7.11-7.18 (2H, m), 7.58 (1H, d, J=8.1 Hz), 7.63 (1H, d, J=8.4 Hz), 9.79 (1H, s), 10.55 (1H, s)

LC/MS (ESI): m/z 357.0 (M+1).

Example 71

2-(2-chloro-5-methoxyphenyl)-7-hydroxy-2,5-dihydro-4H-pyrazolo[4,3-c]quinolin-4-one

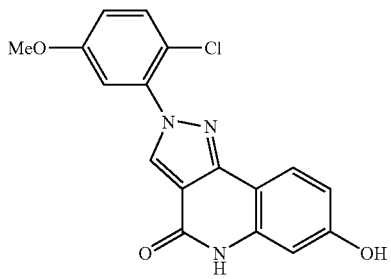

In the same manner as shown in Example 68, the target compound was obtained.

$^1$H-NMR (DMSO-d$_6$, 300 MHz): δ 3.84 (3H, s), 6.66 (1H, dd, J=8.4, 2.3 Hz), 6.77 (1H, d, J=2.3 Hz), 7.16 (1H, dd, J=8.9, 2.9 Hz), 7.33 (1H, d, J=2.9 Hz), 7.62 (1H, d, J=8.9 Hz), 7.84 (1H, d, J=8.4 Hz), 8.84 (1H, s), 9.94 (1H, s), 11.08 (1H, br).

LC/MS (ESI): m/z 342.0 (M+1).

Example 72

3-(3-amino-4-oxo-4,5-dihydro-2H-pyrazolo[4,3-c]quinolin-2-yl)-4-chlorophenyl acetate

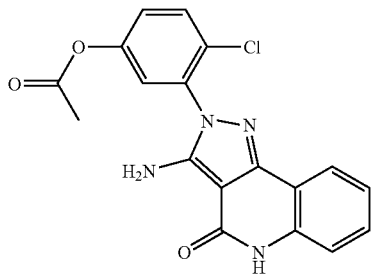

A mixture of 3-amino-2-(2-chloro-5-hydroxyphenyl)-2,5-dihydro-4H-pyrazolo[4,3-c]quinolin-4-one (65 mg), triethylamine (31 μl), acetyl chloride (15 μl) and dichloromethane (1.7 ml) was stirred at room temperature for 12 hours. The reaction mixture was poured into water and extracted with ethyl acetate. The extract was washed with brine and dried over anhydrous magnesium sulfate. The solvent was distilled off under reduced pressure, and chloroform-hexane was added to the residue. The precipitated solid was collected by filtration to obtain the target compound (52 mg).

$^1$H-NMR (DMSO-d$_6$, 300 MHz): δ 2.30 (3H, s), 6.49 (2H, s), 7.08-7.14 (1H, m), 7.24-7.28 (1H, m), 7.35-7.42 (2H, m), 7.49 (1H, d, J=2.7 Hz), 7.74 (1H, d, J=8.7 Hz), 7.82-7.85 (1H, m), 10.73 (1H, s).

LC/MS (ESI): m/z 369.0 (M+1).

Example 73

N-(3-amino-4-oxo-2-phenyl-4,5-dihydro-2H-pyrazolo[4,3-c]quinolin-7-yl)-2-(4-methyl-1-piperazinyl)acetamide

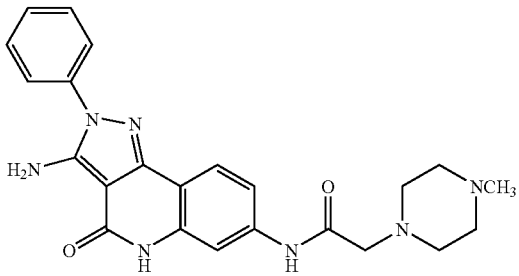

A mixture of 3,7-diamino-2-phenyl-2,5-dihydro-4H-pyrazolo[4,3-c]quinolin-4-one (100 mg), chloroacetyl chloride (28.6 μl), triethylamine (71.7 μl) and tetrahydrofuran (6 ml) was stirred at room temperature for 30 minutes, and 1-methylpiperazine (76.1 μl) was added thereto. The reaction mixture was stirred at room temperature for additional 30 minutes and with heating under reflux for 6 hours. To the reaction mixture was added water, and the mixture was extracted with ethyl acetate. The extract was washed with water and brine, dried over anhydrous magnesium sulfate and then the solvent was distilled off under reduced pressure. Ethyl acetate was added to the residue. The precipitated solid was collected by filtration, and washed with ethyl acetate to obtain the target compound (64 mg).

$^1$H-NMR (DMSO-$d_6$, 300 MHz): δ 2.17 (3H, s), 2.38 (4H, br), 2.53 (4H, br), 3.13 (2H, s), 6.37 (2H, br), 7.32 (1H, dd, J=8.6, 1.9 Hz), 7.41-7.46 (1H, m), 7.53-7.59 (2H, m), 7.64-7.71 (3H, m), 7.81 (1H, d, J=8.4 Hz), 9.86 (1H, br), 10.77 (1H, br).

LC/MS (ESI): m/z 432.2 (M+1).

Example 74

N-(3-amino-4-oxo-2-phenyl-4,5-dihydro-2H-pyrazolo[4,3-c]quinolin-7-yl)-3-(4-methyl-1-piperazinyl)propanamide

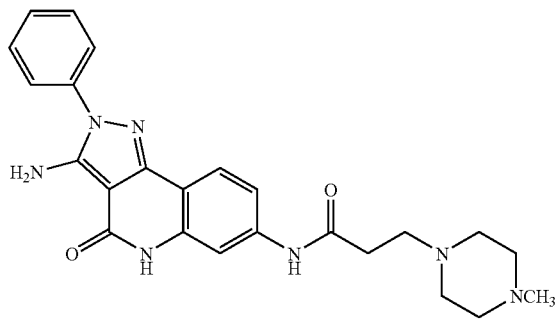

A mixture of 3,7-diamino-2-phenyl-2,5-dihydro-4H-pyrazolo[4,3-c]quinolin-4-one (100 mg), acryloyl chloride (29.3 μl), triethylamine (71.7 μl) and tetrahydrofuran (6 ml) was stirred at 0° C. for 30 minutes. Water was added to the mixture, and the mixture was extracted with ethyl acetate. The extract was washed with water and brine, dried over anhydrous magnesium sulfate and then the solvent was distilled off under reduced pressure. To the residue were added 1-methylpiperazine (0.6 ml) and N,N-dimethylformamide (3 ml), and the mixture was stirred at 80° C. for one night and concentrated under reduced pressure. Ethyl acetate-diisopropyl ether was added to the residue. The precipitated solid was collected by filtration and washed with ethyl acetate-diisopropyl ether to obtain the target compound (83 mg).

$^1$H-NMR (DMSO-$d_6$, 300 MHz): δ 2.14 (3H, s), 2.30 (4H, br), 2.41 (4H, br), 2.44-2.50 (2H, m), 2.61 (2H, t, J=6.9 Hz), 6.36 (2H, br), 7.31 (1H, dd, J=8.5, 1.9 Hz), 7.40-7.45 (1H, m), 7.53-7.58 (2H, m), 7.62-7.67 (3H, m), 7.79 (1H, d, J=8.5 Hz), 10.27 (1H, br), 10.79 (1H, br).

LC/MS (ESI): m/z 446.3 (M+1).

Example 75

N-(3-amino-4-oxo-2-phenyl-4,5-dihydro-2H-pyrazolo[4,3-c]quinolin-7-yl)-2-(4-methyl-1-piperazinyl)ethanesulfonamide

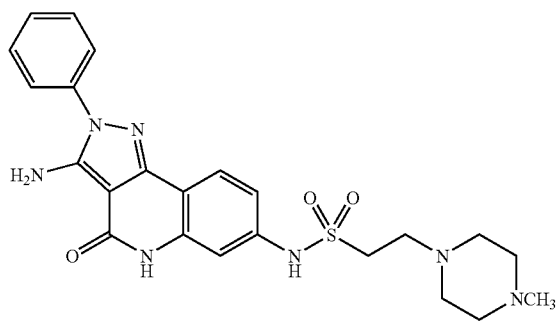

A mixture of 3,7-diamino-2-phenyl-2,5-dihydro-4H-pyrazolo[4,3-c]quinolin-4-one (150 mg), 2-chloroethanesulfonyl chloride (61.8 μl), diisopropylethylamine (108 μl) and tetrahydrofuran (5 ml) was stirred at room temperature for 30 minutes, 1-methylpiperazine (571 μl) and N,N-dimethylformamide (1 ml) were added thereto, and stirred at room temperature for one night. To the reaction mixture was added water, and the mixture was extracted with ethyl acetate. The extract was washed with water and brine, dried over anhydrous magnesium sulfate, and then the solvent was distilled off under reduced pressure. The residue was purified with aminopropylated silica gel column chromatography to obtain the target compound (25 mg).

$^1$H-NMR (DMSO-$d_6$, 300 MHz): δ 2.19 (3H, s), 2.37 (2H, br), 3.17-3.20 (4H, m), 3.28-3.33 (4H, m), 3.42-3.47 (2H, m), 6.16-6.19 (1H, m), 6.29 (2H, br), 6.42-6.45 (2H, m), 7.38-7.43 (1H, m), 7.52-7.66 (5H, m), 10.46 (1H, br).

LC/MS (ESI): m/z 482.3 (M+1).

Example 76

3-amino-2-(3-methoxyphenyl)-7-(2-morpholin-4-ylethoxy)-2,5-dihydro-4H-pyrazolo[4,3-c]quinolin-4-one

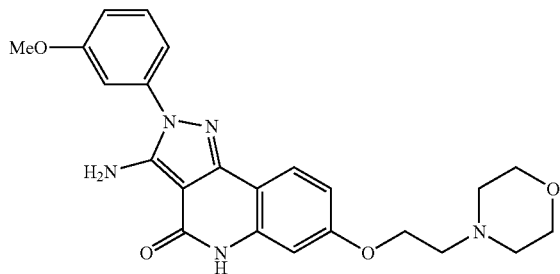

A mixture of 3-amino-2-(3-methoxyphenyl)-7-hydroxy-2,5-dihydro-4H-pyrazolo[4,3-c]quinolin-4-one (150 mg), 4-(2-chloroethyl)morpholine hydrochloride (109 mg), potassium carbonate (163 mg), potassium iodide (5 mg) and N,N-dimethylformamide (5 mg) was stirred at 80° C. for 3 hours. To the reaction mixture was added water, and the mixture was extracted with ethyl acetate. The extract was washed with water and brine, dried over anhydrous magnesium sulfate, and then the solvent was distilled off under reduced pressure. The residue was purified with silica gel column chromatography. To the concentrated residue of fraction was added ethyl acetate. The precipitated solid was collected by filtration, washed with ethyl acetate, and dried to obtain the target compound (73 mg).

$^1$H-NMR (DMSO-d$_6$, 300 MHz): δ 2.47-2.50 (4H, m), 2.71 (2H, t, J=5.5 Hz), 3.59 (4H, t, J=4.4 Hz), 3.84 (3H, s), 4.10 (2H, t, J=5.5 Hz), 6.39 (2H, br), 6.76-6.80 (2H, m), 6.99-7.02 (1H, m), 7.20-7.24 (2H, m), 7.44-7.49 (1H, m), 7.79 (1H, d, J=8.4 Hz), 10.65 (1H, br).

LC/MS (ESI): m/z 436.2 (M+1).

Example 77

3-amino-2-(2-chloro-5-methoxyphenyl)-7-(2-morpholin-4-ylethoxy)-2,5-dihydro-4H-pyrazolo[4,3-c]quinolin-4-one

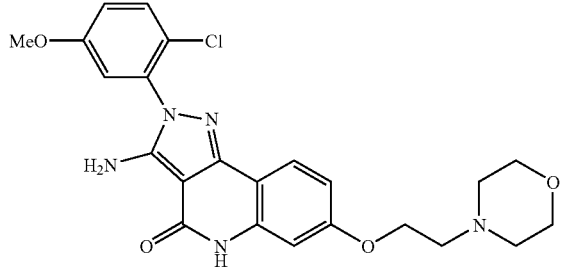

In the same manner as shown in Example 76, the target compound was obtained.

$^1$H-NMR (DMSO-d$_6$, 300 MHz): δ 2.45-2.50 (4H, m), 2.72 (2H, t, J=5.7 Hz), 3.56-3.62 (4H, m), 3.82 (3H, s), 4.10 (2H, t, J=5.7 Hz), 6.32 (2H, s), 6.73 (1H, dd, J=8.7, 2.4 Hz), 6.79 (1H, d, J=2.4 Hz), 7.12-7.18 (2H, m), 7.57 (1H, d, J=8.7 Hz), 7.73 (1H, d, J=8.7 Hz), 10.59 (1H, s).

LC/MS (ESI): m/z 470.0 (M+1).

Example 78

3-amino-2-(2-chloro-5-methoxyphenyl)-7-(3-morpholin-4-ylpropoxy)-2,5-dihydro-4H-pyrazolo[4,3-c]quinolin-4-one

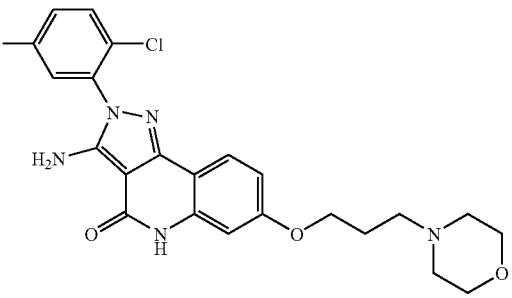

In the same manner as shown in Example 76, the target compound was obtained.

$^1$H-NMR (DMSO-d$_6$, 300 MHz): δ 1.75-2.00 (2H, m), 2.30-2.46 (6H, m), 3.53-3.60 (4H, m), 3.82 (3H, s), 4.03 (2H, t, J=6.6 Hz), 6.33 (2H, s), 6.72 (1H, dd, J=8.7, 2.4 Hz), 6.79 (1H, d, J=2.4 Hz), 7.13-7.20 (2H, m), 7.58 (1H, d, J=8.7 Hz), 7.72 (1H, d, J=8.7 Hz), 10.59 (1H, s).

LC/MS (ESI): m/z 484.1 (M+1).

Example 79

3-amino-2-(5-methoxy-2-methylphenyl)-7-(2-morpholin-4-ylethoxy)-2,5-dihydro-4H-pyrazolo[4,3-c]quinolin-4-one

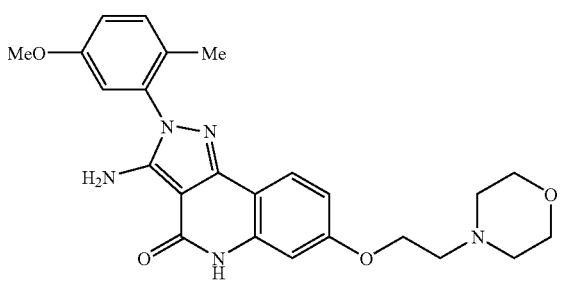

In the same manner as shown in Example 76, the target compound was obtained.

$^1$H-NMR (DMSO-d$_6$, 300 MHz): δ 2.01 (3H, s), 2.46-2.54 (4H, m), 2.71 (2H, t, J=5.7 Hz), 3.54-3.60 (4H, m), 3.78 (3H, s), 4.10 (2H, t, J=5.7 Hz), 6.13 (2H, s), 6.75 (1H, dd, J=8.7, 2.4 Hz), 6.80 (1H, d, J=2.4 Hz), 6.94 (1H, d, J=2.7 Hz), 7.03 (1H, dd, J=8.7, 2.7 Hz), 7.33 (1H, d, J=8.7 Hz), 7.73 (1H, d, J=8.7 Hz), 10.61 (1H, s).

LC/MS (ESI): m/z 450.0 (M+1).

Example 80

3-amino-2-(5-methoxy-2-methylphenyl)-7-(3-morpholin-4-ylpropoxy)-2,5-dihydro-4H-pyrazolo[4,3-c]quinolin-4-one

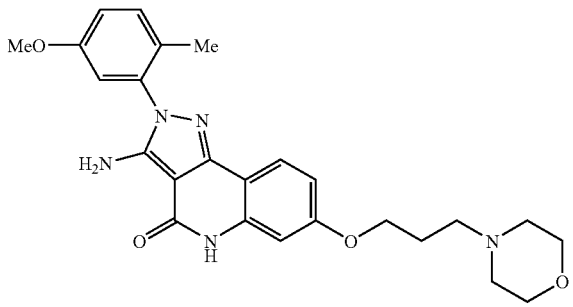

In the same manner as shown in Example 76, the target compound was obtained.

$^1$H-NMR (DMSO-d$_6$, 300 MHz): δ 1.85-1.95 (2H, m), 2.01 (3H, s), 2.33-2.47 (6H, m), 3.55-3.61 (4H, m), 3.78 (3H, s), 4.02 (2H, t, J=6.3 Hz), 6.13 (2H, s), 6.72 (1H, dd, J=8.7, 2.4 Hz), 6.79 (1H, d, J=2.4 Hz), 6.94 (1H, d, J=2.7 Hz), 7.03 (1H, dd, J=8.7, 2.7 Hz), 7.33 (1H, d, J=8.7 Hz), 7.73 (1H, d, J=8.7 Hz), 10.61 (1H, s).

LC/MS (ESI): m/z 464.1 (M+1).

Example 81

3-amino-8-methoxy-2-(5-methoxy-2-methylphenyl)-7-(2-morpholin-4-ylethoxy)-2,5-dihydro-4H-pyrazolo[4,3-c]quinolin-4-one

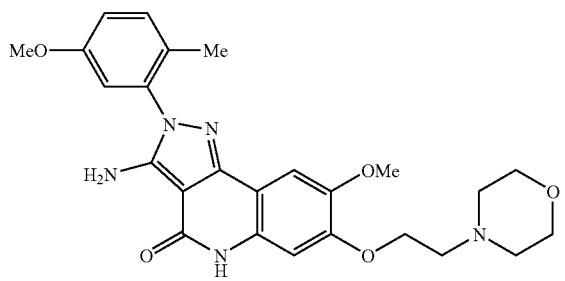

In the same manner as shown in Example 76, the target compound was obtained.

$^1$H-NMR (DMSO-d$_6$, 300 MHz): δ 1.99 (3H, s), 2.48 (4H, br), 2.71 (2H, t, J=6.0 Hz), 3.55-3.58 (4H, m), 3.75 (3H, s), 3.76 (3H, s), 4.05 (2H, t, J=6.0 Hz), 6.08 (2H, br), 6.86 (1H, s), 6.93 (1H, d, J=2.5 Hz), 7.02 (1H, dd, J=8.6, 2.5 Hz), 7.26 (1H, s), 7.31 (1H, d, J=8.6 Hz), 10.46 (1H, br).

LC/MS (ESI): m/z 480.1 (M+1).

Example 82

3-amino-8-methoxy-2-(5-methoxy-2-methylphenyl)-7-(3-morpholin-4-ylpropoxy)-2,5-dihydro-4H-pyrazolo[4,3-c]quinolin-4-one

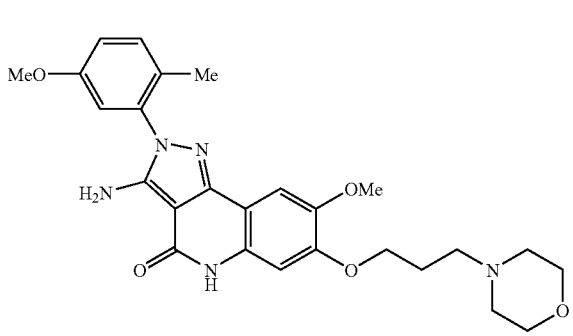

In the same manner as shown in Example 76, the target compound was obtained.

$^1$H-NMR (DMSO-d$_6$, 300 MHz): δ 1.99-2.03 (2H, m), 2.11 (3H, s), 2.46-2.60 (6H, m), 3.60-3.75 (4H, m), 3.87 (6H, s), 4.00-4.20 (2H, m), 6.21 (2H, br), 6.97 (1H, s), 7.04 (1H, s), 7.13 (1H, d, J=8.4 Hz), 7.38 (1H, s), 7.43 (1H, d, J=8.4 Hz), 10.57 (1H, br).

LC/MS (ESI): m/z 494.1 (M+1).

Example 83

3-amino-8-methoxy-2-(5-methoxy-2-methylphenyl)-7-[(1-methylpiperidin-4-yl)methoxy]-2,5-dihydro-4H-pyrazolo[4,3-c]quinolin-4-one

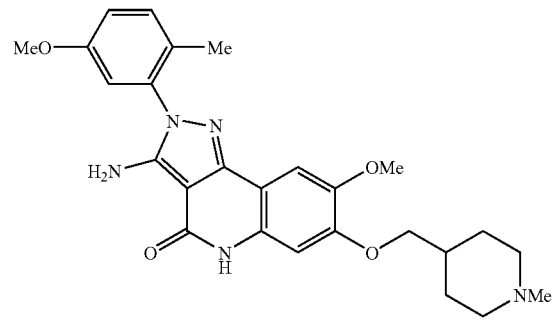

In the same manner as shown in Example 76, the target compound was obtained.

$^1$H-NMR (DMSO-d$_6$, 300 MHz): δ 1.38-1.50 (1H, m), 1.70-2.00 (4H, m), 2.00 (3H, s), 2.05-2.30 (5H, m), 2.35-2.45 (1H, m), 2.60-2.70 (1H, m), 3.77 (3H, s), 3.78 (3H, s), 3.92-3.97 (2H, m), 6.09 (2H, br), 6.86 (1H, s), 6.96 (1H, d, J=2.5 Hz), 7.03 (1H, dd, J=8.5, 2.5 Hz), 7.26 (1H, s), 7.32 (1H, d, J=8.5 Hz), 10.45 (1H, br).

LC/MS (ESI): m/z 478.2 (M+1).

Example 84

3-amino-2-(2-chloro-5-methoxyphenyl)-8-methoxy-(3-morpholin-4-ylpropoxy)-2,5-dihydro-4H-pyrazolo[4,3-c]quinolin-4-one

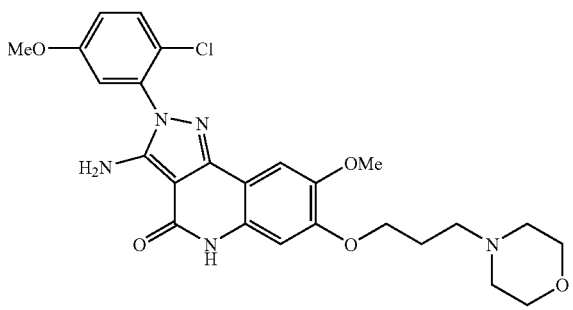

In the same manner as shown in Example 76, the target compound was obtained.

$^1$H-NMR (DMSO-$d_6$, 300 MHz): δ 1.86-1.97 (2H, m), 2.37 (4H, br), 2.43 (2H, t, J=7.1 Hz), 3.56-3.59 (4H, m), 3.77 (3H, s), 3.82 (3H, s), 4.00 (2H, t, J=6.3 Hz), 6.32 (2H, br), 6.86 (1H, s), 7.15 (1H, dd, J=8.6, 2.8 Hz), 7.19 (1H, d, J=2.8 Hz), 7.26 (1H, s), 7.57 (1H, d, J=8.6 Hz), 10.46 (1H, br).

LC/MS (ESI): m/z 514.1 (M+1).

Example 85

3-amino-2-(2-chloro-5-methoxyphenyl)-7-[3-(dimethylamino)propoxy]-8-methoxy-2,5-dihydro-4H-pyrazolo[4,3-c]quinolin-4-one

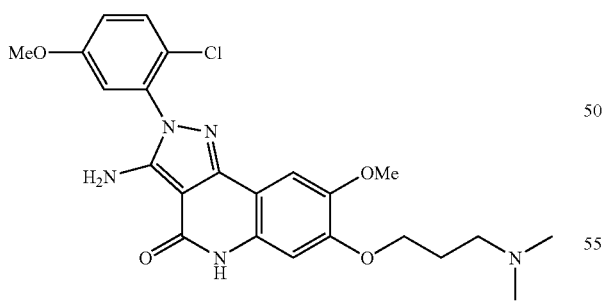

In the same manner as shown in Example 76, the target compound was obtained.

$^1$H-NMR (DMSO-$d_6$, 300 MHz): δ 1.84-1.96 (2H, m), 2.15 (6H, s), 2.37 (2H, t, J=6.7 Hz), 3.78 (3H, s), 3.82 (3H, s), 3.99 (2H, t, J=6.3 Hz), 6.32 (2H, br), 6.87 (1H, s), 7.15-7.19 (2H, m), 7.26 (1H, s), 7.59 (1H, d, J=8.7 Hz), 10.46 (1H, br).

LC/MS (ESI): m/z 472.1 (M+1).

Example 86

2-(2-chloro-5-methoxyphenyl)-7-(2-morpholin-4-ylethoxy)-2,5-dihydro-4H-pyrazolo[4,3-c]quinolin-4-one

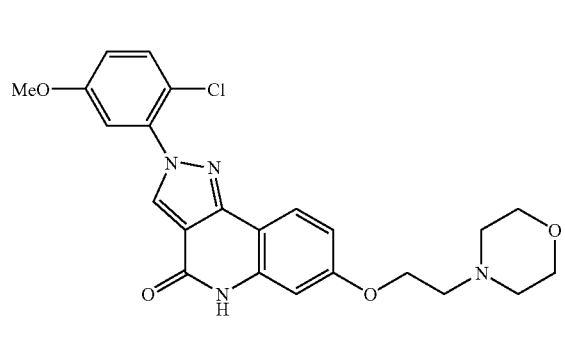

In the same manner as shown in Example 76, the target compound was obtained.

$^1$H-NMR (DMSO-$d_6$, 300 MHz): δ 2.50-2.55 (4H, m), 2.72 (2H, t, J=5.7 Hz), 3.58 (4H, t, J=4.5 Hz), 3.84 (3H, s), 4.13 (2H, t, J=5.7 Hz), 6.85 (1H, dd, J=8.6, 2.2 Hz), 6.89 (1H, d, J=2.2 Hz), 7.17 (1H, dd, J=9.0, 3.0 Hz), 7.34 (1H, d, J=3.0 Hz), 7.63 (1H, d, J=9.0 Hz), 7.93 (1H, d, J=8.6 Hz), 8.89 (1H, s), 11.13 (1H, br).

LC/MS (ESI):. m/z 455.0 (M+1).

Example 87

2-(2-chloro-5-methoxyphenyl)-7-(3-morpholin-4-ylpropoxy)-2,5-dihydro-4H-pyrazolo[4,3-c]quinolin-4-one

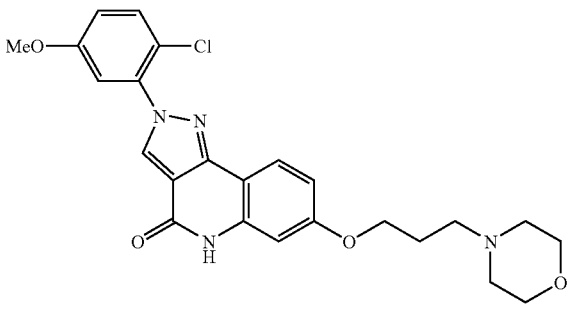

In the same manner as shown in Example 76, the target compound was obtained.

$^1$H-NMR (DMSO-$d_6$, 300 MHz): δ 1.85-1.95 (2H, m), 2.22-2.44 (6H, m), 3.55-3.57 (4H, m), 3.82 (3H, s), 4.04-4.06 (2H, m), 6.82 (1H, d, J=8.7 Hz), 6.88 (1H, s), 7.15-7.18 (1H, m), 7.33-7.34 (1H, m), 7.62 (1H, dd, J=8.8, 1.7 Hz), 8.08-8.45 (1H, m), 8.88 (1H, d, J=2.1 Hz), 11.25 (1H, br).

LC/MS (ESI): m/z 469.1 (M+1).

Example 88

3-amino-8-{3-[4-(3-chlorophenyl)-1-piperazinyl]propoxy}-2-phenyl-2,5-dihydro-4H-pyrazolo[4,3-c]quinolin-4-one

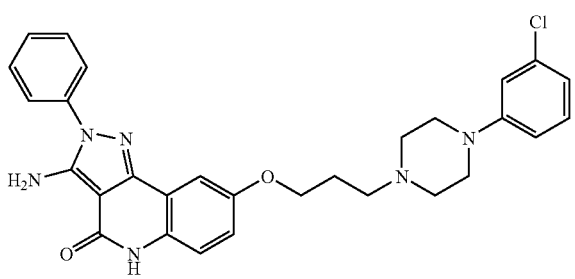

In the same manner as shown in Example 76, the target compound was obtained.

$^1$H-NMR (DMSO-d$_6$, 200 MHz): δ 1.85-2.00 (2H, m), 2.40-2.56 (6H, m), 3.00-3.21 (4H, m), 3.97-4.11 (2H, m), 6.37 (2H, br), 6.72-6.78 (1H, m), 6.80-6.94 (2H, m), 7.00-7.07 (1H, m), 7.15-7.23 (2H, m), 7.30-7.71 (6H, m), 10.65 (1H, br).

Example 89

3-amino-8-[3-(4-methyl-1-piperazinyl)propoxy]-2-phenyl-2,5-dihydro-4H-pyrazolo[4,3-c]quinolin-4-one

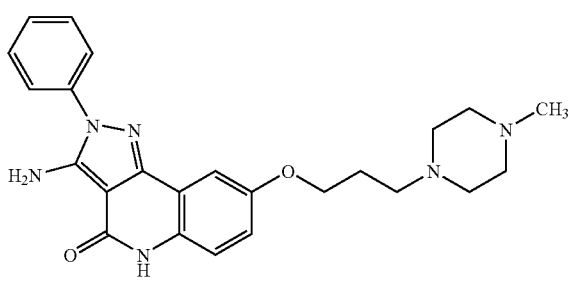

In the same manner as shown in Example 76, the target compound was obtained.

$^1$H-NMR (CDCl$_3$, 200 MHz): δ 1.92-2.04 (2H, m), 2.29 (3H, s), 2.3-2.7 (10H, m), 4.07 (2H, t, J=4.0 Hz), 6.39 (2H, br), 7.01-7.08 (1H, m), 7.17-7.23 (1H, m), 7.37-7.71 (6H, m), 10.68 (1H, br).

Example 90

3-amino-8-[2-(4-morpholinyl)ethoxy]-2-phenyl-2,5-dihydro-4H-pyrazolo[4,3-c]quinolin-4-one

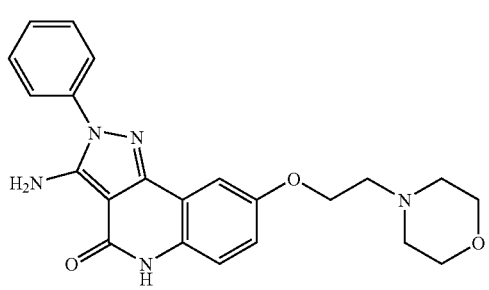

In the same manner as shown in Example 76, the target compound was obtained.

$^1$H-NMR (DMSO-d$_6$, 200 MHz): δ 2.40-2.60 (4H, m), 2.70 (2H, t, J=4.0 Hz), 3.54-3.62 (4H, m), 4.11 (2H, t, J=4.0 Hz), 6.39 (2H, br), 7.01-7.08 (1H, m), 7.17-7.23 (1H, m), 7.37-7.71 (6H, m), 10.68 (1H, br).

Example 91

3-(3-amino-4-oxo-4,5-dihydro-2H-pyrazolo[4,3-c]quinolin-2-yl)benzoic acid

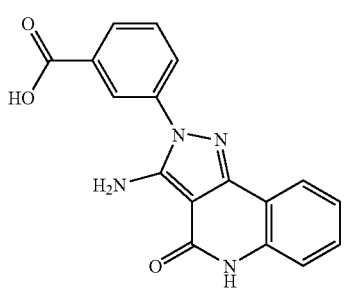

A mixture of methyl 3-(3-amino-4-oxo-4,5-dihydro-2H-pyrazolo[4,3-c]quinolin-2-yl)benzoate (80 mg), an 1N aqueous sodium hydroxide solution (0.5 ml), methanol (5 ml), tetrahydrofuran (5 ml) and water (2.5 ml) was stirred at 50° C. for 1 hour. The reaction mixture was neutralized with 1N hydrochloric acid. The precipitated solid was collected by filtration, washed with water, and dried to obtain the target compound (63 mg).

$^1$H-NMR (DMSO-d$_6$, 300 MHz): δ 6.55 (2H, br), 7.12-7.17 (1H, m), 7.28 (1H, d, J=8.1 Hz), 7.39-7.44 (1H, m), 7.67-7.73 (1H, m), 7.92-8.01 (3H, m), 8.20 (1H, s), 10.81 (1H, br).

LC/MS (ESI) : m/z 321.0 (M+1).

Example 92

3-amino-2-{4-[2-(1-piperidinyl)ethyl]phenyl}-2,5-dihydro-4H-pyrazolo[4,3-c]quinolin-4-one

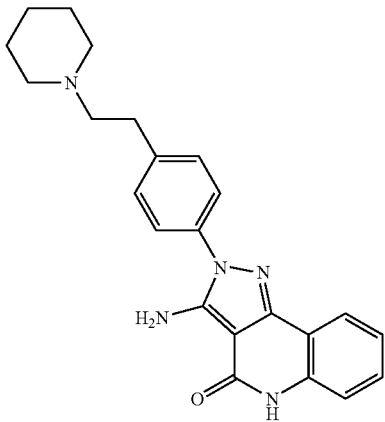

A mixture of N-{5-(4-methoxybenzyl)-4-oxo-2-[4-(2-piperidin-1-ylethyl)phenyl]-4,5-dihydro-2H-pyrazolo[4,3-c]quinolin-3-yl}acetamide (0.13 g), trifluoroacetic acid (2.5 ml), anisole (1 ml) and trifluoromethanesulfonic acid (0.5 ml) was stirred at room temperature for 26 hours. Ice and 2N aqueous sodium hydroxide solution were added to the reaction mixture, and the mixture was extracted with ethyl acetate. The extract was washed with brine, dried over anhydrous magnesium sulfate, and then the solvent was distilled off under reduced pressure. The residue was purified with propylaminated silica gel column chromatography, and the obtained crystals were recrystallized from ethyl acetate to obtain the target compound (0.04 g).

$^1$H-NMR (CDCl$_3$, 200 MHz): δ 1.43-1.72 (6H, m), 2.36-2.64 (6H, m), 2.85-2.94 (2H, m), 5.25 (2H, br), 7.05-7.11 (1H, m), 7.16-7.28 (1H, m), 7.36-7.44 (3H, m), 7.53-7.60 (2H, m), 8.08-8.22 (2H, m).

Example 93

3-amino-2-{4-[2-(4-morpholinyl)ethyl]phenyl}-2,5-dihydro-4H-pyrazolo[4,3-c]quinolin-4-one

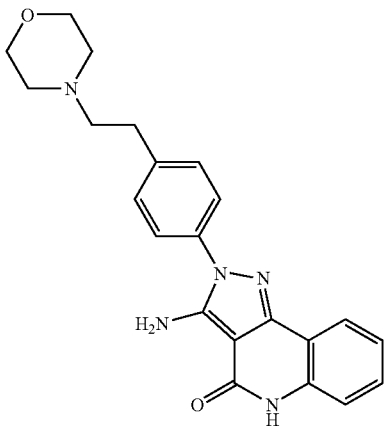

A solution of 2-{4-[3-(acethylamino)-5-(4-methoxybenzyl)-4-oxo-4,5-dihydro-2H-pyrazolo[4,3-c]quinolin-2-yl]phenyl}ethyl methanesulfonate (0.5 g), morpholine (0.23 ml) and triethylamine (0.19 ml) in ethanol (50 ml) was heated under reflux for 24 hours. The solvent was distilled off under reduced pressure, ethyl acetate was added to the residue, and the mixture was extracted with 1N hydrochloric acid. The water layer was washed with ether, basified with 2N aqueous sodium hydroxide solution and extracted with ethyl acetate. The extract was washed brine, dried over anhydrous magnesium sulfate, and concentrated under reduced pressure. The residue was recrystallized from ethyl acetate to obtain the solid (0.12 g). The mother liquor of recrystallization was purified with propylaminated silica gel column chromatography to obtain the solid (0.27 g). The obtained soilds were combined and to the solids were added trifluoroacetic acid (7.5 ml), anisole (3 ml) and trifluoromethanesulfonic acid (1.5 ml). The mixture was stirred at room temperature for 21 hours. An ice and 11N aqueous sodium hydroxide solution were added to the mixture, and the mixture was extracted with ethyl acetate. The extract was dried over anhydrous magnesium sulfate and concentrated under reduced pressure. The residue was purified with propylaminated silica gel column chromatography. The obtained solid was recrystallized from ethyl acetate to obtain the target compound (0.13 g).

$^1$H-NMR (DMSO-d$_6$, 200 MHz): δ 2.30-3.44 (8H, m), 3.45-3.80 (4H, m), 6.37 (2H, br), 7.11-7.16 (1H, m), 7.23-7.30 (1H, m), 7.37-7.82 (5H, m), 7.86-7.93 (1H, m), 10.79 (1H, br).

Example 94

3-amino-2-{4-[2-(4-methyl-1-piperazinyl)ethyl]phenyl}-2,5-dihydro-4H-pyrazolo[4,3-c]quinolin-4-one

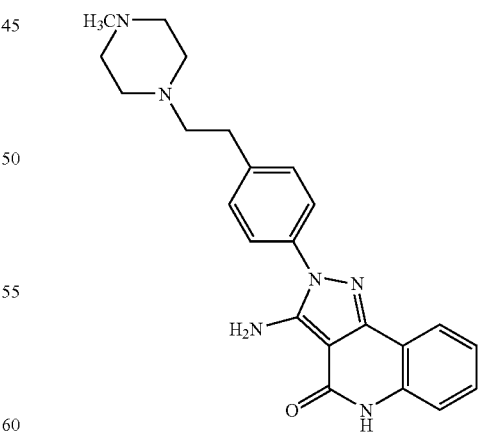

In the same manner as shown in Example 93, the target compound was obtained.

$^1$H-NMR (DMSO-d$_6$, 200 MHz): δ 2.20-3.46 (15H, m), 6.35 (2H, br), 7.10-7.28 (2H, m), 7.36-7.52 (3H, m), 7.54-7.63 (2H, m), 7.85-7.91 (1H, m), 10.79 (1H, br).

Example 95

3-amino-2-{4-[2-(4-hydroxy-1-piperidinyl)ethyl]phenyl}-2,5-dihydro-4H-pyrazolo[4,3-c]quinolin-4-one

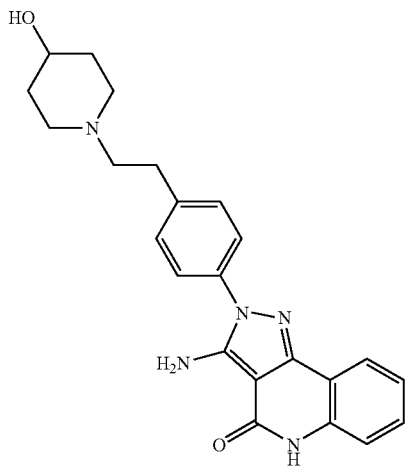

In the same manner as shown in Example 93, the target compound was obtained.

$^1$H-NMR (CDCl$_3$, 200 MHz): δ 1.30-1.54 (2H, m), 1.64-1.80 (2H, m), 2.20-2.18 (2H, m), 2.40-2.58 (2H, m), 2.74-2.88 (4H, m), 4.50-4.60 (1H, m), 6.35 (2H, br), 7.10-7.19 (1H, m), 7.22-7.31 (1H, m), 7.37-7.50 (3H, m), 7.52-7.62 (2H, m), 7.86-7.92 (1H, m), 10.78 (1H, br)

Example 96

3-amino-7,8-dimethoxy-2-(2-methylphenyl)-2,5-dihydro-4H-pyrazolo[4,3-c]quinolin-4-one

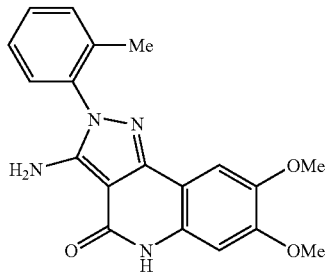

In the same manner as shown in Example 2, the target compound was obtained.

$^1$H-NMR (DMSO-d6, 300 MHz): δ 2.10 (3H, s), 3.76 (3H, s), 3.78 (3H, s), 6.08 (2H, br s), 6.86 (1H, s), 7.26 (1H, s), 7.36-7.44 (4H, m), 10.51 (1H, br s).

LC/MS (ESI): m/z 351.0 (M+1).

Example 97

3-amino-7-hydroxy-8-methoxy-2-(4-phenoxyphenyl)-2,5-dihydro-4H-pyrazolo[4,3-c]quinolin-4-one

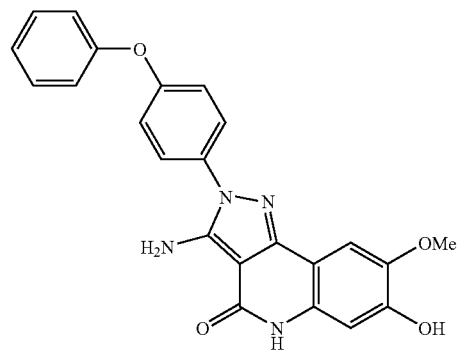

In the same manner as shown in Example 2, the target compound was obtained.

$^1$H-NMR (DMSO-d6, 300 MHz): δ 3.80 (3H, s), 6.31 (2H, br s), 6.74 (1H, s), 7.09-7.22 (5H, m), 7.26 (1H, s), 7.40-7.47 (2H, m), 7.63-7.66 (2H, m), 9.67 (1H, br s), 10.50 (1H, br s).

LC/MS (ESI): m/z 415.0 (M+1).

Example 98

3-amino-7-hydroxy-2-(4-methoxyphenyl)-2,5-dihydro-4H-pyrazolo[4,3-c]quinolin-4-one

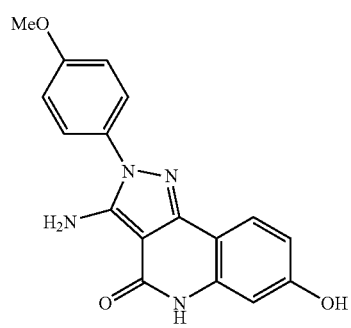

In the same manner as shown in Example 2, the target compound was obtained.

$^1$H-NMR (DMSO-d6, 300 MHz): δ 3.83 (3H, s), 6.20 (2H, br s), 6.57 (1H, dd, J=8.5, 2.5 Hz), 6.68 (1H, d, J=2.5 Hz), 7.10 (2H, d, J=8.9 Hz), 7.54 (2H, d, J=8.9 Hz), 7.68 (1H, d, J=8.5 Hz), 9.80 (1H, br s), 10.59 (1H, br s).

LC/MS (ESI): m/z 323.0 (M+1).

Example 99

3-amino-7-hydroxy-2-(2-methoxy-5-methylpyrimidin-4-yl)-2,5-dihydro-4H-pyrazolo[4,3-c]quinolin-4-one

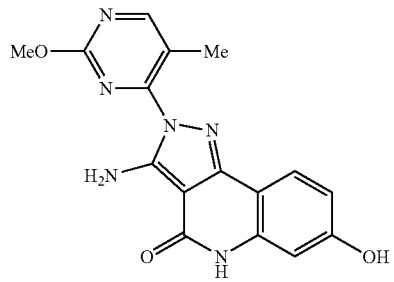

In the same manner as shown in Example 2, the target compound was obtained.

$^1$H-NMR (DMSO-d6, 300 MHz): δ 2.52 (3H, s), 3.95 (3H, s), 6.59 (1H, dd, J=8.5, 2.2 Hz), 6.66 (1H, d, J=2.2 Hz), 7.27 (2H, br s), 7.70 (1H, d, J=8.5 Hz), 8.59 (1H, s), 9.93 (1H, br s), 10.63 (1H, br s).

LC/MS (ESI): m/z 339.0 (M+1).

Example 100

3-amino-8-methoxy-2-(4-phenoxyphenyl)-2,5-dihydro-4H-pyrazolo[4,3-c]quinolin-4-one

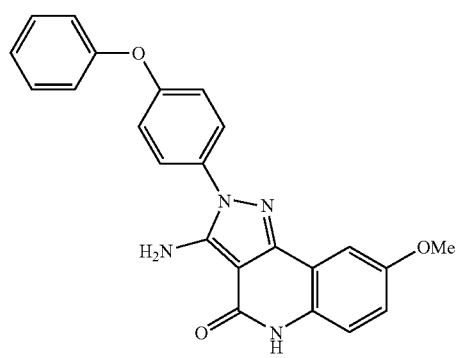

In the same manner as shown in Example 2, the target compound was obtained.

$^1$H-NMR (DMSO-d6, 300 MHz): δ 3.79 (3H, s), 6.38 (2H, br s), 7.03 (1H, dd, J=9.1, 2.8 Hz), 7.09-7.12 (2H, m), 7.17-7.23 (4H, m), 7.35 (1H, d, J=2.8 Hz), 7.43-7.48 (2H, m), 7.66 (2H, d, J=9.1 Hz), 10.67 (1H, br s).

LC/MS (ESI): m/z 399.0 (M+1).

Example 101

3-amino-7-hydroxy-2-(4-phenoxyphenyl)-2,5-dihydro-4H-pyrazolo[4,3-c]quinolin-4-one

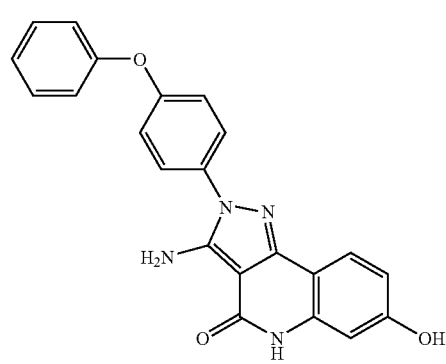

In the same manner as shown in Example 2, the target compound was obtained.

$^1$H-NMR (DMSO-d6, 300 MHz): δ 6.32 (2H, br s), 6.55-6.58 (1H, m), 6.67 (1H, d, J=1.8 Hz), 7.08-7.21 (5H, m), 7.41-7.46 (2H, m), 7.62 (2H, d, J=8.4 Hz), 7.67 (1H, d, J=8.1 Hz), 9.80 (1H, br s), 10.59 (1H, br s).

LC/MS (ESI): m/z 385.0 (M+1).

Example 102

3-amino-7-hydroxy-2-(2-methyl-4-phenoxyphenyl)-2,5-dihydro-4H-pyrazolo[4,3-c]quinolin-4-one

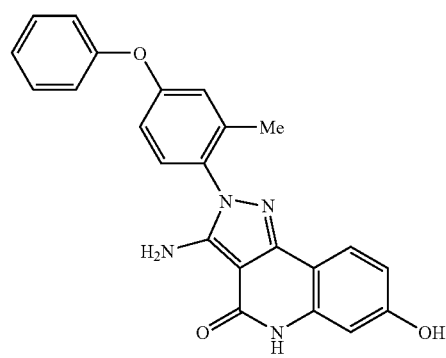

In the same manner as shown in Example 2, the target compound was obtained.

$^1$H-NMR (DMSO-d6, 300 MHz): δ 1.99 (3H, s), 6.15 (2H, br s), 6.55-6.58 (1H, m), 6.68 (1H, s), 6.96 (1H, dd, J=8.7, 2.4 Hz), 7.07-7.22 (4H, m), 7.37 (1H, d, J=8.4 Hz), 7.42-7.47 (2H, m), 7.64 (1H, d, J=8.7 Hz), 9.77 (1H, br s), 10.56 (1H, br s)

LC/MS (ESI): m/z 399.1 (M+1).

Example 103

3-amino-7-hydroxy-2-(3-methoxy-4-phenoxyphenyl)-2,5-dihydro-4H-pyrazolo[4,3-c]quinolin-4-one

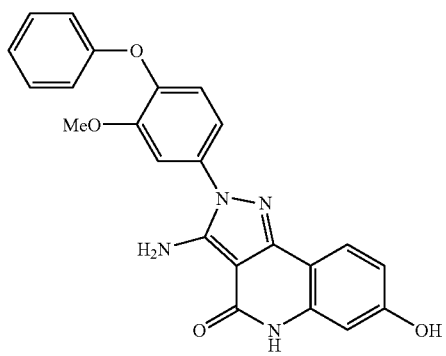

In the same manner as shown in Example 2, the target compound was obtained.

$^1$H-NMR (DMSO-d6, 300 MHz): δ 3.82 (3H, s), 6.41 (2H, br s), 6.58 (1H, d, J=8.7 Hz), 6.68 (1H, s), 6.92-6.94 (2H, m), 7.04-7.09 (1H, m), 7.16-7.23 (2H, m), 7.32-7.37 (3H, m), 7.70 (1H, d, J=8.4 Hz), 9.81 (1H, br s), 10.60 (1H, br s).

LC/MS (ESI): m/z 415.1 (M+1).

Example 104

3-amino-2-(3-methoxy-4-phenoxyphenyl)-2,5-dihydro-4H-pyrazolo[4,3-c]quinolin-4-one

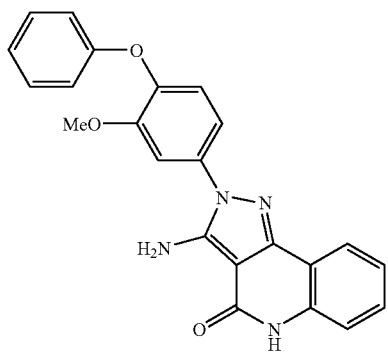

In the same manner as shown in Example 2, the target compound was obtained.

$^1$H-NMR (DMSO-d6, 300 MHz): δ 3.83 (3H, s), 6.50 (2H, br s), 6.95 (2H, d, J=8.7 Hz), 7.05-7.43 (9H, m), 7.92 (1H, d, J=7.8 Hz), 10.73 (1H, br s).

LC/MS (ESI): m/z 399.1 (M+1).

Example 105

3-amino-2-[4-(phenylsulfonyl)phenyl]-2,5-dihydro-4H-pyrazolo[4,3-c]quinolin-4-one

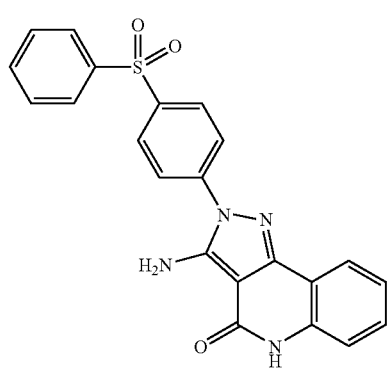

In the same manner as shown in Example 2, the target compound was obtained.

$^1$H-NMR (DMSO-d6, 300 MHz): δ 6.70 (2H, br s), 7.10-7.16 (1H, m), 7.25 (1H, d, J=8.1 Hz), 7.38-7.43 (1H, m), 7.62-7.74 (3H, m), 7.88 (1H, d, J=7.8 Hz), 7.95 (2H, d, J=8.7 Hz), 8.00-8.02 (2H, m), 8.17 (2H, d, J=8.7 Hz), 10.82 (1H, br s).

LC/MS (ESI): m/z 417.1 (M+1).

Example 106

3-amino-2-(5-methoxy-2-methyl-4-phenoxyphenyl)-2,5-dihydro-4H-pyrazolo[4,3-c]quinolin-4-one

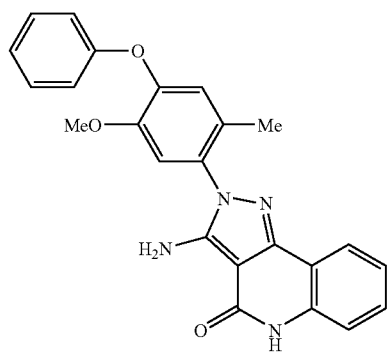

In the same manner as shown in Example 2, the target compound was obtained.

$^1$H-NMR (DMSO-d6, 300 MHz): δ 1.98 (3H, s), 3.74 (3H, s), 6.30 (2H, br s), 6.96 (2H, d, J=8.1 Hz), 7.03-7.16 (3H, m), 7.18 (1H, s), 7.24-7.40 (4H, m), 7.86 (1H, d, J=7.5 Hz), 10.71 (1H, br s).

LC/MS (ESI): m/z 413.1 (M+1).

Example 107

2-(5-methoxy-2-methylphenyl)-1,2-dihydro-5H-pyrazolo[4,3-c]quinoline-3,4-dione

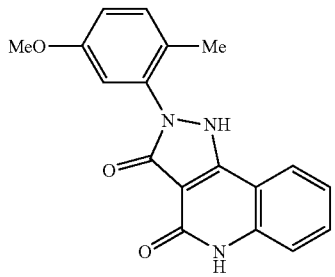

In the same manner as shown in Example 2, the target compound was obtained.

$^1$H-NMR (DMSO-d6, 300 MHz): δ 2.05 (3H, br s), 3.77 (3H, s), 6.96 (1H, s), 7.02 (1H, dd, J=8.6, 2.9 Hz), 7.12-7.17 (1H, m), 7.26-7.32 (2H, m), 7.43 (1H, br s), 7.89 (1H, d, J=7.5 Hz), 10.91 (1H, br s).

LC/MS (ESI): m/z 322.1 (M+1).

Example 108

3-amino-7-hydroxy-8-methoxy-2-(2-methylphenyl)-2,5-dihydro-4H-pyrazolo[4,3-c]quinolin-4-one

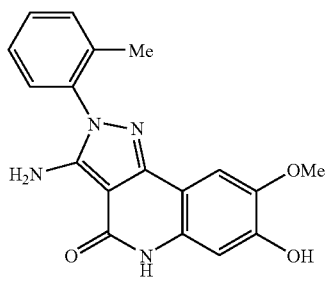

In the same manner as shown in Example 2, the target compound was obtained.

$^1$H-NMR (DMSO-d6, 300 MHz): δ 2.10 (3H, s), 3.77 (3H, s), 6.04 (2H, br s), 6.74 (1H, s), 7.23 (1H, s), 7.35-7.38 (2H, m), 7.42-7.45 (2H, m), 9.49 (1H, br s), 10.45 (1H, br s).

LC/MS (ESI): m/z 337.1 (M+1).

Example 109

3-amino-2-(5-fluoro-2-methylphenyl)-7-hydroxy-2,5-dihydro-4H-pyrazolo[4,3-c]quinolin-4-one

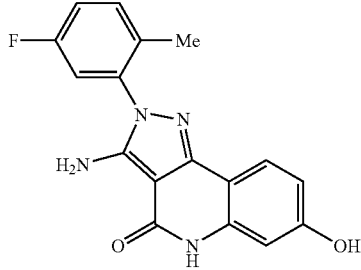

In the same manner as shown in Example 2, the target compound was obtained.

$^1$H-NMR (DMSO-d6, 300 MHz): δ 2.06 (3H, s), 6.22 (2H, br s), 6.56 (1H, dd, J=8.4, 2.4 Hz), 6.67 (1H, d, J=2.4 Hz), 7.27-7.35 (2H, m), 7.43-7.49 (1H, m), 7.63 (1H, d, J=8.4 Hz), 9.80 (1H, br s), 10.57 (1H, br s).

LC/MS (ESI): m/z 325.0 (M+1).

Example 110

3-amino-2-(5-chloro-2-methylphenyl)-7-hydroxy-2,5-dihydro-4H-pyrazolo[4,3-c]quinolin-4-one

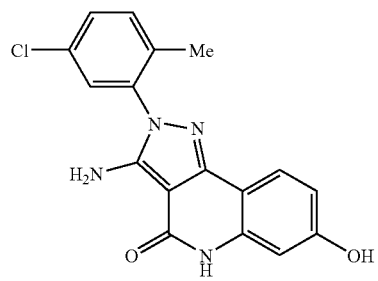

In the same manner as shown in Example 2, the target compound was obtained.

$^1$H-NMR (DMSO-d6, 300 MHz): δ 2.07 (3H, s), 6.25 (2H, br s), 6.56 (1H, dd, J=8.7, 1.5 Hz), 6.67 (1H, d, J=1.5 Hz), 7.45-7.55 (3H, m), 7.63 (1H, d, J=8.7 Hz), 9.80 (1H, br s), 10.57 (1H, br s)

LC/MS (ESI): m/z 340.9 (M+1).

Example 111

3-amino-7-hydroxy-2-(2-isopropylphenyl)-2,5-dihydro-4H-pyrazolo[4,3-c]quinolin-4-one

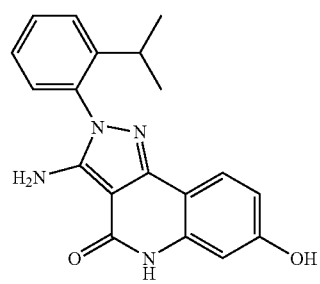

In the same manner as shown in Example 2, the target compound was obtained.

$^1$H-NMR (DMSO-d6, 300 MHz): δ 1.13 (6H, d, J=6.9 Hz), 2.70-2.76 (1H, m), 6.02 (2H, br s), 6.55 (1H, dd, J=8.7, 2.4 Hz), 6.68 (1H, d, J=2.4 Hz), 7.26-7.41 (2H, m), 7.51-7.56 (2H, m), 7.62 (1H, d, J=8.7 Hz), 9.77 (1H, br s), 10.56 (1H, br s).

LC/MS (ESI): m/z 335.0 (M+1).

Example 112

3-amino-7-hydroxy-2-{4-[(6-methylpyridin-3-yl)oxy]phenyl}-2,5-dihydro-4H-pyrazolo[4,3-c]quinolin-4-one

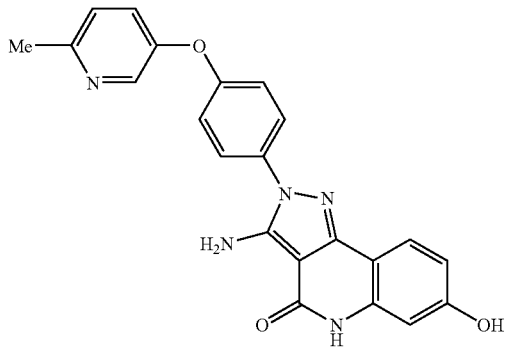

In the same manner as shown in Example 2, the target compound was obtained.

¹H-NMR (DMSO-d6, 300 MHz): δ 2.48 (3H, s), 6.33 (2H, br s), 6.57 (1H, dd, J=8.7, 2.4 Hz), 6.67 (1H, d, J=2.4 Hz), 7.15-7.21 (2H, m), 7.33 (1H, d, J=8.4 Hz), 7.45 (1H, dd, J=8.4, 3.0 Hz), 7.61-7.70 (3H, m), 8.32 (1H, d, J=3.0 Hz), 9.82 (1H, br s), 10.65 (1H, br s).

LC/MS (ESI): m/z 400.0 (M+1).

Example 113

3-amino-2-(5-methyl-1H-benzoimidazol-4-yl)-2,5-dihydro-4H-pyrazolo[4,3-c]quinolin-4-one and
3-amino-2-(6-methyl-1H-benzoimidazol-7-yl)-2,5-dihydro-4H-pyrazolo[4,3-c]quinolin-4-one

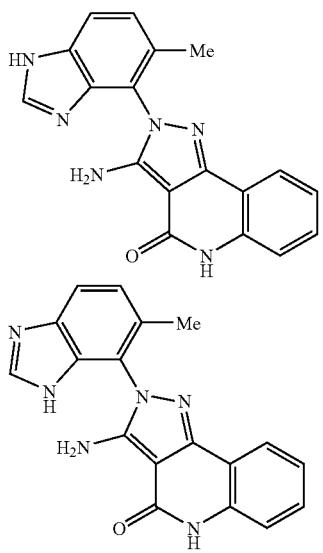

In the same manner as shown in Example 2, the target compound was obtained.

¹H-NMR (DMSO-d6, 300 MHz): δ 2.18 (3H, s), 5.93 (1H, br s), 6.20 (1H, br s), 7.05-7.15 (1H, m), 7.18-7.32 (2H, m), 7.35-7.44 (1H, m), 7.57-7.80 (1H, m), 7.85 (1H, d, J=7.8 Hz), 8.12-8.24 (1H, m), 10.74 (1H, br s), 12.47 (0.5H, br s), 12.69 (0.5H, br s).

LC/MS (ESI): m/z 331.1 (M+1).

Example 114

3-amino-2-(1,3-benzothiazol-2-yl)-2,5-dihydro-4H-pyrazolo[4,3-c]quinolin-4-one

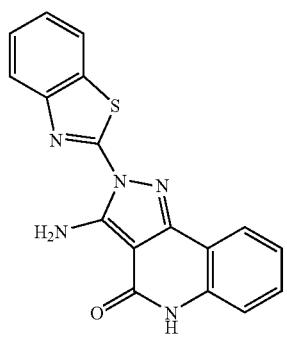

In the same manner as shown in Example 2, the target compound was obtained.

¹H-NMR (DMSO-d6, 300 MHz): δ 7.20 (1H, t, J=7.2 Hz), 7.28 (1H, d, J=8.1 Hz), 7.40-7.59 (3H, m), 7.85-8.02 (4H, m), 8.13 (1H, d, J=7.5 Hz), 10.94 (1H, br s).

LC/MS (ESI): m/z 334.0 (M+1).

Example 115

3-amino-7-hydroxy-2-(5-methoxy-2,4-dimethylphenyl)-2,5-dihydro-4H-pyrazolo[4,3-c]quinolin-4-one

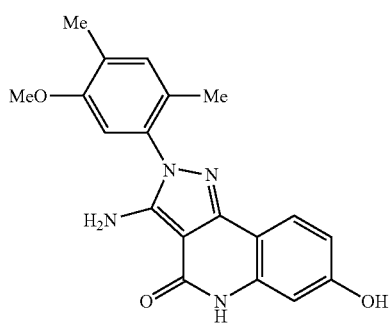

In the same manner as shown in Example 2, the target compound was obtained.

¹H-NMR (DMSO-d6, 300 MHz): δ 1.97 (3H, s), 2.20 (3H, s), 3.79 (3H, s), 6.02 (2H, br s), 6.55 (1H, dd, J=8.4, 2.4 Hz), 6.67 (1H, d, J=2.4 Hz), 6.89 (1H, s), 7.18 (1H, s), 7.63 (1H, d, J=8.4 Hz), 9.78 (1H, br s), 10.53 (1H, br s).

LC/MS (ESI): m/z 351.0 (M+1).

Example 116

3-amino-2-[4-(2-methoxyphenoxy)-2-methylphenyl]-2,5-dihydro-4H-pyrazolo[4,3-c]quinolin-4-one

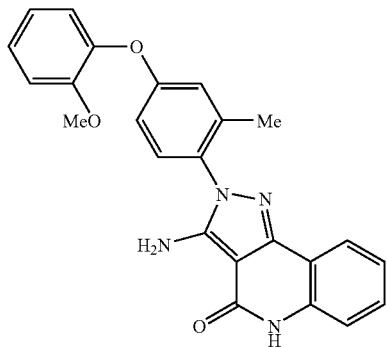

In the same manner as shown in Example 2, the target compound was obtained.

$^1$H-NMR (DMSO-d6, 300 MHz): δ 2.02 (3H, s), 3.78 (3H, s), 6.14 (2H, br s), 6.73 (1H, dd, J=8.4, 2.7 Hz), 6.89-6.91 (1H, m), 6.98-7.11 (3H, m), 7.18-7.38 (5H, m), 7.81 (1H, d, J=7.8 Hz), 10.68 (1H, br s).

LC/MS (ESI): m/z 413.2 (M+1).

Example 117

3-amino-2-(2-methyl-4-phenoxyphenyl)-2,5-dihydro-4H-pyrazolo[4,3-c]quinolin-4-one

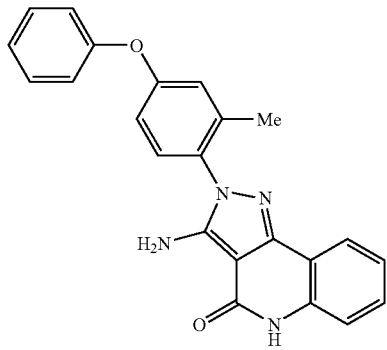

In the same manner as shown in Example 2, the target compound was obtained.

$^1$H-NMR (DMSO-d6, 300 MHz): δ 2.05 (3H, s), 6.23 (2H, br s), 6.96 (1H, dd, J=8.4, 2.4 Hz), 7.08-7.27 (6H, m), 7.35-7.47 (4H, m), 7.85 (1H, d, J=7.8 Hz), 10.73 (1H, br s).

LC/MS (ESI): m/z 383.1 (M+1).

Example 118

3-amino-9-hydroxy-7-methoxy-2-(2-methyl-4-phenoxyphenyl)-2,5-dihydro-4H-pyrazolo[4,3-c]quinolin-4-one

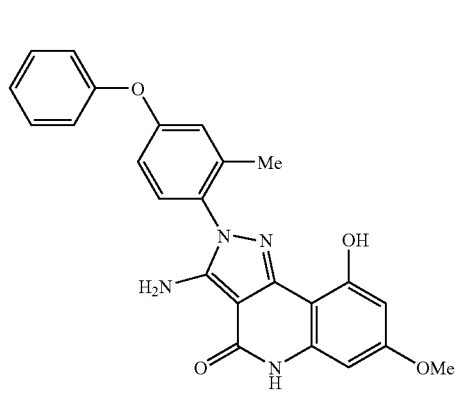

In the same manner as shown in Example 2, the target compound was obtained.

$^1$H-NMR (DMSO-d6, 300 MHz): δ 2.03 (3H, s), 3.72 (3H, s), 6.20 (2H, br s), 6.33 (1H, s), 6.36 (1H, s), 6.94 (1H, dd, J=8.7, 3.0 Hz), 7.06-7.19 (4H, m), 7.37-7.44 (3H, m), 8.94 (1H, br s), 10.62 (1H, br s).

LC/MS (ESI): m/z 429.1 (M+1).

Example 119

3-amino-7,9-dimethoxy-2-(4-phenoxyphenyl)-2,5-dihydro-4H-pyrazolo[4,3-c]quinolin-4-one

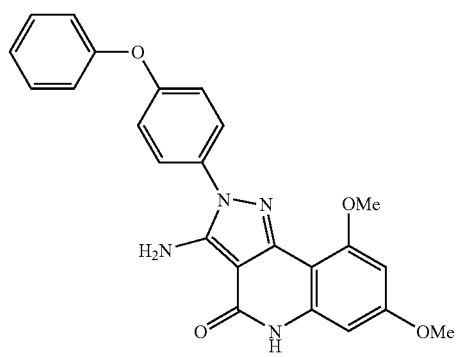

In the same manner as shown in Example 2, the target compound was obtained.

$^1$H-NMR (DMSO-d6, 200 MHz): δ 3.72 (3H, s), 3.78 (3H, s), 6.20 (2H, br s), 6.28 (1H, d, J=2.2 Hz), 6.39 (1H, d, J=2.2 Hz), 7.02-7.14 (5H, m), 7.38 (2H, t, J=8.4 Hz), 7.55 (2H, d, J=9.0 Hz), 10.57 (1H, br s).

LC/MS (ESI): m/z 429.1 (M+1).

Example 120

3-amino-9-hydroxy-7-methoxy-2-(4-phenoxyphenyl)-2,5-dihydro-4H-pyrazolo[4,3-c]quinolin-4-one

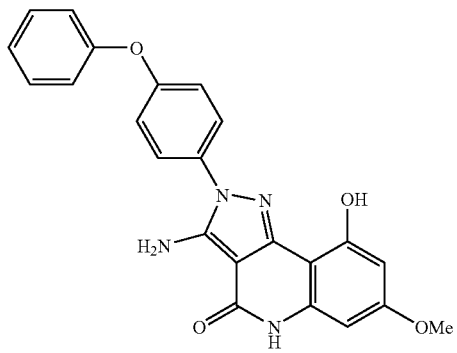

In the same manner as shown in Example 2, the target compound was obtained.

$^1$H-NMR (DMSO-d6, 300 MHz): δ 3.73 (3H, s), 6.22 (1H, s), 6.33 (1H, s), 6.49 (2H, br s), 7.07-7.20 (5H, m), 7.42 (2H, t, J=8.4 Hz), 7.62 (2H, d, J=9.3 Hz), 8.98 (1H, br s), 10.65 (1H, br s).

LC/MS (ESI): m/z 414.9 (M+1).

Example 121

3-amino-7,9-dimethoxy-2-(5-methoxy-2-methylphenyl)-2,5-dihydro-4H-pyrazolo[4,3-c]quinolin-4-one

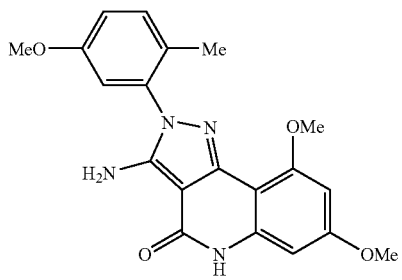

In the same manner as shown in Example 2, the target compound was obtained.

$^1$H-NMR (DMSO-d6, 300 MHz): δ 1.98 (3H, s), 3.78-3.80 (9H, m), 6.21 (2H, br s), 6.32 (1H, d, J=1.8 Hz), 6.45 (1H, d, J=1.8 Hz), 6.94 (1H, s), 7.04 (1H, d, J=8.7 Hz), 7.33 (1H, d, J=8.7 Hz), 10.63 (1H, br s).

LC/MS (ESI): m/z 381.1 (M+1).

Example 122

3-amino-9-hydroxy-7-methoxy-2-(5-methoxy-2-methylphenyl)-2,5-dihydro-4H-pyrazolo[4,3-c]quinolin-4-one

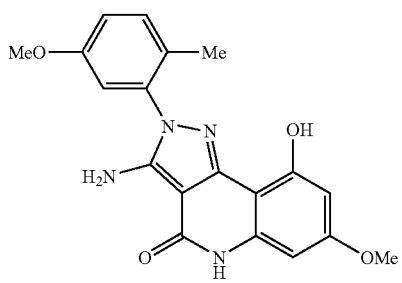

In the same manner as shown in Example 2, the target compound was obtained.

$^1$H-NMR (DMSO-d6, 300 MHz): δ 2.00 (3H, s), 3.74 (3H, s), 6.20 (1H, d, J=2.3 Hz), 6.31 (2H, br s), 6.33 (1H, d, J=2.3 Hz), 7.00 (1H, d, J=2.4 Hz), 7.02 (1H, dd, J=8.4, 2.4 Hz), 7.32 (1H, d, J=8.4 Hz), 8.93 (1H, br s), 10.61 (1H, br s).

LC/MS (ESI): m/z 367.2 (M+1).

Example 123

3-amino-7,9-dimethoxy-2-(2-methylphenyl)-2,5-dihydro-4H-pyrazolo[4,3-c]quinolin-4-one

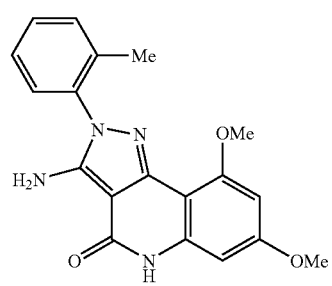

In the same manner as shown in Example 2, the target compound was obtained.

$^1$H-NMR (DMSO-d6, 300 MHz): δ 2.06 (3H, s), 3.76 (3H, s), 3.78 (3H, s), 6.00 (2H, br s), 6.29 (1H, s), 6.43 (1H, s), 7.34-7.42 (4H, m), 10.57 (1H, br s).

LC/MS (ESI): m/z 351.0 (M+1).

Example 124

3-amino-9-hydroxy-7-methoxy-2-(2-methylphenyl)-2,5-dihydro-4H-pyrazolo[4,3-c]quinolin-4-one

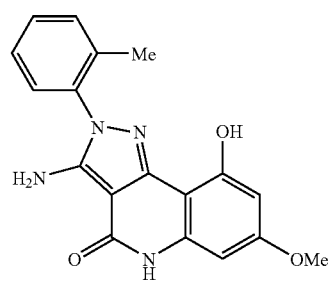

In the same manner as shown in Example 2, the target compound was obtained.

¹H-NMR (DMSO-d6, 300 MHz): δ 2.09 (3H, s), 3.72 (3H, s), 6.20 (2H, br s), 6.29 (1H, s), 6.33 (1H, s), 7.38-7.43 (4H, m), 8.93 (1H, br s), 10.62 (1H, br s).

LC/MS (ESI): m/z 337.1 (M+1).

Example 125

3-amino-2-(2-methoxy-5-methylpyrimidin-4-yl)-2,5-dihydro-4H-pyrazolo[4,3-c]quinolin-4-one

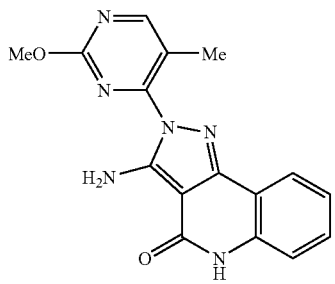

In the same manner as shown in Example 31, the target compound was obtained.

¹H-NMR (DMSO-d6, 300 MHz): δ2.50 (3H, s), 3.96 (3H, s), 7.12-7.17 (1H, m), 7.25 (1H, d, J =8.1 Hz), 7.29 (2H, br s), 7.39-7.45 (1H, m), 7.90 (1H, d, J =7.8 Hz), 8.63 (1H, s), 10.80 (1H, br s).

LC/MS (ESI): m/z 323.1 (M+1).

Example 126

3-amino-2-[4-(2,6-difluorophenoxy)-5-methoxy-2-methyphenyl]-2,5-dihydro-4H-pyrazolo[4,3-c]quinolin-4-one

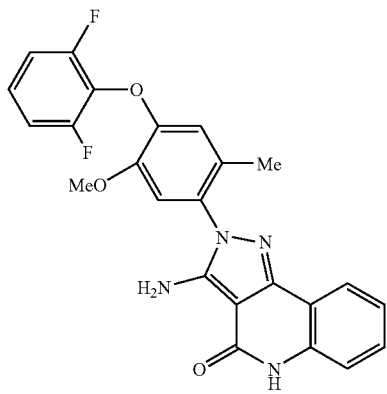

In the same manner as shown in Example 31, the target compound was obtained.

¹H-NMR (DMSO-d6, 300 MHz): δ 1.91 (3H, s), 3.84 (3H, s), 6.21 (2H, br s), 6.69 (1H, s), 7.08-7.12 (1H, m), 7.15 (1H, 5), 7.23-7.42 (5H, m), 7.83 (1H, d, J=7.5 Hz), 10.70 (1H, br s).

LC/MS (ESI): m/z 449.4 (M+1).

Example 127

3-amino-7-hydroxy-2-(5-methoxy-2-methyl-4-phenoxyphenyl)-2,5-dihydro-4H-pyrazolo[4,3-c]quinolin-4-one

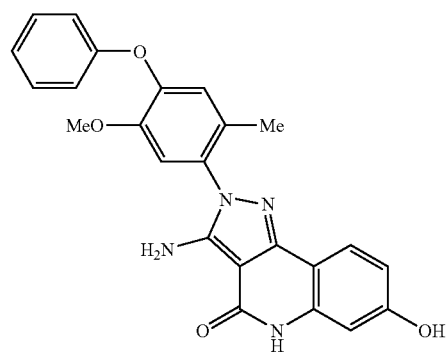

In the same manner as shown in Example 31, the target compound was obtained.

¹H-NMR (DMSO-d6, 300 MHz): δ 1.98 (3H, s), 3.73 (3H, s), 6.21 (2H, br s), 6.55 (1H, dd, J=8.6, 1.9 Hz), 6.66 (1H, d, J=1.9 Hz), 6.93-6.96 (2H, m), 7.03-7.07 (2H, m), 7.14 (1H, s), 7.31-7.36 (2H, m), 7.64 (1H, d, J=8.6 Hz), 9.75 (1H, br s), 10.54 (1H, br s).

LC/MS (ESI): m/z 429.1 (M+1).

Example 128

3-amino-2-[5-methoxy-2-methyl-4-(pyridin-3-yloxy)phenyl]-2,5-dihydro-4H-pyrazolo[4,3-c]quinolin-4-one

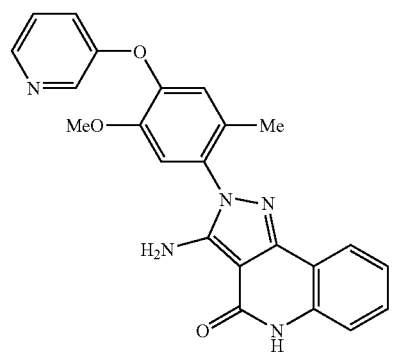

In the same manner as shown in Example 31, the target compound was obtained.

¹H-NMR (DMSO-d6, 300 MHz): δ 1.99 (3H, s), 3.74 (3H, s), 6.35 (2H, br s), 7.08-7.13 (1H, m), 7.21-7.26 (3H, m), 7.32-7.40 (3H, m), 7.86 (1H, d, J=7.8 Hz), 8.28 (1H, dd, J=4.2, 0.9 Hz), 8.34 (1H, d, J=2.7 Hz), 10.72 (1H, br s).

LC/MS (ESI): m/z 414.0 (M+1).

Example 129

3-amino-7-hydroxy-2-[5-methoxy-2-methyl-4-(pyridin-3-yloxy)phenyl]-2,5-dihydro-4H-pyrazolo[4,3-c]quinolin-4-one

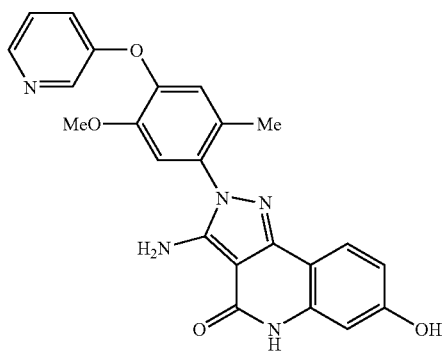

In the same manner as shown in Example 31, the target compound was obtained.

$^1$H-NMR (DMSO-d6, 300 MHz): δ 1.99 (3H, s), 3.73 (3H, s), 6.25 (2H, br s), 6.55 (1H, dd, J=8.4, 2.1 Hz), 6.66 (1H, d, J=2.1 Hz), 7.18 (1H, s), 7.19 (1H, s), 7.33-7.36 (2H, m), 7.64 (1H, d, J=8.4 Hz), 8.28 (1H, dd, J=4.1, 1.6 Hz), 8.33 (1H, d, J=2.7 Hz), 9.75 (1H, br s), 10.54 (1H, br s).

LC/MS (ESI): m/z 430.0 (M+1).

Example 130

3-amino-2-(5-methyl-1H-benzoimidazol-6-yl)-2,5-dihydro-4H-pyrazolo[4,3-c]quinolin-4-one

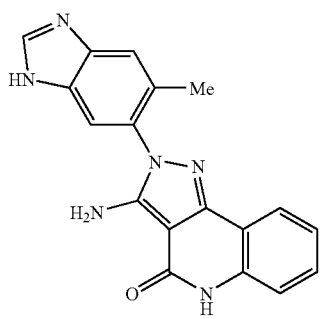

In the same manner as shown in Example 31, the target compound was obtained.

$^1$H-NMR (DMSO-d6, 300 MHz): δ 2.13 (3H, s), 6.07 (2H, br s), 7.08-7.14 (1H, m), 7.25-7.28 (1H, m), 7.35-7.41 (1H, m), 7.61 (2H, s), 7.85 (1H, dd, J=7.8, 1.5 Hz), 8.30 (1H, s), 10.72 (1H, br s), 12.61 (1H, br s).

LC/MS (ESI): m/z 331.1 (M+1).

Example 131

3-amino-2-[4-(2,6-dichlorophenoxy)-2-methylphenyl]-2,5-dihydro-4H-pyrazolo[4,3-c]quinolin-4-one

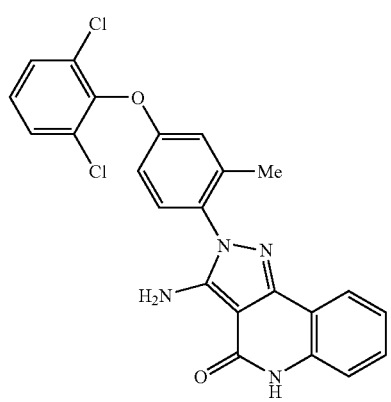

In the same manner as shown in Example 31, the target compound was obtained.

$^1$H-NMR (DMSO-d6, 300 MHz): δ 2.06 (3H, s), 6.20 (2H, br s), 6.73 (1H, dd, J=8.7, 3.0 Hz), 6.97 (1H, d, J=3.0 Hz), 7.06-7.15 (1H, m), 7.22-7.29 (1H, m), 7.33-7.45 (3H, m), 7.70 (2H, d, J=8.1 Hz), 7.83 (1H, dd, J=7.8, 1.2 Hz), 10.73 (1H, br s).

LC/MS (ESI): m/z 450.9 (M+1).

Example 132

3-amino-2-(4-methyl-6-phenoxypyridin-3-yl)-2,5-dihydro-4H-pyrazolo[4,3-c]quinolin-4-one

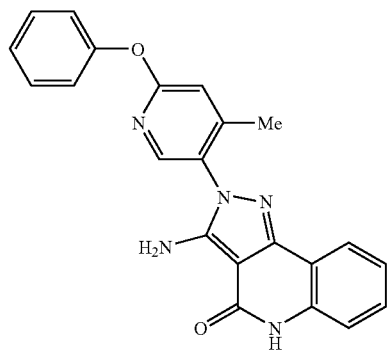

In the same manner as shown in Example 31, the target compound was obtained.

$^1$H-NMR (DMSO-d6, 300 MHz): δ 2.12 (3H, s), 6.43 (2H, br s), 7.08-7.27 (6H, m), 7.35-7.49 (3H, m), 7.84 (1H, dd, J=7.8, 1.2 Hz), 8.17 (1H, s), 10.74 (1H, br s).

LC/MS (ESI): m/z 384.0 (M+1).

Example 133

3-amino-2-[4-phenoxy-2-(trifluoromethyl)phenyl]-2,5-dihydro-4H-pyrazolo[4,3-c]quinolin-4-one

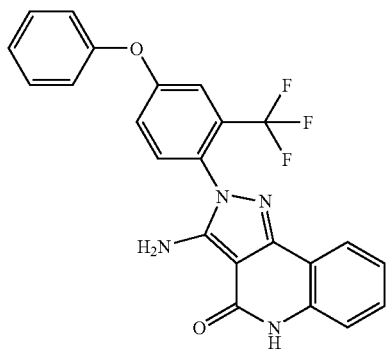

In the same manner as shown in Example 31, the target compound was obtained.

$^1$H-NMR (DMSO-d6, 300 MHz): δ 6.47 (2H, br s), 7.06-7.14 (1H, m), 7.17-7.31 (4H, m), 7.34-7.42 (2H, m), 7.46-7.54 (3H, m), 7.63 (1H, d, J=8.7 Hz), 7.81 (1H, dd, J=7.8, 0.9 Hz), 10.73 (1H, br s).

LC/MS (ESI): m/z 437.0 (M+1).

Example 134

3-amino-2-(3-phenoxyphenyl)-2,5-dihydro-4H-pyrazolo[4,3-c]quinolin-4-one

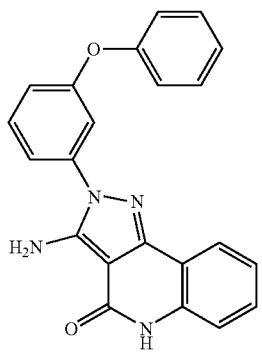

In the same manner as shown in Example 31, the target compound was obtained.

$^1$H-NMR (DMSO-d6, 300 MHz): δ 6.48 (2H, br s), 7.04-7.30 (7H, m), 7.37-7.48 (4H, m), 7.57 (1H, t, J=8.1 Hz), 7.88 (1H, dd, J=7.8, 1.2 Hz), 10.79 (1H, br s).

LC/MS (ESI): m/z 369.0 (M+1).

Example 135

3-amino-2-(5-methoxy-2,4-dimethylphenyl)-2,5-dihydro-4H-pyrazolo[4,3-c]quinolin-4-one

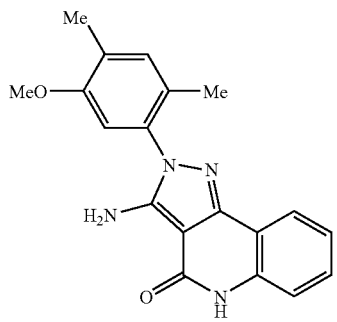

In the same manner as shown in Example 31, the target compound was obtained.

$^1$H-NMR (DMSO-d6, 300 MHz): δ 1.98 (3H, s), 2.21 (3H, s), 3.79 (3H, s), 6.11 (2H, br s), 6.92 (1H, s), 7.08-7.14 (1H, m), 7.20 (1H, s), 7.24-7.27 (1H, m), 7.35-7.41 (1H, m), 7.85 (1H, dd, J=8.1, 1.2 Hz), 10.71 (1H, br s).

LC/MS (ESI): m/z 335.1 (M+1).

Example 136

3-amino-7,8-dimethoxy-2-(4-methyl-6-phenoxypyridin-3-yl)-2,5-dihydro-4H-pyrazolo[4,3-c]quinolin-4-one

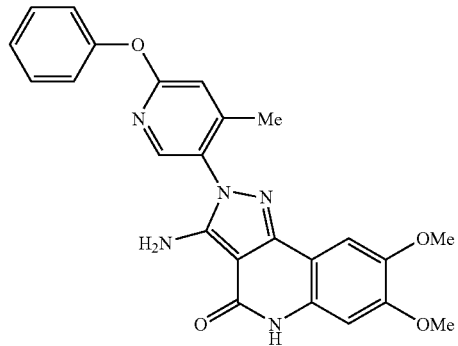

In the same manner as shown in Example 31, the target compound was obtained.

$^1$H-NMR (DMSO-d6, 300 MHz): δ 2.12 (3H, s), 3.77 (3H, s), 3.78 (3H, s), 6.36 (2H, br s), 6.86 (1H, s), 7.12-7.27 (5H, m), 7.41-7.50 (2H, m), 8.15 (1H, s), 10.53 (1H, br s).

LC/MS (ESI): m/z 444.0 (M+1).

Example 137

3-amino-7-hydroxy-2-(4-methyl-6-phenoxypyridin-3-yl)-2,5-dihydro-4H-pyrazolo[4,3-c]quinolin-4-one

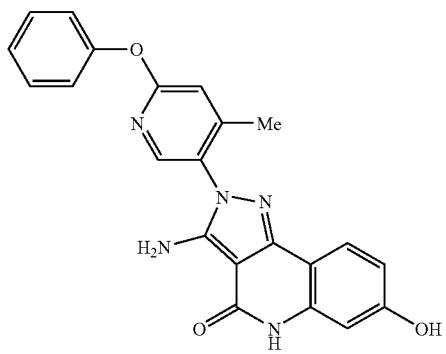

In the same manner as shown in Example 31, the target compound was obtained.

$^1$H-NMR (DMSO-d6, 300 MHz): δ 2.11 (3H, s), 6.34 (2H, br s), 6.55 (1H, dd, J=8.4, 2.4 Hz), 6.67 (1H, d, J=2.4 Hz), 7.13 (1H, s), 7.15-7.27 (3H, m), 7.41-7.49 (2H, m), 7.63 (1H, d, J=8.4 Hz), 8.13 (1H, s), 9.80 (1H, br s), 10.56 (1H, br s).

LC/MS (ESI): m/z 400.0 (M+1).

Example 138

3-amino-2-(4-bromo-5-methoxy-2-methylphenyl)-2,5-dihydro-4H-pyrazolo[4,3-c]quinolin-4-one

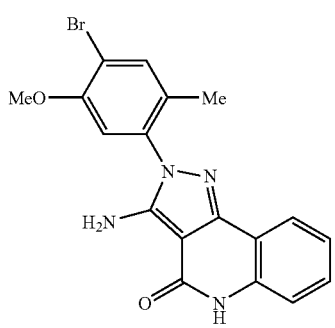

In the same manner as shown in Example 31, the target compound was obtained.

$^1$H-NMR (DMSO-d6, 300 MHz): δ 2.01 (3H, s), 3.86 (3H, s), 6.30 (2H, br s), 7.08-7.15 (2H, m), 7.24-7.42 (2H, m), 7.69 (1H, s), 7.85 (1H, dd, J=7.2, 0.9 Hz), 10.73 (1H, br s).

LC/MS (ESI): m/z 399.0 (M+1).

Example 139

3-amino-2-(2,6-dimethylphenyl)-2,5-dihydro-4H-pyrazolo[4,3-c]quinolin-4-one

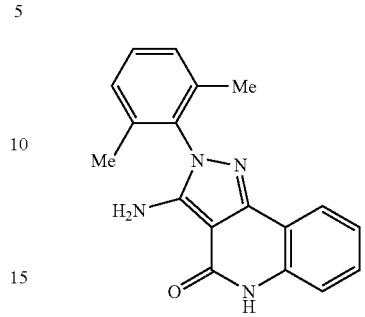

In the same manner as shown in Example 31, the target compound was obtained.

$^1$H-NMR (DMSO-d6, 300 MHz): δ 1.99 (6H, s), 6.09 (2H, br s), 7.08 (1H, t, J=8.1 Hz), 7.22-7.25 (3H, m), 7.31-7.38 (2H, m), 7.82 (1H, d, J=7.8 Hz), 10.71 (1H, br s).

LC/MS (ESI): m/z 305.1 (M+1).

Example 140

3-amino-2-(3-methoxy-2-methylphenyl)-2,5-dihydro-4H-pyrazolo[4,3-c]quinolin-4-one

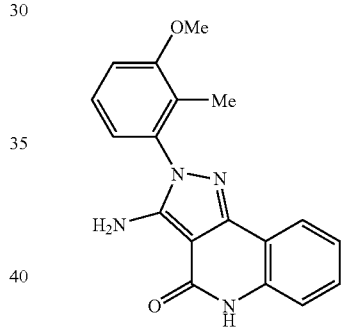

In the same manner as shown in Example 31, the target compound was obtained.

$^1$H-NMR (DMSO-d6, 300 MHz): δ 1.83 (3H, s), 3.81 (3H, s), 6.05 (2H, br s), 6.92 (1H, d, J=8.4 Hz), 7.01-7.11 (2H, m), 7.17-7.35 (3H, m), 7.77 (1H, d, J=7.6 Hz), 10.66 (1H, br s).

LC/MS (ESI): m/z 320.9 (M+1).

Example 141

3-amino-2-cyclohexyl-2,5-dihydro-4H-pyrazolo[4,3-c]quinolin-4-one

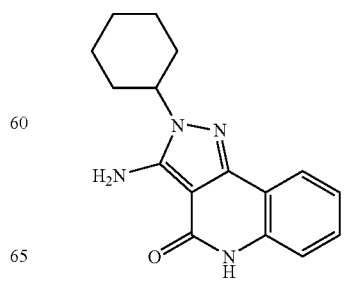

In the same manner as shown in Example 31, the target compound was obtained.

¹H-NMR (DMSO-d6, 300 MHz): δ 1.15-1.99 (10H, m), 4.15-4.25 (1H, m), 6.30 (2H, br s), 7.05-7.12 (1H, m), 7.17-7.25 (1H, m), 7.27-7.37 (1H, m), 7.84 (1H, d, J=6.9 Hz), 10.59 (1H, br s).

LC/MS (ESI): m/z 282.4 (M+1).

Example 142

3-amino-2-(4-hydroxyphenyl)-7-(3-morpholin-4-ylpropoxy)-2,5-dihydro-4H-pyrazolo[4,3-c]quinolin-4-one

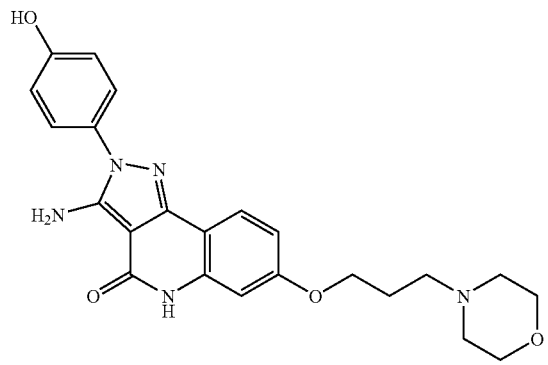

In the same manner as shown in Example 33, the target compound was obtained.

¹H-NMR (DMSO-d6, 300 MHz): δ 1.85-1.94 (2H, m), 2.36-2.45 (6H, m), 3.57 (4H, t, J=4.7 Hz), 4.01 (2H, t, J=6.3 Hz), 6.14 (2H, br s), 6.72 (1H, dd, J=8.7, 2.4 Hz), 6.78 (1H, d, J=2.4 Hz), 6.90 (2H, d, J=8.7 Hz), 7.38 (2H, d, J=8.7 Hz), 7.74 (1H, d, J=8.7 Hz), 9.80 (1H, br s), 10.59 (1H, br s).

LC/MS (ESI): m/z 436.1 (M+1).

Example 143

3-amino-8-hydroxy-2-(4-phenoxyphenyl)-2,5-dihydro-4H-pyrazolo[4,3-c]quinolin-4-one

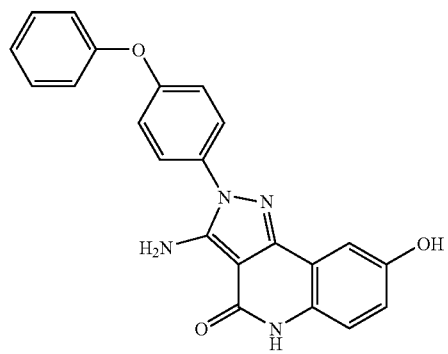

In the same manner as shown in Example 33, the target compound was obtained.

¹H-NMR (DMSO-d6, 300 MHz): δ 6.34 (2H, br s), 6.86 (1H, dd, J=8.9, 2.9 Hz), 7.03-7.37 (7H, m), 7.43-7.48 (2H, m), 7.65 (2H, d, J=9.0 Hz), 9.34 (1H, br s), 10.56 (1H, br s).

LC/MS (ESI): m/z 385.0 (M+1).

Example 144

3-amino-2-(3-hydroxy-4-phenoxyphenyl)-7-(3-morpholin-4-ylpropoxy)-2,5-dihydro-4H-pyrazolo[4,3-c]quinolin-4-one

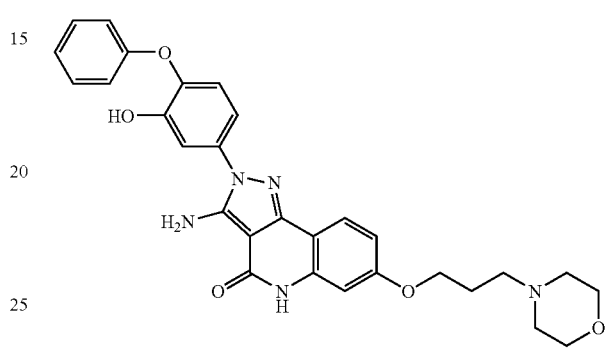

In the same manner as shown in Example 33, the target compound was obtained.

¹H-NMR (DMSO-d6, 300 MHz): δ 1.86-1.95 (2H, m), 2.38-2.46 (6H, m), 3.58 (4H, t, J=4.3 Hz), 4.03 (2H, t, J=5.7 Hz), 6.37 (2H, br s), 6.75 (1H, d, J=8.7 Hz), 6.80 (1H, s), 6.94 (2H, d, J=9.0 Hz), 7.03-7.14 (3H, m), 7.24 (1H, d, J=1.5 Hz), 7.32-7.37 (2H, m), 7.78 (1H, d, J=8.7 Hz), 10.05 (1H, br s), 10.65 (1H, br s).

LC/MS (ESI): m/z 528.3 (M+1).

Example 145

3-amino-2-(3-hydroxy-4-phenoxyphenyl)-2,5-dihydro-4H-pyrazolo[4,3-c]quinolin-4-one

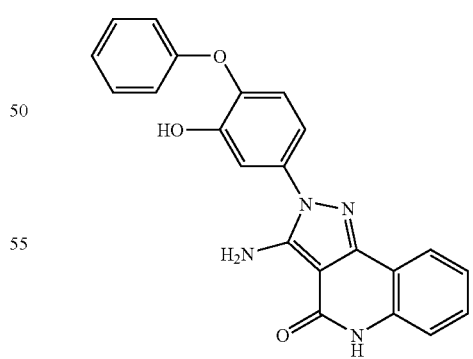

In the same manner as shown in Example 33, the target compound was obtained.

¹H-NMR (DMSO-d6, 300 MHz): δ 6.41 (2H, br s), 6.95 (2H, d, J=8.4 Hz), 7.03-7.17 (4H, m), 7.26-7.43 (5H, m), 7.89 (1H, d, J=7.5 Hz), 9.26 (1H, br s), 10.78 (1H, br s).

LC/MS (ESI): m/z 385.1 (M+1).

Example 146

3-amino-2-(5-hydroxy-2-methyl-4-phenoxyphenyl)-2,5-dihydro-4H-pyrazolo[4,3-c]quinolin-4-one

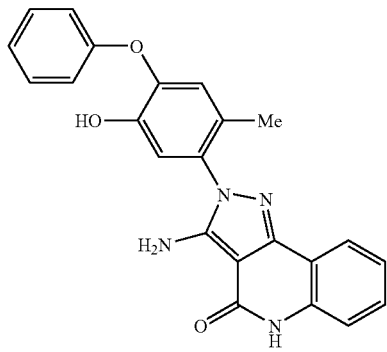

In the same manner as shown in Example 33, the target compound was obtained.

$^1$H-NMR (DMSO-d6, 300 MHz): δ 1.95 (3H, s), 6.26 (2H, br s), 6.92-7.13 (6H, m), 7.25 (1H, d, J=8.1 Hz), 7.31-7.40 (3H, m), 7.84 (1H, d, J=7.2 Hz), 9.76 (1H, br s), 10.71 (1H, br s).

LC/MS (ESI): m/z 399.1 (M+1).

Example 147

2-(5-hydroxy-2-methylphenyl)-1H-pyrazolo[4,3-c]quinoline-3,4(2H,5H)-dione

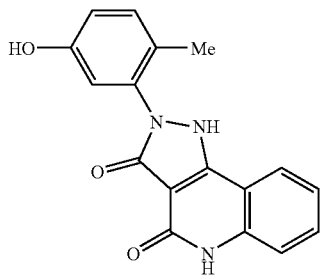

In the same manner as shown in Example 33, the target compound was obtained.

$^1$H-NMR (DMSO-d6, 300 MHz): δ 1.99 (3H, s), 6.75 (1H, s), 6.83 (1H, d, J=8.4 Hz), 7.17-7.41 (4H, m), 7.89 (1H, d, J=6.0 Hz), 9.61 (1H, br s), 10.91 (1H, br s).

LC/MS (ESI): m/z 308.1 (M+1).

Example 148

3-amino-2-[4-(2,6-difluorophenoxy)-5-hydroxy-2-methylphenyl]-2,5-dihydro-4H-pyrazolo[4,3-c]quinolin-4-one

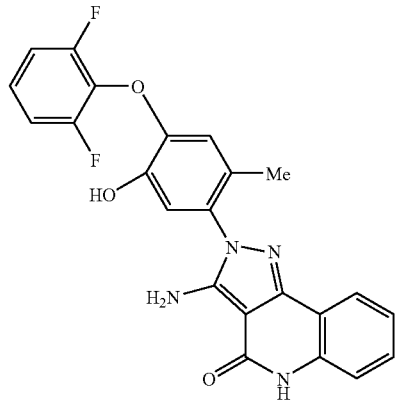

In the same manner as shown in Example 33, the target compound was obtained.

$^1$H-NMR (DMSO-d6, 300 MHz): δ 1.88 (3H, s), 6.16 (2H, br s), 6.64 (1H, s), 6.88 (1H, s), 7.07-7.12 (1H, m), 7.23-7.39 (5H, m), 7.82 (1H, d, J=7.5 Hz), 9.90 (1H, br s), 10.69 (1H, br s).

LC/MS (ESI): m/z 435.3 (M+1).

Example 149

3-amino-7-hydroxy-2-(5-hydroxy-2-methyl-4-phenoxyphenyl)-2,5-dihydro-4H-pyrazolo[4,3-c]quinolin-4-one

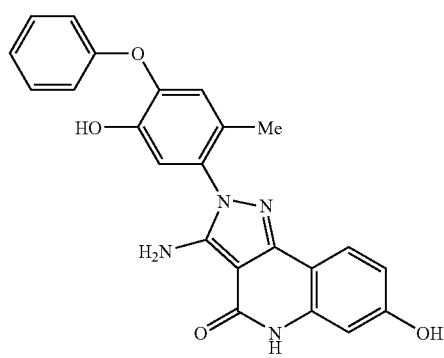

In the same manner as shown in Example 33, the target compound was obtained.

$^1$H-NMR (DMSO-d6, 300 MHz): δ 1.94 (3H, s), 6.17 (2H, br s), 6.55 (1H, dd, J=8.2, 2.0 Hz), 6.66 (1H, d, J=2.0 Hz), 6.90-7.06 (5H, m), 7.30-7.36 (2H, m), 7.63 (1H, d, J=8.2 Hz), 9.75 (2H, br s), 10.54 (1H, br s).

LC/MS (ESI): m/z 415.0 (M+1).

Example 150

{[3-amino-2-(5-hydroxy-2-methyl-4-phenoxyphenyl)-4-oxo-4,5-dihydro-2H-pyrazolo[4,3-c]quinolin-7-yl]oxy}acetic acid

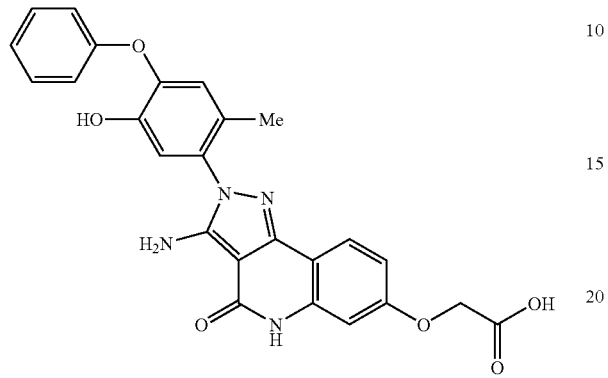

In the same manner as shown in Example 33, the target compound was obtained.

¹H-NMR (DMSO-d6, 300 MHz): δ 1.94 (3H, s), 4.67 (2H, s), 6.22 (2H, br s), 6.71 (1H, dd, J=8.8, 2.2 Hz), 6.76 (1H, d, J=2.2 Hz), 6.91 (1H, s), 6.94-6.97 (2H, m), 7.00 (1H, s), 7.01-7.06 (1H, m), 7.30-7.36 (2H, m), 7.74 (1H, d, J=8.8 Hz), 9.77 (1H, br s), 10.61 (1H, br s).

LC/MS (ESI): m/z 473.1 (M+1).

Example 151

3-amino-2-[5-hydroxy-2-methyl-4-(pyridin-3-yloxy)phenyl]-2,5-dihydro-4H-pyrazolo[4,3-c]quinolin-4-one

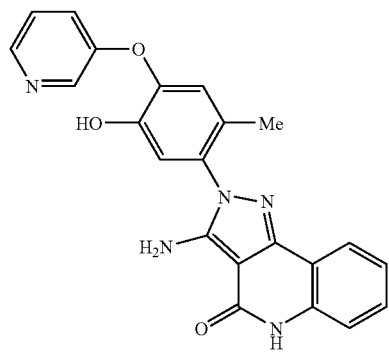

In the same manner as shown in Example 33, the target compound was obtained.

¹H-NMR (DMSO-d6, 300 MHz): δ 1.97 (3H, s), 6.31 (2H, br s), 6.94 (1H, s), 7.08-7.13 (2H, m), 7.22-7.26 (1H, m), 7.32-7.40 (3H, m), 7.85 (1H, d, J=7.8 Hz), 8.27 (1H, dd, J=4.2, 1.2 Hz), 8.35 (1H, d, J=2.4 Hz), 9.94 (1H, br s), 10.72 (1H, br s).

LC/MS (ESI): m/z 400.0 (M+1).

Example 152

3-amino-7-(2-hydroxyethoxy)-2-[5-hydroxy-2-methyl-4-(pyridin-3-yloxy)phenyl]-2,5-dihydro-4H-pyrazolo[4,3-c]quinolin-4-one

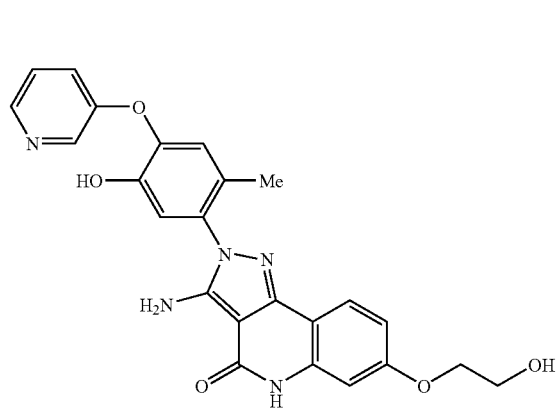

In the same manner as shown in Example 33, the target compound was obtained.

¹H-NMR (DMSO-d6, 300 MHz): δ 1.96 (3H, s), 3.71-3.75 (2H, m), 3.99 (2H, t, J=4.8 Hz), 4.91 (1H, t, J=5.4 Hz), 6.26 (2H, br s), 6.73 (1H, dd, J=8.5, 2.3 Hz), 6.80 (1H, d, J=2.3 Hz), 6.92 (1H, s), 7.12 (1H, s), 7.30-7.38 (2H, m), 7.73 (1H, d, J=8.5 Hz), 8.26 (1H, d, J=3.9 Hz), 8.34 (1H, s), 9.96 (1H, br s), 10.61 (1H, br s).

LC/MS (ESI): m/z 460.1 (M+1).

Example 153

3-amino-7-(2-hydroxyethoxy)-2-(5-hydroxy-2-methylphenyl)-2,5-dihydro-4H-pyrazolo[4,3-c]quinolin-4-one

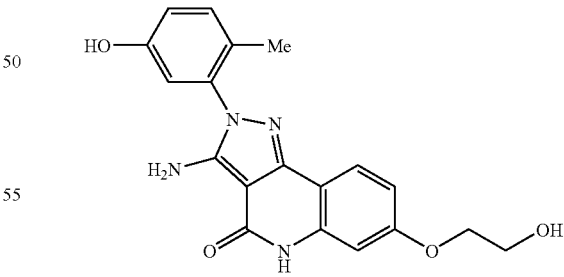

In the same manner as shown in Example 33, the target compound was obtained.

¹H-NMR (DMSO-d6, 300 MHz): δ 1.97 (3H, s), 3.70-3.77 (2H, m), 3.97-4.06 (2H, m), 4.90 (1H, t, J=5.7 Hz), 6.06 (2H, br s), 6.71-6.76 (2H, m), 6.80-6.87 (2H, m), 7.21 (1H, d, J=8.4 Hz), 7.73 (1H, d, J=8.7 Hz), 9.64 (1H, br s), 10.60 (1H, br s).

LC/MS (ESI): m/z 367.0 (M+1).

Example 154

3-amino-2-(5-hydroxy-2,4-dimethylphenyl)-2,5-dihydro-4H-pyrazolo[4,3-c]quinolin-4-one

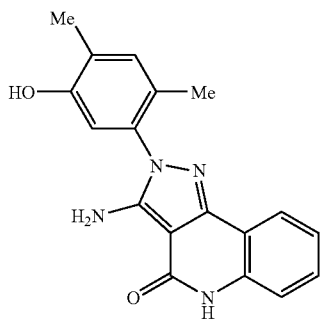

In the same manner as shown in Example 33, the target compound was obtained.

$^1$H-NMR (DMSO-d6, 300 MHz): δ 1.94 (3H, s), 2.18 (3H, s), 6.02 (2H, br s), 6.74 (1H, s), 7.08-7.14 (2H, m), 7.24-7.40 (2H, m), 7.84 (1H, dd, J=8.4, 1.2 Hz), 9.57 (1H, br s), 10.70 (1H, br s).

LC/MS (ESI): m/z 321.0 (M+1).

Example 155

3-amino-2-(5-hydroxy-2,4-dimethylphenyl)-7-(2-hydroxyethoxy)-2,5-dihydro-4H-pyrazolo[4,3-c]quinolin-4-one

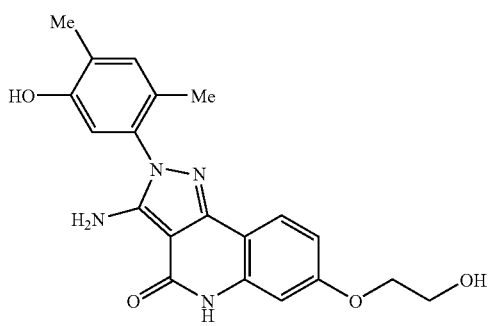

In the same manner as shown in Example 33, the target compound was obtained.

$^1$H-NMR (DMSO-d6, 300 MHz): δ 1.94 (3H, s), 2.17 (3H, s), 3.73 (2H, dt, J=5.7, 5.1 Hz), 3.99 (2H, t, J=5.1 Hz), 4.91 (1H, t, J=5.7 Hz), 6.02 (2H, br s), 6.71-6.82 (3H, m), 7.10 (1H, s), 7.72 (1H, d, J=8.7 Hz), 9.56 (1H, br s), 10.60 (1H, br s).

LC/MS (ESI): m/z 381.0 (M+1).

Example 156

2-{[3-amino-2-(5-hydroxy-2,4-dimethylphenyl)-4-oxo-4,5-dihydro-2H-pyrazolo[4,3-c]quinolin-7-yl]oxy}aectamide

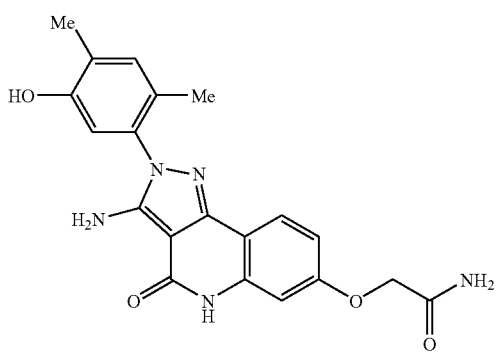

In the same manner as shown in Example 33, the target compound was obtained.

$^1$H-NMR (DMSO-d6, 300 MHz): δ 1.94 (3H, s), 2.17 (3H, s), 4.44 (2H, s), 6.03 (2H, br s), 6.73 (1H, s), 6.75 (1H, dd, J=8.7, 2.4 Hz), 6.81 (1H, d, J=2.4 Hz), 7.10 (1H, s), 7.42 (1H, br s), 7.58 (1H, br s), 7.74 (1H, d, J=8.7 Hz), 9.54 (1H, br s), 10.67 (1H, br s).

LC/MS (ESI): m/z 394.0 (M+1).

Example 157

3-amino-2-(4-bromo-5-hydroxy-2-methylphenyl)-2,5-dihydro-4H-pyrazolo[4,3-c]quinolin-4-one

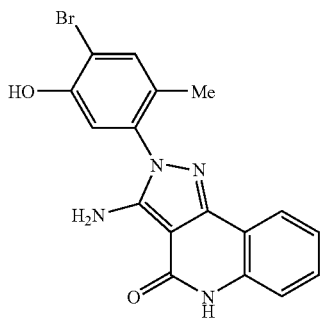

In the same manner as shown in Example 33, the target compound was obtained.

$^1$H-NMR (DMSO-d6, 300 MHz): δ 1.97 (3H, s), 6.26 (2H, br s), 6.89 (1H, s), 7.07-7.15 (1H, m), 7.23-7.42 (2H, m), 7.57 (1H, s), 7.85 (1H, dd, J=7.8, 1.2 Hz), 10.50 (1H, br s), 10.73 (1H, br s).

LC/MS (ESI): m/z 384.9 (M+1).

Example 158

3-amino-2-[4-(2-hydroxyphenoxy)-2-methylphenyl]-2,5-dihydro-4H-pyrazolo[4,3-c]quinolin-4-one

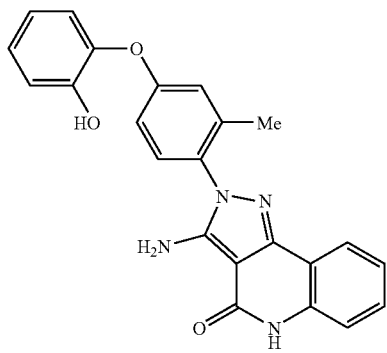

In the same manner as shown in Example 33, the target compound was obtained.

¹H-NMR (DMSO-d6, 300 MHz): δ 2.02 (3H, s), 6.12 (2H, br s), 6.74-6.98 (3H, m), 6.99-7.10 (4H, m), 7.12-7.36 (3H, m), 7.80 (1H, d, J=7.5 Hz), 9.62 (1H, br s), 10.69 (1H, br s).

LC/MS (ESI): m/z 399.1 (M+1).

Example 159

3-amino-2-(3-hydroxy-2-methylphenyl)-2,5-dihydro-4H-pyrazolo[4,3-c]quinolin-4-one

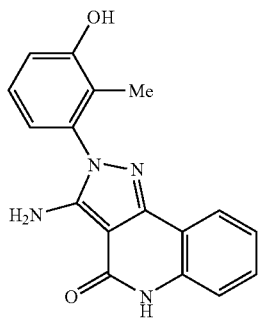

In the same manner as shown in Example 33, the target compound was obtained.

¹H-NMR (DMSO-d6, 300 MHz): δ 1.84 (3H, s), 6.05 (2H, br s), 6.81 (1H, d, J=8.1 Hz), 6.97 (1H, d, J=7.5 Hz), 7.09 (1H, t, J=8.1 Hz), 7.16 (1H, t, J=7.8 Hz), 7.24 (1H, d, J=8.1 Hz), 7.33-7.38 (1H, m), 7.82 (1H, d, J=7.8 Hz), 9.82 (1H, br s), 10.71 (1H, br s).

LC/MS (ESI): m/z 306.9 (M+1).

Example 160

3-amino-7-(2-hydroxyethoxy)-2-(5-hydroxy-2-methyl-4-phenoxyphenyl)-2,5-dihydro-4H-pyrazolo[4,3-c]quinolin-4-one

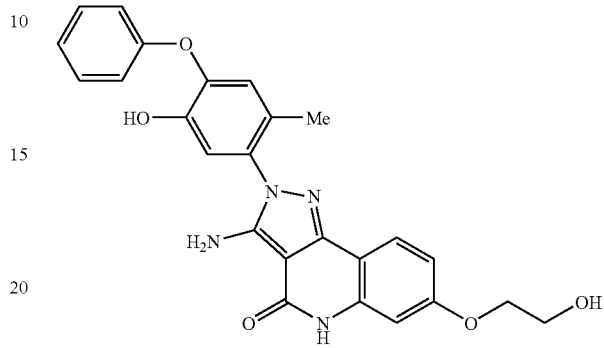

In the same manner as shown in Example 56, the target compound was obtained.

¹H-NMR (DMSO-d6, 300 MHz): δ 1.94 (3H, s), 3.70-3.76 (2H, m), 3.99 (2H, t, J=5.1 Hz), 4.90 (1H, t, J=5.8 Hz), 6.21 (2H, br s), 6.73 (1H, dd, J=8.5, 2.2 Hz), 6.80 (1H, d, J=2.2 Hz), 6.91 (1H, s), 6.94-7.06 (4H, m), 7.30-7.36 (2H, m), 7.73 (1H, d, J=8.5 Hz), 9.71 (1H, br s), 10.60 (1H, br s).

LC/MS (ESI): m/z 459.0 (M+1).

Example 161

3-amino-8-methoxy-7-(3-morpholin-4-ylpropoxy)-2-(4-phenoxyphenyl)-2,5-dihydro-4H-pyrazolo[4,3-c]quinolin-4-one

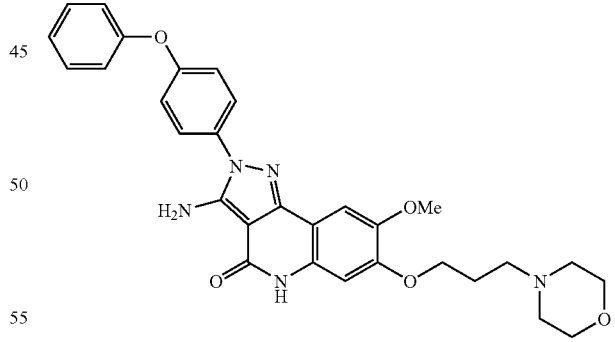

In the same manner as shown in Example 76, the target compound was obtained.

¹H-NMR (DMSO-d6, 300 MHz): δ 1.88-2.01 (2H, m), 2.38-2.50 (6H, m), 3.58 (4H, t, J=4.5 Hz), 3.80 (3H, s), 4.01 (2H, t, J=6.3 Hz), 6.34 (2H, br s), 6.88 (1H, s), 7.09-7.22 (5H, m), 7.29 (1H, s), 7.42-7.48 (2H, m), 7.65 (2H, d, J=9.3 Hz), 10.52 (1H, br s).

LC/MS (ESI): m/z 542.1 (M+1).

Example 162

3-amino-2-(4-methoxyphenyl)-7-(3-morpholin-4-ylpropoxy)-2,5-dihydro-4H-pyrazolo[4,3-c]quinolin-4-one

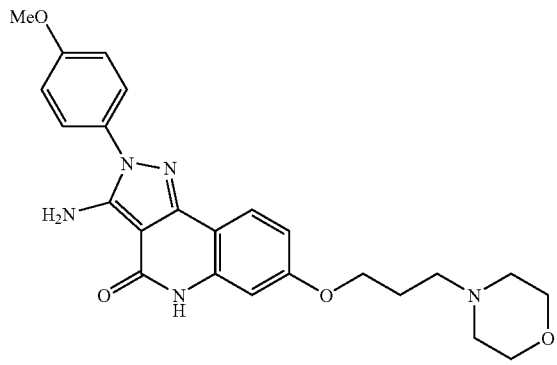

In the same manner as shown in Example 76, the target compound was obtained.

$^1$H-NMR (DMSO-d6, 300 MHz): δ 1.85-1.94 (2H, m), 2.36-2.44 (6H, m), 3.57 (4H, t, J=4.3 Hz), 3.82 (3H, s), 4.01 (2H, t, J=6.3 Hz), 6.22 (2H, br s), 6.72 (1H, dd, J=8.7, 1.7 Hz), 6.79 (1H, d, J=1.7 Hz), 7.09 (2H, d, J=8.9 Hz), 7.53 (2H, d, J=8.9 Hz), 7.76 (1H, d, J=8.7 Hz), 10.61 (1H, br s).

LC/MS (ESI): m/z 450.1 (M+1).

Example 163

3-amino-2-[4-(benzyloxy)phenyl]-7-(3-morpholin-4-ylpropoxy)-2,5-dihydro-4H-pyrazolo[4,3-c]quinolin-4-one

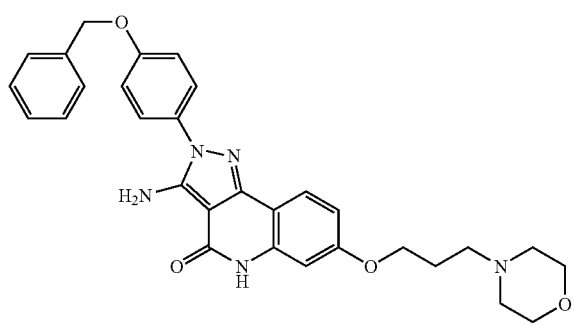

In the same manner as shown in Example 76, the target compound was obtained.

$^1$H-NMR (DMSO-d6, 300 MHz): δ 1.86-1.94 (2H, m), 2.37-2.45 (6H, m), 3.57 (4H, t, J=4.5 Hz), 4.02 (2H, t, J=6.0 Hz), 5.18 (2H, s), 6.23 (2H, br s), 6.72 (1H, dd, J=8.6, 2.3 Hz), 6.79 (1H, d, J=2.3 Hz), 7.17 (2H, d, J=8.7 Hz), 7.34-7.54 (7H, m), 7.75 (1H, d, J=8.6 Hz), 10.62 (1H, br s).

LC/MS (ESI): m/z 526.2 (M+1).

Example 164

3-amino-2-(2-methoxy-5-methylpyrimidin-4-yl)-7-(3-morpholin-4-ylpropoxy)-2,5-dihydro-4H-pyrazolo[4,3-c]quinolin-4-one

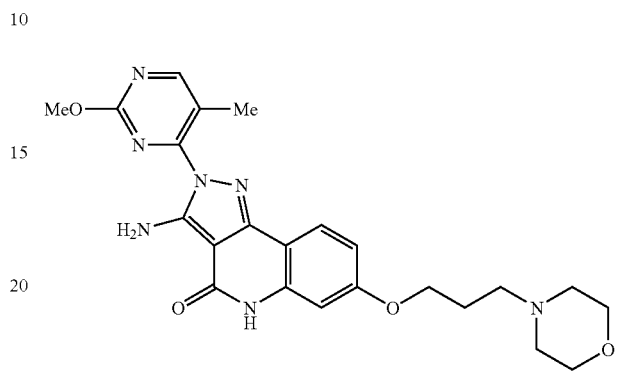

In the same manner as shown in Example 76, the target compound was obtained.

$^1$H-NMR (DMSO-d6, 300 MHz): δ 1.86-1.95 (2H, m), 2.38-2.52 (9H, m), 3.57-3.59 (4H, m), 3.96 (3H, s), 4.03 (2H, t, J=6.5 Hz), 6.75-6.78 (2H, m), 7.31 (2H, br s), 7.80 (1H, d, J=8.4 Hz), 8.62 (1H, s), 10.69 (1H, br s).

LC/MS (ESI): m/z 466.1 (M+1).

Example 165

3-amino-8-(3-morpholin-4-ylpropoxy)-2-(4-phenoxyphenyl)-2,5-dihydro-4H-pyrazolo[4,3-c]quinolin-4-one

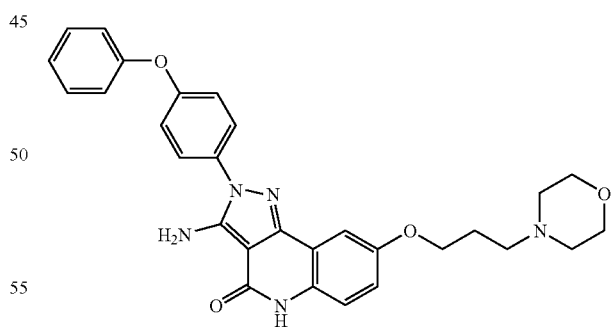

In the same manner as shown in Example 76, the target compound was obtained.

$^1$H-NMR (DMSO-d6, 300 MHz): δ 1.85-1.90 (2H, m), 2.36-2.45 (6H, m), 3.56 (4H, t, J=4.2 Hz), 4.03 (2H, t, J=6.0 Hz), 6.37 (2H, br s), 7.02 (1H, dd, J=9.0, 1.9 Hz), 7.10 (2H, d, J=8.7 Hz), 7.17-7.22 (4H, m), 7.34 (1H, d, J=1.9 Hz), 7.42-7.47 (2H, m), 7.65 (2H, d, J=7.8 Hz), 10.66 (1H, br s).

LC/MS (ESI): m/z 512.2 (M+1).

Example 166

3-amino-8-methoxy-7-(2-morpholin-4-ylethoxy)-2-(4-phenoxyphenyl)-2,5-dihydro-4H-pyrazolo[4,3-c]quinolin-4-one

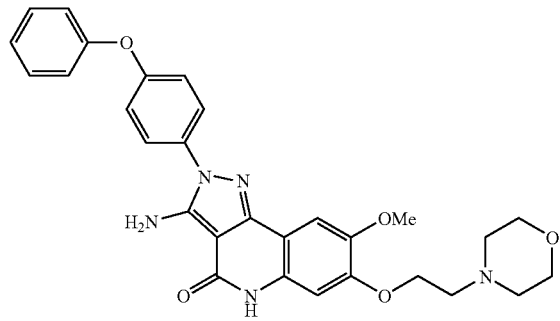

In the same manner as shown in Example 76, the target compound was obtained.

$^1$H-NMR (DMSO-d6, 300 MHz): δ 2.50-2.52 (4H, m), 2.74 (2H, t, J=5.9 Hz), 3.59 (4H, t, J=4.7 Hz), 3.80 (3H, s), 4.08 (2H, t, J=5.9 Hz), 6.34 (2H, br s), 6.89 (1H, s), 7.08-7.12 (2H, m), 7.16-7.22 (3H, m), 7.30 (1H, s), 7.42-7.48 (2H, m), 7.65 (2H, d, J=9.0 Hz), 10.53 (1H, br s).

LC/MS (ESI): m/z 528.0 (M+1).

Example 167

3-amino-7-(3-morpholin-4-ylpropoxy)-2-(4-phenoxyphenyl)-2,5-dihydro-4H-pyrazolo[4,3-c]quinolin-4-one

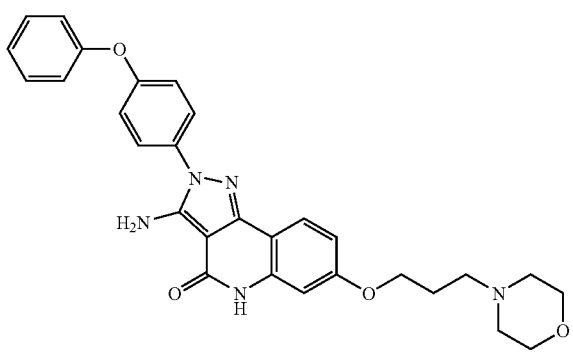

In the same manner as shown in Example 76, the target compound was obtained.

$^1$H-NMR (DMSO-d6, 300 MHz): δ 1.87-1.93 (2H, m), 2.37-2.46 (6H, m), 3.88 (4H, t, J=4.3 Hz), 4.03 (2H, t, J=6.3 Hz), 6.36 (2H, br s), 6.74 (1H, dd, J=8.4, 2.4 Hz), 6.80 (1H, d, J=2.4 Hz), 7.09-7.23 (5H, m), 7.42-7.47 (2H, m), 7.64 (2H, d, J=8.7 Hz), 7.78 (1H, d, J=8.4 Hz), 10.65 (1H, br s).

LC/MS (ESI): m/z 512.2 (M+1).

Example 168

3-amino-2-(2-methyl-4-phenoxyphenyl)-7-(3-morpholin-4-ylpropoxy)-2,5-dihydro-4H-pyrazolo[4,3-c]quinolin-4-one

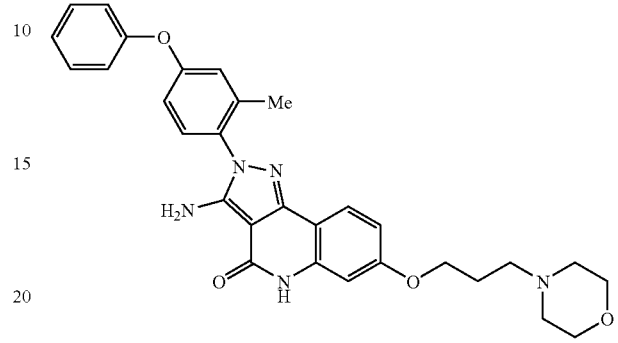

In the same manner as shown in Example 76, the target compound was obtained.

$^1$H-NMR (DMSO-d6, 300 MHz): δ 1.86-1.95 (2H, m), 2.06 (3H, s), 2.37-2.46 (6H, m), 3.58 (4H, t, J=4.0 Hz), 4.03 (2H, t, J=6.5 Hz), 6.19 (2H, br s), 6.73 (1H, d, J=8.4 Hz), 6.79 (1H, s), 6.96 (1H, d, J=8.4 Hz), 7.08-7.13 (3H, m), 7.17-7.22 (1H, m), 7.38 (1H, d, J=8.7 Hz), 7.42-7.47 (2H, m), 7.73 (1H, d, J=8.7 Hz), 10.60 (1H, br s).

LC/MS (ESI): m/z 526.2 (M+1).

Example 169

3-amino-2-(3-methoxy-4-phenoxyphenyl)-7-(3-morpholin-4-ylpropoxy)-2,5-dihydro-4H-pyrazolo[4,3-c]quinolin-4-one

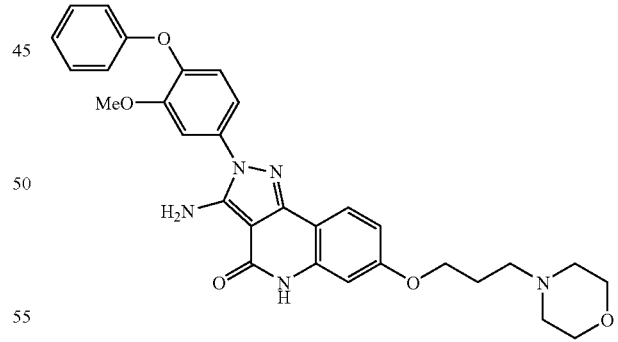

In the same manner as shown in Example 76, the target compound was obtained.

$^1$H-NMR (DMSO-d6, 300 MHz): δ 1.89-1.95 (2H, m), 2.37-2.45 (6H, m), 3.58 (4H, t, J=4.5 Hz), 3.82 (3H, s), 4.03 (2H, t, J=6.5 Hz), 6.44 (2H, br s), 6.74 (1H, dd, J=8.7, 2.4 Hz), 6.79 (1H, d, J=2.4 Hz), 6.92 (2H, d, J=7.8 Hz), 7.03-7.08 (1H, m), 7.15-7.22 (2H, m), 7.31-7.37 (3H, m), 7.78 (1H, d, J=8.7 Hz), 10.63 (1H, br s).

LC/MS (ESI): m/z 542.2 (M+1).

Example 170

3-amino-2-[4-(cyclopentyloxy)phenyl]-7-(3-morpholin-4-ylpropoxy)-2,5-dihydro-4H-pyrazolo[4,3-c]quinolin-4-one

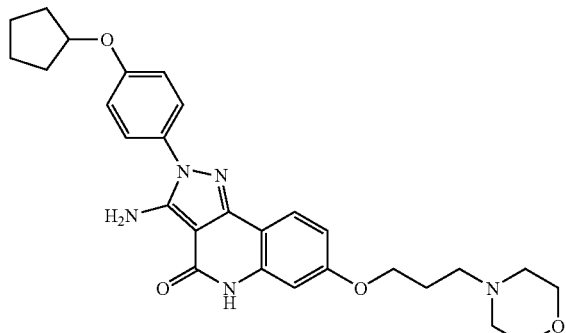

In the same manner as shown in Example 76, the target compound was obtained.

$^1$H-NMR (DMSO-d6, 300 MHz): δ 1.59-1.99 (10H, m), 2.37-2.42 (6H, m), 3.57 (4H, t, J=4.3 Hz), 4.02 (2H, t, J=6.2 Hz), 4.84-4.92 (1H, m), 6.22 (2H, br s), 6.73 (1H, d, J=8.6 Hz), 6.79 (1H, s), 7.05 (2H, d, J=8.9 Hz), 7.50 (2H, d, J=8.9 Hz), 7.77 (1H, d, J=8.6 Hz), 10.63 (1H, br s).

LC/MS (ESI): m/z 504.1 (M+1).

Example 171

3-amino-2-[4-(3-methylbutoxy)phenyl]-7-(3-morpholin-4-ylpropoxy)-2,5-dihydro-4H-pyrazolo[4,3-c]quinolin-4-one

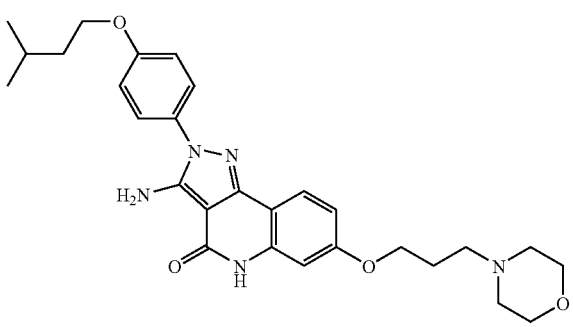

In the same manner as shown in Example 76, the target compound was obtained.

$^1$H-NMR (DMSO-d6, 300 MHz): δ 0.95 (6H, d, J=6.2 Hz), 1.62-1.69 (2H, m), 1.75-1.95 (3H, m), 2.38-2.45 (6H, m), 3.58 (4H, t, J=4.2 Hz), 4.01-4.09 (4H, m), 6.22 (2H, br s), 6.74 (1H, d, J=8.5 Hz), 6.79 (1H, s), 7.10 (2H, d, J=8.7 Hz), 7.52 (2H, d, J=8.7 Hz), 7.77 (1H, d, J=8.5 Hz), 10.63 (1H, br s).

LC/MS (ESI): m/z 506.1 (M+1).

Example 172

Methyl{[3-amino-2-(5-methoxy-2-methyl-4-phenoxyphenyl)-4-oxo-4,5-dihydro-2H-pyrazolo[4,3-c]quinolin-7-yl]oxy}acetate

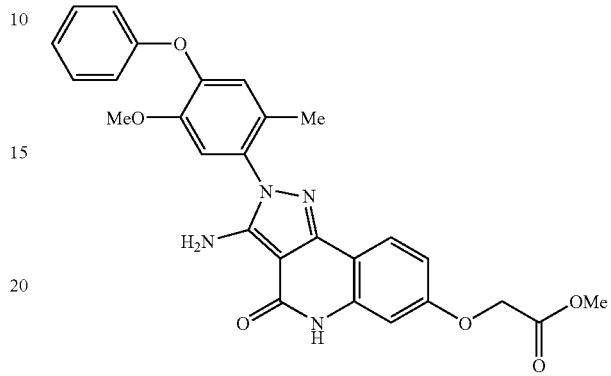

In the same manner as shown in Example 76, the target compound was obtained.

$^1$H-NMR (DMSO-d6, 300 MHz): δ 1.97 (3H, s), 3.72 (3H, s), 3.74 (3H, s), 4.82 (2H, s), 6.28 (2H, br s), 6.72-6.76 (2H, m), 6.95 (2H, d, J=8.4 Hz), 7.03-7.08 (2H, m), 7.17 (1H, s), 7.31-7.36 (2H, m), 7.76 (1H, d, J=8.7 Hz), 10.61 (1H, br s).

LC/MS (ESI): m/z 501.1 (M+1).

Example 173

3-amino-2-(5-methoxy-2-methyl-4-phenoxyphenyl)-7-(3-methoxypropoxy)-2,5-dihydro-4H-pyrazolo[4,3-c]quinolin-4-one

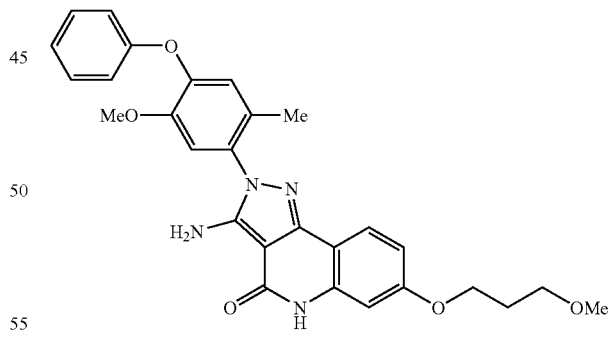

In the same manner as shown in Example 76, the target compound was obtained.

$^1$H-NMR (DMSO-d6, 300 MHz): δ 1.93-2.02 (5H, m), 3.26 (3H, s), 3.48 (2H, t, J=6.1 Hz), 3.74 (3H, s), 4.03 (2H, t, J=6.5 Hz), 6.26 (2H, br s), 6.72 (1H, dd, J=8.7, 2.4 Hz), 6.79 (1H, d, J=2.4 Hz), 6.93-6.96 (2H, m), 7.03-7.05 (1H, m), 7.08 (1H, s), 7.16 (1H, s), 7.31-7.36 (2H, m), 7.74 (1H, d, J=8.7 Hz), 10.59 (1H, br s).

LC/MS (ESI): m/z 501.1 (M+1).

Example 174

3-amino-7-(2,3-dihydroxypropoxy)-2-(5-methoxy-2-methyl-4-phenoxyphenyl)-2,5-dihydro-4H-pyrazolo[4,3-c]quinolin-4-one

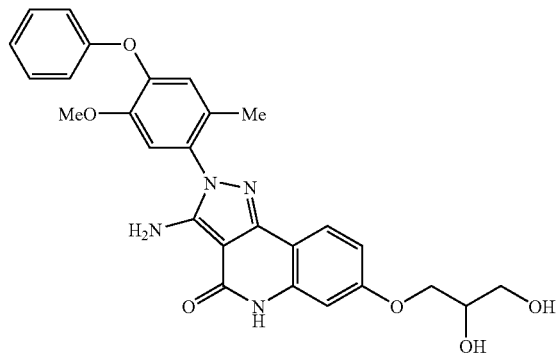

In the same manner as shown in Example 76, the target compound was obtained.

$^1$H-NMR (DMSO-d6, 300 MHz): δ 1.98 (3H, s), 3.45-3.49 (2H, m), 3.74 (3H, s), 3.80-3.90 (2H, m), 3.99-4.04 (1H, m), 4.71 (1H, br s), 5.01 (1H, br s), 6.26 (2H, br s), 6.74 (1H, d, J=8.4 Hz), 6.81 (1H, s), 6.96 (2H, d, J=8.4 Hz), 7.03-7.09 (2H, m), 7.17 (1H, s), 7.32-7.37 (2H, m), 7.75 (1H, d, J=8.4 Hz), 10.63 (1H, br s).

LC/MS (ESI): m/z 503.1 (M+1).

Example 175

{[3-amino-2-(5-methoxy-2-methyl-4-phenoxyphenyl)-4-oxo-4,5-dihydro-2H-pyrazolo[4,3-c]quinolin-7-yl]oxy}acetonitrile

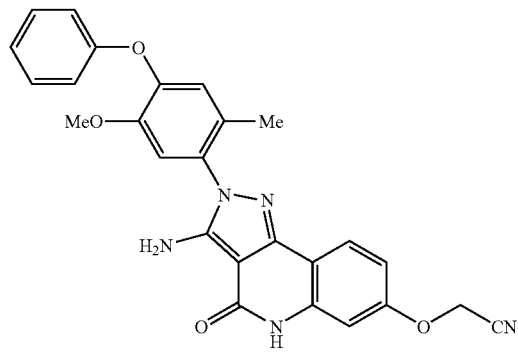

In the same manner as shown in Example 76, the target compound was obtained.

$^1$H-NMR (DMSO-d6, 300 MHz): δ 1.98 (3H, s), 3.74 (3H, s), 5.19 (2H, s), 6.31 (2H, br s), 6.86-6.89 (2H, m), 6.96 (2H, d, J=7.2 Hz), 7.03-7.09 (2H, m), 7.18 (1H, s), 7.32-7.37 (2H, m), 7.85 (1H, d, J=8.1 Hz), 10.74 (1H, br s).

LC/MS (ESI): m/z 468.1 (M+1).

Example 176

3-amino-8-methoxy-2-(2-methylphenyl)-7-(3-morpholin-4-ylpropoxy)-2,5-dihydro-4H-pyrazolo[4,3-c]quinolin-4-one

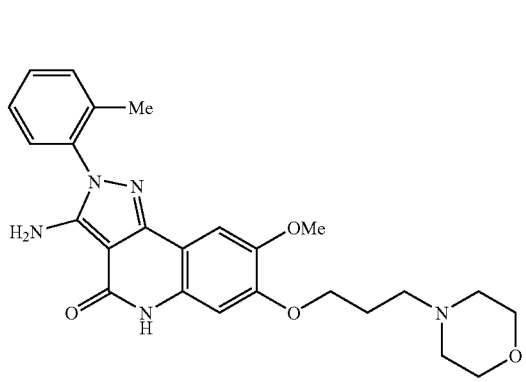

In the same manner as shown in Example 76, the target compound was obtained.

$^1$H-NMR (DMSO-d6, 300 MHz): δ 1.88-1.96 (2H, m), 2.10 (3H, s), 2.37-2.46 (6H, m), 3.55-3.61 (4H, m), 3.77 (3H, s), 4.00 (2H, t, J=6.0 Hz), 6.09 (2H, br s), 6.87 (1H, s), 7.26 (1H, s), 7.37-7.43 (4H, m), 10.47 (1H, br s).

LC/MS (ESI): m/z 464.2 (M+1).

Example 177

3-amino-8-methoxy-2-(2-methylphenyl)-7-[(1-methylpiperidin-4-yl)methoxy]-2,5-dihydro-4H-pyrazolo[4,3-c]quinolin-4-one

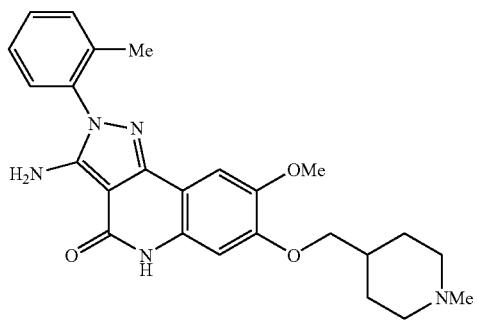

In the same manner as shown in Example 76, the target compound was obtained.

$^1$H-NMR (DMSO-d6, 300 MHz): δ 1.38-1.50 (1H, m), 1.76-2.04 (4H, m), 2.10 (3H, s), 2.22-2.50 (6H, m), 2.63-2.68 (1H, m), 3.77 (3H, s), 3.95 (2H, t, J=6.3 Hz), 6.09 (2H, br s), 6.87 (1H, s), 7.27 (1H, s), 7.38 (2H, s), 7.45 (2H, s), 10.47 (1H, br s).

LC/MS (ESI): m/z 448.2 (M+1).

Example 178

3-amino-7-(2-methoxyethoxy)-2-[5-methoxy-2-methyl-4-(pyridin-3-yloxy)phenyl]-2,5-dihydro-4H-pyrazolo[4,3-c]quinolin-4-one

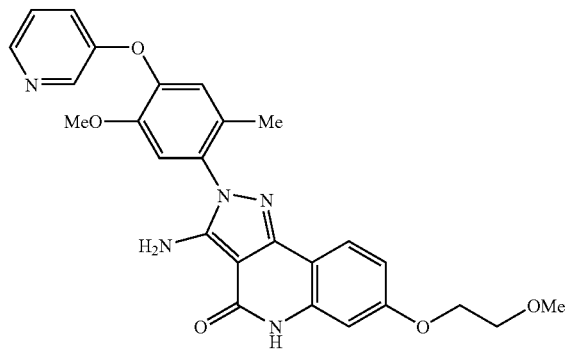

In the same manner as shown in Example 76, the target compound was obtained.

$^1$H-NMR (DMSO-d6, 300 MHz): δ 2.00 (3H, s), 3.32 (3H, s), 3.67-3.70 (2H, m), 3.74 (3H, s), 4.09-4.12 (2H, m), 6.31 (2H, br s), 6.75 (1H, dd, J=8.6, 2.5 Hz), 6.80 (1H, d, J=2.5 Hz), 7.21 (2H, s), 7.32-7.40 (2H, m), 7.76 (1H, d, J=8.6 Hz), 8.29 (1H, dd, J=7.2, 1.5 Hz), 8.35-8.44 (1H, m), 10.63 (1H, br s).

LC/MS (ESI): m/z 488.1 (M+1).

Example 179

3-amino-2-(5-fluoro-2-methylphenyl)-7-(2-morpholin-4-ylethoxy)-2,5-dihydro-4H-pyrazolo[4,3-c]quinolin-4-one

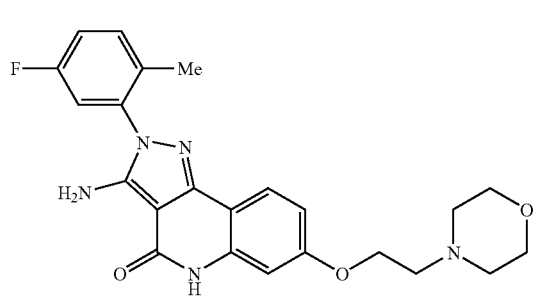

In the same manner as shown in Example 76, the target compound was obtained.

$^1$H-NMR (DMSO-d6, 300 MHz): δ 2.07 (3H, s), 2.45-2.52 (4H, m), 2.71 (2H, t, J=5.7 Hz), 3.55-3.61 (4H, m), 4.10 (2H, t, J=5.7 Hz), 6.28 (2H, br s), 6.75 (1H, dd, J=8.7, 2.4 Hz), 6.79 (1H, d, J=2.4 Hz), 7.28-7.36 (2H, m), 7.43-7.50 (1H, m), 7.73 (1H, d, J=8.7 Hz), 10.63 (1H, br s).

LC/MS (ESI): m/z 437.5 (M+1).

Example 180

3-amino-2-(5-chloro-2-methylphenyl)-7-(2-morpholin-4-ylethoxy)-2,5-dihydro-4H-pyrazolo[4,3-c]quinolin-4-one

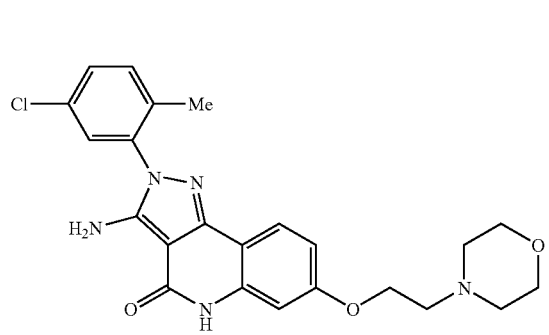

In the same manner as shown in Example 76, the target compound was obtained.

$^1$H-NMR (DMSO-d6, 300 MHz): δ 2.08 (3H, s), 2.45-2.52 (4H, m), 2.71 (2H, t, J=5.7 Hz), 3.55-3.62 (4H, m), 4.10 (2H, t, J=5.7 Hz), 6.31 (2H, br s), 6.75 (1H, dd, J=8.7, 2.4 Hz), 6.79 (1H, d, J=2.4 Hz), 7.44-7.55 (3H, m), 7.73 (1H, d, J=8.7 Hz), 10.63 (1H, br s).

LC/MS (ESI): m/z 454.1 (M+1).

Example 181

3-amino-2-(2-isopropylphenyl)-7-(2-morpholin-4-ylethoxy)-2,5-dihydro-4H-pyrazolo[4,3-c]quinolin-4-one

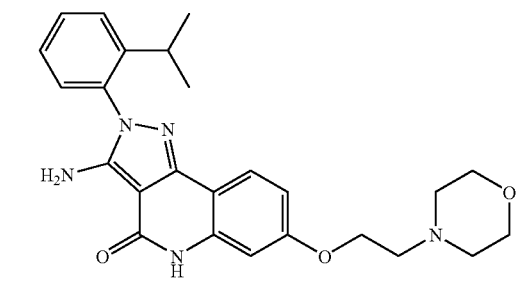

In the same manner as shown in Example 76, the target compound was obtained.

$^1$H-NMR (DMSO-d6, 300 MHz): δ 1.14 (6H, d, J=6.9 Hz), 2.45-2.54 (4H, m), 2.66-2.77 (3H, m), 3.56-3.63 (4H, m), 4.10 (2H, t, J=5.7 Hz), 6.07 (2H, br s), 6.75 (1H, dd, J=8.7, 2.4 Hz), 6.80 (1H, d, J=2.4 Hz), 7.28-7.43 (2H, m), 7.52-7.58 (2H, m), 7.72 (1H, d, J=8.7 Hz), 10.62 (1H, br s).

LC/MS (ESI): m/z 448.1 (M+1).

Example 182

3-amino-2-{4-[(6-methylpyridin-3-yl)oxy]phenyl}-7-(3-morpholin-4-ylpropoxy)-2,5-dihydro-4H-pyrazolo[4,3-c]quinolin-4-one

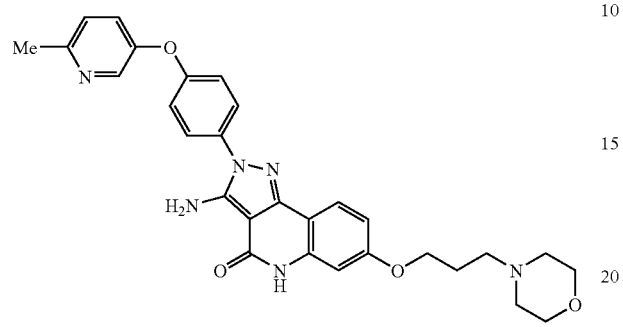

In the same manner as shown in Example 76, the target compound was obtained.

$^1$H-NMR (DMSO-d6, 300 MHz): δ 1.85-1.95 (2H, m), 2.32-2.47 (6H, m), 2.49 (3H, s), 3.54-3.61 (4H, m), 4.03 (2H, t, J=6.3 Hz), 6.37 (2H, br s), 6.74 (1H, dd, J=8.7, 2.4 Hz), 6.80 (1H, d, J=2.4 Hz), 7.14-7.23 (2H, m), 7.33 (1H, d, J=8.4 Hz), 7.45 (1H, dd, J=8.4, 2.7 Hz), 7.61-7.67 (2H, m), 7.77 (1H, d, J=8.7 Hz), 8.32 (1H, d, J=2.7 Hz), 10.65 (1H, br s).

LC/MS (ESI): m/z 527.2 (M+1).

Example 183

3-amino-7-(2-methoxyethoxy)-2-(5-methoxy-2-methylphenyl)-2,5-dihydro-4H-pyrazolo[4,3-c]quinolin-4-one

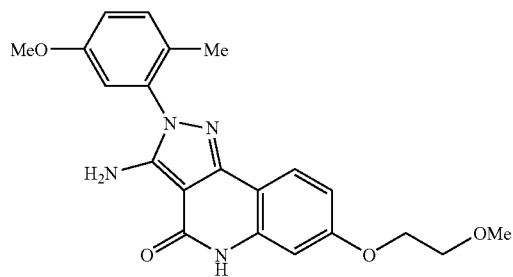

In the same manner as shown in Example 76, the target compound was obtained.

$^1$H-NMR (DMSO-d6, 300 MHz): δ 2.01 (3H, s), 3.32 (3H, s), 3.65-3.71 (2H, m), 3.78 (3H, s), 4.07-4.12 (2H, m), 6.12 (2H, br s), 6.74 (1H, dd, J=8.7, 2.4 Hz), 6.80 (1H, d, J=2.4 Hz), 6.94 (1H, d, J=2.7 Hz), 7.03 (1H, dd, J=8.4, 2.7 Hz), 7.33 (1H, d, J=8.7 Hz), 7.74 (1H, d, J=8.4 Hz), 10.62 (1H, br s).

LC/MS (ESI): m/z 395.1 (M+1).

Example 184

3-amino-2-(5-methoxy-2,4-dimethylphenyl)-7-(2-methoxyethoxy)-2,5-dihydro-4H-pyrazolo[4,3-c]quinolin-4-one

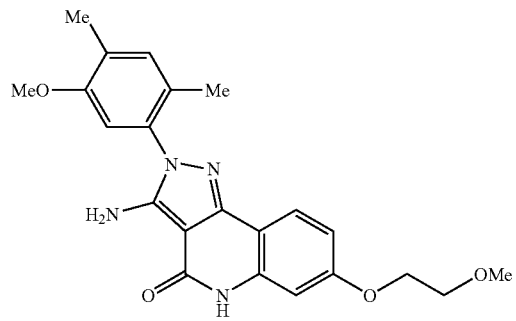

In the same manner as shown in Example 76, the target compound was obtained.

$^1$H-NMR (DMSO-d6, 300 MHz): δ 1.98 (3H, s), 2.20 (3H, s), 3.32 (3H, s), 3.65-3.70 (2H, m), 3.79 (3H, s), 4.08-4.12 (2H, m), 6.07 (2H, br s), 6.74 (1H, dd, J=8.7, 2.4 Hz), 6.80 (1H, d, J=2.4 Hz), 6.91 (1H, s), 7.19 (1H, s), 7.74 (1H, d, J=8.7 Hz), 10.60 (1H, br s).

LC/MS (ESI) : m/z 409.1 (M+1).

Example 185

2-{[3-amino-2-(5-methoxy-2,4-dimethylphenyl)-4-oxo-4,5-dihydro-2H-pyrazolo[4,3-c]quinolin-7-yl]oxy}acetamide

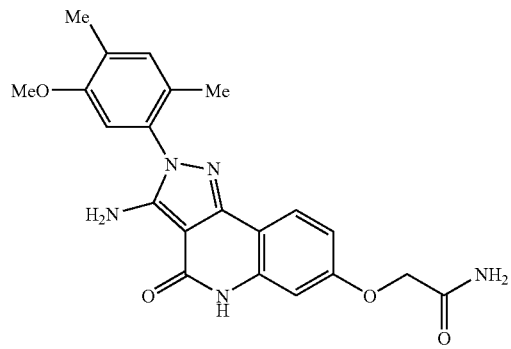

In the same manner as in Example 76, the target compound was obtained.

$^1$H-NMR (DMSO-d6, 300 MHz): δ 1.97 (3H, s), 2.20 (3H, s), 3.79 (3H, s), 4.44 (2H, s), 6.07 (2H, br s), 6.75 (1H, dd, J=8.7, 2.4 Hz), 6.81 (1H, d, J=2.4 Hz), 6.91 (1H, s), 7.19 (1H, s), 7.41 (1H, br s), 7.58 (1H, br s), 7.76 (1H, d, J=8.7 Hz), 10.65 (1H, br s).

LC/MS (ESI): m/z 408.0 (M+1).

Example 186

3-amino-2-(4-methyl-6-phenoxypyridin-3-yl)-7-(3-morpholin-4-ylpropoxy)-2,5-dihydro-4H-pyrazolo[4,3-c]quinolin-4-one

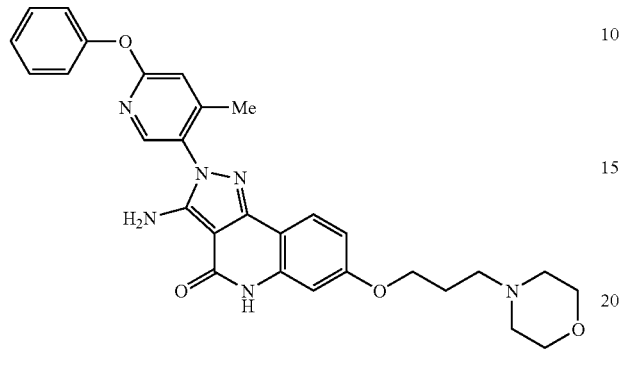

In the same manner as shown in Example 76, the target compound was obtained.

¹H-NMR (DMSO-d6, 300 MHz): δ 1.84-1.95 (2H, m), 2.11 (3H, s), 2.30-2.47 (6H, m), 3.55-3.60 (4H, m), 4.02 (2H, t, J=6.0 Hz), 6.38 (2H, br s), 6.72 (1H, dd, J=8.7, 1.5 Hz), 6.79 (1H, d, J=1.5 Hz), 7.14 (1H, s), 7.15-7.27 (3H, m), 7.41-7.49 (2H, m), 7.72 (1H, d, J=8.7 Hz), 8.15 (1H, s), 10.61 (1H, br s).

LC/MS (ESI): m/z 527.1 (M+1).

Example 187

3-amino-7-(2-methoxyethoxy)-2-(4-methyl-6-phenoxypyridin-3-yl)-2,5-dihydro-4H-pyrazolo[4,3-c]quinolin-4-one

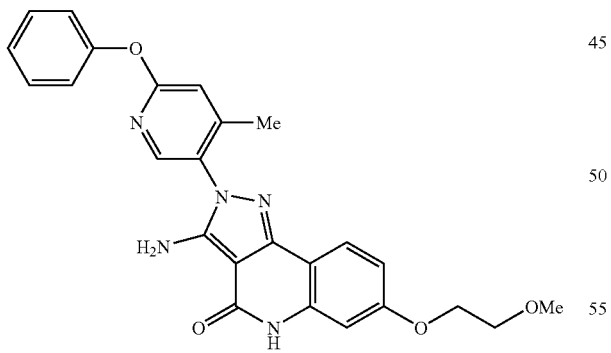

In the same manner as shown in Example 76, the target compound was obtained.

¹H-NMR (DMSO-d6, 300 MHz): δ 2.11 (3H, s), 3.32 (3H, s), 3.65-3.70 (2H, m), 4.07-4.12 (2H, m), 6.39 (2H, br s), 6.74 (1H, dd, J=8.7, 2.4 Hz), 6.79 (1H, d, J=2.4 Hz), 7.14 (1H, s), 7.15-7.27 (3H, m), 7.41-7.49 (2H, m), 7.73 (1H, d, J=8.7 Hz), 8.15 (1H, s), 10.63 (1H, br s).

LC/MS (ESI): m/z 458.1 (M+1).

Example 188

3-amino-9-isopropoxy-7-methoxy-2-(4-phenoxyphenyl)-2,5-dihydro-4H-pyrazolo[4,3-c]quinolin-4-one In the same manner as shown in Example 76, the target compound was obtained.

¹H-NMR (DMSO-d6, 300 MHz): δ 1.29-1.31 (6H, m), 3.75 (3H, s), 4.64 (1H, sept, J=5.7 Hz), 6.30-6.31 (3H, m), 6.43 (1H, s), 7.06-7.19 (5H, m), 7.42 (2H, t, J=7.5 Hz), 7.66 (2H, d, J=8.4 Hz), 10.59 (1H, br s).

LC/MS (ESI): m/z 457.3 (M+1).

Example 189

3-amino-9-isopropoxy-7-methoxy-2-(2-methyl-4-phenoxyphenyl)-2,5-dihydro-4H-pyrazolo[4,3-c]quinolin-4-one In the same manner as shown in Example 76, the target compound was obtained.

¹H-NMR (DMSO-d6, 300 MHz): δ 1.25 (6H, d, J=5.7 Hz), 2.04 (3H, s), 3.74 (3H, s), 4.60 (1H, sept, J=5.7 Hz), 6.05 (2H, br s), 6.30 (1H, s), 6.48 (1H, s), 6.93 (1H, dd, J=8.7, 2.7 Hz), 7.05-7.20 (4H, m), 7.34-7.45 (3H, m), 10.53 (1H, br s).

LC/MS (ESI): m/z 471.1 (M+1).

Example 190

3-amino-7-methoxy-2-(2-methyl-4-phenoxyphenyl)-9-(tetrahydro-2H-pyran-4-ylmethoxy)-2,5-dihydro-4H-pyrazolo[4,3-c]quinolin-4-one

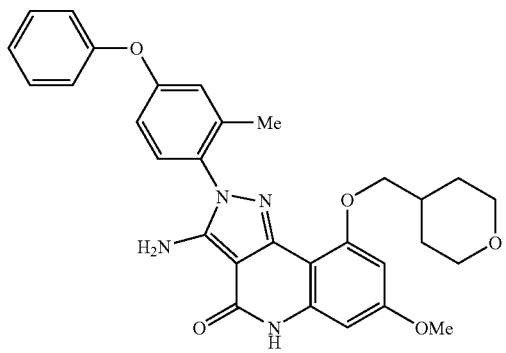

In the same manner as shown in Example 76, the target compound was obtained.

¹H-NMR (DMSO-d6, 300 MHz): δ 1.28-1.31 (1H, m), 1.78-1.85 (4H, m), 2.12 (3H, s), 3.16-3.20 (4H, m), 3.75 (3H, s), 3.87 (2H, d, J=6.3 Hz), 6.09 (2H, br s), 6.29 (1H, s), 6.41 (1H, s), 6.94 (1H, d, J=8.7, 2.7 Hz), 7.05-7.18 (4H, m), 7.32 (1H, d, J=8.7 Hz), 7.41 (2H, t, J=7.2 Hz), 10.53 (1H, br s).

LC/MS (ESI): m/z 527.1 (M+1).

Example 191

3-amino-9-isopropoxy-7-methoxy-2-(5-methoxy-2-methylphenyl)-2,5-dihydro-4H-pyrazolo[4,3-c]quinolin-4-one

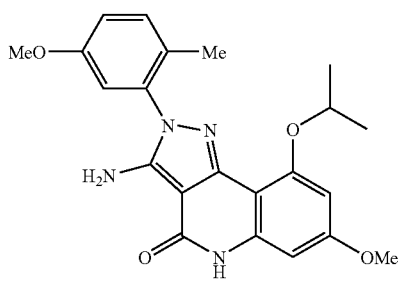

In the same manner as shown in Example 76, the target compound was obtained.

¹H-NMR (DMSO-d6, 300 MHz): δ 1.29-1.31 (6H, m), 2.11 (3H, s), 3.70 (3H, s), 3.75 (3H, s), 4.51-4.75 (1H, m), 6.21 (2H, br s), 6.35 (1H, s), 6.45 (1H, s), 6.96 (1H, s), 6.97 (1H, d, J=8.3 Hz), 7.38 (1H, d, J=8.3 Hz), 10.51 (1H, br s).

LC/MS (ESI): m/z 409.1 (M+1).

Example 192

3-amino-7-methoxy-2-(5-methoxy-2-methylphenyl)-9-(tetrahydro-2H-pyran-4-ylmethoxy)-2,5-dihydro-4H-pyrazolo[4,3-c]quinolin-4-one

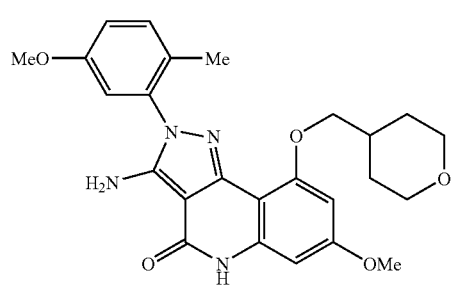

In the same manner as shown in Example 76, the target compound was obtained.

¹H-NMR (DMSO-d6, 300 MHz): δ 1.22-1.34 (1H, m), 1.98-2.10 (7H, m), 3.14-3.18 (4H, m), 3.73 (3H, s), 3.75 (3H, s), 3.88 (2H, d, J=6.6 Hz), 6.07 (2H, br s), 6.30 (1H, s), 6.41 (1H, s), 6.88. (1H, s), 6.97 (1H, d, J=8.3 Hz), 7.30 (1H, d, J=8.3 Hz), 10.53 (1H, br s).

LC/MS (ESI): m/z 465.1 (M+1).

Example 193

3-amino-7-methoxy-9-(3-methoxypropoxy)-2-(2-methylphenyl)-2,5-dihydro-4H-pyrazolo[4,3-c]quinolin-4-one

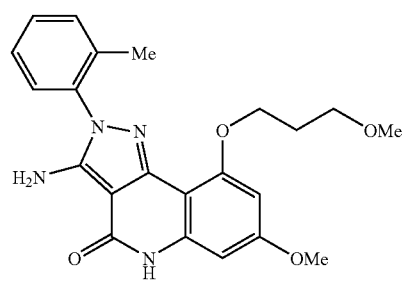

In the same manner as shown in Example 76, the target compound was obtained.

¹H-NMR (DMSO-d6, 300 MHz): δ 1.84-1.88 (2H, m), 2.13 (3H, s), 3.03 (3H, s), 3.51-3.55 (2H, m), 3.74 (3H, s), 4.02-4.06 (2H, m), 6.00 (2H, br s), 6.29 (1H, s), 6.42 (1H, s), 7.35-7.42 (4H, m), 10.55 (1H, br s).

LC/MS (ESI): m/z 409.0 (M+1).

Example 194

3-amino-9-(3-hydroxypropoxy)-7-methoxy-2-(2-methylphenyl)-2,5-dihydro-4H-pyrazolo[4,3-c]quinolin-4-one

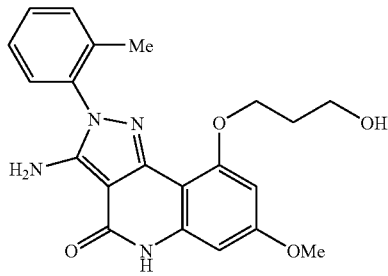

In the same manner as shown in Example 76, the target compound was obtained.

$^1$H-NMR (DMSO-d6, 300 MHz): δ 1.76-1.81 (2H, m), 2.06 (3H, s), 3.74-3.50 (2H, m), 3.70 (3H, s), 4.03-4.08 (2H, m), 4.74-4.80 (1H, m), 5.98 (2H, br s), 6.28 (1H, s), 6.39 (1H, s), 7.28-7.35 (4H, m), 10.57 (1H, br s).

LC/MS (ESI): m/z 395.1 (M+1).

Example 195

Ethyl 4-{[3-amino-7-methoxy-2-(2-methylphenyl)-4-oxo-4,5-dihydro-2H-pyrazolo[4,3-c]quinolin-9-yl]oxy}butanoate

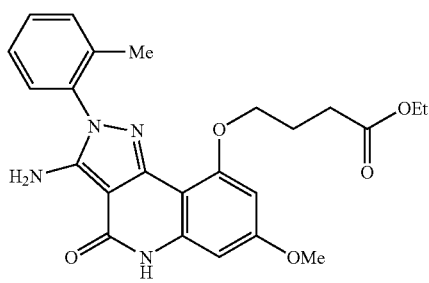

In the same manner as shown in Example 76, the target compound was obtained.

$^1$H-NMR (DMSO-d6, 300 MHz): δ 1.01-1.08 (3H, m), 1.83-1.88 (2H, m), 2.09 (3H, s), 2.57-2.61 (2H, m), 3.71 (3H, s), 3.83-4.00 (4H, m), 5.97 (2H, br s), 6.26 (1H, s), 6.37 (1H, s), 7.34-7.39 (4H, m), 10.56 (1H, br s).

LC/MS (ESI): m/z 451.0 (M+1).

Example 196

Methyl 4-{[3-amino-7-methoxy-2-(2-methylphenyl)-4-oxo-4,5-dihydro-2H-pyrazolo[4,3-c]quinolin-9-yl]oxy}butanoate

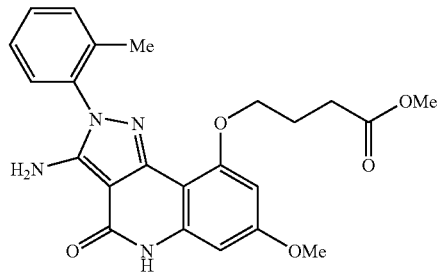

In the same manner as shown in Example 76, the target compound was obtained.

$^1$H-NMR (DMSO-d6, 300 MHz): δ 1.81-1.86 (2H, m), 2.10 (3H, s), 2.60-2.73 (2H, m), 3.74 (3H, s), 3.82-4.00 (5H, m), 6.00 (2H, br s), 6.25 (1H, s), 6.49 (1H, s), 7.38-7.48 (4H, m), 10.50 (1H, br s).

LC/MS (ESI): m/z 437.0 (M+1).

Example 197

Methyl{[3-amino-7-methoxy-2-(2-methylphenyl)-4-oxo-4,5-dihydro-2H-pyrazolo[4,3-c]quinolin-9-yl]oxy}acetate

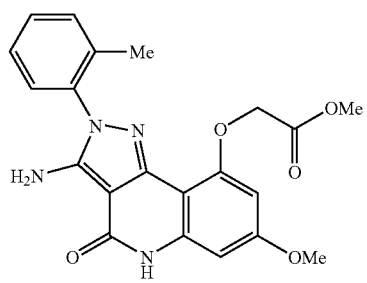

In the same manner as shown in Example 76, the target compound was obtained.

$^1$H-NMR (DMSO-d6, 300 MHz): δ 2.02 (3H, s), 3.59 (3H, s), 3.69 (3H, s), 4.82 (2H, s), 5.99 (2H, br s), 6.09 (1H, s), 6.44 (1H, s), 7.31-7.39 (4H, m), 10.58 (1H, br s).

LC/MS (ESI): m/z 409.2 (M+1).

Example 198

3-amino-7-methoxy-9-(2-methoxyethoxy)-2-(2-methylphenyl)-2,5-dihydro-4H-pyrazolo[4,3-c]quinolin-4-one

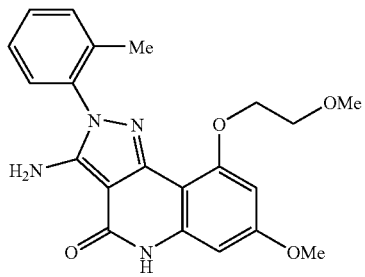

In the same manner as shown in Example 76, the target compound was obtained.

$^1$H-NMR (DMSO-d6, 300 MHz): δ 2.13 (3H, s), 3.25 (3H, s), 3.61-3.64 (2H, m), 3.75 (3H, s), 4.12-4.15 (2H, m), 6.01 (2H, br s), 6.31 (1H, s), 6.44 (1H, s), 7.32-7.41 (4H, m), 10.57 (1H, br s)

LC/MS (ESI): m/z 395.2 (M+1).

Example 199

3-amino-9-(benzyloxy)-7-methoxy-2-(2-methylphenyl)-2,5-dihydro-4H-pyrazolo[4,3-c]quinolin-4-one

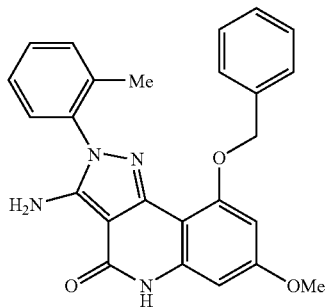

In the same manner as shown in Example 76, the target compound was obtained.

$^1$H-NMR (DMSO-d6, 300 MHz): δ 2.10 (3H, s), 3.71 (3H, s), 5.34 (2H, br s), 6.18 (2H, br s), 6.28 (1H, s), 6.38 (1H, s), 6.75-6.97 (3H, m), 7.18-7.24 (2H, m), 7.38-7.45 (4H, m), 10.67 (1H, br s)

LC/MS (ESI): m/z 427.1 (M+1).

Example 200

3-amino-2-[3-(2-hydroxyethoxy)phenyl]-2,5-dihydro-4H-pyrazolo[4,3-c]quinolin-4-one

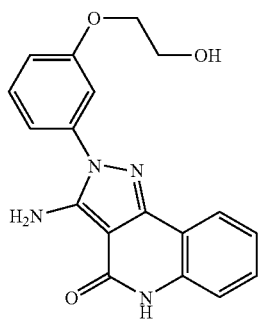

In the same manner as shown in Example 76, the target compound was obtained.

$^1$H-NMR (DMSO-d6, 300 MHz): δ 3.70-3.74 (2H, m), 4.05-4.08 (2H, m), 4.91 (1H, t, J=5.4 Hz), 6.41 (2H, br s), 7.01 (1H, d, J=8.4 Hz), 7.12 (1H, t, J=7.5 Hz), 7.20-7.25 (3H, m), 7.38 (1H, t, J=7.5 Hz), 7.45 (1H, t, J=7.8 Hz), 7.88 (1H, d, J=7.5 Hz), 10.77 (1H, br s).

LC/MS (ESI): m/z 337.1 (M+1).

Example 201

3-amino-2-[3-(2-methoxyethoxy)phenyl]-2,5-dihydro-4H-pyrazolo[4,3-c]quinolin-4-one

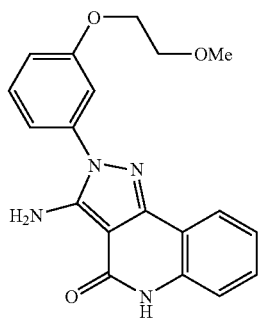

In the same manner as shown in Example 76, the target compound was obtained.

$^1$H-NMR (DMSO-d6, 300 MHz): δ 3.30 (3H, s), 3.66-3.69 (2H, m), 4.16-4.19 (2H, m), 6.41 (2H, br s), 7.01 (1H, dd, J=8.1, 2.4 Hz), 7.19-7.25 (4H, m), 7.35 (1H, t, J=8.1 Hz), 7.44 (1H, t, J=8.1 Hz), 7.88 (1H, d, J=8.1 Hz), 10.76 (1H, br s).

LC/MS (ESI): m/z 351.0 (M+1).

Example 202

Methyl[3-amino-4-oxo-4,5-dihydro-2H-pyrazolo[4,3-c]quinolin-2-yl]phenoxy]acetate

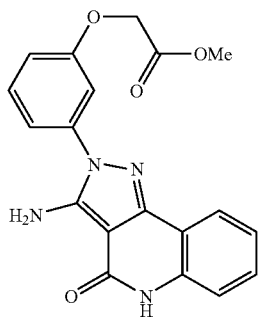

In the same manner as shown in Example 76, the target compound was obtained.

$^1$H-NMR (DMSO-d6, 300 MHz): δ 3.70 (3H, s), 4.90 (2H, s), 6.41 (2H, br s), 7.01 (1H, dd, J=8.1, 2.4 Hz), 7.19-7.25 (4H, m), 7.35 (1H, t, J=8.1 Hz), 7.44 (1H, t, J=8.1 Hz), 7.88 (1H, d, J=8.1 Hz), 10.76 (1H, br s).

LC/MS (ESI): m/z 365.1 (M+1).

Example 203

3-amino-2-[3-(3-hydroxypropoxy)phenyl]-2,5-dihydro-4H-pyrazolo[4,3-c]quinolin-4-one

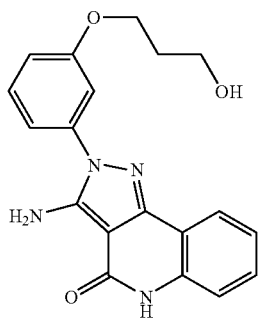

In the same manner as shown in Example 76, the target compound was obtained.

$^1$H-NMR (DMSO-d6, 300 MHz): δ 1.83-1.92 (2H, m), 3.53-3.59 (2H, m), 4.08-4.13 (2H, m), 4.53-4.58 (1H, m), 6.40 (2H, br s), 6.99 (1H, dd, J=7.5, 2.1 Hz), 7.11 (1H, t, J=7.5 Hz), 7.17-7.25 (3H, m), 7.35-7.48 (2H, m), 7.88 (1H, d, J=7.5 Hz), 10.09 (1H, br s).

LC/MS (ESI): m/z 351.1 (M+1).

Example 204

3-amino-2-[2-(2-hydroxyethoxy)phenyl]-2,5-dihydro-4H-pyrazolo[4,3-c]quinolin-4-one

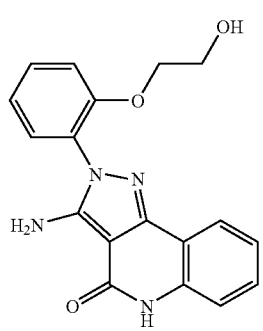

In the same manner as shown in Example 76, the target compound was obtained.

$^1$H-NMR (DMSO-d6, 300 MHz): δ 3.65-3.66 (2H, m), 4.13-4.16 (2H, m), 4.91-4.94 (1H, m), 6.05 (2H, br s), 7.07-7.14 (2H, m), 7.23-7.34 (2H, m), 7.34-7.39 (1H, m), 7.41-7.49 (2H, m), 7.84 (1H, dd, J=7.8, 1.2 Hz), 10.73 (1H, br s).

LC/MS (ESI): m/z 337.2 (M+1).

Example 205

3-amino-2-[2-(2-methoxyethoxy)phenyl]-2,5-dihydro-4H-pyrazolo[4,3-c]quinolin-4-one

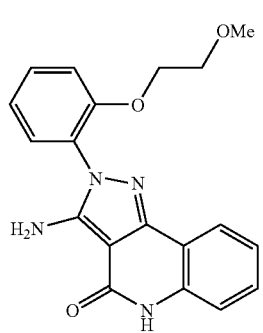

In the same manner as shown in Example 76, the target compound was obtained.

$^1$H-NMR (DMSO-d6, 300 MHz): δ 3.19 (3H, s), 3.58-3.61 (2H, m), 4.20-4.23 (2H, m), 6.03 (2H, br s), 7.07-7.26 (2H, m), 7.27 (2H, t, J=8.1 Hz), 7.33-7.39 (1H, m), 7.41-7.49 (2H, m), 7.83 (1H, d, J=7.8 Hz), 10.70 (1H, br s).

LC/MS (ESI): m/z 351.0 (M+1).

Example 206

Methyl[2-(3-amino-4-oxo-4,5-dihydro-2H-pyrazolo[4,3-c]quinolin-2-yl)phenoxy]acetate

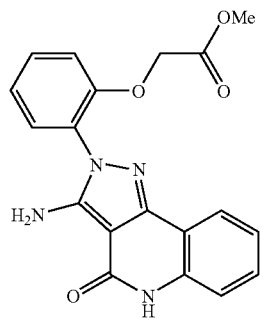

In the same manner as shown in Example 76, the target compound was obtained.

$^1$H-NMR (DMSO-d6, 300 MHz): δ 3.69 (3H, s), 4.96 (2H, s), 6.06 (2H, br s), 7.07-7.18 (3H, m), 7.24 (1H, d, J=8.1 Hz), 7.36 (1H, t, J=7.8 Hz), 7.43-7.48 (2H, m), 7.84 (1H, d, J=7.8 Hz), 10.71 (1H, br s).

LC/MS (ESI): m/z 365.1 (M+1).

Example 207

3-amino-2-[5-(2-hydroxyethoxy)-2-methylphenyl]-2,5-dihydro-4H-pyrazolo[4,3-c]quinolin-4-one

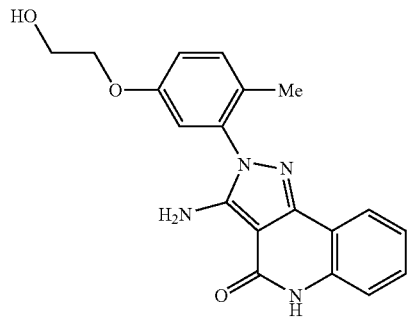

In the same manner as shown in Example 76, the target compound was obtained.

$^1$H-NMR (DMSO-d6, 300 MHz): δ 1.97 (3H, s), 3.66-3.71 (2H, m), 3.97-4.01 (2H, m), 6.14 (2H, br s), 6.93 (1H, d, J=2.7 Hz), 7.03 (1H, dd, J=8.4, 2.7 Hz), 7.09 (1H, t, J=7.5 Hz), 7.24 (1H, t, J=8.1 Hz), 7.29-7.38 (2H, m), 7.82 (1H, d, J=8.1 Hz), 10.70 (1H, br s).

LC/MS (ESI): m/z 351.1 (M+1).

Example 208

3-amino-2-[3-(2-hydroxyethoxy)-2-methylphenyl]-2,5-dihydro-4H-pyrazolo[4,3-c]quinolin-4-one

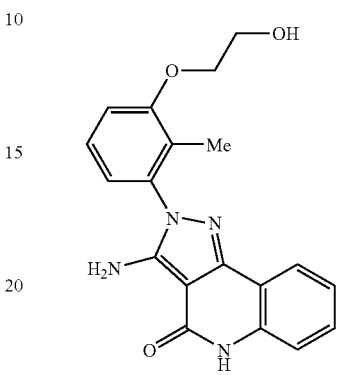

In the same manner as shown in Example 76, the target compound was obtained.

$^1$H-NMR (DMSO-d6, 300 MHz): δ 1.90 (3H, s), 3.75-3.76 (2H, m), 4.04-4.06 (2H, m), 4.88-4.90 (1H, m), 6.10 (2H, br s), 6.96 (1H, d, J=7.5 Hz), 7.06-7.14 (2H, m), 7.23-7.39 (3H, m), 7.82 (1H, d, J=8.1 Hz), 10.72 (1H, br s).

LC/MS (ESI): m/z 351.0 (M+1).

Example 209

Methyl[3-(3-amino-4-oxo-4,5-dihydro-2H-pyrazolo[4,3-c]quinolin-2-yl)-2-methylphenoxy]acetate

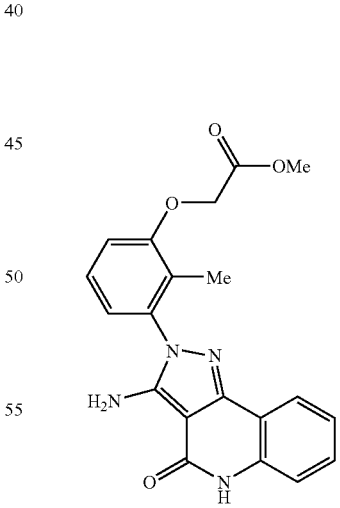

In the same manner as shown in Example 76, the target compound was obtained.

$^1$H-NMR (DMSO-d6, 300 MHz): δ 1.93 (3H, s), 3.71 (3H, s), 4.90 (2H, s), 6.14 (2H, br s), 7.00-7.11 (3H, m), 7.22-7.39 (3H, m), 7.82 (1H, d, J=7.8 Hz), 10.72 (1H, br s).

LC/MS (ESI): m/z 379.0 (M+1).

Example 210

3-amino-2-[3-(2-methoxyethoxy)-2-methylphenyl]-2,5-dihydro-4H-pyrazolo[4,3-c]quinolin-4-one

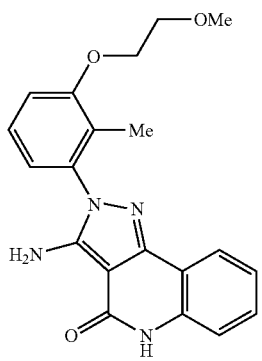

In the same manner as shown in Example 76, the target compound was obtained.

¹H-NMR (DMSO-d6, 300 MHz): δ 1.84 (3H, s), 3.27 (3H, s), 3.64-3.68 (2H, m), 4.11-4.15 (2H, m), 6.07 (2H, br s), 6.92 (1H, d, J=8.0 Hz), 7.00-7.12 (2H, m), 7.17-7.35 (3H, m), 7.77. (1H, d, J=7.6 Hz), 10.67 (1H, br s).

LC/MS (ESI): m/z 365.0 (M+1).

Example 211

[3-(3-amino-4-oxo-4,5-dihydro-2H-pyrazolo[4,3-c]quinolin-2-yl)-2-methylphenoxy]acetonitrile

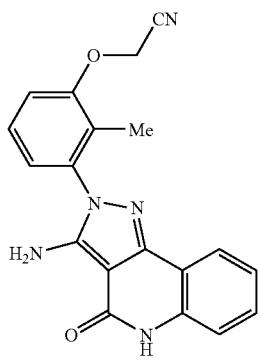

In the same manner as shown in Example 76, the target compound was obtained.

¹H-NMR (DMSO-d6, 300 MHz): δ 1.93 (3H, s), 5.29 (2H, s), 6.23 (2H, br s), 7.08-7.15 (2H, m), 7.25 (1H, d, J=8.4 Hz), 7.30 (1H, d, J=8.4 Hz), 7.36-7.46 (2H, m), 7.83 (1H, d, J=7.8 Hz), 10.75 (1H, br s).

LC/MS (ESI): m/z 346.0 (M+1).

Example 212

4-{[3-amino-7-methoxy-2-(2-methylphenyl)-4-oxo-4,5-dihydro-2H-pyrazolo[4,3-c]quinolin-9-yl]oxy}butanoic acid

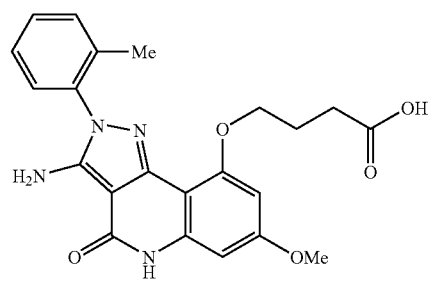

In the same manner as shown in Example 91, the target compound was obtained.

¹H-NMR (DMSO-d6, 300 MHz): δ 1.83-1.88 (2H, m), 2.06 (3H, s), 2.07-2.13 (2H, m), 3.75 (3H, s), 4.04-4.06 (2H, m), 6.01 (2H, br s), 6.31 (1H, s), 6.42 (1H, s), 7.34-7.39 (4H, m), 10.56 (1H, br s), 11.92 (1H, br s).

LC/MS (ESI): m/z 423.0 (M+1).

Example 213

{[3-amino-7-methoxy-2-(2-methylphenyl)-4-oxo-4,5-dihydro-2H-pyrazolo[4,3-c]quinolin-9-yl]oxy}acetic acid

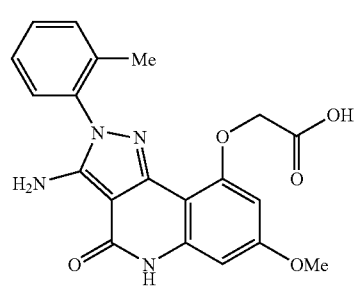

In the same manner as shown in Example 91, the target compound was obtained.

¹H-NMR (DMSO-d6, 300 MHz): δ 2.02 (3H, s), 3.71 (3H, s), 4.72 (2H, s), 6.18 (2H, br s), 6.30 (1H, s), 6.46 (1H, s), 7.31-7.41 (4H, m), 10.71 (1H, br s).

LC/MS (ESI): m/z 395.2 (M+1).

Example 214

[3-(3-amino-4-oxo-4,5-dihydro-2H-pyrazolo[4,3-c]quinolin-2-yl]phenoxy}acetic acid

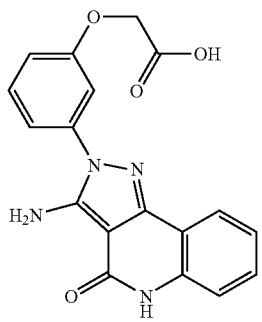

In the same manner as shown in Example 91, the target compound was obtained.

$^1$H-NMR (DMSO-d6, 300 MHz): δ 4.78 (2H, s), 6.42 (2H, br s), 6.97-7.05 (1H, m), 7.09-7.17 (2H, m), 7.23-7.26 (2H, m), 7.38 (1H, t, J=7.8 Hz), 7.45 (1H, t, J=8.4 Hz), 7.88 (1H, d, J=7.5 Hz), 10.77 (1H, br s).

LC/MS (ESI): m/z 351.2 (M+1).

Example 215

[2-(3-amino-4-oxo-4,5-dihydro-2H-pyrazolo[4,3-c]quinolin-2-yl)phenoxy]acetic acid

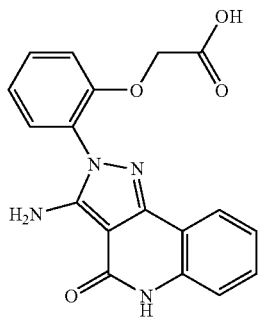

In the same manner as shown in Example 91, the target compound was obtained.

$^1$H-NMR (DMSO-d6, 300 MHz): δ 4.69 (2H, s), 6.64 (2H, br s), 7.05-7.12 (3H, m), 7.23 (1H, d, J=8.4 Hz), 7.33-7.44 (3H, m), 7.84 (1H, d, J=8.4 Hz), 10.67 (1H, br s).

LC/MS (ESI): m/z 351.0 (M+1).

Example 216

[3-(3-amino-4-oxo-4,5-dihydro-2H-pyrazolo[4,3-c]quinolin-2-yl)-2-methylphenoxy]acetic acid

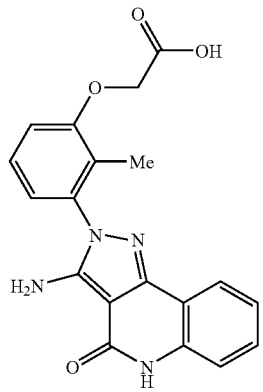

In the same manner as shown in Example 91, the target compound was obtained.

$^1$H-NMR (DMSO-d6, 300 MHz): δ 1.88 (3H, s), 4.73 (2H, s), 6.08 (2H, br s), 6.93-7.08 (3H, m), 7.17-7.36 (3H, m), 7.78 (1H, d, J=7.6 Hz), 10.67 (1H, br s).

LC/MS (ESI): m/z 365.1 (M+1).

Example 217

3-[3-(3-amino-4-oxo-4,5-dihydro-2H-pyrazolo[4,3-c]quinolin-2-yl)-2-methylphenoxy]propanoic acid

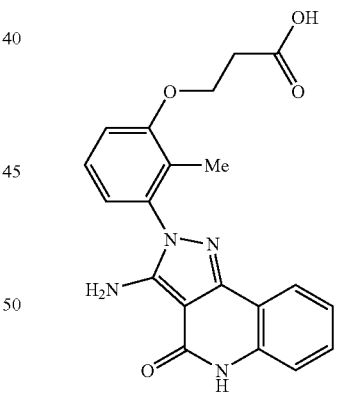

To a mixture of 3-amino-2-(3-hydroxy-2-methylphenyl)-2,5-dihydro-4H-pyrazolo[4,3-c]quinolin-4-one (100 mg), 1N aqueous sodium hydroxide solution (326 μl) and water (3 ml) was added dropwise γ-propiolactone (25 μl) at 80° C. The mixture was stirred at 80° C. for 2 hours, after stirring, cooled to room temperature, and the insoluble materials were filtered off. pH of the filtrate was adjusted to about 2 by adding 1N hydrochloric acid. The precipitated solid was collected by filtration, washed with water, and dried to obtain the target compound (8 mg).

$^1$H-NMR (DMSO-d6, 300 MHz): δ 1.87 (3H, s), 2.74 (2H, t, J=5.9 Hz), 4.26 (2H, t, J=5.9 Hz), 6.14 (2H, br s), 7.00 (1H, d, J=7.8 Hz), 7.09-7.14 (1H, m), 7.18 (1H, d, J=8.4 Hz), 7.26 (1H, d, J=7.5 Hz), 7.32-7.41 (2H, m), 7.84 (1H, d, J=7.8 Hz), 10.74 (1H, br s).
LC/MS (ESI): m/z 379.0 (M+1).

Example 218

3-amino-2-[2-methyl-3-(1H-tetrazol-5-ylmethoxy)phenyl]-2,5-dihydro-4H-pyrazolo[4,3-c]quinolin-4-one

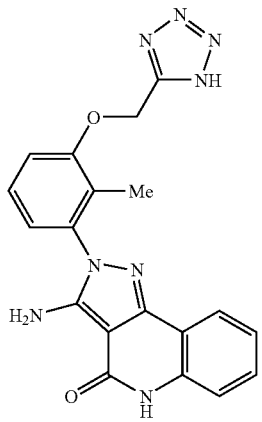

A mixture of [3-(3-amino-4-oxo-4,5-dihydro-2H-pyrazolo[4,3-c]quinolin-2-yl)-2-methylphenoxy]acetonitrile (65 mg), sodium azide (37 mg), ammonium chloride (30 mg) and N,N-dimethylformamide (6 ml) was stirred at 60° C. for 3 hours and then at 100° C. for 2 days. After cooling to room temperature, the reaction mixture was diluted with water, and then pH of the reaction mixture was adjusted to about 2 by adding 1N hydrochloric acid. The precipitated solid was collected by filtration, washed with water, and dried to obtain the target compound (72 mg).
$^1$H-NMR (DMSO-d6, 300 MHz): δ 1.94 (3H, s), 5.60 (2H, s), 6.17 (2H, br s), 7.06-7.14 (2H, m), 7.25-7.41 (4H, m), 7.84 (1H, d, J=7.8 Hz), 10.75 (1H, br s).
LC/MS (ESI): m/z 389.1 (M+1).

Example 219

Methyl{[3-amino-2-(5-hydroxy-2-methyl-4-phenoxyphenyl)-4-oxo-4,5-dihydro-2H-pyrazolo[4,3-c]quinolin-7-yl]oxy}acetate

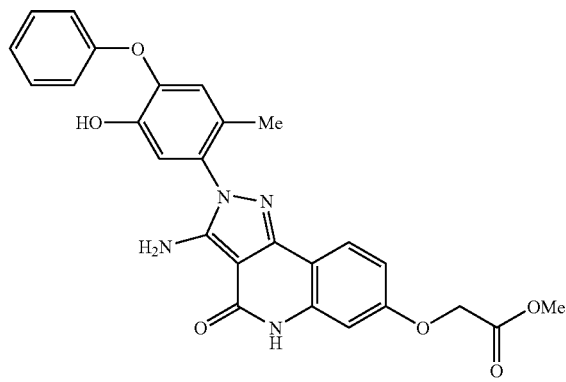

To a mixture of acetyl chloride (2 ml) and methanol (20 ml) was added {[3-amino-2-(5-hydroxy-2-methyl-4-phenox- yphenyl)-4-oxo-4,5-dihydro-2H-pyrazolo[4,3-c]quinolin-7-yl]oxy}acetic acid (145 mg). The mixture was heated under reflux with stiring for one night. The reaction mixture was cooled, a 5% aqueous sodium hydrogen carbonate solution was added thereto, and extracted with ethyl acetate. The extract was washed with water and saturated brine, dried over anhydrous magnesium sulfate, and then concentrated under reduced pressure. To the residue was added ethyl acetate-hexane, the precipitated solid was collected by filtration, washed with ethyl acetate-hexane to obtain the target compound (130 mg).
$^1$H-NMR (DMSO-d6, 300 MHz): δ 1.94 (3H, s), 3.72 (3H, s), 4.82 (2H, s), 6.23 (2H, br s), 6.73-6.76 (2H, m), 6.92-7.07 (5H, m), 7.31-7.36 (2H, m), 7.75 (1H, d, J=7.2 Hz), 9.76 (1H, br s), 10.62 (1H, br s).
LC/MS (ESI): m/z 487.1 (M+1).

Example 220

Ethyl{[3-amino-2-(5-hydroxy-2-methyl-4-phenoxyphenyl)-4-oxo-4,5-dihydro-2H-pyrazolo[4,3-c]quinolin-7-yl]oxy}acetate

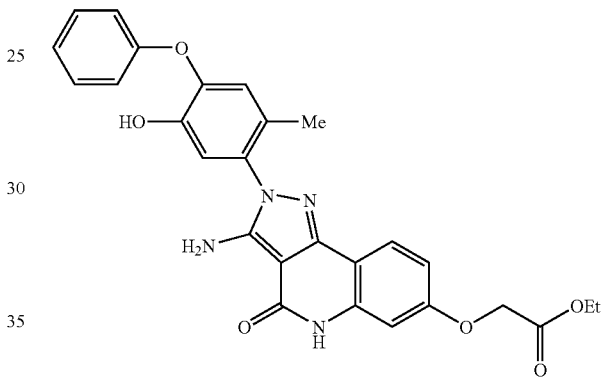

In the same manner as shown in Example 219, the target compound was obtained.
$^1$H-NMR (DMSO-d6, 300 MHz): δ 1.24 (3H, t, J=7.1 Hz), 1.94 (3H, s), 4.19 (2H, q, J=7.1 Hz), 4.79 (2H, s), 6.24 (2H, br s), 6.72-6.75 (2H, m), 6.91 (1H, s), 6.95-7.07 (4H, m), 7.31-7.36 (2H, m), 7.75 (1H, d, J=8.4 Hz), 9.77 (1H, br s), 10.64 (1H, br s).
LC/MS (ESI): m/z 501.3 (M+1).

Example 221

3-amino-7,9-dimethoxy-2-(2-methyl-4-phenoxyphenyl)-2,5-dihydro-4H-pyrazolo[4,3-c]quinolin-4-one

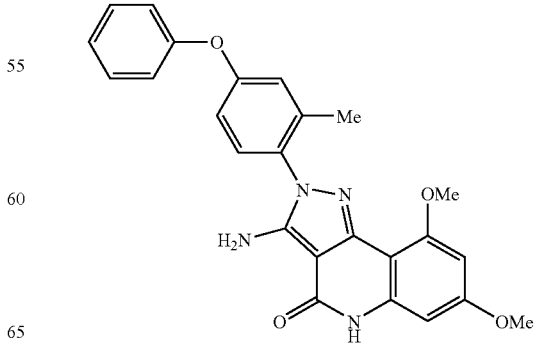

A mixture of 4-chloro-5,7-dimethoxy-1-(4-methoxybenzyl)-2-oxo-1,2-dihydroquinoline-3-carbonitrile (1.50 g), 2-methyl-4-phenoxyphenylhydrazine hydrochloride (1.27 g), triethylamine (1.3 ml) and ethanol (20 ml) was stirred at 80° C. for 2 hours. After cooling, water was added to the mixture. The precipitated solid was collected by filtration, washed with water and ethyl acetate-hexane, and dried to obtain the solid (1.79 g). A mixture of the obtained solid (655 mg), anisole (0.8 ml), trifluoroacetic acid (2.3 ml) and trifluoromethanesulfonic acid (0.5 ml) was stirred at room temperature for 4 hours, and concentrated under reduced pressure. The residue was cooled with ice water bath, dissolved in ethyl acetate, was basified with an 8N aqueous sodium hydroxide solution, and then was extracted with ethyl acetate. The extract was washed with water and brine, dried over anhydrous magnesium sulfate, and the solvent was distilled off under reduced pressure. The residual solid was washed with ethyl acetate-hexane, and recrystallized from ethyl acetate-ethanol to obtain the target compound (194 mg).

$^1$H-NMR (DMSO-d6, 300 MHz): δ 2.02 (3H, s), 3.76 (3H, s), 3.79 (3H, s), 6.08 (2H, br s), 6.30 (1H, s), 6.43 (1H, s), 6.94 (1H, dd, J=8.4, 2.4 Hz), 7.05 (1H, d, J=2.4 Hz), 7.09 (2H, d, J=7.5 Hz), 7.16 (1H, t, J=7.5 Hz), 7.34 (1H, d, J=8.4 Hz), 7.42 (2H, t, J=7.5 Hz), 10.57 (1H, br s).

LC/MS (ESI): m/z 443.3 (M+1).

Example 222

2-{[3-amino-7-methoxy-2-(2-methylphenyl)-4-oxo-4,5-dihydro-2H-pyrazolo[4,3-c]quinolin-9-yl]oxy}-N-[2-(dimethylamino)ethyl]acetamide

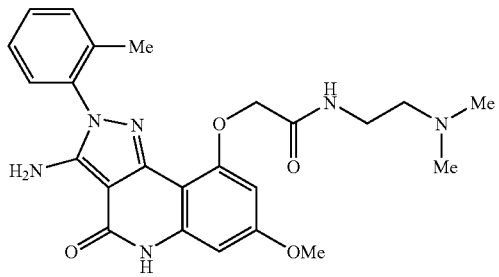

A mixture of {[3-amino-7-methoxy-2-(2-methylphenyl)-4-oxo-4,5-dihydro-2H-pyrazolo[4,3-c]quinolin-9-yl]oxy}acetic acid (80 mg), N,N-dimethylethylenediamine (33 μl), (3-dimethylaminopropyl)ethylcarbodiimide hydrochloride (58 mg), 1-hydroxybenzotriazole (41 mg), triethylamine (43 μl) and N,N-dimethylformamide (2 ml) was stirred at room temperature for one night. The reaction mixture was concentrated under reduced pressure, and the residue was purified with column chromatography to obtain the target compound (61 mg).

$^1$H-NMR (DMSO-d6, 300 MHz): δ 1.61-1.66 (2H, m), 1.88 (6H, s), 2.10 (3H, s), 2.75-2.77 (2H, m), 3.77 (3H, s), 4.51 (2H, s), 6.17 (2H, br s), 6.34 (1H, s), 6.46 (1H, s), 1.40-7.44 (4H, m), 9.02 (1H, br), 10.71 (1H, br s).

LC/MS (ESI): m/z 465.1 (M+1).

Example 223

3-amino-7-methoxy-2-(2-methylphenyl)-9-[2-(4-methylpiperazin-1-yl)-2-oxoethoxy]-2,5-dihydro-4H-pyrazolo[4,3-c]quinolin-4-one

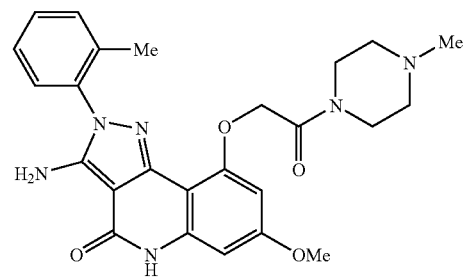

In the same manner as shown in Example 222, the target compound was obtained.

$^1$H-NMR (DMSO-d6, 300 MHz): δ 2.02 (3H, s), 2.08 (3H, s), 2.08-2.17 (2H, m), 2.92-2.98 (2H, m), 3.33-3.35 (2H, m), 3.48-3.50 (2H, m), 3.73 (3H, s), 4.83 (2H, s), 6.03 (2H, br s), 6.18 (1H, s), 6.45 (1H, s), 7.33-7.42 (4H, m), 10.60 (1H, br s).

LC/MS (ESI): m/z 477.1 (M+1).

Example 224

2-{[3-amino-7-methoxy-2-(2-methylphenyl)-4-oxo-4,5-dihydro-2H-pyrazolo[4,3-c]quinolin-9-yl]oxy}-N-1H-pyrazol-3-ylacetamide

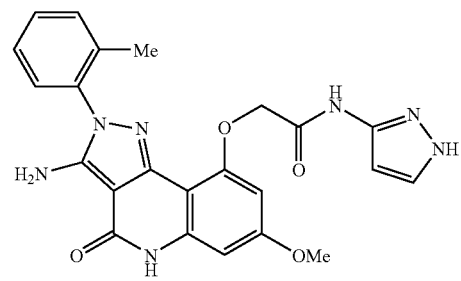

In the same manner as shown in Example 222, the target compound was obtained.

$^1$H-NMR (DMSO-d6, 300 MHz): δ 2.02 (3H, s), 3.78 (3H, s), 4.74 (2H, s), 6.08 (2H, br s), 6.44 (1H, s), 6.50 (1H, s), 7.22-7.55 (6H, m), 10.50 (1H, br s), 10.73 (1H, br s), 12.00 (1H, br s).

LC/MS (ESI): m/z 460.2 (M+1).

Example 225

2-{[3-amino-7-methoxy-2-(2-methylphenyl)-4-oxo-4,5-dihydro-2H-pyrazolo[4,3-c]quinolin-9-yl]oxy}-N-1H-imidazol-3-ylacetamide

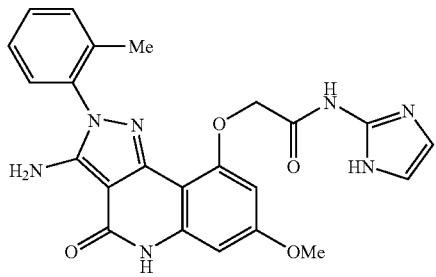

In the same manner as shown in Example 222, the target compound was obtained.

$^1$H-NMR (DMSO-d6, 300 MHz): δ 2.02 (3H, s), 3.78 (3H, s), 4.82 (2H, s), 6.08 (2H, br s), 6.45-6.50 (3H, m), 6.69 (1H, br s), 7.12-7.30 (4H, m), 10.74 (1H, br s), 10.99 (1H, br s), 11.50 (1H, br s).

LC/MS (ESI): m/z 460.2 (M+1).

Example 226

2-[2-(3-amino-4-oxo-4,5-dihydro-2H-pyrazolo[4,3-c]quinolin-2-yl)phenoxy]-N-(2-hydroxyethyl)acetamide

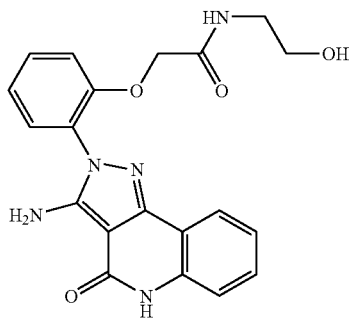

In the same manner as shown in Example 222, the target compound was obtained.

$^1$H-NMR (DMSO-d6, 300 MHz): δ 3.14-3.19 (2H, m), 3.31-3.36 (2H, m), 4.74 (2H, s), 6.46 (2H, br s), 7.07-7.15 (3H, m), 7.24 (1H, d, J=8.4 Hz), 7.37 (1H, t, J=6.9 Hz), 7.43-7.48 (2H, m), 7.85 (1H, d, J=7.5 Hz), 8.22 (1H, t, J=5.7 Hz), 10.77 (1H, br s).

LC/MS (ESI): m/z 394.0 (M+1).

Example 227

2-[3-(3-amino-4-oxo-4,5-dihydro-2H-pyrazolo[4,3-c]quinolin-2-yl)-2-methylphenoxy]-N-(methylsulfonyl)acetamide

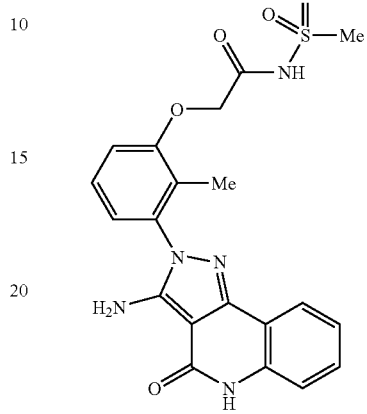

A mixture of [3-(3-amino-4-oxo-4,5-dihydro-2H-pyrazolo[4,3-c]quinolin-2-yl)-2-methylphenoxy]acetic acid (64 mg), methanesulfonamide (50 mg), 4-(dimethylamino)pyridine (25 mg), (3-dimethylaminopyropyl)ethylcarbodiimide hydrochloride (40 mg) and N,N-dimethylformamide (6 ml) was stirred at room temperature for 2 days. The reaction mixture was concentrated under reduced pressure. To the residue was added water, and then pH of the residue was adjusted to about 2 by adding a 1N hydrochloric acid. The precipitated solid was collected by filtration, washed with water, and dried to obtain the target compound (29 mg).

$^1$H-NMR (DMSO-d6, 300 MHz): δ 1.96 (3H, s), 3.26 (3H, s), 4.79 (2H, s), 6.16 (2H, br s), 7.00-7.05 (2H, m), 7.09-7.14 (1H, m), 7.26 (1H, d, J=7.8 Hz), 7.32-7.41 (2H, m), 7.84 (1H, d, J=7.8 Hz), 10.74 (1H, br s), 12.10 (1H, br s).

LC/MS (ESI): m/z 442.0 (M+1).

Example 228

4-{[3-amino-7-methoxy-2-(2-methylphenyl)-4-oxo-4,5-dihydro-2H-pyrazolo[4,3-c]quinolin-9-yl]oxy}butanamide

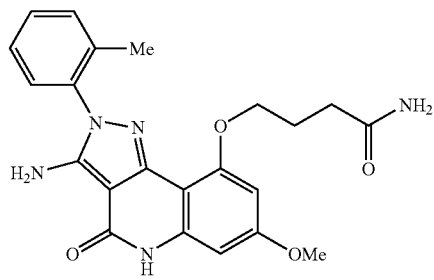

A mixture of methyl 4-{[3-amino-7-methoxy-2-(2-methylphenyl)-4-oxo-4,5-dihydro-2H-pyrazolo[4,3-c]quinolin-9-yl]oxy}butanoate (60 mg) and 2N solution of ammonia in methanol was stirred at room temperature for 5 hours. The reaction mixture was concentrated under reduced pressure, and the residue was purified with column chromatography to obtain the target compound (37 mg).

¹H-NMR (DMSO-d6, 300 MHz): δ 1.76-1.93 (4H, m), 2.02 (3H, s), 2.08 (2H, br s), 3.71 (3H, s), 3.95-4.02 (2H, m), 5.94 (2H, br s), 6.36 (2H, s), 7.31-7.37 (4H, m), 10.53 (1H, br s).

LC/MS (ESI): m/z 422.1 (M+1).

Example 229

4-{[3-amino-7-methoxy-2-(2-methylphenyl)-4-oxo-4,5-dihydro-2H-pyrazolo[4,3-c]quinolin-9-yl]oxy}-N,N-dimethylbutanamide

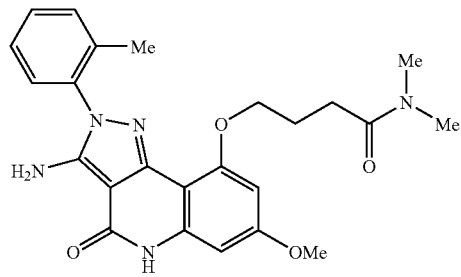

In the same manner as shown in Example 228, the target compound was obtained.

¹H-NMR (DMSO-d6, 300 MHz): δ 1.80-1.85 (2H, m), 2.02 (3H, s), 2.05-2.09 (2H, m), 2.42-2.52 (6H, m), 3.71 (3H, s), 3.95-4.00 (2H, m), 5.97 (2H, br s), 6.26 (1H, s), 6.38 (1H, s), 7.30-7.38 (4H, m), 10.52 (1H, br s).

LC/MS (ESI): m/z 450.1 (M+1).

Example 230

4-{[3-amino-7-methoxy-2-(2-methylphenyl)-4-oxo-4,5-dihydro-2H-pyrazolo[4,3-c]quinolin-9-yl]oxy}-N-methylbutanamide

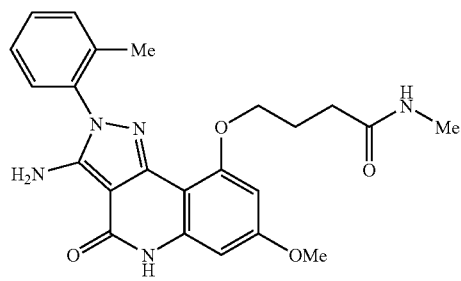

In the same manner as shown in Example 228, the target compound was obtained.

¹H-NMR (DMSO-d6, 300 MHz): δ 1.81-1.85 (2H, m), 2.06 (3H, s), 2.10-2.26 (5H, m), 3.75 (3H, s), 4.04-4.08 (2H, m), 6.06 (2H, br s), 6.35 (1H, s), 6.43 (1H, s), 7.37-7.42 (4H, m), 7.67 (1H, br s), 10.57 (1H, br s).

LC/MS (ESI): m/z 436.0 (M+1).

Example 231

2-{[3-amino-7-methoxy-2-(2-methylphenyl)-4-oxo-4,5-dihydro-2H-pyrazolo[4,3-c]quinolin-9-yl]oxy}-N-methylacetamide

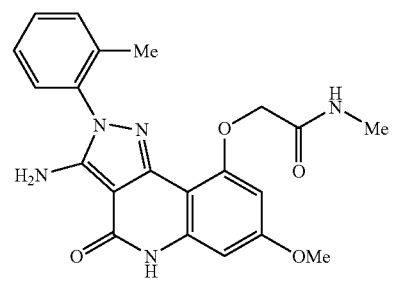

In the same manner as shown in Example 228, the target compound was obtained.

¹H-NMR (DMSO-d6, 300 MHz): δ 2.02 (3H, s), 2.05 (3H, s), 3.72 (3H, s), 4.47 (2H, s), 6.20 (2H, br s), 6.31 (1H, s), 6.41 (1H, s), 7.38-7.41 (4H, m), 9.23-9.26 (1H, m), 10.67 (1H, br s).

LC/MS (ESI) : m/z 408.0 (M+1).

Example 232

2-[3-(3-amino-4-oxo-4,5-dihydro-2H-pyrazolo[4,3-c]quinolin-2-yl)phenoxy]-N-methylacetamide

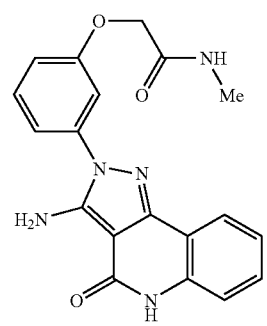

In the same manner as shown in Example 228, the target compound was obtained.

¹H-NMR (DMSO-d6, 300 MHz): δ 2.65 (3H, d, J=4.8 Hz), 4.56 (2H, s), 6.44 (2H, br s), 7.03 (1H, d, J=7.5 Hz), 7.12 (1H, t, J=7.5 Hz), 7.23-7.27 (3H, m), 7.35-7.47 (2H, m), 7.88 (1H, d, J=8.1 Hz), 8.09 (1H, br q, J=4.8 Hz), 10.77 (1H, br s).

LC/MS (ESI): m/z 364.2 (M+1).

Example 233

2-[2-(3-amino-4-oxo-4,5-dihydro-2H-pyrazolo[4,3-c]quinolin-2-yl)phenoxy]-N-methylacetamide

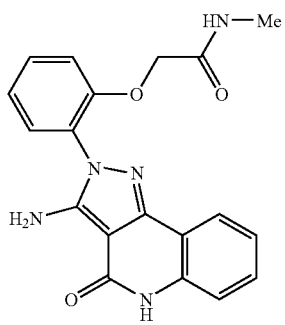

In the same manner as shown in Example 228, the target compound was obtained.

$^1$H-NMR (DMSO-d6, 300 MHz): δ 2.63 (3H, d, J=4.8 Hz), 4.72 (2H, s), 6.46 (2H, br s), 7.08-7.16 (3H, m), 7.25 (1H, d, J=8.1 Hz), 7.37 (1H, t, J=7.8 Hz), 7.43-7.48 (2H, m), 7.84 (1H, d, J=7.8 Hz), 8.15 (1H, br q, J=4.8 Hz), 10.71 (1H, br s).

LC/MS (ESI): m/z 364.1 (M+1).

Example 234

2-[2-(3-amino-4-oxo-4,5-dihydro-2H-pyrazolo[4,3-c]quinolin-2-yl)phenoxy]acetamide

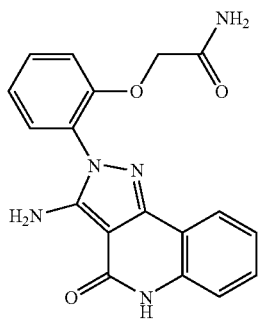

In the same manner as shown in Example 228, the target compound was obtained.

$^1$H-NMR (DMSO-d6, 300 MHz): δ 4.70 (2H, s), 6.45 (2H, br s), 7.05-7.15 (3H, m), 7.24 (1H, d, J=7.8 Hz), 7.37 (1H, t, J=6.9 Hz), 7.44-7.48 (2H, m), 7.58 (1H, br s), 7.73 (1H, br s), 7.83 (1H, d, J=7.5 Hz), 10.71 (1H, br s).

LC/MS (ESI): m/z 350.0 (M+1).

Example 235

2-[3-(3-amino-4-oxo-4,5-dihydro-2H-pyrazolo[4,3-c]quinolin-2-yl)-2-methylphenoxy]-N-methylacetamide

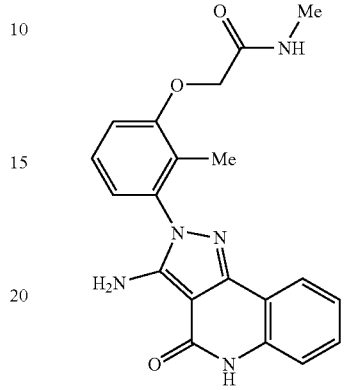

In the same manner as shown in Example 228, the target compound was obtained.

$^1$H-NMR (DMSO-d6, 200 MHz): δ 1.93 (3H, s), 2.62 (3H, d, J=4.4 Hz), 4.52 (2H, s), 6.07 (2H, br s), 6.95-7.08 (3H, m), 7.18-7.36 (3H, m), 7.77 (1H, d, J=8.0 Hz), 7.85 (1H, br q, J=4.4 Hz), 10.68 (1H, br s).

LC/MS (ESI): m/z 378.0 (M+1).

Example 236

2-{[3-amino-2-(5-hydroxy-2-methyl-4-phenoxyphenyl)-4-oxo-4,5-dihydro-2H-pyrazolo[4,3-c]quinolin-7-yl]oxy}-N-methylacetamide

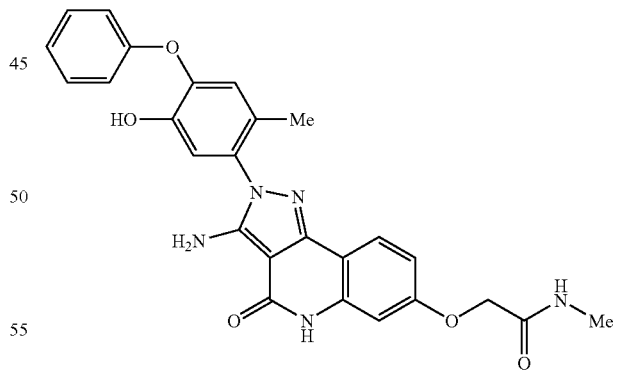

In the same manner as shown in Example 228, the target compound was obtained.

$^1$H-NMR (DMSO-d6, 300 MHz): δ 1.94 (3H, s), 2.66 (3H, d, J=4.8 Hz), 4.47 (2H, s), 6.23 (2H, br s), 6.76 (1H, dd, J=8.5, 2.3 Hz), 6.81 (1H, d, J=2.3 Hz), 6.91 (1H, s), 6.94-7.07 (4H, m), 7.30-7.36 (2H, m), 7.76 (1H, d, J=8.5$^1$Hz), 8.08 (1H, br q, J=4.8 Hz), 9.76 (1H, br s), 10.67 (1H, br s).

LC/MS (ESI): m/z 486.0 (M+1).

| Preparation Example 1 (Dosage per a Tablet) | |
|---|---|
| (1) Compound obtained in Example 37 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 37, 60.0 mg of lactose and 35.0 mg of corn starch was granulated through a 1 mm-mesh sieve using 0.03 ml of a 10% by weight aqueous solution of gelatin (3.0 mg as gelatin), and then dried at 40° C. and sieved again. The obtained granules were mixed with 2.0 mg of magnesium stearate and compressed. The obtained core tablets were sugar-coated with a suspension of sucrose, titanium dioxide, talc and gum Arabic. The coated core tablets were glazed with bees wax to obtain sugar-coated tablets (carrier is a suitable products in the Japanese Pharmacopoeia Fourteenth Edition).

| Preparation Example 2 (Dosage per a Tablet) | |
|---|---|
| (1) Compound obtained in Example 37 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 37 and 3.0 mg of magnesium stearate were granulated with 0.07 ml (7.0 mg as soluble starch) of an aqueous soluble starch solution, dried, and mixed with 70.0 mg of lactose and 50.0 mg of corn starch. The mixture was compressed to obtain tablets (carrier is a suitable products in the Japanese Pharmacopoeia Fourteenth Edition).

Test Example 1

Inhibition activity of the test compound for Src tyrosine kinase was measured by the method described as below. p60$^{c\text{-}src}$ (a preparation purified partically, purchased from Upstate Biotechnology, Inc.) was usded as an enzyme. A biotin-labeled polypeptide (co-polymer of glutamic acid and tyrosine, glutamic acid:tyrosine=4:1, purchased from Nihon Schering K. K. (Japan), prepared by CIS Bio International) was used as a substrate. A solution having composition of 50 mM Tris-HCl (pH 7.5), 5 mM of $MgCl_2$, 5 mM of $MnCl_2$, 2 mM of dithiothreitol, 0.01% of Tween-20 was used as a buffer solution for measuring the activity of tyrosine-kinase. The amount of phosphorylation of tyrosine in the substrate after the reaction was measured by the method using phosphotyrosine recognition antibody. In the concrete, α-screen phosphotyrosine (p-tyr-100) assay kit (manufactured by PerkinElmer, Inc.) was used. Fusion™ (manufactured by PerkinElmer, Inc.) was used as a plate reader. The test compound was dissolved in dimethylsulfoxide, and diluted with the above-mentioned buffer solution for measuring the activity of tyrosine-kinase. To 5 μl of the solution of test compound was added 10 μl of a buffer solution containing 75 ng/ml of the enzyme (p60 $^{c\text{-}src}$) and 250 ng/ml of the substrate (biotin-labeled polypeptide), and then added 10 μl of a buffer solution containing 5 μM ATP, and then the tyrosine-kinase reaction was initiated. Accordingly the tyrosine-kinase reaction was meant by a kinase reaction in a solution containing the test compound having designated concentration, 30 ng/ml of p60$^{c\text{-}src}$, 100 ng/ml of polypeptide, 2 μM of ATP, 50 mM of Tris-HCl (pH 7.5), 5 mM of $MgCl_2$, 5 mM of $MnCl_2$, 2 mM of dithiothreitol and 0.01% of Tween-20, and the amount of the reaction liquid was 25 μl. After the reaction was continued at room temperature for 10 minutes, the kinase reaction was terminated by adding 25 μl of a solution containing 100 mM of EDTA-2 sodium salt (Ethylene Diamine Tetraacetic Acid, disodium salt), 62.5 mM of HEPES (pH 7.4), 250 mM of NaCl, 0.1% of Bovine Serum Albumin, 10 μg/ml of streptavidine donor beads for α-screen assay, 10 μg/ml of acceptor beads binding anti-phosphotyrosin recognition antibody PY-100 for α-screen assay (Anti-phosphotyrisine(P-Tyr-100) Acceptor beads), and then the binding reaction between phosphotyrosine recognition antibody and phosphorylating tyrosine was continued at room temperature for 16 hours, and then the amount of tyrosine phosphorylation was measured by using plate reader Fusion™. The inhibition rate (%) of the kinase by the test compound was determinated by the equation represented below.

Inhibition rate (%)=100-[(count of the test compound-blank)/(control-blank)]×100

Wherein, the [control] was defined as the count of the solution which was reacted without adding the compound, the [blank] was defined as the count of the solution which was reacted without adding the compound and ATP.

The concentration of the compound required for 50% inhibition of the enzyme activity (the value of $IC_{50}$) was calculated with graph analysis software PRISM Ver3.02 (prepared by Graphpad software, Inc.).

The compound of Example 37, Example 38, Example 61 and Example 62 were showed the inhibiton activity of $10^{-9}$ M order in $IC_{50}$ values.

Industrial Applicability

The compound (I) or the compound (I') of the present invention or a salt thereof or a prodrug thereof, has kinase inhibitory activity (particularly, Src inhibitory activity) and low toxicity, and therefore, can be used for preventing or treating kinase-dependent diseases in a mammal. The kinase-dependent disease involves cell proliferation hyperkinetic diseases caused by abnormal kinase enzyme activity. Further, the compound (I) or the compound (I') of the present invention or a salt thereof or a prodrug thereof specifically inhibits kinase (particularly, Src), and therefore, is useful as a therapeutic agent for inhibiting proliferation of cancer with activated Src and an agent for the prophylaxis and/or treatment of bone and/or articulation diseases.

The present application is based on Patent application No. 2004-42491 applicated in Japan. Accordingly the whole of its contents is involved in the application.

The invention claimed is:

1. A compound represented by the formula:

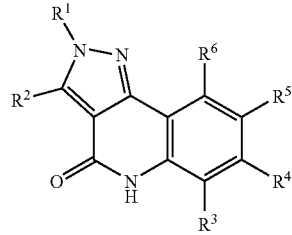

(I)

wherein $R^1$ is:
(1) a $C_{6-12}$ aryl group which may be substituted with 1 to 3 substituents selected from:
   (a) a $C_{1-6}$ alkyl group which may be substituted with 1 to 3 substituents selected from (i) a halogen atom,
(ii) a hydroxy group, and
(iii) a 5- to 8-membered heterocyclic group which may be substituted with a substituent selected from a hydroxy group and a $C_{1-6}$ alkyl group, and has 1 to 3 heteroatoms selected from a nitrogen atom, an oxygen atom and a sulfur atom;
(b) a $C_{1-6}$ alkoxy group which may be substituted with a substituent selected from
(i) a hydroxy group,
(ii) a $C_{1-6}$ alkoxy group,
(iii) a carboxy group,
(iv) a $C_{1-6}$ alkoxy-carbonyl group,
(v) a carbamoyl group,
(vi) a carbamoyl group which is mono- or di-substituted with a $C_{1-6}$ alkyl group which may be substituted with a substituent selected from a hydroxy group and a $C_{1-6}$ alkylsulfonyl group,
(vii) a cyano group, and
(viii) a 5- to 8-membered heterocyclic group having 1 to 3 heteroatoms selected from a nitrogen atom, an oxygen atom and a sulfur atom;
(c) a halogen atom;
(d) a hydroxy group;
(e) an amino group;
(f) a nitro group;
(g) a carboxy group;
(h) a $C_{1-6}$ alkoxy-carbonyl group;
(i) a $C_{1-6}$ alkyl-carbonyloxy group;
(j) a $C_{6-12}$ aryloxy group which may be substituted with a substituent selected from a halogen atom, a hydroxy group and a $C_{1-6}$ alkoxy group;
(k) a $C_{6-14}$ aralkyloxy group;
(l) a $C_{3-7}$ cycloalkyloxy group;
(m) a 5- to 8-membered heterocyclic-oxy group which may be substituted with a $C_{1-6}$ alkyl group, and has 1 to 3 heteroatoms selected from a nitrogen atom, an oxygen atom and a sulfur atom;
(n) a $C_{1-6}$ alkylsulfonyl group; and
(o) a $C_{6-12}$ arylsulfonyl group, or
(2) a 5- or 6-membered aromatic heterocyclic group which may be substituted with 1 to 3 substituents selected from:
(a) a $C_{1-6}$ alkyl group, and
(b) a $C_{1-6}$ alkoxy group,
and has 1 to 3 heteroatoms selected from a nitrogen atom, an oxygen atom and a sulfur atom, or a group resulting from condensation of the 5- or 6-membered aromatic heterocyclic group with a benzene ring;
$R^2$ is:
(1) a hydrogen atom, or
(2) an amino group which may be mono- or di-substituted with a $C_{1-6}$ alkyl group;
$R^3$ is a hydrogen atom;
$R^4$ is:
(1) an amino group,
(2) a hydroxy group, or
(3) a group represented by the formula:

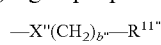
—X"(CH$_2$)$_{b''}$—R$^{11''}$ wherein X" is —O—, —NHSO$_2$—, —NHCO— or —NR$^{12''}$— (wherein R$^{12''}$ is a hydrogen atom, or a $C_{1-6}$ alkyl group which may be substituted with a 5- to 8-membered heterocyclic group having 1 to 3 heteroatoms selected from a nitrogen atom, an oxygen atom and a sulfur atom), b" is an integer from 1 to 4, and
R$^{11''}$ is a 5- to 8-membered heterocyclic group which may be substituted with a substituent selected from
(a) a hydroxy group, and
(b) a $C_{1-6}$ alkyl group,
and has 1 to 3 heteroatoms selected from a nitrogen atom, an oxygen atom and a sulfur atom;
$R^5$ is:
(1) a hydrogen atom,
(2) a $C_{1-6}$ alkoxy group, or
(3) a group represented by the formula:

—O—(CH$_2$)$_{b'''}$—R$^{11'''}$ wherein b''' is an integer from 2 to 4, and
R$^{11'''}$ is a 5- to 8-membered heterocyclic group which may be substituted with a substituent selected from
(a) a $C_{1-6}$ alkyl group, and
(b) a $C_{6-14}$ aryl group which may be substituted with a halogen atom, and has 1 to 3 heteroatoms selected from a nitrogen atom, an oxygen atom and a sulfur atom;
$R^6$ is:
(1) a hydrogen atom,
(2) a hydroxy group,
(3) a $C_{1-6}$ alkoxy group which may be substituted with a substituent selected from:
(a) a hydroxy group,
(b) a $C_{1-6}$ alkoxy group,
(c) a carboxy group,
(d) a $C_{1-6}$ alkoxy-carbonyl group,
(e) a carbamoyl group,
(f) a carbamoyl group which is mono- or di-substituted with a $C_{1-6}$ alkyl group which may be substituted with an amino group which may be mono- or di-substituted with a $C_{1-6}$ alkyl group,
(g) a carbamoyl group which is mono- or di-substituted with a 5- to 8-membered heterocyclic group having 1 to 3 heteroatoms selected from a nitrogen atom, an oxygen atom and a sulfur atom, and
(h) a 5- to 8-membered heterocyclic-carbonyl group which may be substituted with a $C_{1-6}$ alkyl group, and has 1 to 3 heteroatoms selected from a nitrogen atom, an oxygen atom and a sulfur atom,
(4) a $C_{7-14}$ aralkyloxy group, or
(5) a group represented by the formula:

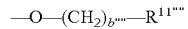
—O—(CH$_2$)$_{b''''}$—R$^{11''''}$ wherein b'''' is an integer from 1 to 4, and
R$^{11''''}$ is a 5- to 8-membered heterocyclic group having 1 to 3 heteroatoms selected from a nitrogen atom, an oxygen atom and a sulfur atom.

2. The compound according to claim 1, wherein $R^1$ is a $C_{6-12}$ aryl group which may be substituted with 1 to 3 substituents selected from:
(a) a $C_{1-6}$ alkyl group which may be substituted with 1 to 3 substituents selected from:
(i) a halogen atom,
(ii) a hydroxy group, and
(iii) a 5- to 8-membered heterocyclic group which may be substituted with a substituent selected from a hydroxy group, a halogen atom and a $C_{1-6}$ alkyl group, and has 1 to 3 heteroatoms selected from a nitrogen atom, an oxygen atom and a sulfur atom,
(b) a $C_{1-6}$ alkoxy group which may be substituted with a substituent selected from:
(i) a hydroxy group,
(ii) a $C_{1-6}$ alkoxy group, (iii) a carboxy group,
(iv) a $C_{1-6}$ alkoxy-carbonyl group,
(v) a carbamoyl group, and
(vi) a carbamoyl group which is mono- or di-substituted with a $C_{1-6}$ alkyl group,
(c) a halogen atom,
(d) a hydroxy group,
(i) a $C_{1-6}$ alkyl-carbonyloxy group,
(j) a $C_{6-12}$ aryloxy group which may be substituted with a halogen atom, and
(m) a 5- to 8-membered heterocyclic-oxy group which may be substituted with a $C_{1-6}$ alkyl group, and has 1 to 3 heteroatoms selected from a nitrogen atom, an oxygen atom and a sulfur atom;

$R^2$ is:
(1) a hydrogen atom, or
(2) an amino group which may be mono- or di-substituted with a $C_{1-6}$ alkyl group;

$R^3$ is a hydrogen atom;

$R^4$ is:
(1) an amino group,
(2) a hydroxy group, or
(3) a group represented by the formula:

$$-X''(CH_2)_{b''}-R^{11''}$$

wherein X" is —O—, —NR$^{12''}$-(wherein R$^{12''}$ is a hydrogen atom, or a $C_{1-6}$ alkyl group which may be substituted with a 5- to 8-membered heterocyclic group having 1 to 3 heteroatoms selected from a nitrogen atom, an oxygen atom and a sulfur atom);

b" is an integer from 1 to 4; and

R$^{11''}$ is a 5- to 8-membered heterocyclic group which may be substituted with a substituent selected from:
(a) a hydroxy group, and
(b) a $C_{1-6}$ alkyl group,
and has 1 to 3 heteroatoms selected from a nitrogen atom, an oxygen atom and a sulfur atom;

$R^5$ is:
(1) a hydrogen atom, or
(2) a $C_{1-6}$ alkoxy group;

$R^6$ is:
(1) a hydrogen atom, or
(2) a $C_{1-6}$ alkoxy group which may be substituted with a substituent selected from:
(a) a hydroxy group,
(b) a $C_{1-6}$ alkoxy group,
(c) a carboxy group,
(d) a $C_{1-6}$ alkoxy-carbonyl group,
(e) a carbamoyl group,
(f) a carbamoyl group which is mono- or di-substituted with a $C_{1-6}$ alkyl group which may be substituted with an amino group which may be mono- or di-substituted with a $C_{1-6}$ alkyl group,
(g) a carbamoyl group which is mono- or di-substituted with a 5- to 8-membered heterocyclic group having 1 to 3 heteroatoms selected from a nitrogen atom, an oxygen atom and a sulfur atom, and
(h) a 5- to 8-membered heterocyclic-carbonyl group which may be substituted with a $C_{1-6}$ alkyl group, and has 1 to 3 heteroatoms selected from a nitrogen atom, an oxygen atom and a sulfur atom.

3. The compound according to claim 1, which is 3-amino-2-(2-chloro-5-hydroxyphenyl)-7-(3-morpholin-4-ylpropoxy)-2,5-dihydro-4H-pyrazolo[4,3-c]quinolin-4-one, 3-amino-2-(2-chloro-5-hydroxyphenyl)-7-(2-morpholin-4-ylethoxy)-2,5-dihydro-4H-pyrazolo [4,3-c]quinolin-4-one, 3-amino-2-(5-hydroxy-2-m ethylphenyl)-7-(3-m orpholin-4-2,5-dihydro-4H-pyrazolo[4,3-c]quinolin-4-one, 3-amino-2-(5-hydroxy-2-ylpropoxy) methylphenyl)-7-(2-morpholin-4-ylethoxy)-2,5-dihydro-4H-pyrazolo[4,3-c]quinolin-4-one, or a salt thereof.

4. A medicine comprising the compound according to claim 1.

* * * * *

UNITED STATES PATENT AND TRADEMARK OFFICE
CERTIFICATE OF CORRECTION

Page 1 of 1

PATENT NO. : 7,842,701 B2
APPLICATION NO. : 10/589443
DATED : November 30, 2010
INVENTOR(S) : Fukumoto et al.

It is certified that error appears in the above-identified patent and that said Letters Patent is hereby corrected as shown below:

Column 238, line 30, (claim 3): "...3-amino-2-(5-hydroxy-2-m ethylpenyl)..." should read --...3-amino-2-(5-hydroxy-2-methylpenyl)--

Column 238, line 30, (claim 3): "...(3-m orpholin-4-2,5-dihydro-4H-pyrazolo..." should read --(3-morpholin-4-ylpropoxy)-2,5-dihydro-4H-pyrazolo...--

Column 238, line 31-32, (claim 3): "...3-amino-2-(5-hydroxy-2-ylpropoxy) methylphenyl) -7-(2-morpholin-4-ylethoxy)-2,5-dihydro-4H-pyrazolo[4,3-c]quinolin-4-one, or a salt thereof." should read --"...3-amino-2- (5-hydroxy-2-~~ylpropoxy)~~-methylphenyl)-7-(2-morpholin-4-ylethoxy)-2,5-dihydro-4H-pyrazolo[4,3-c]quinolin-4-one, or a salt thereof.--

Signed and Sealed this
Twenty-eighth Day of February, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,842,701 B2 | Page 1 of 1 |
| APPLICATION NO. | : 10/589443 | |
| DATED | : November 30, 2010 | |
| INVENTOR(S) | : Fukumoto et al. | |

It is certified that error appears in the above-identified patent and that said Letters Patent is hereby corrected as shown below:

Column 238, lines 30-34 (claim 3): "...3-amino-2-(5-hydroxy-2-m ethylpenyl)-7-(3-m orpholin-4-2,5-dihydro- 4H-pyrazolo[4,3-c]quinolin-4-one, 3-amino-2-(5-hydroxy-2-ylpropoxy) methylphenyl)-7-(2-morpholin-4-ylethoxy)-2,5-dihydro-4H-pyrazolo[4,3-c]quinolin-4-one, or a salt thereof."

should read

-- ...3-amino-2-(5-hydroxy-2-methylpenyl)-7-(3-morpholin-4-ylpropoxy)-2,5-dihydro-4H-pyrazolo[4,3-c]quinolin-4-one, 3-amino-2-(5-hydroxy-2-methylphenyl)-7-(2-morpholin-4-ylethoxy)-2,5-dihydro-4H-pyrazolo[4,3-c]quinolin-4-one, or a salt thereof. --

This certificate supersedes the Certificate of Correction issued February 28, 2012.

Signed and Sealed this
First Day of May, 2012

David J. Kappos
*Director of the United States Patent and Trademark Office*